United States Patent
Dacey, Jr. et al.

(10) Patent No.: US 9,687,670 B2
(45) Date of Patent: Jun. 27, 2017

(54) SYSTEMS, DEVICES, AND METHODS INCLUDING INFECTION-FIGHTING AND MONITORING SHUNTS

(75) Inventors: Ralph G. Dacey, Jr., St. Louis, MO (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Nathan P. Myhrvold, Bellevue, WA (US); Dennis J. Rivet, Portsmouth, VA (US); Michael A. Smith, Phoenix, AZ (US); Elizabeth A. Sweeney, Seattle, WA (US); Clarence T. Tegreene, Bellevue, WA (US); Lowell L. Wood, Jr., Bellevue, WA (US); Victoria Y. H. Wood, Livermore, CA (US)

(73) Assignee: Gearbox, LLC, Bellevue, WA (US)

( * ) Notice: Subject to any disclaimer, the term of this patent is extended or adjusted under 35 U.S.C. 154(b) by 1272 days.

(21) Appl. No.: 12/800,798

(22) Filed: May 21, 2010

(65) Prior Publication Data
US 2010/0241055 A1 Sep. 23, 2010

Related U.S. Application Data

(63) Continuation of application No. 12/660,156, filed on Feb. 19, 2010, now Pat. No. 8,366,652, which is a
(Continued)

(51) Int. Cl.
*A61M 37/00* (2006.01)
*A61N 5/06* (2006.01)
(Continued)

(52) U.S. Cl.
CPC .......... *A61N 5/0601* (2013.01); *A61B 5/0084* (2013.01); *A61B 5/145* (2013.01); *A61B 5/14503* (2013.01); *A61B 5/14539* (2013.01); *A61B 5/14546* (2013.01); *A61L 2/0011* (2013.01); *A61L 2/08* (2013.01); *A61L 2/14* (2013.01); *A61M 5/14276* (2013.01);
(Continued)

(58) Field of Classification Search
CPC ....................... A61M 27/006; A62M 5/14276
USPC ......................................... 604/6.08, 8, 9, 20
See application file for complete search history.

(56) References Cited

U.S. PATENT DOCUMENTS

| | | |
|---|---|---|
| 3,274,406 A | 9/1966 | Sommers, Jr. |
| 3,825,016 A | 7/1974 | Lale et al. |

(Continued)

FOREIGN PATENT DOCUMENTS

| | | |
|---|---|---|
| EP | 1 614 442 A2 | 1/2006 |
| JP | H11117194 | 4/1999 |

(Continued)

OTHER PUBLICATIONS

Hashimoto et al, TiO2 Photocatalysis: A Historical Overview and Future Prospects, Japanese Journal of Applied Physics, 44:12, 8269-8285 (2005).*

(Continued)

*Primary Examiner* — Leslie Deak

(57) ABSTRACT

Systems, devices, methods, and compositions are described for providing an actively controllable shunt configured to, for example, monitor, treat, or prevent an infection.

32 Claims, 36 Drawing Sheets

Related U.S. Application Data continuation of application No. 12/315,880, filed on Dec. 4, 2008, now Pat. No. 8,162,924, and a continuation-in-part of application No. 12/315,881, filed on Dec. 4, 2008, now abandoned, and a continuation-in-part of application No. 12/315,882, filed on Dec. 4, 2008, now abandoned, and a continuation-in-part of application No. 12/315,883, filed on Dec. 4, 2008, now abandoned, and a continuation-in-part of application No. 12/315,884, filed on Dec. 4, 2008, now abandoned, and a continuation-in-part of application No. 12/315,885, filed on Dec. 4, 2008, now abandoned, and a continuation-in-part of application No. 12/380,553, filed on Feb. 27, 2009, now abandoned, application No. 12/800,798, which is a continuation-in-part of application No. 12/315,885, filed on Dec. 4, 2008, now abandoned.

(51) Int. Cl.
    *A61L 2/00*            (2006.01)
    *A61L 2/08*            (2006.01)
    *A61L 2/14*            (2006.01)
    *A61N 1/20*           (2006.01)
    *A61M 27/00*         (2006.01)
    *A61B 5/00*            (2006.01)
    *A61B 5/145*          (2006.01)
    *A61M 5/142*         (2006.01)
    *A61N 1/372*         (2006.01)
    *A61N 1/378*         (2006.01)
    *A61N 1/40*           (2006.01)
    *A61N 5/02*           (2006.01)
    *A61N 5/10*           (2006.01)
    *A61N 7/00*           (2006.01)
    *A61B 5/053*          (2006.01)
    *A61B 5/1459*        (2006.01)
    *A61B 5/1473*        (2006.01)
    *A61B 18/20*         (2006.01)

(52) U.S. Cl.
    CPC .......... *A61M 27/006* (2013.01); *A61N 1/205* (2013.01); *A61N 5/0624* (2013.01); *A61B 5/053* (2013.01); *A61B 5/1459* (2013.01); *A61B 5/1473* (2013.01); *A61B 5/14532* (2013.01); *A61B 5/412* (2013.01); *A61B 18/20* (2013.01); *A61L 2202/24* (2013.01); *A61N 1/3785* (2013.01); *A61N 1/3787* (2013.01); *A61N 1/37252* (2013.01); *A61N 1/40* (2013.01); *A61N 1/403* (2013.01); *A61N 5/02* (2013.01); *A61N 5/10* (2013.01); *A61N 7/00* (2013.01); *A61N 2005/0651* (2013.01); *A61N 2005/0652* (2013.01); *A61N 2005/0661* (2013.01)

(56) References Cited

U.S. PATENT DOCUMENTS

| | | |
|---|---|---|
| 4,081,764 A | 3/1978 | Christmann et al. |
| 4,598,579 A | 7/1986 | Cummings et al. |
| 4,698,058 A | 10/1987 | Greenfeld et al. |
| 4,718,417 A | 1/1988 | Kittrell et al. |
| 4,788,975 A | 12/1988 | Shturman et al. |
| 4,863,849 A | 9/1989 | Melamede |
| 4,900,553 A | 2/1990 | Silver et al. |
| 5,000,731 A | 3/1991 | Wong et al. |
| 5,127,735 A | 7/1992 | Pitt |
| 5,155,707 A | 10/1992 | Fisher |
| 5,156,839 A | 10/1992 | Pennell et al. |
| 5,240,675 A | 8/1993 | Wilk et al. |
| 5,260,020 A | 11/1993 | Wilk et al. |
| 5,281,199 A | 1/1994 | Ensminger et al. |
| 5,302,345 A | 4/1994 | Oksman et al. |
| 5,324,275 A | 6/1994 | Raad et al. |
| 5,326,567 A | 7/1994 | Capelli |
| 5,431,694 A | 7/1995 | Snaper et al. |
| 5,445,608 A | 8/1995 | Chen et al. |
| 5,594,544 A | 1/1997 | Horiuchi et al. |
| 5,607,683 A | 3/1997 | Capelli |
| 5,622,848 A | 4/1997 | Morrow |
| 5,651,767 A | 7/1997 | Schulman et al. |
| 5,681,260 A | 10/1997 | Ueda et al. |
| 5,704,352 A | 1/1998 | Tremblay et al. |
| 5,733,270 A | 3/1998 | Ling et al. |
| 5,735,276 A | 4/1998 | Lemelson |
| 5,750,093 A | 5/1998 | Menon et al. |
| 5,766,934 A | 6/1998 | Guiseppi-Elie |
| 5,797,898 A | 8/1998 | Santini, Jr. et al. |
| 5,810,015 A | 9/1998 | Flaherty |
| 5,855,203 A | 1/1999 | Matter |
| 5,865,744 A | 2/1999 | Lemelson |
| 5,961,923 A | 10/1999 | Nova et al. |
| 5,978,713 A | 11/1999 | Prutchi et al. |
| 5,993,378 A | 11/1999 | Lemelson |
| 5,993,382 A | 11/1999 | Pruitt, Sr. |
| 6,008,896 A | 12/1999 | Sabsabi et al. |
| 6,057,561 A | 5/2000 | Kawasaki et al. |
| 6,086,851 A | 7/2000 | Boni et al. |
| 6,135,990 A | 10/2000 | Heller et al. |
| 6,143,035 A | 11/2000 | McDowell |
| 6,146,409 A | 11/2000 | Overholt et al. |
| 6,162,242 A | 12/2000 | Peyman |
| 6,222,953 B1 | 4/2001 | Hoekstra et al. |
| 6,266,551 B1 | 7/2001 | Osadchy et al. |
| 6,280,604 B1 | 8/2001 | Allen et al. |
| 6,282,444 B1 | 8/2001 | Kroll et al. |
| 6,304,786 B1 | 10/2001 | Heil, Jr. et al. |
| 6,312,770 B1 | 11/2001 | Sage et al. |
| 6,348,042 B1 | 2/2002 | Warren, Jr. |
| 6,350,263 B1 | 2/2002 | Wetzig et al. |
| 6,403,337 B1 | 6/2002 | Bailey et al. |
| 6,418,342 B1 | 7/2002 | Owen et al. |
| 6,426,066 B1 | 7/2002 | Najafi et al. |
| 6,428,491 B1 | 8/2002 | Weiss |
| 6,440,097 B1 | 8/2002 | Kupiecki |
| 6,443,147 B1 | 9/2002 | Matter |
| 6,451,003 B1 | 9/2002 | Prosl et al. |
| 6,461,569 B1 | 10/2002 | Boudreaux |
| 6,470,212 B1 | 10/2002 | Weijand et al. |
| 6,470,888 B1 | 10/2002 | Matter |
| 6,478,778 B1 | 11/2002 | Jacobsen et al. |
| 6,488,704 B1 | 12/2002 | Connelly et al. |
| 6,491,666 B1 | 12/2002 | Santini, Jr. et al. |
| 6,506,416 B1 | 1/2003 | Okauchi et al. |
| 6,533,733 B1 | 3/2003 | Ericson et al. |
| 6,542,767 B1 | 4/2003 | McNichols et al. |
| 6,551,346 B2 | 4/2003 | Crossley |
| 6,562,295 B1 | 5/2003 | Neuberger |
| 6,585,677 B2 | 7/2003 | Cowan, Jr. et al. |
| 6,599,274 B1 | 7/2003 | Kucharczyk et al. |
| 6,626,902 B1 | 9/2003 | Kucharczyk et al. |
| 6,667,807 B2 | 12/2003 | Lieberman |
| 6,730,113 B2 | 5/2004 | Eckhardt et al. |
| 6,743,190 B2 | 6/2004 | Connelly et al. |
| 6,750,055 B1 | 6/2004 | Connelly et al. |
| 6,764,501 B2 | 7/2004 | Ganz |
| 6,789,183 B1 | 9/2004 | Smith et al. |
| 6,793,642 B2 | 9/2004 | Connelly et al. |
| 6,793,880 B2 | 9/2004 | Kippenhan, Jr. |
| 6,802,811 B1 | 10/2004 | Slepian |
| 6,831,748 B2 | 12/2004 | Tittel et al. |
| 6,838,292 B1 | 1/2005 | Rajan et al. |
| 6,844,028 B2 | 1/2005 | Mao et al. |
| 6,849,463 B2 | 2/2005 | Santini, Jr. et al. |
| 6,853,765 B1 | 2/2005 | Cochran |
| 6,887,202 B2 | 5/2005 | Currie et al. |
| 6,908,460 B2 | 6/2005 | DiStefano |
| 6,913,589 B2 | 7/2005 | Dextradeur et al. |

(56) References Cited

U.S. PATENT DOCUMENTS

| | | |
|---|---|---|
| 6,914,279 B2 | 7/2005 | Lu et al. |
| 6,918,869 B2 | 7/2005 | Shaw et al. |
| 6,932,787 B2 | 8/2005 | Cowan et al. |
| 6,939,290 B2 | 9/2005 | Iddan |
| 6,960,201 B2 | 11/2005 | Cumbie |
| 6,969,382 B2 | 11/2005 | Richter |
| 6,980,716 B1 | 12/2005 | Diaz et al. |
| 7,020,355 B2 | 3/2006 | Lahann et al. |
| 7,030,989 B2 | 4/2006 | Yager et al. |
| 7,041,130 B2 | 5/2006 | Santini, Jr. et al. |
| 7,052,488 B2 | 5/2006 | Uhland |
| 7,070,590 B1 | 7/2006 | Santini, Jr. et al. |
| 7,070,592 B2 | 7/2006 | Santini, Jr. et al. |
| 7,078,903 B2 | 7/2006 | Paliwal et al. |
| 7,116,857 B2 | 10/2006 | Faris |
| 7,117,807 B2 | 10/2006 | Bohn, Jr. et al. |
| 7,118,548 B2 | 10/2006 | Børgesen |
| 7,130,459 B2 | 10/2006 | Anderson et al. |
| 7,134,999 B2 | 11/2006 | Brauker et al. |
| 7,143,709 B2 | 12/2006 | Brennan et al. |
| 7,151,139 B2 | 12/2006 | Tiller et al. |
| 7,159,590 B2 | 1/2007 | Rife |
| 7,160,931 B2 | 1/2007 | Cheng et al. |
| 7,167,734 B2 | 1/2007 | Khalil et al. |
| 7,167,755 B2 | 1/2007 | Seeberger et al. |
| 7,183,048 B2 | 2/2007 | Felkner et al. |
| 7,195,608 B2 | 3/2007 | Burnett |
| 7,217,425 B2 | 5/2007 | Serhan et al. |
| 7,221,456 B2 | 5/2007 | Kanai et al. |
| 7,226,441 B2 | 6/2007 | Kulessa |
| 7,232,429 B2 | 6/2007 | Moreci |
| 7,236,821 B2 | 6/2007 | Cates et al. |
| 7,238,363 B2 | 7/2007 | Mansouri et al. |
| 7,244,232 B2 | 7/2007 | Connelly et al. |
| 7,250,615 B1 | 7/2007 | Soong et al. |
| 7,253,152 B2 | 8/2007 | Panero et al. |
| 7,276,255 B2 | 10/2007 | Selkon |
| 7,288,232 B2 | 10/2007 | Morrow et al. |
| 7,306,620 B2 | 12/2007 | Cumbie |
| 7,309,330 B2 | 12/2007 | Bertrand et al. |
| 7,310,459 B1 | 12/2007 | Rahman |
| 7,322,965 B2 | 1/2008 | Gibson et al. |
| 7,334,594 B2 | 2/2008 | Ludin |
| 7,345,372 B2 | 3/2008 | Roberts et al. |
| 7,348,021 B2 | 3/2008 | Klein |
| 7,354,575 B2 | 4/2008 | Shachar et al. |
| 7,365,859 B2 | 4/2008 | Yun et al. |
| 7,367,342 B2 | 5/2008 | Butler |
| 7,390,310 B2 | 6/2008 | McCusker et al. |
| 7,396,676 B2 | 7/2008 | Robotti et al. |
| 7,442,372 B2 | 10/2008 | Kakkis |
| 7,455,667 B2 | 11/2008 | Uhland et al. |
| 7,524,298 B2 | 4/2009 | Gharib et al. |
| 7,535,692 B2 | 5/2009 | Krupenkin et al. |
| 7,621,905 B2 | 11/2009 | Penner et al. |
| 7,650,848 B2 | 1/2010 | Brennan et al. |
| 7,691,684 B2 | 4/2010 | Breitwisch et al. |
| 7,691,894 B2 | 4/2010 | Ono et al. |
| 7,706,178 B2 | 4/2010 | Parkinson |
| 7,714,326 B2 | 5/2010 | Kim et al. |
| 7,837,719 B2 | 11/2010 | Brogan et al. |
| 8,197,452 B2 | 6/2012 | Harding et al. |
| 8,496,610 B2 | 7/2013 | Levenson et al. |
| 2002/0030196 A1 | 3/2002 | Iwata et al. |
| 2002/0090388 A1 | 7/2002 | Humes et al. |
| 2002/0123787 A1 | 9/2002 | Weiss |
| 2002/0182262 A1 | 12/2002 | Selkon |
| 2002/0188323 A1 | 12/2002 | Penner et al. |
| 2002/0192366 A1 | 12/2002 | Cramer et al. |
| 2002/0192680 A1 | 12/2002 | Chan et al. |
| 2003/0012688 A1 | 1/2003 | Kippenhan, Jr. |
| 2003/0014091 A1 | 1/2003 | Rastegar et al. |
| 2003/0017073 A1 | 1/2003 | Eckhardt et al. |
| 2003/0092996 A1 | 5/2003 | Lowe et al. |
| 2003/0097121 A1 | 5/2003 | Jolly et al. |
| 2003/0109907 A1 | 6/2003 | Shadduck |
| 2003/0163079 A1 | 8/2003 | Burnett |
| 2003/0165702 A1 | 9/2003 | Disse et al. |
| 2003/0195415 A1 | 10/2003 | Iddan |
| 2003/0199806 A1 | 10/2003 | Kieval |
| 2003/0204163 A1 | 10/2003 | Marchitto et al. |
| 2003/0214579 A1 | 11/2003 | Iddan |
| 2003/0225331 A1 | 12/2003 | Diederich et al. |
| 2004/0022669 A1 | 2/2004 | Ruan et al. |
| 2004/0073278 A1 | 4/2004 | Pachys |
| 2004/0098005 A1 | 5/2004 | Mirza et al. |
| 2004/0098055 A1 | 5/2004 | Kroll et al. |
| 2004/0149582 A1 | 8/2004 | Kovacs |
| 2004/0186546 A1 | 9/2004 | Mandrusov et al. |
| 2004/0208940 A1 | 10/2004 | Selkon |
| 2004/0253138 A1 | 12/2004 | Malak |
| 2004/0260249 A1 | 12/2004 | Kulessa |
| 2005/0008285 A1 | 1/2005 | Kim et al. |
| 2005/0042743 A1 | 2/2005 | Kawai et al. |
| 2005/0043894 A1 | 2/2005 | Fernandez |
| 2005/0045183 A1 | 3/2005 | Callister et al. |
| 2005/0049181 A1 | 3/2005 | Madhyastha |
| 2005/0063647 A1 | 3/2005 | Thornton et al. |
| 2005/0089890 A1 | 4/2005 | Cubicciotti |
| 2005/0095351 A1 | 5/2005 | Zumeris et al. |
| 2005/0100937 A1 | 5/2005 | Holmes |
| 2005/0105077 A1 | 5/2005 | Padmanabhan et al. |
| 2005/0107289 A1 | 5/2005 | Ghadiri et al. |
| 2005/0142157 A1 | 6/2005 | Alimi |
| 2005/0164169 A1 | 7/2005 | Malak |
| 2005/0171434 A1 | 8/2005 | Madden et al. |
| 2005/0171437 A1 | 8/2005 | Carberry |
| 2005/0175658 A1 | 8/2005 | DiMauro et al. |
| 2005/0180678 A1 | 8/2005 | Panepucci et al. |
| 2005/0192478 A1 | 9/2005 | Williams et al. |
| 2005/0196421 A1 | 9/2005 | Hunter et al. |
| 2005/0203495 A1 | 9/2005 | Malak |
| 2005/0203582 A1 | 9/2005 | Healy et al. |
| 2005/0209665 A1 | 9/2005 | Hunter et al. |
| 2005/0245557 A1 | 11/2005 | Schoenhard et al. |
| 2005/0255604 A1 | 11/2005 | Gjerde et al. |
| 2005/0256554 A1 | 11/2005 | Malak |
| 2005/0263386 A9 | 12/2005 | Pitts, Jr. et al. |
| 2005/0266081 A1 | 12/2005 | Rogozinski |
| 2005/0266582 A1 | 12/2005 | Modlin et al. |
| 2005/0268921 A1 | 12/2005 | Zumeris et al. |
| 2005/0272974 A1 | 12/2005 | Iddan |
| 2005/0288654 A1 | 12/2005 | Nieman et al. |
| 2006/0004317 A1* | 1/2006 | Mauge et al. .................. 604/8 |
| 2006/0004431 A1 | 1/2006 | Fuller et al. |
| 2006/0009805 A1 | 1/2006 | Jensen et al. |
| 2006/0020186 A1 | 1/2006 | Brister et al. |
| 2006/0020239 A1 | 1/2006 | Geiger et al. |
| 2006/0047283 A1 | 3/2006 | Evans, III et al. |
| 2006/0047329 A1 | 3/2006 | Krespi et al. |
| 2006/0052782 A1 | 3/2006 | Morgan et al. |
| 2006/0074479 A1 | 4/2006 | Bailey et al. |
| 2006/0079740 A1 | 4/2006 | Silver et al. |
| 2006/0079762 A1 | 4/2006 | Norris et al. |
| 2006/0105275 A1 | 5/2006 | Maloney et al. |
| 2006/0121087 A1 | 6/2006 | Williams et al. |
| 2006/0122543 A1 | 6/2006 | Mayer et al. |
| 2006/0139667 A1 | 6/2006 | Morimoto et al. |
| 2006/0140911 A1 | 6/2006 | Sharp et al. |
| 2006/0147492 A1 | 7/2006 | Hunter et al. |
| 2006/0159916 A1 | 7/2006 | Dubrow et al. |
| 2006/0204738 A1 | 9/2006 | Dubrow et al. |
| 2006/0210602 A1 | 9/2006 | Sehl et al. |
| 2006/0247525 A1 | 11/2006 | Huo et al. |
| 2006/0253259 A1 | 11/2006 | Fernandez |
| 2006/0271112 A1 | 11/2006 | Martinson et al. |
| 2006/0276713 A1 | 12/2006 | Maier |
| 2006/0287660 A1 | 12/2006 | Syed et al. |
| 2006/0289761 A1 | 12/2006 | Nabet et al. |
| 2007/0016163 A1 | 1/2007 | Santini, Jr. et al. |
| 2007/0031777 A1 | 2/2007 | Wang et al. |
| 2007/0073135 A1 | 3/2007 | Lee et al. |
| 2007/0087445 A1 | 4/2007 | Tearney et al. |
| 2007/0106333 A1 | 5/2007 | Fernandez |

(56) References Cited

U.S. PATENT DOCUMENTS

| | | |
|---|---|---|
| 2007/0111201 A1 | 5/2007 | Doranz |
| 2007/0142874 A1 | 6/2007 | John |
| 2007/0150019 A1 | 6/2007 | Youker et al. |
| 2007/0156039 A1 | 7/2007 | Casciani et al. |
| 2007/0156211 A1 | 7/2007 | Ferren et al. |
| 2007/0173755 A1 | 7/2007 | Alimi et al. |
| 2007/0176117 A1 | 8/2007 | Redmond et al. |
| 2007/0187626 A1 | 8/2007 | Gaska et al. |
| 2007/0196357 A1 | 8/2007 | Alimi et al. |
| 2007/0197890 A1 | 8/2007 | Boock et al. |
| 2007/0205382 A1 | 9/2007 | Gaska et al. |
| 2007/0208245 A1 | 9/2007 | Brauker et al. |
| 2007/0209143 A1 | 9/2007 | Choi et al. |
| 2007/0225634 A1 | 9/2007 | Ferren et al. |
| 2007/0225800 A1 | 9/2007 | Sahatjian et al. |
| 2007/0244423 A1 | 10/2007 | Zumeris et al. |
| 2007/0249969 A1 | 10/2007 | Shields, Jr. |
| 2007/0259017 A1 | 11/2007 | Francis |
| 2007/0274909 A1 | 11/2007 | Justel et al. |
| 2007/0275068 A1 | 11/2007 | Martens et al. |
| 2007/0276208 A1 | 11/2007 | Connelly et al. |
| 2007/0280852 A1 | 12/2007 | Skubal et al. |
| 2007/0282190 A1 | 12/2007 | Dekel et al. |
| 2007/0299384 A1 | 12/2007 | Faul et al. |
| 2008/0007885 A1 | 1/2008 | Mehrl et al. |
| 2008/0014632 A1 | 1/2008 | Cunningham et al. |
| 2008/0033519 A1 | 2/2008 | Burwell et al. |
| 2008/0039678 A1 | 2/2008 | Montpetit et al. |
| 2008/0039768 A1* | 2/2008 | Francis .......................... 604/8 |
| 2008/0051691 A1 | 2/2008 | Dragoon et al. |
| 2008/0051736 A1 | 2/2008 | Rioux et al. |
| 2008/0058798 A1 | 3/2008 | Wallace et al. |
| 2008/0064980 A1 | 3/2008 | Lee et al. |
| 2008/0095977 A1 | 4/2008 | Aizenberg et al. |
| 2008/0118546 A1 | 5/2008 | Thatcher et al. |
| 2008/0119421 A1 | 5/2008 | Tuszynski et al. |
| 2008/0125838 A1 | 5/2008 | Francis |
| 2008/0195170 A1 | 8/2008 | Asgari |
| 2008/0223717 A1 | 9/2008 | Isaksson et al. |
| 2008/0234786 A1 | 9/2008 | Cumbie |
| 2008/0243231 A1 | 10/2008 | Flanagan et al. |
| 2008/0248993 A1 | 10/2008 | Hannappel et al. |
| 2008/0253712 A1 | 10/2008 | Allen et al. |
| 2008/0257355 A1 | 10/2008 | Rao et al. |
| 2008/0265179 A1 | 10/2008 | Havens et al. |
| 2009/0012626 A1 | 1/2009 | Thompson et al. |
| 2009/0015841 A1 | 1/2009 | Downey |
| 2009/0018424 A1 | 1/2009 | Kamath et al. |
| 2009/0048542 A1 | 2/2009 | Varadan et al. |
| 2009/0048648 A1 | 2/2009 | Dacey, Jr. et al. |
| 2009/0054824 A1 | 2/2009 | Melsheimer et al. |
| 2009/0054827 A1 | 2/2009 | Eide |
| 2009/0066195 A1 | 3/2009 | Wang et al. |
| 2009/0110711 A1 | 4/2009 | Trollsas et al. |
| 2009/0118661 A1 | 5/2009 | Moehle et al. |
| 2009/0118813 A1 | 5/2009 | Scheuermann et al. |
| 2009/0156460 A1 | 6/2009 | Jiang et al. |
| 2009/0177254 A1 | 7/2009 | Boyden et al. |
| 2009/0185988 A1 | 7/2009 | Maleski et al. |
| 2009/0195120 A1 | 8/2009 | Knospe |
| 2009/0209897 A1 | 8/2009 | Limaye et al. |
| 2009/0209904 A1 | 8/2009 | Peeters |
| 2009/0281412 A1 | 11/2009 | Boyden et al. |
| 2009/0299153 A1 | 12/2009 | Gerber et al. |
| 2009/0316195 A1 | 12/2009 | Tseng et al. |
| 2010/0063404 A1 | 3/2010 | Kaplan et al. |
| 2010/0100160 A1 | 4/2010 | Edman et al. |
| 2010/0145286 A1 | 6/2010 | Zhang et al. |
| 2010/0174346 A1 | 7/2010 | Boyden et al. |
| 2010/0198357 A1 | 8/2010 | Fuller et al. |
| 2010/0204802 A1 | 8/2010 | Wilson et al. |
| 2010/0234792 A1 | 9/2010 | Dacey, Jr. et al. |
| 2010/0249692 A1 | 9/2010 | Dacey, Jr. et al. |
| 2010/0256607 A1 | 10/2010 | Burnett |
| 2011/0116967 A1 | 5/2011 | Roy et al. |
| 2011/0117582 A1 | 5/2011 | Malima et al. |
| 2011/0160643 A1 | 6/2011 | Dacey, Jr. et al. |
| 2013/0273564 A1 | 10/2013 | Quinn |

FOREIGN PATENT DOCUMENTS

| | | |
|---|---|---|
| WO | WO 91/06855 A2 | 5/1991 |
| WO | WO/92/01222 | 1/1992 |
| WO | WO/97/00586 | 1/1997 |
| WO | WO/00/09733 | 2/2000 |
| WO | WO/00/29613 | 5/2000 |
| WO | WO/00/56185 | 9/2000 |
| WO | WO/01/13926 A2 | 3/2001 |
| WO | WO/01/54704 | 8/2001 |
| WO | WO 02/068049 A1 | 9/2002 |
| WO | WO/02/102421 A1 | 12/2002 |
| WO | WO/2004/027116 A2 | 4/2004 |
| WO | WO/2004/031077 A2 | 4/2004 |
| WO | WO/2005/100100 | 10/2005 |
| WO | WO/2005/117914 A2 | 12/2005 |
| WO | WO 2006/000764 A1 | 1/2006 |
| WO | WO/2006/044324 | 4/2006 |
| WO | WO/2007/070801 A3 | 6/2007 |
| WO | WO/2007/085021 | 7/2007 |
| WO | WO 2007/140544 A1 | 12/2007 |
| WO | WO/2008/020770 A1 | 2/2008 |
| WO | WO/2008/073774 A1 | 6/2008 |
| WO | WO/2008/083390 A2 | 10/2008 |
| WO | WO 2009/067682 A2 | 5/2009 |

OTHER PUBLICATIONS

PCT International Search Report; International App. No. PCT/US2010/003088; Apr. 1, 2011; pp. 1-4.
PCT International Search Report; International App. No. PCT/US11/01883; May 3, 2012; pp. 1-5.
U.S. Appl. No. 12/218,214, Hyde et al.
U.S. Appl. No. 12/231,676, Hyde et al.
U.S. Appl. No. 11/973,010, Hyde et al.
Albert, Richard K. and Condie, Frances; "Medical Intelligence: Hand-Washing Patterns in Medical Intensive-Care Units"; New England Journal of Medicine; Jun. 1981; pp. 1465-1466; vol. 304, No. 24.
Aarabi, Shahram et al.; "Research in Translation: Hypertrophic Scar Formation Following Burns and Trauma: New Approaches to Treatment"; PLoS Medicine; Sep. 2007; pp. 1464-1470; vol. 4, Issue 9, No. e234; located at: www.plosmedicine.org.
Abdollahi, Amir; "Apoptosis Signals in Lymphoblasts Induced by Focused Ultrasound"; The FASEB Journal-FJ Express; Sep. 2004; pp. 1413-1414; vol. 18; FASEB.
"Arglaes® Controlled-Release Silver Technology"; Medline; 2003; 6 pages; Medline Industries, Inc.; located at: www.medline.com.
Ashush, Hagit et al.; "Apoptosis Induction of Human Myeloid Leukemic Cells by Ultrasound Exposure"; Cancer Research; bearing a date of Feb. 15, 2000; pp. 1014-1020; vol. 60.
Bozhevolnyi, Sergey I. et al.; "Photonic bandgap.structures for long-range surface plasmon polaritons"; Optics Communications; bearing a date of 2005; pp. 328-333; vol. 250; Elsevier B.V.
Brogden, Kim A.; "Antimicrobial Peptides: Pore Formers or Metabolic Inhibitors in Bacteria?"; Nature Reviews, Microbiology; Mar. 2005; pp. 238-250; vol. 3.
Carcillo, Joseph A. et al.; "Early Markers of Infection and Sepsis in Newborns and Children"; Leading Article, Advances in Sepsis; 2006; pp. 118-125; vol. 5, No. 4.
Caricchio, Roberto et al.; "Ultraviolet B Radiation-Induced Cell Death: Critical Role of Ultraviolet Dose in Inflammation and Lupus Autoantigen Redistribution"; The Journal of Immunology; 2003; pp. 5778-5786; vol. 171; The American Association of Immunologists, Inc.
Chen, Ting-Hsuan et al.; "A Wettability SWitchable Surface Driven by Electrostatic Induced Surface Morphology Change Without Energy Interference on Reagents in Droplets"; MEMS; Jan. 2006; pp. 178-181; IEEE.

(56) References Cited

OTHER PUBLICATIONS

Cheng, Gang et al.; "Switchable Polymer Surfaces: A Switchable Biocompatible Polymer Surface with Self-Sterilizing and Nonfouling Capabilities"; Angewandte Chemie; 2008; pp. 8831-8834; vol. 47; Wiley-VCH Verlag GmbH & Co.

De Fabo, Edward C.; "Advances in Brief: Ultraviolet B but not Ultraviolet A Radiation Initiates Melanoma"; Cancer Research; bearing a date of Sep. 15, 2004; pp. 6372-6376; vol. 64; American Association for Cancer Research.

Donlan, R. M. et al.; "Model Systems for Growing and Quantifying *Streptococcus Pneumoniae* Biofilms In Situ and in Real Time"; Applied and Environmental Microbiology; Aug. 2004; pp. 4980-4988; vol. 70, No. 8; American Society for Microbiology.

Dubinsky et al.; "High-Intensity Focused Ultrasound: Current Potential and Oncologic Applications"; Ultrasound Imaging-Review, AJR; bearing a date of Jan. 2008; pp. 191-199; vol. 190; American Roentgen Ray Society.

ESR European Search Report; European App. No. EP 08 25 1153; Dec. 15, 2008; p. 1.

"Fact Sheet: Cerebrospinal Fluid Shunt Systems for the Management of Hydrocephalus"; Hydrocephalus Association; 2000; 7 pages; Hydrocephalus Association; located at: www.hydroassoc.org.

Feng, Xinjian et al.; "Reversible Super-Hydrophobicity to Super-Hydrophilicity Transition of Aligned ZnO Nanorod Films"; JACS Communications; 2004; pp. 62-63; vol. 126; American Chemical Society.

Feng, Yi et al.; "Gastric Cancer: Low Intensity Ultrasound-Induced Apoptosis in Human Gastric Carcinoma Cells"; World Journal of Gastroenterology; bearing a date of Aug. 21, 2008; pp. 4873-4879; vol. 14, No. 31; The WJG Press; located at: www.wjgnet.com.

Fogh-Andersen, Niels et al.; "Composition of Interstitial Fluid"; General Clinical Chemistry; 1995; pp. 1522-1525; vol. 41, No. 10.

Forbes, Peter; "Scientific American: Self-Cleaning Materials: Lotus Leaf-Inspired Nanotechnology"; Scientific American Magazine; bearing a date of Jul. 30, 2008; pp. 1-5; printed on Nov. 21, 2008.

Goclawski, Jaroslaw et al.; "The Measurement of Wetting Angle by Applying and ADSA Model of Sessile Drop on Selected Textile Surfaces"; Fibres and Textiles in Eastern Europe; Apr./Jun. 2008; pp. 84-88; vol. 16, No. 2(67).

Gavrieli et al.; "Identification of Programmed Cell Death in situ via Specific Labeling of Nuclear DNA Fragmentation"; The Journal of Cell Biology; bearing a date of Nov. 1992; pp. 493-501; vol. 119, No. 3; The Rockefeller University Press; located at: http://jcb.rupress.org/.

Grunfeld, Carl; "Lipids, Lipoproteins, Triglyceride Clearance, and Cytokines in Human Immunodeficiency Virus Infection and the Acquired Immunodeficiency Syndrome"; Journal of Clinical Endocrinology and Metabolism; 1992; pp. 1045-1052; vol. 74, No. 5; The Endocrine Society.

Harmon et al.; "Cell Death Induced in a Murine Mastocytoma by 42-47°C Heating in vitro: Evidence that the Form of Death Changes From Apoptosis to Necrosis Above a Critical Heat Load"; Int. J. Radiat. Biol., Rights Links; 1990; pp. 845-858; vol. 58, No. 5; Taylor & Francis Ltd.

Imam, S.K. et al.; "Radiotracers for Imaging of Infection and Inflammation—A Review"; World Journal Nuclear Medicine.; Jan. 2006; pp. 40-55; vol. 5, No. 1.

Khan et al.; "The Effect of Hyperthermia on the Induction of Cell Death in Brain, Testis, and Thymus of the Adult and Developing Rat"; Cell Stress & Chaperones; 2002; pp. 73-90; vol. 7, No. 1; Cell Stress Society International.

Killer, H. E. et al.; "The Optic Nerve: A New Window into Cerebrospinal Fluid Composition?"; Brain; 2006; pp. 1027-1030; vol. 129.

Lahann, Joerg; "A Reversibly Switching Surface"; Reports, Science; bearing a date of Jan. 17, 2003; pp. 371-374 (plus Erratum); vol. 299; located at: www.sciencemag.org.

Lepock, James R.; "Cellular Effects of Hyperthermia: Relevance to the Minimum Dose for Thermal Damage"; International Journal of Hyperthermia, Taylor & Francis healthsciences; May-Jun. 2003; pp. 252-266; vol. 19, No. 3; Taylor & Francis Ltd.

Lin, Yi-Hsin; "Electrically Tunable Wettability of Liquid Crystal/Polymer Composite Films"; Optics Express; bearing a date of Oct. 27, 2008; pp. 17591-17598; vol. 16, No. 22; OSA.

Masteikova, Ruta et al.; "Stimuli-Sensitive Hydrogels in Controlled and Sustained Drug Delivery"; Medicina; 2003; pp. 19-24; vol. 39, No. 2.

McDannold et al.; "Microbubble Contrast Agent with Focused Ultrasound to Create Brain Lesions at Low Power Levels: MR Imaging and Histologic Study in Rabbits[1]"; Original Research, Experimental Studies, Radiology; bearing a date of Oct. 2006; pp. 95-106; vol. 241, No. 1; RSNA.

McKenna, Susan M. et al.; "The Inhibition of Bacterial Growth by Hypochlorous Acid"; Biochemistry; 1988; pp. 685-692; vol. 254.

Nejat, Farideh et al.; "Original Article: A Randomized Trial of Ceftriaxone Versus Trimethoprimsulfamethoxazole to Prevent Ventriculoperitoneal Shunt Infection"; Journal of Microbiology, Immunology and Infection; 2008; pp. 112-117; vol. 41; Journal of Microbiology, Immunology and Infection.

NG, P C; "Review: Diagnostic Markers of Infection in Neonates"; Arch Dis Child Fetal Neonatal Ed; 2004; pp. F229-F235; vol. 89; located at: www.archdischild.com.

Okada, Ayako et al.; "Inhibition of Biofilm Formation Using Newly Developed Coating Materials with Self-Cleaning Properties"; Dental Materials Journal; 2008; pp. 565-572; vol. 27, No. 4.

Rathmell, James P. et al.; "Infectious Risks of Chronic Pain Treatments: Injection Therapy, Surgical Implants, and Intradiscal Techniques"; Regional Anesthesia and Pain Medicine; 2006; pp. 346-352; vol. 31, No. 4.

Rediske, Andrea M. et al.; "Pulsed Ultrasound Enhances the Killing of *Escherichia Coli* Biofilms by Aminoglycoside Antibiotics In Vivo"; Antimicrobial Agents and Chemotherapy; Mar. 2000; pp. 771-772; vol. 44, No. 3; American Society for Microbiology; downloaded on Aug. 24, 2009.

Reid, Marvin et al.; "The Acute-Phase Protein Response to Infection in Edematous and Nonedematous Protein-Energy Malnutrition"; The American Journal of Clinical Nutrition; 2002; pp. 1409-1415; vol. 76; American Society for Clinical Nutrition.

Roti Roti, Joseph L.; "Review: Cellular Responses to Hyperthermia (40-46°C): Cell Killing and Molecular Events"; Informa healthcare; Feb. 2008; pp. 3-15; vol. 24, No. 1; Informa UK Ltd.

Seehusen, Dean A. et al.; "Cerebrospinal Fluid Analysis"; American Family Physician; bearing a date of Sep. 15, 2003; pp. 1103-1108; vol. 68, No. 6; located at: www.aafg.org/afp.

Setroikromo, R.; "Heat Shock Proteins and Bc1-2 Expression and Function in Relation to the Differential Hyperthermic Sensitivity between Leukemic and Normal Hematopoietic Cells"; Cell Stress & Chaperones; 2007; pp. 320-330; vol. 12, No. 4; Cell Stress Society International.

Shellman et al.; "Hyperthermia Induces Endoplasmic Reticulum-Mediated Apoptosis in Melanoma and Non-Melanoma Skin Cancer Cells" Original Article, Journal of Investigative Dermatology; 2008; pp. 949-956; vol. 128; The Society of Investigative Dermatology; located at: www.jidonline.org.

"SilvaSorb® Targeted Antimicrobial Protection"; Medline; 2005; 16 pages; Medline Industries Inc.; located at www.medline.com.

Sodja, Caroline; "Splenic T Lymphocytes Die Preferentially During Heat-Induced Apoptosis: NuMA Reorganization as a Marker"; Journal of Cell Science; 1998; pp. 2305-2313; vol. 111; The Company of Biologists Limited.

Somwaru et al.; "Heat Induced Apoptosis of Mouse Meiotic Cells is Suppressed by Ectopic Expression of Testis-Specific Calpastatin"; Journal of Andrology; bearing a date of Jul./Aug. 2004; pp. 506-513; vol. 25, No. 4; American Society of Andrology.

Stankiewicz, Adam R.; "Hsp70 Inhibits Heat-Induced Apoptosis Upstream of Mitochondria by Preventing Bax Translocation"; The Journal of Biological Chemistry; Bearing a date of Nov. 18, 2005; pp. 38729-38739; vol. 280, No. 46; The American Society for Biochemistry and Molecular Biology, Inc.

Tuteja, Anish et al.; "Robust Omniphobic Surfaces"; PNAS; bearing a date of Nov. 25, 2008; pp. 18200-18205; vol. 105, No. 47; The National Academy of Sciences of the USA.

(56) References Cited

OTHER PUBLICATIONS

Vykhodtseva et al.; "Induction of Apoptosis in vivo in the Rabbit Brain with Focused Ultrasound and Optison®"; Original Contribution, Ultrasound in Med. & Biol.; 2006; pp. 1923-1929; vol. 32, No. 12; World Federation for Ultrasound in Medicine & Biology.
Wang, Shutao; "Review: Photoresponsive Surfaces with Controllable Wettability"; Journal of Photochemistry and Photobiology C: Photochemistry Review, Science Direct; 2007; pp. 18-29; vol. 8; Elsevier B.V.
Wang, Zhe et al.; "APD: The Antimicrobial Peptide Database"; Nucleic Acids Research; 2004; pp. D590-D592; vol. 32; Oxford University Press.
Watson, Mark A.; "Review: Clinical Utility of Biochemical Analysis of Cerebrospinal Fluid"; Clinical Chemistry; 1995; pp. 343-360; vol. 41, No. 3.
Wentworth, Jr., Paul et al.; "Reports: Evidence for Antibody-Catalyzed Ozone Formation in Bacterial Killing and Inflammation"; Science AAAS; 2002; pp. 2195-2199; vol. 298; downloaded on Jul. 14, 2009; located at: www.sciencemag.org.
Zhong, Yinghui et al.; "Review: Biomaterials for the Central Nervous System"; Journal of the Royal Society Interface; 2008; pp. 957-975; vol. 5; The Royal Society.
PCT International Search Report; International App. No. PCT/US10/00579; May 3, 2010; pp. 1-2.
PCT International Search Report; International App. No. PCT/US09/06393; May 13, 2010; pp. 1-4.
McCarthy et al.; "Steroid Modulation of Astrocytes in the Neonatal Brain: Implications for Adult Reproductive Function"; Biology of Reproduction; bearing a date of Apr. 5, 2002; pp. 691-698; vol. 67; Society for the Study of Reproduction, Inc.
Dienel et al.; Astrocyte activation in vivo during graded photic stimulation ; Journal of Neurochemistry; bearing a date of 2007; pp. 1506-1522; vol. 103; International Society for Neurochemistry.
Apple et al.; "Review: Future Biomarkers for Detection of Ischemia and Risk Stratification in Acute Coronary Syndrome"; Clinical Chemistry; bearing a date of 2005; pp. 810-824; vol. 51, No. 5; American Association for Clinical Chemistry.
Barnes et al.; "Novel Biomarkers Associated with Deep Venous Thrombosis: A Comprehensive Review"; Biomarker Insights; bearing a date of 2008; pp. 93-100; vol. 3; Creative Commons Attribution.
Beebe et al.; "Nanosecond, High-Intensity Pulsed Electric Fields Induce Apoptosis in Human Cells"; The FASEB Journal; bearing a date of Jun. 17, 2003; pp. 1-23.
Cheng et al.; "Electrically Switchable and Optically Rewritable Reflective Fresnel Zone Plate in Dye-Doped Cholesteric Liquid Crystals"; Optics Express; bearing a date of Oct. 17, 2007; pp. 14078-14085; vol. 15, No. 21; OSA.
Coppola et al.; "Visualization of Optical Deflection and Switching Operations by a Domain-Engineered-Based LinbO$_3$ Electro-Optic Device"; Optics Express; bearing a date of May 19, 2003; vol. 11, No. 10; OSA.
Davis et al.; "A New Electro-Optic Waveguide Architecture and the Unprecedented Devices it Enables"; Proc. of SPIE; bearing a date of 2008; pp. 697503-1-697503-12; vol. 6975.
Frasca et al.; "Review: Prevention of Central Venous Catheter-Related Infection in the Intensive Care Unit"; Critical Care; bearing a date of 2010; pp. 1-8; vol. 14, No. 212; Springer-Verlag Berlin Heidelberg.
Feng et al.; "Plasmonic Effects in Dynamic Tunable Metal-Dielectric Composites"; PIERS Online; bearing a date of 2008; pp. 625-630; vol. 4, No. 6.
European Search Report; European App. No. EP 08 25 1153; Jul. 10, 2009; pp. 1-2.
Giannitsis et al.; "Risk Stratification in Pulmonary Embolism Based on Biomarkers and Echocardiography"; Circulation: Journal of the American Heart Association; bearing a date of 2005; pp. 1520-1521; American Heart Association; located at: http://circ.ahajournals.org/cgi/content/full/112/11/1520.

Hall et al.; "Nanosecond Pulsed Electric Fields Induce Apoptosis in p53-wildtype and p53-null HCT116 Colon Carcinoma Cells"; Apoptosis; bearing a date of May 23, 2007; pp. 1721-1731; vol. 12; Springer Science+Business Media, LLC.
Horng et al.; "Tunable Optical Switch Using Magnetic Fluids"; Applied Physics Letters; bearing a date of Dec. 6, 2004; pp. 5592-5594; vol. 85, No. 23; American Institute of Physics.
Jaffer et al.; "In Vivo Imaging of Thrombin Activity in Experimental Thrombi with Thrombin-Sensitive Near-Infrared Molecular Probe"; Arteriosclerosis, Thrombosis, and Vascular Biology: Journal of the American Heart Association; bearing a date of Aug. 8, 2002; pp. 1929-1935; American Heart Association, Inc.; located at: http://atvb.ahajournals.org/cgi/content/full/22/11/1929.
Jaiswal et al.; "Long-Term Multiple Color Imaging of Live Cells Using Quantum Dot Bioconjugates"; Nature Biotechnology; bearing a date of Jan. 2003; pp. 47-51; vol. 21; Nature Publishing Group.
Kamphuisen et al.; "Can Anticoagulant Treatment be Tailored with Biomarkers in Patients with Venous Thromboembolism?"; Journal of Thrombosis and Haemostasis; bearing a date of 2006; pp. 1206-1207; vol. 4; International Society on Thrombosis and Haemostasis.
Krupenkin et al.; "Electrically Tunable Superhydrophobic Nanostructured Surfaces"; Bell Labs Technical Journal; bearing a date of 2005; pp. 161-170; vol. 10, No. 3; Lucent Technologies Inc.
Li et al.; "Feasibility of Interstitial Doppler Optical Coherence Tomography for In Vivo Detection of Microvascular Changes During Photodynamic Therapy"; Lasers in Surgery and Medicine; bearing a date of Jul. 2, 2006; pp. 754-761; vol. 38; Wiley-Liss Inc.
Liou et al.; "An ASIC Control Circuit for Thermal Actuated Large Optical Packet Switch Array"; Proceedings of the World Congress of Engineering; bearing a date of Jul. 2-4, 2008; pp. 1-6; vol. I; WCE.
Olcum et al.; "Tunable Surface Plasmon Resonance on an Elastomeric Substrate"; Optics Express; bearing a date of May 11, 2009; pp. 8542-8547; vol. 17, No. 10; OSA.
Piccolo et al.; "Antifuse Injectors for SOI LEDs"; printed in 2009; pp. 573-575.
Reynolds et al.; "Early Biomarkers of Stroke"; Clinical Chemistry: Oak Ridge Conference; bearing a date of Apr. 7, 2003; pp. 1733-1739; vol. 49, No. 10; American Association for Clinical Chemistry.
Rosalki et al.; "Cardiac Biomarkers for Detection of Myocardial Infarction: Perspectives from Past to Present"; Clinical Chemistry; bearing a date of Aug. 17, 2004; pp. 2205-2213; vol. 50, No. 11; American Association for Clinical Chemistry.
Shackleford et al.; "Integrated Plasmonic Iens Photodetector"; Applied Physics Letters; bearing a date of Nov. 24, 2008; pp. 1-3; vol. 94, No. 083501; American Institute of Physics.
Smith et al.; "Evanescent Wave Imaging in Optical Lithography"; printed on Dec. 10, 2010; pp. 1-9.
Spori et al.; "Cassie-State Wetting Investigated by Means of a Hole-to-Pillar Density Gradient"; Langmuir Article; bearing a date Dec. 15, 2009; pp. 9465-9473; vol. 26, No. 12; American Chemical Society.
Thai et al.; "Development of a Fully-Integrated Ultrasensitive Wireless Sensor Utilizing Carbon Nanotubes and Surface Plasmon Theory"; Electronic Components and Technology Conference; bearing a date of 2008; pp. 436-439; IEEE.
Timko et al.; "Remotely Triggerable Drug Delivery Systems"; Advanced Materials; bearing a date of Jun. 4, 2010; pp. 4925-4943; vol. 22; Wiley-VCH Verlag GmbH&Co.
Tsutsui et al.; "Research: The use of Microbubbles to Target Drug Delivery"; BioMed Central-Open Access; bearing a date of Aug. 17, 2004; pp. 1-7; vol. 2, No. 23; BioMed Central Ltd.
Vàzquez et al.; "Optical Router for Optical Fiber Sensor Networks Based on a Liquid Crystal Cell"; IEEE Sensors Journal; bearing a date of Aug. 2003; pp. 513-518; vol. 3, No. 4; IEEE.
Wang et al.; "Effective in Plane Launching and Focusing Surface Plasmons by a Plasmonic Lens"; OSA; bearing a date of 2009; pp. 1-2; IEEE.
Yang et al.; "Polyimide-Waveguide-Based Thermal Optical Switch Using Total-Internal-Reflection Effect"; Applied Physics Letters; bearing a date of Oct. 14, 2002; pp. 2947-2949; vol. 81, No. 16; American Institute of Physics.

(56) References Cited

OTHER PUBLICATIONS

European Search Report; European App. No. EP 08 83 4851; Dec. 2, 2010 (received by our Agent on Dec. 14, 2010); pp. 1-6.

European Patent Office; Extended Supplementary European Search Report; Application No. EP 09 83 0731; Dec. 18, 2012; (Received by our associate Dec. 19, 2012) ; pp. 1-3.

Elmore, Susan; "Apoptosis: A Review of Programmed Cell Death"; Toxicol Pathology; Dec. 6, 2007; pp. 495-516 (pp. 1-40 as provided); vol. 35, No. 4; National Institute of Health.

European Patent Office; Extended European Search Report; App. No. EP 10 74 6554; Apr. 5, 2013 (received by our agent on Apr. 8, 2013); 8 pages (1 cover page, 1 supplementary European search report, 6 European search opinion pages).

Gal'China et al.; "Electroluminescence Spectra of Ultraviolet Light-Emitting Diodes Based on *p-n*-Heterostructures Coated with Phosphors"; Semiconductors; bearing a date of 2007; pp. 1126-1131; vol. 41, No. 9; Pleiades Publishing Ltd.; ISSN 1063-7826.

Kim et al.; "Realization of p-type ZnO thin films via phosphorus doping and thermal activation of the dopant"; Applied Physics Letters; bearing a date of Jul. 7, 2003; pp. 63-65; vol. 83, No. 1; American Institute of Physics.

Könenkamp et al.; "Ultraviolet Electroluminescence from ZnO/Polymer Heterojunction Light-Emitting Diodes"; Nano Letters; bearing a date of 2005; pp. 2005-2008; vol. 5, No. 10; American Chemical Society.

Li et al.; "Ultraviolet nanophosphors"; Journal of Luminescence; bearing a date of 2007; pp. 345-347; vol. 122-123; Elsevier B.V.

Lim et al.; "UV Electroluminescence Emission from ZnO Light-Emitting Diodes Grown by High-Temperatures Radiofrequencey Sputtering"; Advanced Materials; bearing a date of 2006; pp. 2720-2724; vol. 18; WILEY-VCH Verlag GmbH & Co.

Sun et al.; "Realization of ultraviolet electroluminescence from ZnO homojunction with n-ZnO/p-ZnO:As/GaAs structure"; Applied Physics Letters; bearing a date of 2007; pp. 121128-1-121128-3; vol. 90; American Institute of Physics.

Tang et al.; "Cerium Phosphate Nanotubes: Synthesis, Valence State, and Optical Properties"; Angew. Chem. Int. Ed.; bearing a date of 2005; pp. 576-579; vol. 44; Wiley-VCH Verlag GmbH.

Zhang et al.; "Milliwatt power deep ultraviolet light-emitting diodes over sapphire with emission at 278 nm"; Applied Physics Letters; bearing a date of Dec. 23, 2002; pp. 4910-4912; vol. 81, No. 26; American Institute of Physics.

Gjerde, Kjetil, "Carbon nanotube forests: a non-stick workbench for nanomanipulation," Institute of Physics Publishing, 2006, pp. 4917-4922, Nanotechnology 17, IOP Publishing Ltd, UK.

Dostálek et al.; "Multichannel surface plasmon resonance biosensor with wavelength division multiplexing"; Sensors and Actuators B 108 Chemical; Feb. 5, 2005; pp. 758-764; Elsevier B.V.

Nugaeva et al.; :Micromechanical cantilever array sensors for selective fungal immobilization and fast growth detection; Biosensors & Bioelectronics 21; Mar. 2, 2005; pp. 849-856; Elsevier B.V.

\* cited by examiner

Fig. 20  2000 →

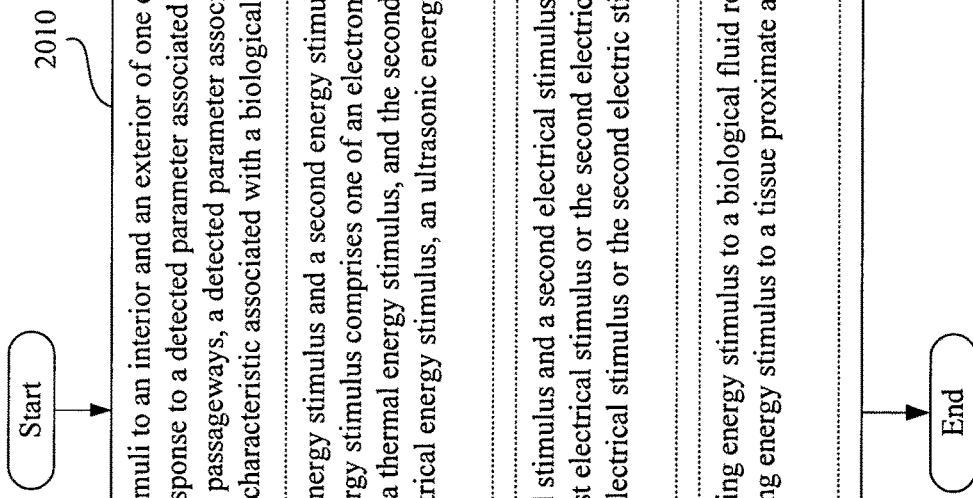

Start 2010 concurrently or sequentially delivering two or more energy stimuli to an interior and an exterior of one or more fluid-flow passageways of an indwelling cerebrospinal fluid management apparatus in response to a detected parameter associated with one or more of a cerebrospinal fluid received within the one or more fluid-flow passageways, a detected parameter associated with a tissue proximate an outer surface of the one or more fluid-flow passageways, or a characteristic associated with a biological subject 2012 concurrently or sequentially delivering at least a first energy stimulus and a second energy stimulus, the second energy stimulus different than the first energy stimulus; wherein the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus 2014 concurrently or sequentially delivering a first electrical stimulus and a second electrical stimulus, *in vivo*, to target tissue proximate the implanted or inserted surgical implant, the first electrical stimulus or the second electric stimulus of a character or duration to inhibit scar formation, and the other of the first electrical stimulus or the second electric stimulus of a character or duration to promote growth of tissue.

2016 concurrently or sequentially delivering the first sterilizing energy stimulus to a biological fluid received within at least one of the one or more fluid-flow passageways and the second sterilizing energy stimulus to a tissue proximate an outer surface of the indwelling cerebrospinal fluid management apparatus End

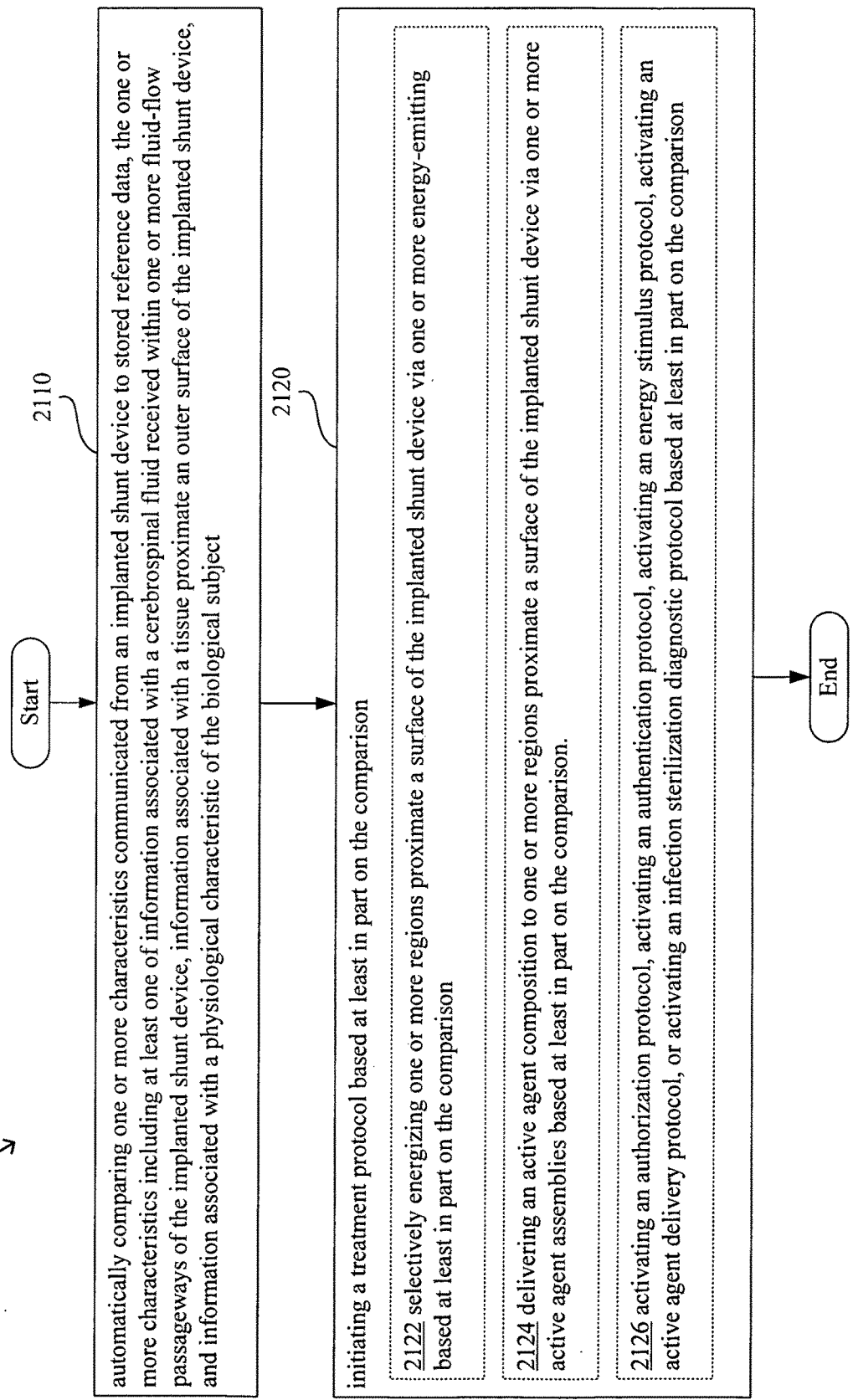

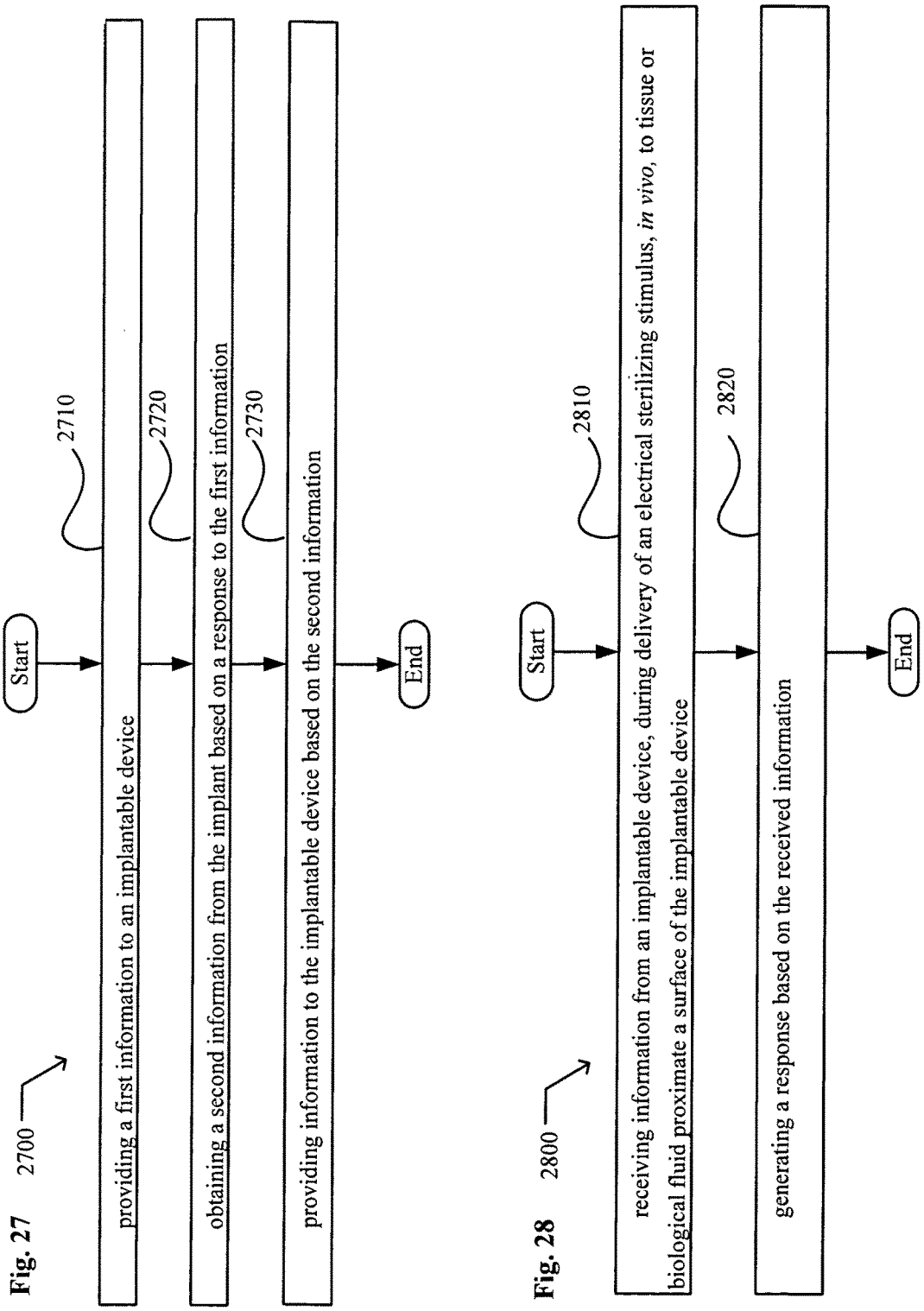

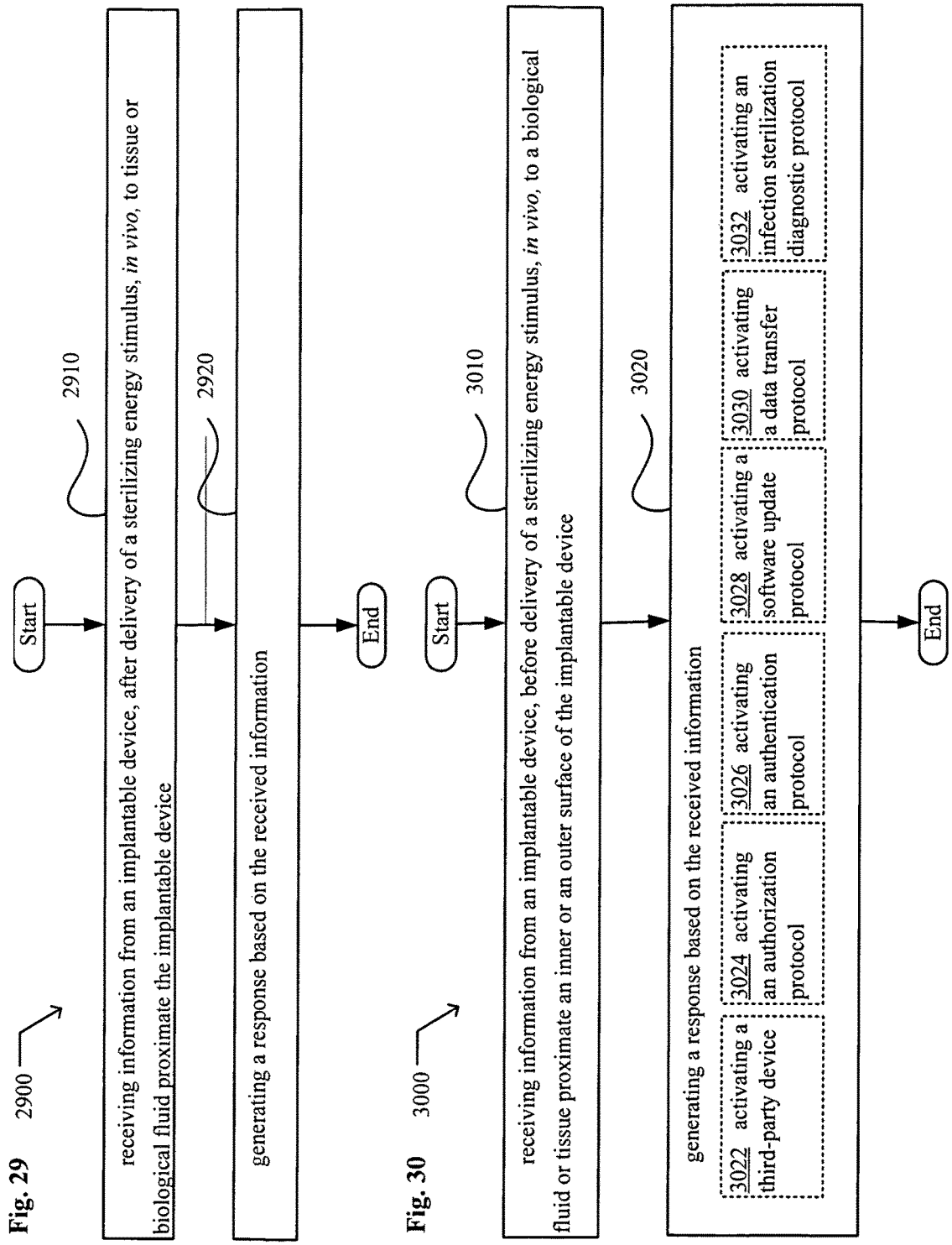

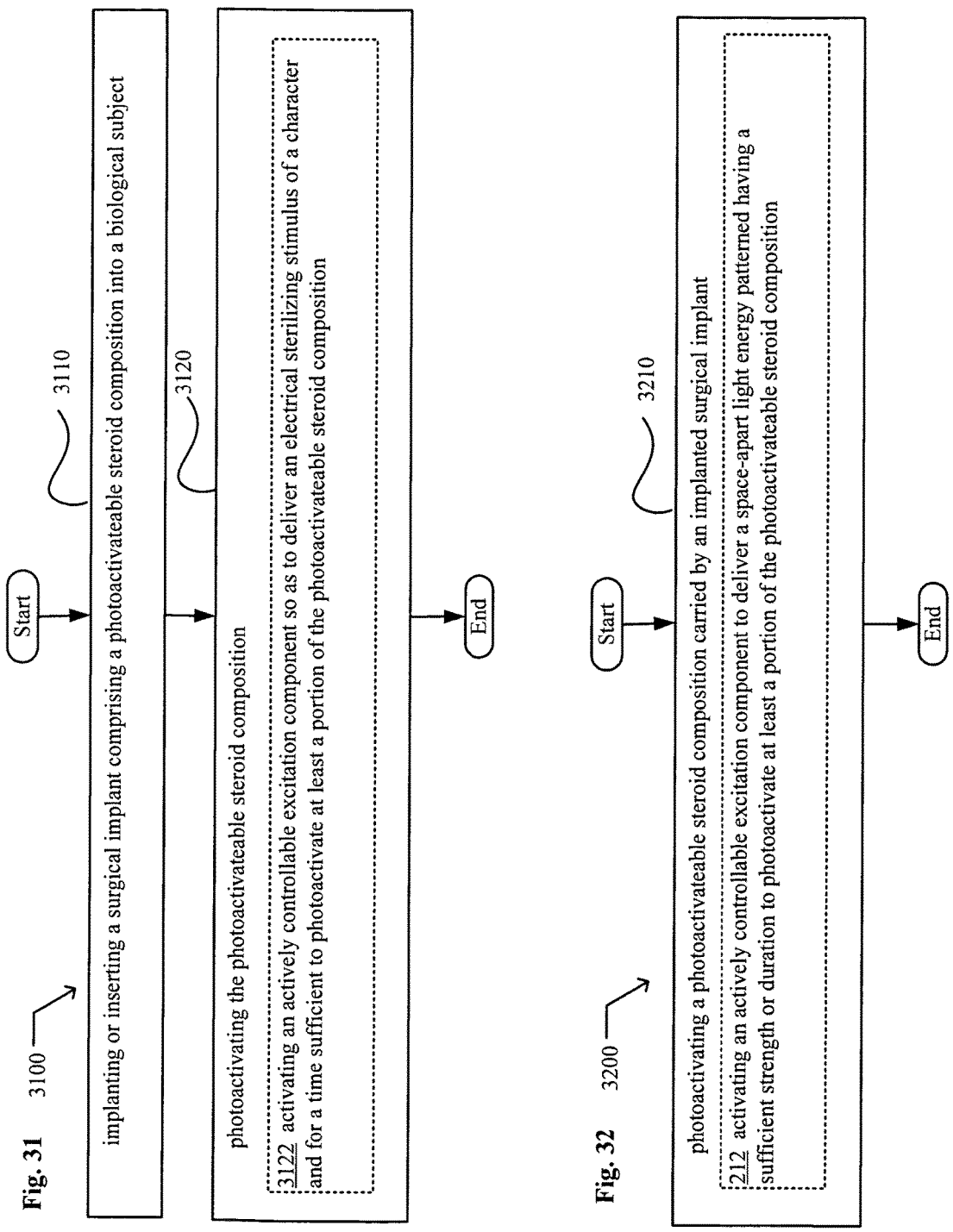

Fig. 38

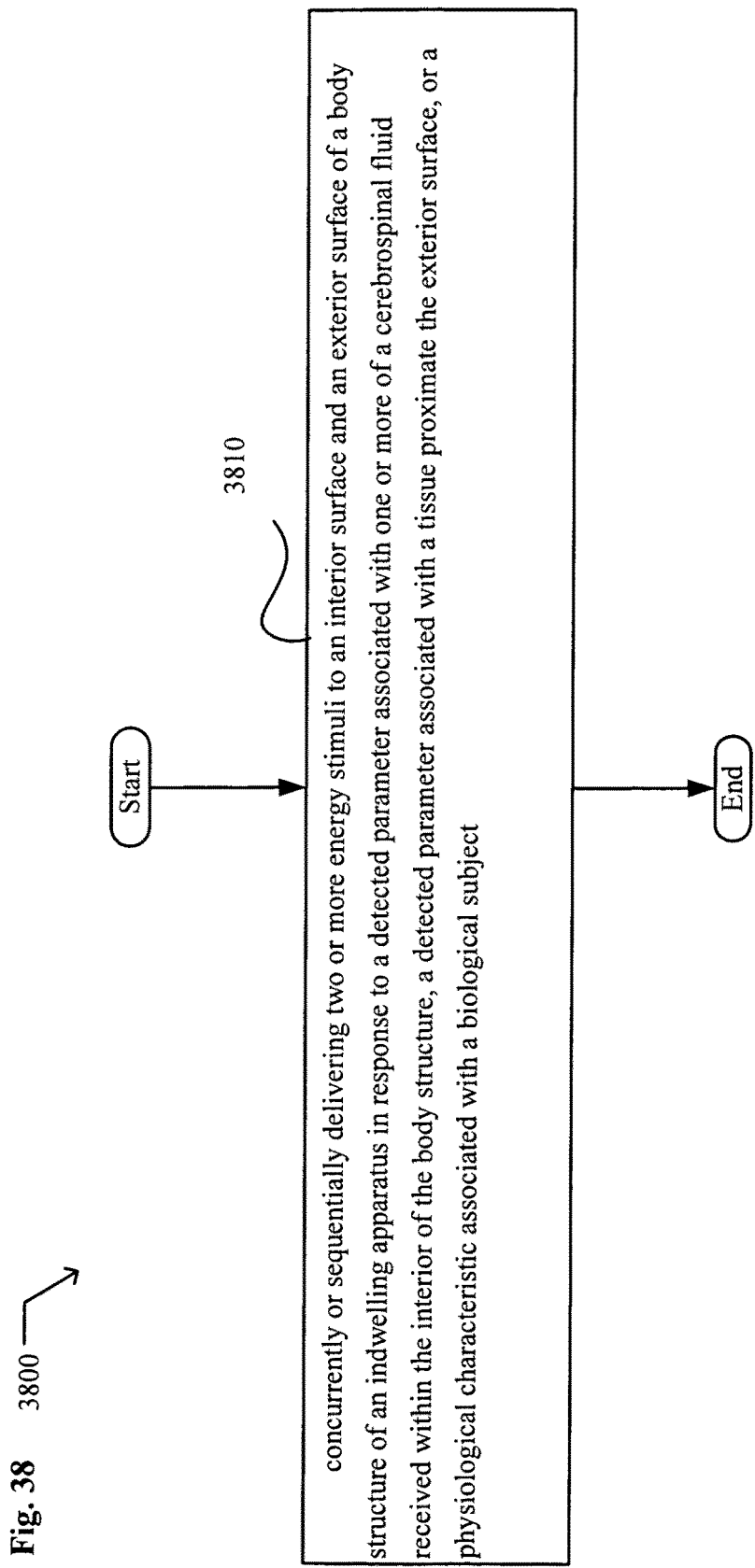

3800

3810: concurrently or sequentially delivering two or more energy stimuli to an interior surface and an exterior surface of a body structure of an indwelling apparatus in response to a detected parameter associated with one or more of a cerebrospinal fluid received within the interior of the body structure, a detected parameter associated with a tissue proximate the exterior surface, or a physiological characteristic associated with a biological subject

SYSTEMS, DEVICES, AND METHODS INCLUDING INFECTION-FIGHTING AND MONITORING SHUNTS

CROSS-REFERENCE TO RELATED APPLICATIONS

The present application is related to and claims the benefit of the earliest available effective filing dates from the following listed applications (the "Related Applications") (e.g., claims earliest available priority dates for other than provisional patent applications or claims benefits under 35 U.S.C. §116(e) for provisional patent applications, for any and all parent, grandparent, great-grandparent, etc. applications of the Related Applications). All subject matter of the Related Applications and of any and all parent, grandparent, great-grandparent, etc. applications of the Related Applications is incorporated herein by reference to the extent such subject matter is not inconsistent herewith.

Related Applications

For purposes of the USPTO extra-statutory requirements, the present application constitutes a continuation of U.S. patent application Ser. No. 12/660,156, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 19 Feb. 2010 now U.S. Pat. No. 8,366,652, which is a continuation-in-part of U.S. patent application Ser. No. 12/315,880, filed 4 Dec. 2008, a continuation-in-part of U.S. patent application Ser. No. 12/315,881, filed 4 Dec. 2008, a continuation-in-part of U.S. patent application Ser. No. 12/315,882, filed 4 Dec. 2008, a continuation-in-part of U.S. patent application Ser. No. 12/315,883, filed 4 Dec. 2008, a continuation-in-part of U.S. patent application Ser. No. 12/315,884, filed 4 Dec. 2008, a continuation-in-part of U.S. patent application Ser. No. 12/315,885, filed 4 Dec. 2008, and a continuation-in-part of U.S. patent application Ser. No. 12/380,553, filed 27 Feb. 2009, and which is currently co-pending, or is an application of which a currently co-pending application is entitled to the benefit of the filing date.

For purposes of the USPTO extra-statutory requirements, the present application is related to U.S. patent application Ser. No. 12/800,792, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C, LEUTHARDT, NATHAN P. MYHRVOLD, DENNIS J, RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,793, entitled SYSTEMS, DEVICES, AND METHODS INCLUDING INFECTION-FIGHTING AND MONITORING SHUNTS, naming RALPH G, DACEY, JR., RODERICK A. HYDE, MURIEL Y. ISHIKAWA, JOR-DIN T, KARE, ERIC C, LEUTHARDT, NATHAN P. MYHRVOLD, DENNIS J, RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,760, entitled SYSTEMS, DEVICES, AND METHODS INCLUDING INFECTION-FIGHTING AND MONITORING SHUNTS, naming RALPH G. DACEY, JR., RODERICK A. HYDE, MURIEL V, ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,774, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,780, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,778, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,779, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,791, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,781, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,786, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the USPTO extra-statutory requirements, the present application is related to U.S. patent application Ser. No. 12/800,790, entitled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C, LEUTHARDT, NATHAN P. MYHRVOLD, DENNIS J, RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010.

For purposes of the United States Patent and Trademark Office (USPTO) extra-statutory requirements, the present application constitutes a continuation-in-part of U.S. patent application Ser. No. 12/315,880, titled SYSTEM, DEVICES, AND METHODS INCLUDING ACTIVELY CONTROLLABLE SUPEROXIDE WATER GENERATING SYSTEMS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,881, titled SYSTEM, DEVICES, AND METHODS INCLUDING STERILIZING EXCITATION DELIVERY IMPLANTS WITH CRYPTOGRAPHIC LOGIC COMPONENTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,882, titled SYSTEM, DEVICES, AND METHODS INCLUDING STERILIZING EXCITATION DELIVERY IMPLANTS WITH GENERAL CONTROLLERS AND ONBOARD POWER, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,883, titled SYSTEM, DEVICES, AND METHODS INCLUDING ACTIVELY CONTROLLABLE ELECTROMAGNETIC ENERGY-EMITTING DELIVERY SYSTEMS AND ENERGY-ACTIVATABLE DISINFECTING AGENTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,884, titled SYSTEM, DEVICES, AND METHODS INCLUDING ACTIVELY CONTROLLABLE STERILIZING EXCITATION DELIVERY IMPLANTS, naming Edward S. Boyden, Ralph G. Dacey, Jr., Gregory J. Della Rocca, Joshua L. Dowling, Roderick A. Hyde, Muriel Y. Ishikawa, Jordin T. Kare, Eric C. Leuthardt, Nathan P. Myhrvold, Dennis J. Rivet, Paul Santiago, Michael A. Smith, Todd J. Stewart, Elizabeth A. Sweeney, Clarence T. Tegreene, Lowell L. Wood, Jr., Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,885, titled SYSTEM, DEVICES, AND METHODS INCLUDING ACTIVELY-CONTROLLABLE ELECTROSTATIC AND ELECTROMAGNETIC STERILIZING EXCITATION DELIVERY SYSTEMS naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/380,553, titled SYSTEM, DEVICES, AND METHODS INCLUDING ACTIVELY CONTROLLABLE STERILIZING EXCITATION DELIVERY IMPLANTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood; and Jr.; and Victoria Y. H. Wood as inventors, filed 27 Feb. 2009, which is currently co-pending, or is an application of which a currently co-pending application is entitled to the benefit of the filing date.

The USPTO has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In an aspect, the present disclosure is directed to, among other things, an implantable shunt system. The implantable shunt system includes, but is not limited to, one or more fluid-flow passageways configured to receive a cerebrospinal fluid (CSF) of a biological subject and one or more energy emitters. In an embodiment, the one or more energy emitters are configured to deliver at least one of an electromagnetic energy stimulus, an electrical energy stimulus, an ultrasonic energy stimulus, and a thermal energy stimulus. In an embodiment, the one or more energy emitters are configured to emit an energy stimulus of a character and for a time sufficient to inactivate an infectious agent within a cerebrospinal fluid received within at least one of the one or more fluid-flow passageways. In an embodiment, the one or more energy emitters are configured to emit at least one of an electromagnetic energy stimulus, an electrical energy stimulus, an ultrasonic energy stimulus, and a thermal energy stimulus of a character and for a time sufficient to induce programmed cell death (PCD) (e.g., apoptosis, death of a cell mediated by an intracellular program, or the like) without substantially inducing necrosis of at least a portion of cells within a cerebrospinal fluid received within at least one of the one or more fluid-flow passageways.

The implantable shunt system can include, but is not limited to, a surface region that is energetically actuatable between an optically transparent state and an optically reflective state. In an embodiment, a body structure defining at least one of the one or more fluid-flow passageways includes one or more regions that are actively controllable between a transmissive state and a reflective state. In an embodiment, a body structure defining at least one of the one or more fluid-flow passageways includes one or more regions that are actively controllable between a transmissive state and a less transmissive state. The implantable shunt system can include, but is not limited to, one or more actively controllable reflective or transmissive components configured to outwardly transmit or internally reflect an energy stimulus propagated through at least one of the one or more fluid-flow passageways. In an embodiment, at least one of the one or more fluid-flow passageways includes one or more regions that are controllably actuatable between an optically transparent state and an optically reflective state.

The implantable shunt system can include, but is not limited to, a sensor component configured to detect at least one of a characteristic of a cerebrospinal fluid received within one or more fluid-flow passageways, a characteristic of a tissue proximate the one or more fluid-flow passageways, and a physiological characteristic of the biological subject. The implantable shunt system can include, but is not limited to, a controller configured to cause an outward-transmission or internal-reflection of an energy stimulus propagated through at least one of the one or more fluid-flow passageways based on detected information from the sensor component.

The implantable shunt system can include, but is not limited to, one or more optical materials forming at least a portion of a body structure defining the one or more fluid-flow passageways. In an embodiment, one or more of the optical materials are configured to limit an amount of an energy stimulus that can traverse within the one or more fluid-flow passageways and through an outer surface of the body structure. The implantable shunt system can include, but is not limited to, one or more optical materials on at least a portion of a body structure defining the one or more fluid-flow passageways. In an embodiment, one or more of the optical materials are present in a sufficient amount to internally reflect at least a portion of an emitted energy stimulus from the one or more energy emitters into an interior of at least one of the one or more fluid-flow passageways. The implantable shunt system can include, but is not limited to, at least one of an outer internally reflective coating and an inner internally reflective coating on a body structure defining the one or more fluid-flow passageways.

In an embodiment, a body structure defining at least one of the one or more fluid-flow passageways includes one or more surface regions that are energetically actuatable between a substantially hydrophobic state and a substantially hydrophilic state. In an embodiment, a body structure defining at least one of the one or more fluid-flow passageways includes one or more surface regions energetically actuatable between at least a first hydrophilic state and a second hydrophilic state. In an embodiment, a body structure defining at least one of the one or more fluid-flow passageways includes one or more surface regions energetically actuatable between a hydrophobic state and a hydrophilic state. In an embodiment, a body structure defining at least one of the one or more fluid-flow passageways includes one or more surface regions having a material that is switchable between a zwitterionic state and a non-zwitterionic state. In an embodiment, one of the one or more fluid-flow passageways includes one or more surface regions energetically actuatable between an antimicrobial state and a non-fouling state.

The implantable shunt system can include, but is not limited to, one or more sensors configured to detect at least one characteristic associated with the cerebrospinal fluid of the biological subject. The implantable shunt system can include, but is not limited to, a means for detecting at least one characteristic associated with the cerebrospinal fluid of the biological subject. The implantable shunt system can include, but is not limited to, one or more processors configured to perform a comparison of the at least one characteristic associated with the cerebrospinal fluid to stored reference data, and to generate a response based at least in part on the comparison.

The implantable shunt system can include, but is not limited to, one or more sensors configured to detect at least one characteristic associated with a tissue proximate the one or more fluid-flow passageways. The implantable shunt system can include, but is not limited to, an active agent assembly including at least one disinfecting agent reservoir. In an embodiment, the active agent assembly is configured to deliver one or more disinfecting agents from the at least one disinfecting agent reservoir to an interior of at least one of the one or more fluid-flow passageways.

The implantable shunt system can include, but is not limited to, circuitry configured to obtain information and circuitry configured for providing information. In an embodiment, the circuitry configured to obtain information includes circuitry configured to obtain information associated with a delivery of the energy stimulus. In an embodiment, the circuitry configured to obtain information includes circuitry configured to obtain at least one of a command stream, a software stream, and a data stream. The implantable shunt system can include, but is not limited to, at least one of a receiver configured to acquire information based at least in part on a sensed characteristic associated with a cerebrospinal fluid received within at least one of the one or more fluid-flow passageways; a receiver configured to acquire information based at least in part on a detected characteristic associated with a tissue proximate the one or more fluid-flow passageways; a receiver configured to acquire information based at least in part on a detected physiological characteristic associated with the biological subject; a transmitter configured to send information based at least in part on a detected characteristic associated with a cerebrospinal fluid received within at least one of the one or more fluid-flow passageways; and a transmitter configured to send a request for transmission of at least one of data, a command, an authorization, an update, and a code.

The implantable shunt system can include, but is not limited to, one or more computer-readable memory media having cerebrospinal fluid information configured as a data structure. In an embodiment, the data structure includes at least one of psychosis state marker information, psychosis trait marker information, and psychosis indication information. In an embodiment, the data structure includes at least one of psychosis state indication information, psychosis trait indication information, and predisposition for a psychosis indication information. In an embodiment, the data structure includes at least one of infection indication information, inflammation indication information, diseased state indication information (e.g., an absence, a presence, or a severity indication information), and diseased tissue indication information.

The implantable shunt system can include, but is not limited to, an actively controllable excitation component configured to deliver an energy stimulus, in vivo, to a tissue proximate a portion of the one or more fluid-flow passageways. In an embodiment, the actively controllable excitation component is configured to deliver a sterilizing stimulus, in vivo, to a tissue proximate a portion of the one or more fluid-flow passageways.

In an aspect, the present disclosure is directed to, among other things, an indwelling shunt apparatus including a body structure having an outer surface and an inner surface defining one or more fluid-flow passageways configured to receive a cerebrospinal fluid of a biological subject. The body structure of the indwelling shunt apparatus can include, among other things, a plurality of actuatable regions that are independently actuatable between at least a first transmissive state and a second transmissive state. In an embodiment, the indwelling shunt apparatus includes a sensor component including one or more sensors configured to detect at least one characteristic associated with a biological sample proximate at least one of the outer surface and the inner surface of the body structure. In an embodiment, the indwelling shunt apparatus includes one or more energy emitters configured to emit an energy stimulus based at least in part on at least one detected characteristic associated with the biological sample.

In an aspect, the present disclosure is directed to, among other things, an implantable fluid management device. The implantable fluid management device can include, but is not limited to, a shunt assembly defining one or more fluid-flow passageways configured to receive a biological fluid (e.g., bodily fluid, blood, amniotic fluid, ascites, bile, cerebrospinal fluid, interstitial fluid, pleural fluid, transcellular fluid, or the like) of a subject. The implantable fluid management device can include, but is not limited to, a first actively-controllable excitation component configured to deliver, in vivo, a first sterilizing energy stimulus to a biological fluid received within at least one of the one or more fluid-flow passageways. The implantable fluid management device can include, but is not limited to, a second actively controllable excitation component configured to deliver, in vivo, a second sterilizing energy stimulus to a tissue proximate an outer surface of the implantable fluid management device. In an embodiment, the implantable fluid management device is configured to concurrently or sequentially deliver a first sterilizing stimulus to a biological fluid received within at least one of the one or more fluid-flow passageways and a second sterilizing energy stimulus to a tissue proximate an outer surface of the implantable fluid management device. In an embodiment, the first sterilizing stimulus includes at least one of a delivery of a sterilizing energy stimulus and a delivery of a sterilizing agent, and the second sterilizing stimulus includes the other of the delivery of the sterilizing energy stimulus or the delivery of the sterilizing agent. In an embodiment, the first sterilizing stimulus includes at least one of an electromagnetic sterilizing stimulus, an electrical sterilizing stimulus, an ultrasonic sterilizing stimulus, and a thermal sterilizing stimulus, and the second sterilizing stimulus includes a different one of an electromagnetic sterilizing stimulus, an electrical sterilizing stimulus, an ultrasonic sterilizing stimulus, or a thermal sterilizing stimulus. In an embodiment, the implantable fluid management device is configured to concurrently or sequentially deliver the first sterilizing energy stimulus to a biological fluid received within at least one of the one or more fluid-flow passageways and the second sterilizing energy stimulus to a tissue proximate an outer surface of the implantable fluid management device. The implantable fluid management device can include, but is not limited to, a control means operably coupled to at least one of the first actively controllable excitation component and the second actively controllable excitation component.

In an aspect, the present disclosure is directed to, among other things, an implantable fluid management device including a shunt assembly defining one or more fluid-flow passageways configured to receive a biological fluid of a subject. The implantable fluid management device can include, but is not limited to, one or more of shunts (e.g., blalock-taussig shunts, cardiac shunts, cerebral shunts (e.g., cerebrospinal fluid shunts, ventriculo-atrial shunts, ventriculo-peritoneal shunts, or the like) glaucoma shunts, mechanical shunts, pulmonary shunts, portosystemic shunts, portoacaval shunts, ventricle-to-pulmonary artery conduits, or the like), reservoirs (e.g., active agent reservoirs, cerebrospinal fluid reservoirs, drainage reservoirs, or the like), valve assemblies (including one or more adjustable pressure valves, mono-pressure valves, mechanical valves, electromechanical values, programmable valves, pulsar valves, shunt valves, or the like), and valve mechanisms (e.g., ball-in-cone mechanism).

The implantable fluid management device can include, but is not limited to, an actively controllable excitation component configured to independently deliver, in vivo, at least one of a first sterilizing energy stimulus to a biological fluid received within at least one of the one or more fluid-flow passageways and a second sterilizing energy stimulus to a tissue proximate an outer surface of the implantable fluid management device. The implantable fluid management device can include, but is not limited to, a control means operably coupled to the actively controllable excitation component.

In an aspect, the present disclosure is directed to, among other things, an in vivo method of treating an infectious agent. The method includes, but is not limited to, providing an energy stimulus for a time and amount sufficient to inactivate an infectious agent within a cerebrospinal fluid received within one or more fluid-flow passageways of an indwelling implant. The method includes, but is not limited to, providing an energy stimulus for a time and amount sufficient to induce programmed cell death of an infectious agent within a cerebrospinal fluid received within one or more fluid-flow passageways of an indwelling implant. In an embodiment, the method includes providing an energy stimulus to an interior of an indwelling implant via one or more energy-emitting components that are energetically coupleable to an interior of the one or more fluid-flow passageways. The method can include, but is not limited to, delivering an antimicrobial agent composition to a cerebrospinal fluid received within at least one or more fluid-flow passageways.

In an aspect, the present disclosure is directed to, among other things, a method of inhibiting a microbial colonization in the cerebrospinal fluid of a biological subject. The method includes, but is not limited to, selectively energizing one or more regions of at least one fluid-flow passageway of an indwelling cerebrospinal fluid management system via one or more energy-emitting components in optical communication with an interior of the least one fluid-flow passageway. In an embodiment, the method includes energizing a cerebrospinal fluid received within the one or more regions of the at least one fluid-flow passageway with an energy stimulus having an operational fluence of the one or more energy emitters is less than about 80 milli-joules per square centimeter.

In an aspect, a method includes, but is not limited to, selectively energizing one or more regions of at least one fluid-flow passageway of an in vivo implanted cerebrospinal fluid management system in response to an automatically detected optical density parameter associated with a cerebrospinal fluid received within the at least one fluid-flow passageway.

In an aspect, a method includes, but is not limited to, providing an energy stimulus to an interior of one or more fluid-flow passageways of an in vivo implanted cerebrospinal fluid management device in response to a change in a refractive index parameter associated with a cerebrospinal fluid received within the at least one fluid-flow passageway. In an embodiment, the method includes providing a spatially patterned energy stimulus having at least a first region and a second region different from the first region. In an embodiment, the first regions comprises one of a spatially patterned electromagnetic energy stimulus, a spatially patterned electrical energy stimulus, a spatially patterned ultrasonic energy stimulus, or a spatially patterned thermal energy stimulus, and the second region comprises a different one of a spatially patterned electromagnetic energy stimulus, a spatially patterned electrical energy stimulus, a spatially patterned ultrasonic energy stimulus, or a spatially patterned thermal energy stimulus.

In an aspect, a method includes, but is not limited to, delivering one or more energy stimuli to at least one of an interior and an exterior of one or more fluid-flow passageways of an indwelling cerebrospinal fluid management apparatus in response to an in vivo detected change in a refractive index parameter associated with a cerebrospinal fluid received within the one or more fluid-flow passageways. In an embodiment, the method includes directing a first portion of an emitted energy stimulus along a substantially lateral direction in the interior of at least one of the one or more fluid-flow passageways and directing a second portion of the emitted energy stimulus along a substantially longitudinal direction in the interior of at least one of the one or more fluid-flow passageways. In an embodiment, the method includes directing at least a first portion of an emitted energy stimuli, via a first optical component, along a substantially lateral direction in a first region of at least one of the one or more fluid-flow passageways and directing at a second portion of the emitted energy stimulus, via a second optical component, along a substantially lateral direction in a second region of the one or more fluid-flow passageways, the second region different from the first region. In an embodiment, the method includes directing a portion of an emitted energy stimulus along a substantially longitudinal direction in a first region of at least one of the one or more fluid-flow passageways and directing a portion of the emitted energy stimulus along a substantially longitudinal direction in a second region of the one or more fluid-flow passageways, the second region different from the first region. In an embodiment, the method includes directing at least a portion of an emitted energy stimulus along a substantially lateral direction in a first region of at least one of the one or more fluid-flow passageways and directing at least a portion of the emitted energy stimulus along a substantially lateral direction in a second region of the one or more fluid-flow passageways, the second region different from the first region.

In an aspect, a method includes, but is not limited to, concurrently or sequentially delivering two or more energy stimuli to an interior and an exterior of one or more fluid-flow passageways of an indwelling cerebrospinal fluid management apparatus in response to a detected parameter. In an embodiment, the detected parameter is associated with one or more of a cerebrospinal fluid received within the one or more fluid-flow passageways, a tissue proximate an outer surface of the one or more fluid-flow passageways, or a physiological characteristic associated with a biological subject. In an embodiment, the method includes concurrently or sequentially delivering at least a first energy stimulus and a second energy stimulus, the second energy stimulus different from the first energy stimulus. In an embodiment, the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus. In an embodiment, the second energy stimulus comprises a different spatial pattern from the first energy stimulus. In an embodiment, the second energy stimulus comprises a different temporal pattern from the first energy stimulus.

In an aspect, a method includes, but is not limited to, comparing, via integrated circuitry, one or more characteristics communicated from an implanted shunt device to stored reference data. In an embodiment, the one or more characteristics include at least one of information associated with a cerebrospinal fluid received within one or more fluid-flow passageways of the implanted shunt device, information associated with a tissue proximate a surface of the implanted shunt device, and information associated with a physiological characteristic of the biological subject. The method can include, but is not limited to, initiating a treatment protocol based at least in part on the comparison.

In an aspect, the present disclosure is directed to, among other things, an implantable shunt system. The implantable shunt system includes, among other things, a body structure having a surface defining one or more fluid-flow passageways configured to receive a biological fluid of a biological subject, and one or more energy emitters configured to emit a pulsed thermal sterilizing stimulus of a character and for a time sufficient to induce programmed cell death (PCD) (e.g., apoptosis) without substantially inducing necrosis of at least a portion of cells within the biological fluid proximate the surface of the body structure in response to a determination that an infectious agent is present within the biological fluid. In an embodiment, the one or more energy emitters configured to emit a pulsed thermal sterilizing stimulus of a character and for a time sufficient to induce PCD without substantially inducing necrosis of at least a portion of cells proximate the body structure in response to the comparison. In an embodiment, at least one of the one or more energy emitters is configured to emit a pulsed thermal sterilizing stimulus of a character and for a time sufficient to induce PCD without substantially inducing necrosis of an infectious agent within a tissue proximate body structure in response to a detect level of an infectious agent.

In an aspect, the present disclosure is directed to, among other things, a method of inhibiting a microbial colonization in the cerebrospinal fluid of a biological subject. The method includes selectively energizing one or more regions of at least one cerebrospinal fluid-flow passageway of an indwelling implant via one or more pulsed thermal stimuli emitting components in response to an automatically detected optical density parameter associated with a cerebrospinal fluid received within the at least one cerebrospinal fluid-flow passageway. In an embodiment, selectively energizing includes concurrently or sequentially delivering at least a first pulsed thermal stimulus to a first region and a second pulsed thermal stimulus to a second region.

In an aspect, a method includes, but is not limited to, providing a pulsed thermal sterilizing stimulus to an interior of at least one cerebrospinal fluid-flow passageway of an implanted device in response to a change in a refractive index parameter indicative of a presence of an infectious agent within the at least one cerebrospinal fluid-flow passageway of the implanted device. In an embodiment, providing the pulsed thermal sterilizing stimulus includes providing a spatially patterned pulsed thermal sterilizing stimulus having at least a first region and a second region different from the first region. In an embodiment, providing the pulsed thermal sterilizing stimulus includes delivering a pulsed thermal sterilizing stimulus including at least a first pulsed waveform segment and a second pulsed waveform segment, the second pulsed waveform segment having a spatial profile different from the first pulsed waveform segment.

In an aspect, a method includes, but is not limited to, delivering one or more pulsed thermal stimuli to at least one of an interior or an exterior of a cerebrospinal fluid-flow passageway of an indwelling implant apparatus in response to an in vivo detected change in a refractive parameter indicative of a presence of an infectious agent proximate the exterior or the interior of the cerebrospinal fluid-flow passageway. In an embodiment, delivering the one or more pulsed thermal stimuli includes delivering one or more pulsed thermal stimuli to at least one of an interior or an exterior of a cerebrospinal fluid-flow passageway of an indwelling cerebrospinal fluid management implant.

In an aspect, a method includes, but is not limited to, concurrently or sequentially delivering two or more energy stimuli to an interior surface and an exterior surface of a body structure of an indwelling apparatus in response to a detected parameter associated with one or more of a cerebrospinal fluid received within the interior of the body structure, a detected parameter associated with a tissue proximate the exterior surface, and a physiological characteristic associated with a biological subject.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 20 is a flow diagram of a method according to one illustrated embodiment.

FIG. 21 is a flow diagram of a method according to one illustrated embodiment.

FIG. 27 is a flow diagram of a method according to one illustrated embodiment.

FIG. 28 is a flow diagram of a method according to one illustrated embodiment.

FIG. 29 is a flow diagram of a method according to one illustrated embodiment.

FIG. 30 is a flow diagram of a method according to one illustrated embodiment.

FIG. 31 is a flow diagram of a method according to one illustrated embodiment.

FIG. 32 is a flow diagram of a method according to one illustrated embodiment.

FIG. 32 is a flow diagram of a method according to one illustrated embodiment.

FIG. 38 is a flow diagram of a method according to one illustrated embodiment.

DETAILED DESCRIPTION

Figures 1A, 1B:
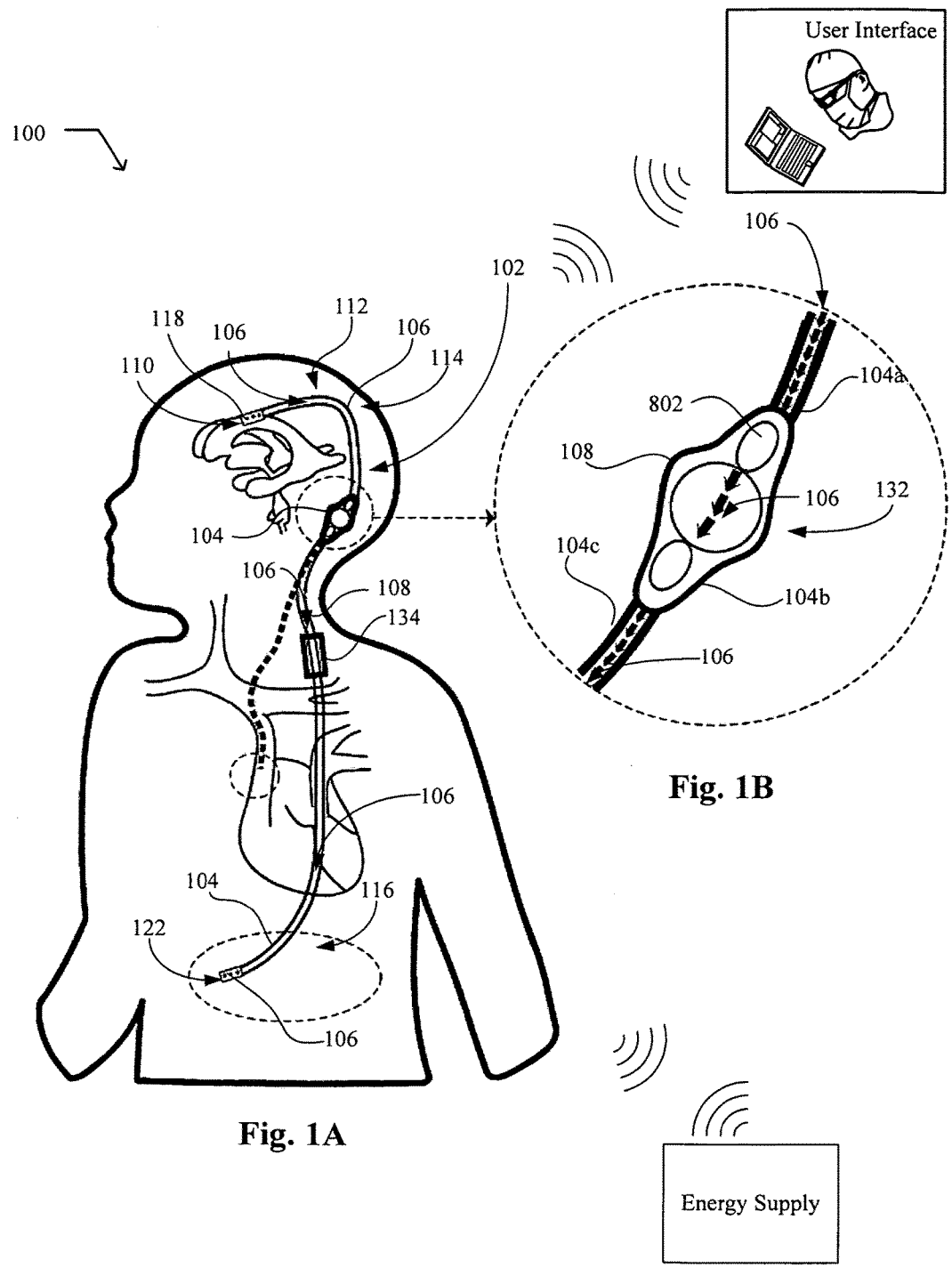
FIG. 1A is a perspective view of a system including an implantable device according to one illustrated embodiment.
FIG. 1B is a top plan view of a portion of an implantable device including a flow-regulating device according to one illustrated embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

Implantable shunts (e.g., cardiac shunts, cerebral shunts, portacaval shunts, portosystemic shunts, pulmonary shunts, or the like), catheters (e.g., central venous catheters, multi-lumen catheters, peripherally inserted central catheters, Quinton catheters, Swan-Ganz catheters, tunneled catheters, or the like), or medical ports (e.g., arterial ports, low profile ports, multi-lumen ports, vascular ports, or the like) are useful for, among other things, managing movement of fluids; directly detecting (e.g., assessing, calculating, evaluating, determining, gauging, identifying, measuring, monitoring, quantifying, resolving, sensing, or the like) mechanical, physical, or biochemical information (e.g., the presence of a biomarker, intracranial pressure, blood pressure, a disease state, or the like) associated with a biological subject; draining or collecting body fluids; as well as for administering therapeutics, medications, pharmaceuticals, intravenous fluids, blood products, or parenteral nutrition.

Infections, malfunctions (e.g., blocked or clogged fluid-flow passageways), and failures account for many of the complications associated with implantable devices and pose tremendous consequences for patients. For example, during an infection, an infectious agent (e.g., fungi, micro-organisms, parasites, pathogens (e.g., viral pathogens, bacterial pathogens, or the like), prions, viroids, viruses, or the like) generally interferes with the normal functioning of a biological subject, and causes, in some cases, chronic wounds, gangrene, loss of an infected tissue, loss of an infected limb, and occasionally death of the biological subject. Implant-associated infections account for a significant amount of nosocomial infections and despite sterilization and aseptic procedures, remain as a major impediment to medical implants including artificial hearts, artificial joints, artificial prosthetics, breast implants, catheters, contact lens, implantable biological fluid drainage system, mechanical heart valves, stents, subcutaneous sensors, shunts, vertebral spacers, and the like. Implant-associated infections are often difficult to detect, problematic to cure, and at times expensive to manage. For example, in cases where the infection does not quickly subside, it sometimes becomes necessary to remove the implant. Implant-associated infections can result from bacterial adhesion and subsequent biofilm formation proximate an implantation site. For example, biofilm-forming microorganisms sometimes colonize implants. Once a biofilm-induced infection takes hold, it can prove difficult to treat.

An aspect includes systems, devices, and methods, described herein provide an implantable device configured to, for example, detect (e.g., assess, calculate, evaluate, determine, gauge, identify, measure, monitor, quantify, resolve, sense, or the like) an infectious agent present in, for example, a biological fluid. A non-limiting example includes systems, devices, and methods including an implantable device configured to, for example, detect an infectious agent present in, for example, a tissue proximate an implantable device.

An aspect includes systems, devices, methods, and compositions for actively detecting, treating, or preventing an infection, a fluid vessel abnormality (e.g., an obstruction), a biological fluid abnormality (e.g., cerebrospinal fluid abnormality, hematological abnormality, components concentration or level abnormality, flow abnormality, or the like), or the like. A non-limiting example includes systems, devices, and methods for actively detecting, treating, or preventing an infection associated with a shunt or catheter. An aspect includes systems, devices, and methods for managing movement of fluids; directly detecting and monitoring functions or conditions (e.g., mechanical, physical, physiological, or biochemical functions or conditions) associated with a biological subject; draining or collecting body fluids; providing access to an interior of a biological subject; distending at least one passageway; as well as for administering therapeutics, medications, pharmaceuticals, intravenous fluids, or parenteral nutrition. A non-limiting example includes systems, devices, and methods for actively detecting, treating, or preventing fluid-flow obstructions in shunts or catheters.

FIGS. 1A and 1B show a system 100 (e.g., an implantable system, an implantable shunt system, an implantable catheter system, a partially implantable system, or the like) in which one or more methodologies or technologies can be implemented such as, for example, managing a transport of biological fluids and actively detecting, treating, or preventing an infection (e.g., an implant-associated infection, a hematogenous associated infection, an infection present in tissue or biological fluid, or the like), a biological fluid abnormality (e.g., a cerebral spinal fluid abnormality, a hematological abnormality, or the like), or the like.

In an embodiment, the system 100 is configured to, among other things, treat a condition associated with an infection. In an embodiment, the system 100 is configured to, among other things, inhibit a microbial colonization in a biological fluid (e.g., bodily fluid, blood, amniotic fluid, ascites, bile, cerebrospinal fluid, interstitial fluid, pleural fluid, transcellular fluid, or the like) of a biological subject. In an embodiment, the system 100 is configured to, among other things, reduce the in vivo concentration of, for example, an infectious agent present in a biological fluid managed by the system 100. In an embodiment, the system 100 is configured to, among other things, reduce the concentration of, for example, an infectious agent in the immediate vicinity of an indwelling implant. In an embodiment, the system 100 is configured to, among other things, reduce the risk of infection. In an embodiment, the system 100 is configured to, among other things, controllably deliver one or more energy stimuli to at least one of an interior and an exterior of one or more fluid-flow passageways of an indwelling implant. In an embodiment, the system 100 is configured to provide antimicrobial therapy.

The system 100 can include, but is not limited to, one or more implantable devices 102. An implantable device 102 is configured to, among other things, have numerous configurations. In an embodiment, the implantable device 102 is configured to manage a transport of biological fluids and actively detect, treat, or prevent an infection, a biological fluid abnormality, or the like. For example, in an embodiment, the implantable device 102 is configured to treat a pathological condition associated with an imbalance between the production and absorption of cerebrospinal fluid. The system 100 can include partially or completely implantable devices 102 or components that are partially or completely implantable.

Among implantable devices 102 examples include, but are not limited to, shunts (e.g., cardiac shunts, cerebral shunts, cerebrospinal fluid shunts (an example of which is shown on FIG. 1), lumbo-peritoneal shunts, portacaval shunts, portosystemic shunts, pulmonary shunts, or the like), catheters (e.g., central venous catheters, multi-lumen catheters, peripherally inserted central catheters, Quinton catheters, Swan-Ganz catheters, tunneled catheters, urinary catheters, vascular catheters, or the like), medical ports (e.g., arterial ports, low profile ports, multi-lumen ports, vascular ports, or the like), and the like. Further non-limiting examples of implantable devices 102 include bio-implants, bioactive implants, breast implants, cochlear implants, dental implants, neural implants, orthopedic implants, ocular implants, prostheses, implantable electronic device, implantable medical devices, and the like.

Further non-limiting examples of implantable devices 102 include replacements implants (e.g., joint replacements implants such, for example, elbows, hip, knee, shoulder, wrists replacements implants, or the like), subcutaneous drug delivery devices (e.g., implantable pills, drug-eluting stents, or the like), stents (e.g., coronary stents, peripheral vascular stents, prostatic stents, ureteral stents, vascular stents, or the like), biological fluid flow controlling implants, and the like. Further non-limiting examples of implantable devices 102 include artificial hearts, artificial joints, artificial prosthetics, contact lens, mechanical heart valves, subcutaneous sensors, and the like.

The implantable device 102 can include, but is not limited to, a body structure 104 having one or more fluid-flow passageways 106. In an embodiment, the body structure 104 includes at least one outer surface 108 and at least one inner surface 110 defining one or more fluid-flow passageways 106. The one or more fluid-flow passageways 106 can take a variety of shapes, configurations, and geometric forms including regular or irregular forms and can have a cross-section of substantially any shape including, but not limited to, circular, triangular, square, rectangular, polygonal, regular or irregular shapes, or the like, as well as other symmetrical and asymmetrical shapes, or combinations thereof. In an embodiment, one or more portions of the body structure 104 take a substantially cylindrical geometric form (e.g., a tubular structure) having an inner surface 110 defining one or more fluid-flow passageways 106. The substantially cylindrical geometric form can have a cross-section of substantially any shape including but not limited to circular, triangular, square, rectangular, polygonal, regular or irregular shapes, or the like, as well as other symmetrical and asymmetrical shapes, or combinations thereof. In an embodiment, the substantially cylindrical geometric form includes multi-lumen structures (e.g., multi-lumen tubing) having multiple fluid-flow passageways 106 running therethrough. In an embodiment, the body structure 104 includes one or more tubular structures (e.g., multilayer tubular structures, tubular catheter body structures, tubular shunt body structures, multi-lumen tubular structures, or the like)

defining one or more fluid-flow passageways 106. In an embodiment, the implantable device 102 includes a body structure 104 having one or more fluid-flow passageways 106 configured to receive a cerebrospinal fluid of a biological subject.

In an embodiment, the body structure 104 includes a plurality of connected segments 104a, 104b, 104c. In an embodiment, the body structure 104 includes a plurality of segments 104a, 104b, 104c coupled along a longitudinal length. In an embodiment, the body structure 104 includes a plurality of segments 104a, 104b, 104c in fluid communication. In an embodiment, the body structure 104 includes a plurality of segment 104a, 104b, 104c connected via separate components. In an embodiment, the body structure 104 is configured as a monolithically structure. In an embodiment, the body structure 104 comprises an integrally formed component assembly. In an embodiment, the body structure 104 includes a plurality of segments configured in fluid communication 104a, 104b, 104c that are configured to transport a biological fluid.

In an embodiment, the implantable device 102 includes a body structure 104 including one or more shunts 112. In an embodiment, the implantable device 102 includes one or more shunts 112 configured to manage the transport of a body fluid (e.g., cerebrospinal fluid) from one region within the body (e.g. cerebral ventricle, lumbar sub-arachnoid spaces, or the like) to another (e.g., right atrium of the heart, peritoneal cavity, or the like). The implantable device 102 can include, but is not limited to, a body structure 104 including one or more shunts 112 each having a proximal portion 114, a distal portion 116, and at least one inner fluid-flow passageway 106 extending therethrough.

Among shunts, examples include, but are not limited to, blalock-taussig shunts, cardiac shunts, cerebral shunts (e.g., cerebrospinal fluid shunts, ventriculo-atrial shunts, ventriculo-peritoneal shunts, or the like) glaucoma shunts, mechanical shunts, pulmonary shunts, portosystemic shunts, portoacaval shunts, ventricle-to-pulmonary artery conduits, and the like. Further non-limiting examples of shunts may be found in, for example the following documents (the contents of which are incorporated herein by reference): U.S. Patent Publication Nos. 2008/0039768 (published Feb. 14, 2008) and 2006/0004317 (published Jan. 5, 2006).

In an embodiment, one or more of the shunts 112 are configured to regulate a pressure or flow of fluid (e.g., cerebrospinal fluid) from the ventricles. For example, an implantable device 102 including one or more shunts 112 may be useful to manage a cerebrospinal fluid transport associated with hydrocephalus (a condition including enlarged ventricles). In hydrocephalus, pressure from the cerebrospinal fluid generally increases. Hydrocephalus develops when cerebrospinal fluid cannot flow through the ventricular system, or when absorption into the blood stream is not the same as the amount of cerebrospinal fluid produced. Indicators for hydrocephalus include headache, personality disturbances and loss of intellectual abilities (dementia), problems in walking, irritability, vomiting, abnormal eye movements, a low level of consciousness, and the like. Normal pressure hydrocephalus is associated with progressive dementia, problems in walking, and loss of bladder control (urinary incontinence).

The implantable device 102 is configured to, among other things, manage a transport of biological fluids. The implantable device 102 can include, but is not limited to, one or more ports 118 configured to provide access from, or to, an interior environment of at least one of the one or more fluid-flow passageways 106. In an embodiment, the implantable device 102 includes one or more fluid entry ports 120 and fluid exit ports 122 in fluid communication with an interior environment of at least one of the one or more fluid-flow passageways 106 to an exterior environment. The implantable device 102 can include, but is not limited to, one or more fluid entry ports 120 configured to provide fluidic access to an interior of at least one of the one or more fluid-flow passageways 106. The implantable device 102 can include, but is not limited to, one or more fluid exit ports 122 configured to provide fluidic access to an exterior of at least one of the one or more fluid-flow passageways 106. In an embodiment, the implantable device 102 includes one or more cannulas configured to drain a cerebrospinal fluid from a ventricle of a brain of the biological subject. In an embodiment, the implantable device 102 includes one or more ventriculoperitoneal shunts.

In an embodiment, the implantable device 102 includes one or more cerebrospinal fluid shunts configured to drain cerebrospinal fluid from a region of a brain of the biological subject. The cerebrospinal fluid shunt can include for example, but is not limit to, entry conduits, such as a proximal (ventricular) catheter, into cranium and lateral ventricle, subcutaneous conduits, such as a distal catheter, and one or more flow-regulating devices for regulation flow of fluid out of the brain and into a peritoneal cavity.

In an embodiment, the implantable device 102 is configured to bypass malfunctioning arachnoidal granulations and to drain an excess fluid from the cerebral ventricles into one or more internal delivery regions (e.g., peritoneal cavity, pleural cavity, right atrium, gallbladder, or the like). For example, an implantable device 102 including one or more shunts 112 is surgically implanted to provide a controllable fluid-flow passageway 106 that diverts cerebrospinal fluid away from central nervous system fluid compartments (e.g., ventricles, fluid spaces near the spine, or the like) to one or more internal delivery regions including, for example, the peritoneal cavity (ventriculo-peritoneal shunt), the pleural cavity (ventriculo-pleural shunt), the right atrium (ventriculo-atrial shunt), or the gallbladder.

In an embodiment, the implantable device 102 includes one or more flow-regulating devices 132. Among flow-regulating devices 132 examples include, but are not limited to, adjustable pressure valves, mono-pressure valves, mechanical valves, electro-mechanical valves, programmable valves, pulsar valves, catheter valves, shunt valves, flow controlling mechanism that can be non-invasively adjusted to comport, for example, with patient's needs, or the like. Further non-limiting examples of flow-regulating devices 132 include differential pressure valves, one-way valves, flow-regulating or restricting valves, fixed pressure valves, (e.g., DELTA valves by Medtronic Neurological and Spinal), adjustable pressure valves (PS MEDICAL STRATA and STRATA valves by Medtronic Neurological and Spinal), CEREBROSPINAL FLUID—flow control valves (Medtronic Neurological and Spinal). In an embodiment, the implantable device 102 includes one or more flow-regulating devices 132 within at least one fluid-flow passageway 106 of a shunt 114. In an embodiment, the implantable device 102 includes one or more flow-regulating devices 132 within at least one fluid-flow passageway 106 of a catheter 122.

In an embodiment, the one or more flow-regulating devices 132 include at least one valve assemblies having one or more of a housing, inlet and outlet ports, fluid-flow passageways 106, adjustable pressure valves, mono-pressure valves, mechanical valves, electro-mechanical valves, programmable valves, one-way valves, two-way valves, pulsar valves, shunt valves, electro-mechanical valve actuators, valve mechanisms (e.g., ball-in-cone mechanism, controllable diaphragms, valve diaphragms, or the like), valve seats, pressure control valves, shunt valves, flow restriction devices, flow control devices, shunts, catheters, and the like. In an embodiment, the implantable device 102 includes one or more pressure (e.g., intracranial pressure) regulating devices 132. In an embodiment, the implantable device 102 includes a pressure-regulated valve means positioned within at least one fluid-flow passageway 106 for providing fluid flow therethrough at selected fluid pressures.

In an embodiment, the implantable device 102 is configured to regulate a transport of a material into or out of a biological subject. For example, in an embodiment, the implantable device 102 includes one or more flow-regulating devices 132 configured to configured to regulate a transport of a material into or out of a biological subject. Among flow-regulating devices 132 examples include, but are not limited to, adjustable pressure valves, mono-pressure valves, mechanical valves, electro-mechanical valves, programmable valves, pulsar valves, catheter valves, shunt valves, flow controlling mechanism that can be non-invasively adjusted to comport, for example, with patient's needs, or the like. Further non-limiting examples of flow-regulating devices 132 include differential pressure valves, one-way valves, flow-regulating or restricting valves, fixed pressure valves, (e.g., DELTA valves by Medtronic Neurological and Spinal), adjustable pressure valves (PS MEDICAL STRATA and STRATA valves by Medtronic Neurological and Spinal), CEREBROSPINAL FLUID—flow control valves (Medtronic Neurological and Spinal). In an embodiment, the implantable device 102 includes one or more flow-regulating devices 132 within at least one fluid-flow passageway 106 of a shunt 114. In an embodiment, the implantable device 102 includes one or more flow-regulating devices 132 within at least one fluid-flow passageway 106 of a catheter 122.

In an embodiment, the implantable device 102 is configured to regulate a transport of a material within a biological subject. In an embodiment, the implantable device 102 is configured to regulate fluidic flow in or out of a biological subject. In an embodiment, the implantable device 102 is configured to regulate fluidic flow from at least a first location of the body to at least a second location of the body. In an embodiment, the implantable device 102 is configured to regulate fluidic flow of cerebrospinal fluid from a ventricle of the brain to a drainage location in the body.

Figure 2:
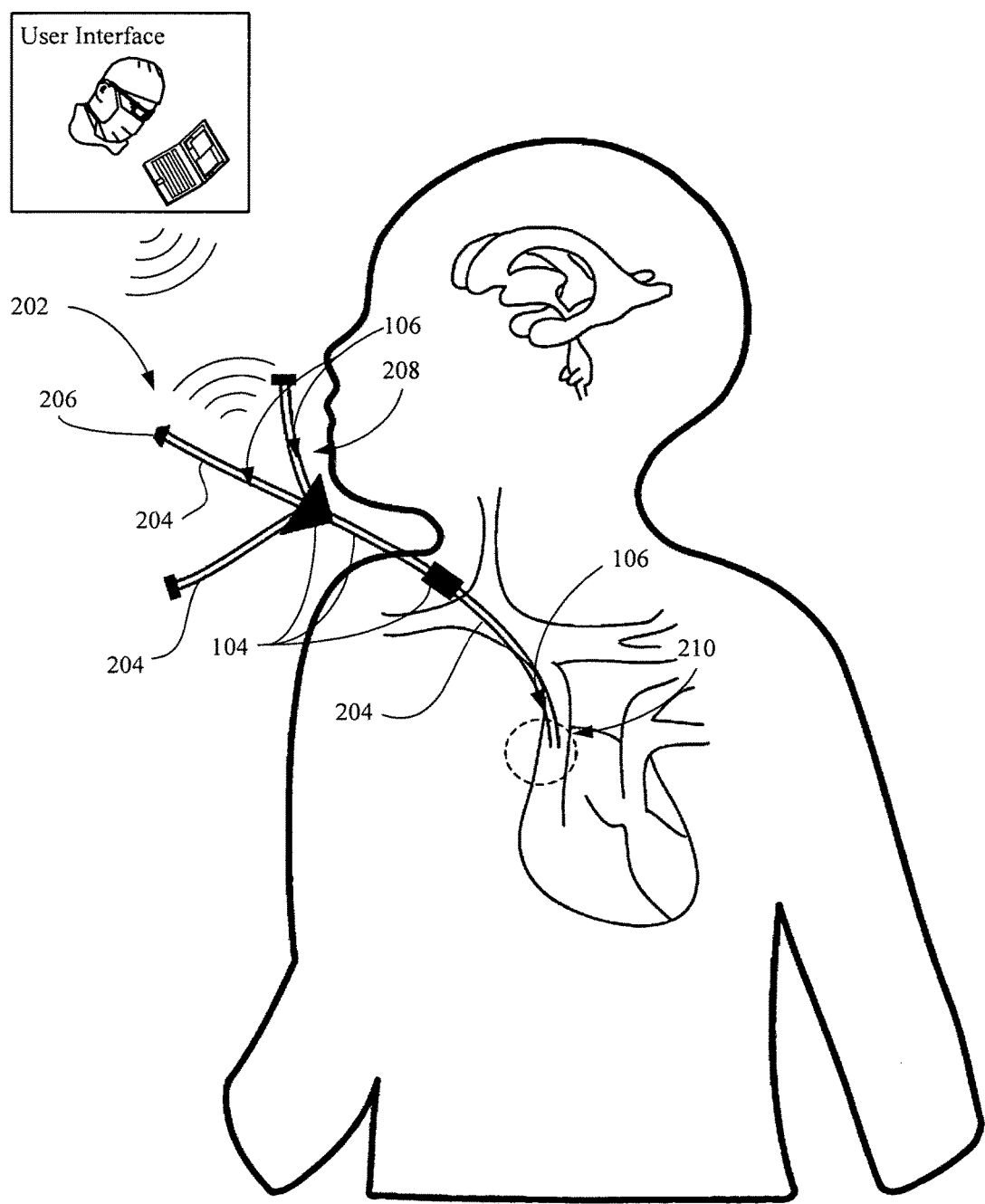
FIG. 2 is a perspective view of a system including an implantable device according to one illustrated embodiment.

Referring to FIG. 2, in an embodiment, the implantable device 102 includes a body structure 104 including a catheter assembly 202 having one or more catheters 204. In an embodiment, the implantable device 102 includes one or more catheters 204 configured to directly detecting and monitoring mechanical, physical, or biochemical functions associated with a biological subject; draining or collecting body fluids; providing access to an interior of a biological subject; distending at least one passageway; as well as for administering therapeutics, medications, pharmaceuticals, intravenous fluids, or nutrition. In an embodiment, the implantable device 102 includes one or more at least partially implantable catheters 204. The implantable device 102 can include, but is not limited to, one or more ports 206 configured to provide access from, or to, an interior environment of at least one of the one or more fluid-flow passageways 106.

The implantable device 102 can include, but is not limited to, a body structure 104 including one or more catheters 204 each having a proximal portion 208, a distal portion 210, and at least one inner fluid-flow passageway 106 extending therethrough. Among catheters 204, examples include, but are not limited to, arterial catheters, dialysis catheters, drainage catheters, indwelling catheters, long term non-tunneled central venous catheters, long term tunneled central venous catheters, mechanical catheters, peripheral venous catheters, peripherally insertable central venous catheters, peritoneal catheters, pulmonary artery Swan-Ganz catheters, short-term central venous catheters, urinary catheters, ventricular catheters, and the like. In an embodiment, one or more of the catheters 204 are configured for insertion into a body cavity, a duct, or a vessel of a subject in need thereof. In an embodiment, an implantable device 102 including a catheter assembly 202 is positioned to facilitate the transport of cerebrospinal fluid from a cerebral ventricle or subarachnoid space into, for example, a collection site, an ex vivo drainage reservoir, a partially implanted catheter assembly 202, or the like.

In an embodiment, the implantable device 102 includes one or more catheters 204. In an embodiment, the implantable device 102 includes one or more proximal catheters. In an embodiment, the implantable device 102 includes one or more distal catheters. In an embodiment, the implantable device 102 includes one or more brain ventricle catheters. In an embodiment, the implantable device 102 includes one or more sinus sagittalis catheters. In an embodiment, the implantable device 102 includes one or more biocompatible materials, polymeric materials, thermoplastics, silicone materials (e.g., polydimethysiloxanes), polyvinyl chloride materials, laytex rubber materials, or the like. Non-limiting examples of catheters 204 or shunts 112, or components thereof may be found in, for example the following documents (the contents of each of which are incorporated herein by reference): U.S. Pat. No. 7,524,298 (issued Apr. 28, 2009), U.S. Pat. No. 7,390,310 (issued Jun. 24, 2008), U.S. Pat. No. 7,334,594 (issued Feb. 26, 2008), U.S. Pat. No. 7,309,330 (issued Dec. 18, 2007), U.S. Pat. No. 7,226,441 (issued Jun. 5, 2007), U.S. Pat. No. 7,118,548 (issued Oct. 10, 2006), U.S. Pat. No. 6,932,787 (issued Aug. 23, 2005), U.S. Pat. No. 6,913,589 (issued Jul. 5, 2005), U.S. Pat. No. 6,743,190 (issued Jun. 1, 2004), U.S. Pat. No. 6,585,677 (issued Jul. 1, 2003); and U.S. Patent Publication Nos. 2009/0118661 (published May 7, 2009), 2009/0054824 (published Feb. 26, 2009, 2009/0054827 (published Feb. 26, 2009), 2008/0039768 (published Feb. 14, 2008), 2006/0004317 (published Jan. 5, 2006).

Figure 3:
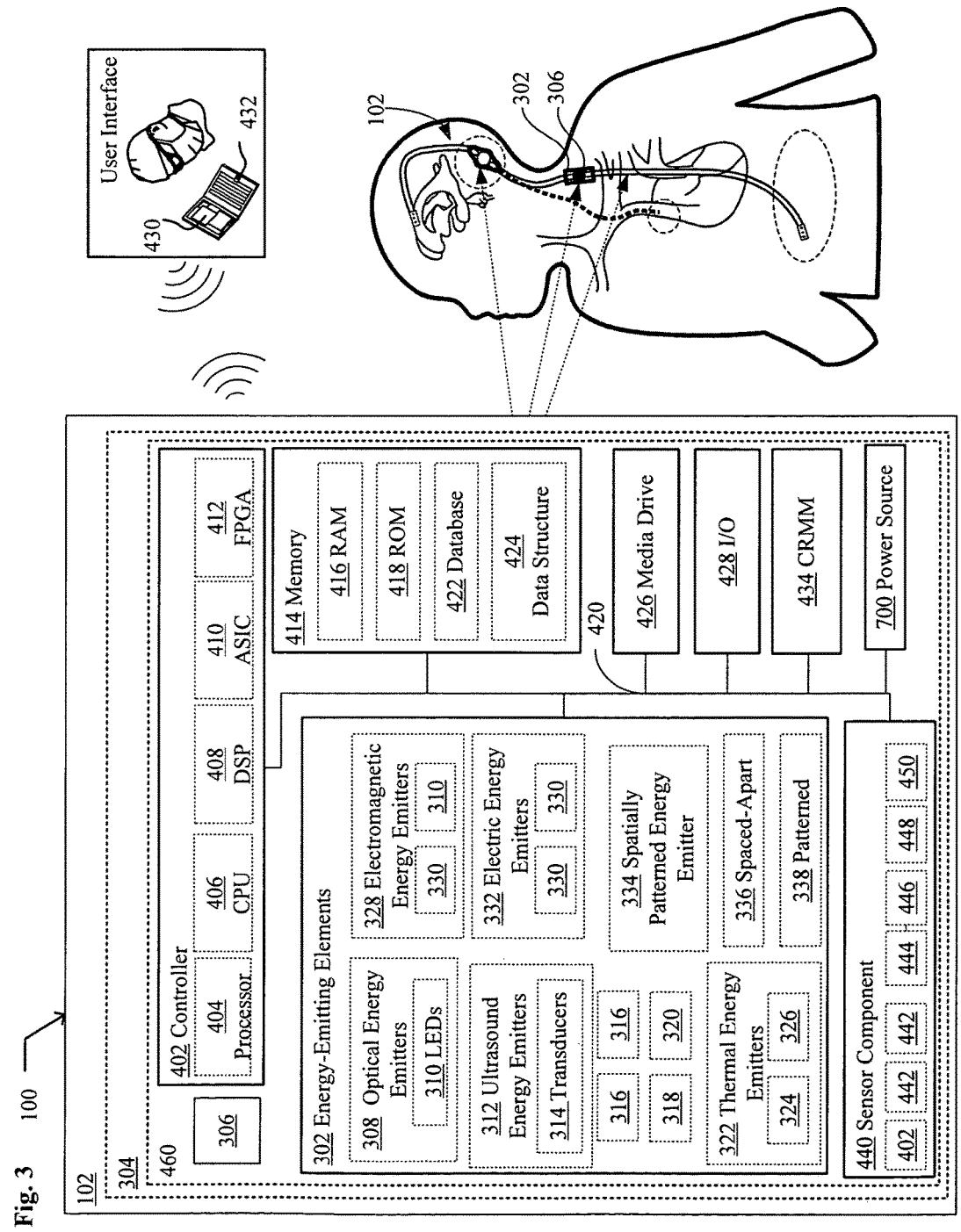
FIG. 3 is a schematic diagram of a system including an implantable device according to one illustrated embodiment.

FIG. 3 shows various configurations of a system 100 in which one or more methodologies or technologies can be implemented. The system 100 can include, but is not limited to, one or more energy emitters 302. In an embodiment, the system 100 includes a means for emitting an energy stimulus 304 including, for example, one or more energy emitters 302 having one or more energy waveguides 306. In an embodiment, the implantable device 102 includes one or more energy emitters 302. In an embodiment, the one or more energy emitters 302 are configured to emit at least one of an electromagnetic stimulus, an electrical stimulus, an ultrasonic stimulus, and a thermal stimulus. In an embodiment, the one or more energy emitters 302 are configured to generate a sterilizing energy stimulus. In an embodiment, the one or more energy emitters 302 are configured to emit at least one of an electromagnetic sterilizing stimulus, an electrical sterilizing stimulus, an ultrasonic sterilizing stimulus, and a thermal sterilizing stimulus. In an embodiment, the one or more energy emitters 302 are configured to deliver an in vivo stimulus waveform to a biological subject. In an embodiment, the one or more energy emitters 302 are configured to generate one or more continuous or a pulsed energy waves, or combinations thereof. In an embodiment, the one or more energy emitters 302 are configured to deliver an emitted energy to a biological fluid or tissue proximate at least one of an outer surface 108 and an inner surface 110 of the implantable device 102.

In an embodiment, the one or more energy emitters 302 are configured to emit at least one of an electromagnetic stimulus, an electrical stimulus, an ultrasonic stimulus, and a thermal stimulus of a character and for a time sufficient to inactivate an infectious agent proximate an outer or inner portion of the implantable device 102. In an embodiment, the one or more energy emitters 302 are configured to emit at least one of an electromagnetic stimulus, an electrical stimulus, an ultrasonic stimulus, and a thermal stimulus of a character and for a time sufficient to inhibit a DNA replication process of an infectious agent. In an embodiment, the one or more energy emitters 302 are configured to emit at least one of an electromagnetic stimulus, an electrical stimulus, an ultrasonic stimulus, and a thermal stimulus of a character and for a time sufficient to induce PCD of at least a portion of cells within a cerebrospinal fluid proximate the implantable device 102.

PCD can be induced using a variety of methodologies and technologies including, for example, pulsed electric fields, pulsed ultrasound, focused ultrasound, low intensity ultrasound, ultraviolet radiation, or the like. Further non-limiting examples of methodologies and technologies for inducing PCD can be found the following documents (the contents of which are incorporated herein by reference): Abdollahi et al., *Apoptosis signals in Lymphoblasts Induced by Focused Ultrasound*, FASEB Journal Express Article doi:10.1096/fj.04-1601fje (Published online Jul. 1, 2004); Ashush et al., *Apoptosis Induction of Human Myeloid Leukemic Cells by Ultrasound Exposure*, Cancer Res. 60: 1014-1020 (2000); Beebe et al., *Nanosecond, High-intensity Pulsed Electric Fields Induce Apoptosis in Human Cells*, The FASEB Journal express article 10.1096/fj.02-0859fje (Published online Jun. 17, 2003); Caricchio et al., *Ultraviolet B Radiation-Induced Cell Death: Critical Role of Ultraviolet Dose in Inflammation and Lupus Autoantigen Redistribution*, J. Immunol., 171: 5778-5786 (2003); Fabo et al., *Ultraviolet B but not Ultraviolet A Radiation Initiates Melanoma*, Cancer Res. 64 (18): 6372-376 (2004); Fent et al., *Low Intensity Ultrasound-induced Apoptosis in Human Gastric Carcinoma Cells*, World J Gastroenterol, 14(31):4873-879 (2008); Hall et al., *Nanosecond Pulsed Electric Fields Induce Apoptosis in p53-Wildtype and p53-Null HCT116 Colon Carcinoma Cells*, Apoptosis, 12(9):1721-31 (2007); and Rediske et al., *Pulsed Ultrasound Enhances the Killing of Escherichia coli Biofilms by Aminoglycoside Antibiotics In Vivo*, Antimicrob. Agents Chemother., 44 (3): 771-72 (2000). In an embodiment, the one or more energy emitters 302 are configured to emit a sufficient amount at least one of an electromagnetic stimulus, an electrical stimulus, an ultrasonic stimulus, and a thermal stimulus to induce PCD without substantially inducing necrosis of a portion of cells proximate an outer or inner portion of the implantable device 102. In an embodiment, the one or more energy emitters 302 are configured to deliver electromagnetic radiation of a character and for a time sufficient to induce PCD without substantially inducing necrosis of a tissue proximate the outer portion of the one or more fluid-flow passageways 106. In an embodiment, one or more energy emitters 302 are configured to deliver a sufficient amount of an ultraviolet radiation to induce cell death by PCD. In an embodiment, the one or more energy emitters 302 are configured to deliver an effective dose of optical energy at which a cell preferentially undergoes PCD compared to necrosis. In an embodiment, the one or more energy emitters 302 are configured to deliver a sufficient amount of an optical energy to initiate ultraviolet energy induced PCD. In an embodiment, the one or more energy emitters 302 include at least one ultraviolet energy emitter. In an embodiment, the one or more energy emitters 302 include at least one ultraviolet B energy emitter. In an embodiment, the one or more energy emitters 302 include at least one ultraviolet C energy emitter. In an embodiment, at least one of the one or more energy emitters 302 comprises a peak emission wavelength ranging from about 100 nanometers to about 400 nanometers. In an embodiment, at least one of the one or more energy emitters 302 comprises a peak emission wavelength ranging from about 100 nanometers to about 320 nanometers. In an embodiment, at least one of the one or more energy emitters 302 comprises a peak emission wavelength ranging from about 280 nanometers to about 320 nanometers.

Among energy emitters 302 examples include, but are not limited to, electric circuits, electrical conductors, electrodes (e.g., nano- and micro-electrodes, patterned-electrodes, electrode arrays (e.g., multi-electrode arrays, micro-fabricated multi-electrode arrays, patterned-electrode arrays, or the like), electrocautery electrodes, or the like), cavity resonators, conducting traces, ceramic patterned electrodes, electro-mechanical components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency UV light-emitting diodes, or the like), arc flashlamps, incandescent emitters, transducers, heat sources, continuous wave bulbs, ultrasound emitting elements, ultrasonic transducers, thermal energy emitting elements, and the like. In an embodiment, the one or more energy emitters 302 include at least one two-photon excitation component. In an embodiment, the one or more energy emitters 302 include at least one of an exciplex laser, a diode-pumped solid state laser, and a semiconductor laser. Further non-limiting examples of energy emitters 302 include radiation emitters, ion emitters, photon emitters, electron emitters, gamma emitters, and the like.

Energy emitters 302 forming part of the implantable device 102, can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, or the like, or any combination thereof. One or more of the energy emitters 302 can have a peak emission wavelength in the x-ray, ultraviolet, visible, infrared, near infrared, terahertz, microwave, or radio frequency spectrum.

In an embodiment, the one or more energy emitters 302 include one or more optical energy emitters 308. In an embodiment, the one or more optical energy emitters 308 are configured to emit a sterilizing energy stimulus having one or more peak emission wavelengths in the infrared, visible, or ultraviolet spectrum, or combinations thereof. In an embodiment, an operational fluence of the one or more optical energy emitters 308 is less than about 80 milli-joules per square centimeter. In an embodiment, an operational fluence of the one or more optical energy emitters 308 is less than about 35 milli-joules per square centimeter. In an embodiment, an operational fluence of the one or more optical energy emitters 308 is less than about 15 milli joules per square centimeter. In an embodiment, an average energy density of the one or more optical energy emitters 308 ranges from about less than about 15 milli-joules per square centimeter to about less than about 80 milli-joules per square centimeter.

In an embodiment, the one or more energy emitters 302 are configured to generate one or more non-ionizing laser pulses in an amount and for a time sufficient to induce the formation of sound waves associated with changes in a biological mass present along an optical path. In an embodiment, the one or more energy emitters 302 are configured to direct a pulsed optical energy waveform along an optical path of a character and for a time sufficient to cause a biological mass within a cerebrospinal fluid interrogated by the pulsed optical energy waveform to temporarily expand. In an embodiment, the one or more energy emitters 302 are configured to direct a pulsed optical energy stimulus along an optical path in an amount and for a time sufficient to elicit the formation of acoustic waves associated with changes in a biological mass present along the optical path. In an embodiment, the one or more energy emitters 302 are configured to direct a pulsed optical energy waveform along an optical path of sufficient strength or duration to cause at least a portion of cells within a cerebrospinal fluid interrogated by the pulsed optical energy waveform to temporarily expand. In an embodiment, the one or more energy emitters 302 are configured to direct a pulsed optical energy waveform along an optical path in an amount and for a time sufficient to cause at least a portion of cells within a cerebrospinal fluid interrogated by the pulsed optical energy waveform to temporarily fluoresce.

In an embodiment, the one or more energy emitters 302 are configured to direct optical energy along the optical path for a time sufficient to interact with a cerebrospinal fluid received within one or more fluid-flow passageways 106. In an embodiment, the one or more energy emitters 302 are further configured to direct a portion of an emitted optical energy to a sensor component in optical communication along the optical path.

In an embodiment, the one or more energy emitters 302 are configured to concurrently or sequentially deliver one or more electromagnetic stimuli, electrical stimuli, ultrasonic stimuli, or thermal stimuli. In an embodiment, at least one of the one or more energy emitters 302 is configured to deliver an electromagnetic stimulus, in vivo, to a cerebrospinal fluid received within at least one of the one or more fluid-flow passageways 106. In an embodiment, at least one of the one or more energy emitters 302 is configured to deliver an electrical stimulus, in vivo, to a cerebrospinal fluid received within at least one of the one or more fluid-flow passageways 106. In an embodiment, at least one of the one or more energy emitters 302 is configured to deliver an ultrasonic stimulus, in vivo, to a cerebrospinal fluid received within at least one of the one or more fluid-flow passageways 106. In an embodiment, at least one of the one or more energy emitters 302 is configured to deliver a thermal stimulus, in vivo, to a cerebrospinal fluid received within at least one of the one or more fluid-flow passageways 106.

In an embodiment, at least one of the one or more energy emitters 302 is configured to emit at least one of an electromagnetic stimulus, an electrical stimulus, an ultrasonic stimulus, and a thermal stimulus having a character and for a time sufficient to induce PCD without substantially inducing necrosis of an infectious agent within a cerebrospinal fluid received within at least one of the one or more fluid-flow passageways 106. In an embodiment, at least one of the one or more energy emitters 302 is configured to emit an energy stimulus of a character and for a time sufficient to induce PCD without substantially inducing necrosis of a pathogen within a cerebrospinal fluid received within at least one of the one or more fluid-flow passageways 106. In an embodiment, at least one of the one or more energy emitters 302 is configured to deliver an energy stimulus of a character and for a time sufficient to induce poration (e.g., electroporation) of a plasma membrane in at least a portion of cells within a cerebrospinal fluid received within at least one of the one or more fluid-flow passageways 106. In an embodiment, one or more of the energy emitters 302 are configured to emit an energy stimulus of a character and for a time sufficient to induce PCD without substantially inducing necrosis of at least a portion of cells within a cerebrospinal fluid received within at least one of the one or more fluid-flow passageways 106.

In an embodiment, at least one of the one or more energy emitters 302 is photonically coupleable to an interior of one or more of the one or more fluid-flow passageways 106. In an embodiment, at least one of the one or more energy emitters 302 is photonically coupleable to an exterior of one or more of the one or more fluid-flow passageways 106. In an embodiment, at least one of the one or more energy emitters 302 is photonically coupleable, via one or more waveguides 306, to an interior of at least one of the one or more fluid-flow passageways 106. In an embodiment, at least one of the one or more energy emitters 302 is configured to emit an energy stimulus from an interior of at least one of the one or more fluid-flow passageways to an exterior of at least one of the one or more fluid-flow passageways 106.

In an embodiment, the one or more energy emitters 302 are configured to deliver an energy stimulus to a region proximate the implantable device 102. In an embodiment, the one or more energy emitters 302 are configured to deliver an emitted energy to tissue proximate the implantable device 102. In an embodiment, the one or more energy emitters 302 are configured to deliver an emitted energy to tissue proximate an outer 108 or inner 110 surface of the implantable device 102.

In an embodiment, the one or more energy emitters 302 are configured to emit an energy stimulus having one or more peak emission wavelengths in the x-ray, ultraviolet, visible, infrared, near infrared, terahertz, microwave, or radio frequency spectrum. In an embodiment, least one of the one or more energy emitters 302 is configured to deliver one or more charged particles. In an embodiment, the one or more energy emitters 302 include one or more lasers, laser diodes, light-emitting diodes, arc flashlamps, incandescent emitters, transducers, heat sources, or continuous wave bulbs. In an embodiment, the one or more energy emitters 302 include one or more light-emitting diodes, quantum dots, organic light-emitting diodes, microcavity light-emitting diodes, or polymer light-emitting diodes.

In an embodiment, the one or more energy emitters 302 are configured to provide a voltage across at least a portion of cells within a cerebrospinal fluid received within at least one of the one or more fluid-flow passageways 106. In an embodiment, the voltage is of sufficient strength or duration to exceed a nominal dielectric strength of at least one cell plasma membrane. In an embodiment, the voltage is of sufficient strength or duration to exceed a nominal dielectric strength of a cell plasma membrane without substantially interfering with a normal operation of the implantable shunt system 100.

In an embodiment, the one or more energy emitters 302 are implanted within a biological subject. In an embodiment, the one or more energy emitters 302 are configured to apply energy (e.g., electrical energy, electromagnetic energy, thermal energy, ultrasonic energy, or the like, or combinations thereof) to tissue proximate an implantable device 102 to, for example, treat or prevent an infection (e.g., an implant-associated infection, hematogenous implant-associated infection, or the like), a hematological abnormality, or the like. In an embodiment, the one or more energy emitters 302 are configured to apply energy to tissue proximate an implantable device 102 to promote at least one of a tissue healing process, a tissue growing process, a tissue scarring process, and the like. In an embodiment, the one or more energy emitters 302 are configured to apply energy of sufficient strength or duration to tissue proximate an implant to inhibit a tissue scarring process. In an embodiment, the one or more energy emitters 302 are configured to apply energy to tissue proximate an implant to treat, prevent, inhibit, or reduce post-operative adhesion, fibrin sheath formation, or scar tissue formation. In an embodiment, the one or more energy emitters 302 are configured to apply an energy stimulus to tissue proximate an implantable device 102 to treat, prevent, inhibit, or reduce the presence or concentration of an infectious agent within at least a portion of the tissue proximate the implantable device 102.

In an embodiment, the one or more energy emitters 302 are configured to concurrently or sequentially deliver at least a first energy stimulus and a second energy stimulus, the second energy stimulus different from the first energy stimulus. In an embodiment, the second energy stimulus differs in at least one of a spatial distribution and a temporal distribution. In an embodiment, the first energy stimulus comprises an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus. In an embodiment, at least one of the one or more energy emitters 302 is configured to provide an illumination pattern comprising at least a first region and a second region. In an embodiment, the second region includes at least one of an illumination intensity, an energy-emitting pattern, a peak emission wavelength, an ON-pulse duration, an OFF-pulse duration, and a pulse frequency different from the first region. In an embodiment, the second region includes at least one of a spatial pattern and a temporal pattern different from the first region.

In an embodiment, an energy emitter 302 is operably coupled to a plurality of waveguides 902 that are configured to deliver a spatially pattern energy stimulus. In an embodiment, an energy emitter 302 is configures to emit a multiplex energy stimulus having two or more peak emission wavelengths. In an embodiment, a multiplex energy stimulus can be routed to respective waveguides 902 configured to deliver a spatially pattern energy stimulus base on a wavelength, an intensity, a spectral power distribution, a waveguide-specific address, or the like.

The system 100 can include, but is not limited to, one or more light-emitting diodes 310. In an embodiment, the implantable device 102 includes one or more light-emitting diodes 310. Light-emitting diodes 310 come in a variety of forms and types including, for example, standard, high intensity, super bright, low current types, or the like. Typically, the light-emitting diode's color is determined by the peak wavelength of the light emitted. For example, red light-emitting diodes have a peak emission ranging from about 610 nm to about 660 nm. Non-limiting examples of light-emitting diode colors include amber, blue, red, green, white, yellow, orange-red, ultraviolet, and the like. Further non-limiting examples of light-emitting diodes include bi-color, tri-color, and the like. Light-emitting diode's emission wavelength may depend on a variety of factors including, for example, the current delivered to the light-emitting diode. The color or peak emission wavelength spectrum of the emitted light may also generally depends on the composition or condition of the semi-conducting material used, and can include, but is not limited to, peak emission wavelengths in the infrared, visible, near-ultraviolet, or ultraviolet spectrum, or combinations thereof.

Light-emitting diodes 310 can be mounted on, for example, but not limited to a surface, a substrate, a portion, or a component of the implantable device 102 using a variety of methodologies and technologies including, for example, wire bonding, flip chip, controlled collapse chip connection, integrated circuit chip mounting arrangement, and the like. In an embodiment, the light-emitting diodes 310 are mounted on a surface, substrate, portion, or component of the implantable device 102 using, for example, but not limited to a flip-chip arrangement. A flip-chip is one type of integrated circuit chip mounting arrangement that generally does not require wire bonding between chips. In an embodiment, instead of wire bonding, solder beads or other elements are positioned or deposited on chip pads such that when the chip is mounted, electrical connections are established between conductive traces carried by circuitry within the system 100. In an embodiment, the one or more energy emitters 302 include one or more light-emitting diode arrays. In an embodiment, the one or more energy emitters 302 include at least one of a one-dimensional light-emitting diode array, a two-dimensional light-emitting diode array, and a three-dimensional light-emitting diode array.

The system 100 can include, but is not limited to, include one or more ultrasound energy emitters 312. In an embodiment, the implantable device 102 includes one or more ultrasound energy emitters 312. In an embodiment, the one or more energy emitters 302 include one or more transducers 314 (e.g., ultrasonic transducers, ultrasonic sensors, or the like). In an embodiment, the one or more transducers 314 are configured to deliver an ultrasonic energy stimulus (e.g., an ultrasonic non-thermal stimulus, an ultrasonic thermal stimulus, a low or high intensity ultrasonic stimulus, a pulsed ultrasonic stimulus, a focused ultrasonic stimulus, or the like) to a region within the biological subject. In an embodiment, the one or more transducers 314 are configured to generate an ultrasonic stimulus. In an embodiment, the one or more transducers 314 are configured to detect an ultrasonic signal. In an embodiment, the one or more transducers 314 are configured to transmit and receive ultrasonic waves. In an embodiment, the one or more transducers 314 are configured to deliver an ultrasonic stimulus to a region proximate the implantable device 102. In an embodiment, the one or more transducers 314 are configured to deliver an in vivo ultrasonic interrogation waveform to a biological subject. In an embodiment, the one or more transducers 314 are configured to generate one or more continuous or a pulsed ultrasonic waves, or combinations thereof.

Among transducers 314, examples include, but are not limited to, acoustic transducers, composite piezoelectric transducers, conformal transducers, flexible transducers, flexible ultrasonic multi-element transducer arrays, flexible ultrasound transducers, immersible ultrasonic transducers, integrated ultrasonic transducers, micro-fabricated ultrasound transducers, piezoelectric materials (e.g., lead-zirconate-titanate, bismuth titanate, lithium niobate, piezoelectric ceramic films or laminates, sol-gel sprayed piezoelectric ceramic composite films or laminates, piezoelectric crystals, or the like), piezoelectric ring transducers, piezoelectric transducers, ultrasonic sensors, ultrasonic transducers, and the like. In an embodiment, the one or more energy emitters 302 include one or more one-dimensional transducer arrays, two-dimensional transducer arrays, or three-dimensional transducer arrays. The one or more transducers 314 can include, but are not limited to, a single design where a single piezoelectric component outputs one single waveform at a time, or can be compound where two or more piezoelectric components are utilized in a single transducer 314 or in multiple transducers 314 thereby allowing multiple waveforms to be output sequentially or concurrently.

The effects of therapeutic ultrasound on living tissues vary. For example, ultrasound typically has a greater affect on highly organized, structurally rigid tissues such as bone, tendons, ligaments, cartilage, and muscle. Due to their different depths within the body, however, the different tissue types require different ultrasonic frequencies for effective treatment. See, e.g., U.S. Publication No. 2007/0249969 (published Oct. 25, 2007) (the contents of which are incorporated herein by reference). Ultrasound can cause increases in tissue relaxation, local blood flow, and scar tissue breakdown. In an embodiment, the effect of the increase in local blood flow are used to, for example, aid in reducing local swelling and chronic inflammation, as well as promote bone fracture healing. In an embodiment, applying a sufficient ultrasonic energy to tissue infected with, for example, pathogenic bacteria, can lead to a reduction of the pathogenic bacteria in at least a portion of the infected tissue. In an embodiment, applying a sufficient ultrasonic energy to tissue infected with, for example, pathogenic bacteria, in the presence of one or more disinfecting agents can lead to a reduction of the pathogenic bacteria in at least a portion of the infected tissue. In an embodiment, applying a sufficient ultrasonic energy to tissue infected with, for example, pathogenic bacteria, in the presence of one or more disinfecting agents can reduce biofilm viability, as well as actively-impeding biofilm formation on an implant.

In an embodiment, the system 100 includes electromechanical components for generating, transmitting, or receiving waves (e.g., ultrasonic waves, electromagnetic waves, or the like). For example, in an embodiment, the system 100 includes one or more waveform generators 316, as well as any associated hardware, software, and the like. In an embodiment, the system 100 includes one or more controllers configured to concurrently or sequentially operate multiple transducers 314. In an embodiment, the system 100 includes multiple drive circuits (e.g., one drive circuit for each transducer 314) and is configured to generate varying waveforms from each coupled transducer 314 (e.g., multiple waveform generators, or the like). The system 100 can include, but is not limited to, an electronic timing controller coupled to an ultrasonic waveform generator. In an embodiment, one or more controllers are configured to automatically control one or more of a frequency, a duration, a pulse rate, a duty cycle, an amount of energy, or the like associated with the ultrasonic energy generated by the one or more transducers 314.

In an embodiment, the one or more transducers 314 are communicatively coupled to one or more waveform generators 316. In an embodiment, a waveform generator 316 can include, but is not limited to, an oscillator 318 and a pulse generator 320 configured to generate one or more drive signals for causing one or more transducer 314 to ultrasonically vibrate and generate ultrasonic energy.

The system 100 can include, but is not limited to, one or more thermal energy emitters 322. In an embodiment, the implantable device 102 includes one or more thermal energy emitters 322. In an embodiment, the one or more thermal energy emitters 322 include one or more transducers 314. In an embodiment, the one or more thermal energy emitters 322 include one or more metallic heat-radiating elements. In an embodiment, the one or more thermal energy emitters 322 include one or more power light-emitting diodes 324. In an embodiment, the one or more thermal energy emitters 322 include one or more thermal energy emitting elements. In an embodiment, the one or more thermal energy emitters 322 include one or more thermal energy conducting elements. In an embodiment, the one or more thermal energy emitters 322 include one or more thermal energy dissipating elements. In an embodiment, the one or more thermal energy emitters 322 include one or more electrodes 326. In an embodiment, the one or more thermal energy emitters 322 are configured to emit a sufficient amount of an energy stimulus to inactivate an infectious agent. In an embodiment, the one or more thermal energy emitters 322 are configured to thermally shock an infectious agent. In an embodiment, the one or more thermal energy emitters 322 are configured to emit a thermal energy stimulus of a character and for a duration to thermally induce PCD of a portion of infected cells proximate the implantable device 102. In an embodiment, the one or more thermal energy emitters 322 are operable to emit a sufficient amount of an energy stimulus to increase the temperature of at least a portion of a cerebrospinal fluid received within at least one of the one or more fluid-flow passageways 106 by about 5° C. to about 20° C. In an embodiment, the one or more thermal energy emitters 322 are operable to emit a sufficient amount of an energy stimulus to increase the temperature of at least a portion of a cerebrospinal fluid received within at least one of the one or more fluid-flow passageways 106 by about 5° C. to about 6° C.

The system 100 can include, but is not limited to, one or more energy emitters 302 configured to deliver a pulsed thermal sterilizing stimulus of a character and for a duration sufficient to elevate a temperature of at least a portion of cells proximate an indwelling medical implant. Elevated temperatures or hyperthermia therapy caused by the one or more energy emitters 302 in a region including cells and or tissue can induce death of the cells and or tissue through, for example, a process of programmed cell death (e.g., apoptosis) or necrosis, depending upon the temperature experienced by the cells and or tissue. For example, hyperthermia therapy between 40° C. and 60° C. can result in disordered cellular metabolism and membrane function and in many instances, cell death. In general, at temperatures below 60° C., hyperthermia is more likely to induce PCD in cells without substantially inducing necrosis. At temperatures greater than about 60° C., the likelihood of inducing coagulation necrosis of cells and tissue increases. Relatively small increases in temperature, e.g., 3° C., above the normal functioning temperature of a cell can cause apoptotic cell death. For example, temperatures ranging from 40° C. to 47° C. can induce cell death in a reproducible time and temperature dependent manner in cells normally functioning at 37° C.

Elevating the temperature of a mammalian cell, for example, to 43° C. can cause changes in cellular protein expression and increased PCD. In some instances, hyperthermia can be induced by exposure to high intensity focused ultrasound (HIFU). High acoustic intensities associated with HIFU can cause rapid heat generation in cells and tissue due to absorption of the acoustic energy. Using HIFU, the temperature in a region including cells and or tissue can rise very rapidly, inducing thermal stressing of the targeted cells and or tissue which in turn can lead to apoptotic cell death. The degree of thermal stressing of cells may be a function of the character or duration of the energy stimulus delivered to induce a temperature change. For example, rapid heating of cells using HIFU may be advantageous for rapidly attenuating an infectious activity by inducing cell death as opposed to slow increases in temperature to which the cells may become adapted. See, e.g., Somwaru, et al., *J. Androl.* 25:506-513, 2004 (the contents of which are incorporated herein by reference); Stankiewicz, et al., *J. Biol. Chem.* 280:38729-38739, 2005 (the contents of which are incorporated herein by reference); Sodja, et al., *J. Cell Sci.* 111:2305-2313, 1998 (the contents of which are incorporated herein by reference); Setroikromo, et al., *Cell Stress Chaperones* 12:320-330, 2007 (the contents of which are incorporated herein by reference); Dubinsky, et al., *AJR* 190:191-199, 2008 (the contents of which are incorporated herein by reference); Lepock. *Int. J. Hyperthermia,* 19:252-266, 2003 (the contents of which are incorporated herein by reference); Roti Roti *Int. J. Hyperthermia* 24:3-15, 2008 (the contents of which are incorporated herein by reference); Fuchs, et al., "The Laser's Position in Medicine" pp 187-198 in *Applied Laser Medicine*. Ed. Hans-Peter Berlien, Gerhard J. Muller, Springer-Verlag New York, LLC, 2003 (the contents of which are incorporated herein by reference).

In an embodiment, an implantable device 102 includes a sensor component 902 configured to perform a real-time comparison of a measurand associated with a biological sample proximate one or more regions of at least one surface of the implantable device 102 to stored reference data. The implantable device 102 can include, among other things, one or more energy emitters 302 configured to emit a pulsed thermal sterilizing stimulus of a character and for a time sufficient to induce PCD without substantially inducing necrosis of at least a portion of cells proximate the implantable device 102 in response to the comparison. In an embodiment, at least one of the one or more energy emitters 302 is configured to emit a pulsed thermal sterilizing stimulus of a character and for a time sufficient to induce PCD without substantially inducing necrosis of an infectious agent within a tissue proximate the implantable device 102 in response to a detect level of an infectious agent.

In an embodiment, at least one of the one or more energy emitters 302 is configured to emit a pulsed thermal sterilizing stimulus of a character and for a duration sufficient to induce PCD without substantially inducing necrosis of a pathogen within a region proximate the implantable device 102. In an embodiment, at least one of the one or more energy emitters 302 is configured to deliver a pulsed thermal sterilizing stimulus of a character and for a duration sufficient to induce thermal poration of a plasma membrane in at least a portion of cells within a tissue proximate the implantable device 102. In an embodiment, at least of the one or more energy emitters 302 is configured to deliver a pulsed thermal sterilizing stimulus of a character and for a time sufficient to induce poration of a plasma membrane in at least a portion of cells on a surface of the implantable device 102.

In an embodiment, the one or more energy emitters 302 are operable to emit a sufficient amount of a pulsed thermal sterilizing stimulus to increase the temperature of at least a portion of cells proximate the implantable device 102 by about 3° C. to about 22° C. In an embodiment, the one or more energy emitters 108 are operable to emit a sufficient amount of a pulsed thermal sterilizing stimulus to increase the temperature of at least a portion of cells proximate the indwelling medical implant 102 by about 3° C. to about 10° C. In an embodiment, the one or more energy emitters 302 are operable to emit a sufficient amount of a pulsed thermal sterilizing stimulus to increase the temperature of at least a portion of cells proximate the implantable device 102 by about 3° C. to about 4° C. In an embodiment, at least one of the one or more energy emitters 302 is configured to deliver a pulsed thermal sterilizing stimulus of a character and for a duration sufficient to elevate a temperature of at least a portion of cells proximate the implantable device 102 from about 37° C. to less than about 60° C. In an embodiment, at least one of the one or more energy emitters 302 is configured to deliver a pulsed thermal sterilizing stimulus of a character and for a duration sufficient to elevate a temperature of at least a portion of cells proximate the indwelling medical implant from about 37° C. to less than about 47° C. In an, embodiment, at least one of the one or more energy emitters 108 is configured to deliver a pulsed thermal sterilizing stimulus 37° C. of a character and for a duration sufficient to elevate a temperature of at least a portion of cells proximate the implantable device 102 from about 37° C. to less than about 45° C. In an embodiment, at least one of the one or more energy emitters 302 is configured to deliver a pulsed thermal sterilizing stimulus of a character and for a duration sufficient to elevate a temperature of at least a portion of cells proximate the implantable device 102 from about 37° C. to less than about 42° C. In an embodiment, least one of the one or more energy emitters 302 is configured to deliver a pulsed thermal sterilizing stimulus of a character and for a duration sufficient to elevate a temperature of at least a portion of cells proximate the indwelling medical implant 102 from about 37° C. to a temperature ranging from greater than about 41° C. to less than about 63° C.

In an embodiment, the system 100 includes, among other things, a body structure 104 having a surface defining one or more fluid-flow passageways configured to receive a biological fluid of a biological subject, and one or more energy emitters 302 configured to emit a pulsed thermal sterilizing stimulus of a character and for a time sufficient to induce PCD without substantially inducing necrosis of at least a portion of cells within the biological fluid proximate the surface of the body structure 104 in response to a determination that an infectious agent is present within the biological fluid.

In an embodiment, the one or more energy emitters 302 are configure to emit a sufficient amount of a pulsed thermal sterilizing stimulus to increase the temperature of at least a portion of a cerebrospinal fluid received within at least one of the one or more fluid-flow passageways by about 3° C. to about 22° C. In an embodiment, the one or more energy emitters 302 are configure to emit a sufficient amount of a pulsed thermal sterilizing stimulus to increase the temperature of at least a portion of a cerebrospinal fluid received within at least one of the one or more fluid-flow passageways by about 3° C. to about 10° C. In an embodiment, the one or more energy emitters 302 are configure to emit a sufficient amount of a pulsed thermal sterilizing stimulus to increase the temperature of at least a portion of cells within a cerebrospinal fluid received within at least one of the one or more fluid-flow passageways by about 3° C. to about 4° C.

In an embodiment, at least one of the one or more energy emitters 302 is configured to deliver a pulsed thermal sterilizing stimulus of a character and for a duration sufficient to elevate a temperature at least a portion of cells within a cerebrospinal fluid received within at least one of the one or more fluid-flow passageways from about 37° C. to less than about 60° C. In an embodiment, at least one of the one or more energy emitters 302 is configured to deliver a pulsed thermal sterilizing stimulus of a character and for a duration sufficient to elevate a temperature at least a portion of cells within a cerebrospinal fluid received within at least one of the one or more fluid-flow passageways from about 37° C. to less than about 47° C. In an embodiment, at least one of the one or more energy emitters 302 is configured to deliver a pulsed thermal sterilizing stimulus of a character and for a duration sufficient to elevate a temperature of at least a portion of cells within a cerebrospinal fluid received within at least one of the one or more fluid-flow passageways from about 37° C. to less than about 45° C. In an embodiment, at least one of the one or more energy emitters 302 is configured to deliver a pulsed thermal sterilizing stimulus of a character and for a duration sufficient to elevate a temperature of at least a portion of cells within a cerebrospinal fluid received within at least one of the one or more fluid-flow passageways from about 37° C. to less than about 42° C. In an embodiment, at least one of the one or more energy emitters 302 is configured to deliver a pulsed thermal sterilizing stimulus of a character and for a duration sufficient to elevate temperature of at least a portion of cells within a cerebrospinal fluid received within at least one of the one or more fluid-flow passageways from about a normal body temperature to a temperature ranging from greater than about 41° C. to less than about 63° C.

In an embodiment, at least one of the one or more energy emitters 302 is configured to emit a pulsed thermal sterilizing stimulus of a character and for a time sufficient to induce PCD without substantially inducing necrosis of an infectious agent within a cerebrospinal fluid proximate the surface of the body structure 104. In an embodiment, at least one of the one or more energy emitters 302 is configured to emit an energy stimulus of a character and for a time sufficient to induce PCD without substantially inducing necrosis of a pathogen within a cerebrospinal proximate the surface of the body structure 104.

In an embodiment, the body structure 104 includes one or more cerebrospinal fluid shunts configured to drain cerebrospinal fluid from a region of a brain of the biological subject. In an embodiment, the body structure 104 includes one or more cannulas configured to drain a cerebrospinal fluid from a ventricle of a brain of the biological subject. In an embodiment, the body structure 104 includes a ventriculo-peritoneal shunt.

The system 100 can include, but is not limited to, one or more electromagnetic energy emitters 328. In an embodiment, the implantable device 102 includes one or more electromagnetic energy emitters 328. In an embodiment, the one or more electromagnetic energy emitters 328 are configured to provide a voltage across at least a portion of cells proximate an outer surface 108 of the implantable device 102. In an embodiment, the one or more electromagnetic energy emitters 328 include one or more electrodes 330. In an embodiment, the one or more electromagnetic energy emitters 328 include one or more light-emitting diodes 310. In an embodiment, the one or more electromagnetic energy emitters 328 include at least one electron emitting material.

In an embodiment, the one or more electromagnetic energy emitters 328 are configured to provide a voltage across at least a portion of tissue proximate the implantable device 102, and to induce pore formation in a plasma membrane of at least a portion of infectious agents within a region proximate the implantable device 102. In an embodiment, the voltage is of sufficient strength or duration to exceed a nominal dielectric strength of at least one cell plasma membrane. In an embodiment, the one or more electromagnetic energy emitters 328 are configured to provide a voltage across at least a portion of cells within a biological fluid received within at least one of the one or more fluid-flow passageways 106. In an embodiment, the voltage is of sufficient strength and duration to exceed a nominal dielectric strength of at least one cell plasma membrane. In an embodiment, the voltage is of sufficient strength and duration to exceed a nominal dielectric strength of a cell plasma membrane without substantially interfering with a normal operation of the implantable shunt system.

The system 100 can include, but is not limited to, one or more electrical energy emitters 332. In an embodiment, the implantable device 102 includes one or more electrical energy emitters 332. In an embodiment, the one or more electrical energy emitters 326 include at least one electrode 330. In an embodiment, a plurality of electrodes 330 are configured to energize a region proximate the implantable device 102 in the presence of an applied potential. In an embodiment, the applied potential is sufficient to produce superoxidized water from an aqueous salt composition proximate the plurality of electrodes 330. In an embodiment, the applied potential is sufficient to produce at least one of a triplet excited-state specie, a reactive oxygen specie, a reactive nitrogen specie, a free radical, a peroxide, and any other inorganic or organic ion and molecules that include oxygen ions.

In an embodiment, a plurality of electrodes 330 are configured to provide an electrical energy stimulus. Electrodes 330 can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, and the like, and any combination thereof. Techniques suitable for making patterned electrodes include, but are not limited to, electro-deposition, electro-deposition onto laser-drilled polymer molds, laser cutting and electro-polishing, laser micromachining, surface micro-machining, soft lithography, x-ray lithography, LIGA techniques (e.g., X-ray lithography, electroplating, and molding), conductive paint silk screen techniques, conventional pattering techniques, injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, or the like), complementary-symmetry/metal-oxide semiconductor (CMOS) technology, deep x-ray exposure techniques, and the like.

In an embodiment, the one or more energy emitters 302 deliver an energy stimulus to a biological fluid received within the one or more fluid-flow passageways 106. In an embodiment, the one or more energy emitters 302 deliver an emitted energy stimulus to a biological fluid proximate a surface of implantable device 102. In an embodiment, the one or more energy emitters 302 deliver an energy stimulus along a substantially longitudinal direction of at least one of the one or more fluid-flow passageways 106. In an embodiment, the one or more energy emitters 302 deliver an energy stimulus along a substantially lateral direction of at least one of the one or more fluid-flow passageways 106. In an embodiment, the one or more energy emitters 302 deliver a first portion of an emitted energy stimulus along a substantially lateral direction in one or more regions of at least one of the one or more fluid-flow passageways 106 and deliver a second portion of the emitted energy stimulus along a substantially longitudinal direction in one or more regions of at least one of the one or more fluid-flow passageways 106. In an embodiment, the one or more energy emitters 302 deliver at least a portion of an emitted energy stimulus along a substantially lateral direction in a first region of at least one of the one or more fluid-flow passageways 106 and deliver at least a portion of the emitted energy stimulus along a substantially lateral direction in a second region of the one or more fluid-flow passageways 106, the second region different from the first region. In an embodiment, the one or more energy emitters 302 deliver at least a portion of an emitted energy stimulus along a substantially longitudinal direction in a first region of at least one of the one or more fluid-flow passageways 106 and deliver at least a portion of the emitted energy stimulus along a substantially longitudinal direction in a second region of the one or more fluid-flow passageways 106, the second region different from the first region. In an embodiment, the one or more energy emitters 302 deliver at least a portion of an emitted energy stimulus along a substantially lateral direction in a first region of at least one of the one or more fluid-flow passageways 106 and at least a portion of the emitted energy stimulus along a substantially lateral direction in a second region of the one or more fluid-flow passageways 106, the second region different from the first region.

The system 100 can include, but is not limited to, one or more spatially patterned energy emitters 334. The system 100 can include, but is not limited to, one or more spaced-apart energy emitters 336. The system 100 can include, but is not limited to, one or more patterned energy emitters 338. Patterned energy emitters 338 can be sized and shaped to provide a spatially patterned energy stimulus to, for example, a region proximate an implantable device 102. In an embodiment, a plurality of energy emitters 302 provide a spatially patterned energy stimulus. The spatially patterned energy stimulus can take a variety forms, configurations, and geometrical patterns including for example, but not limited to, lines, circles, ellipses, triangles, rectangles, polygons, any regular or irregular geometrical patterns, one-dimensional patterns, two-dimensional patterns, three-dimensional patterns, and the like, and any combination thereof. In an embodiment, a plurality of energy emitters 302 includes a patterned energy-emitting source. In an embodiment, at least one of the one or more energy emitters 302 includes at least one of a patterned electromagnetic energy-emitting source, a patterned electrical energy-emitting source, a patterned ultrasonic energy-emitting source, and a patterned thermal energy-emitting source. In an embodiment, at least one of the one or more energy emitters 302 includes a patterned electrode.

Figure 4A:
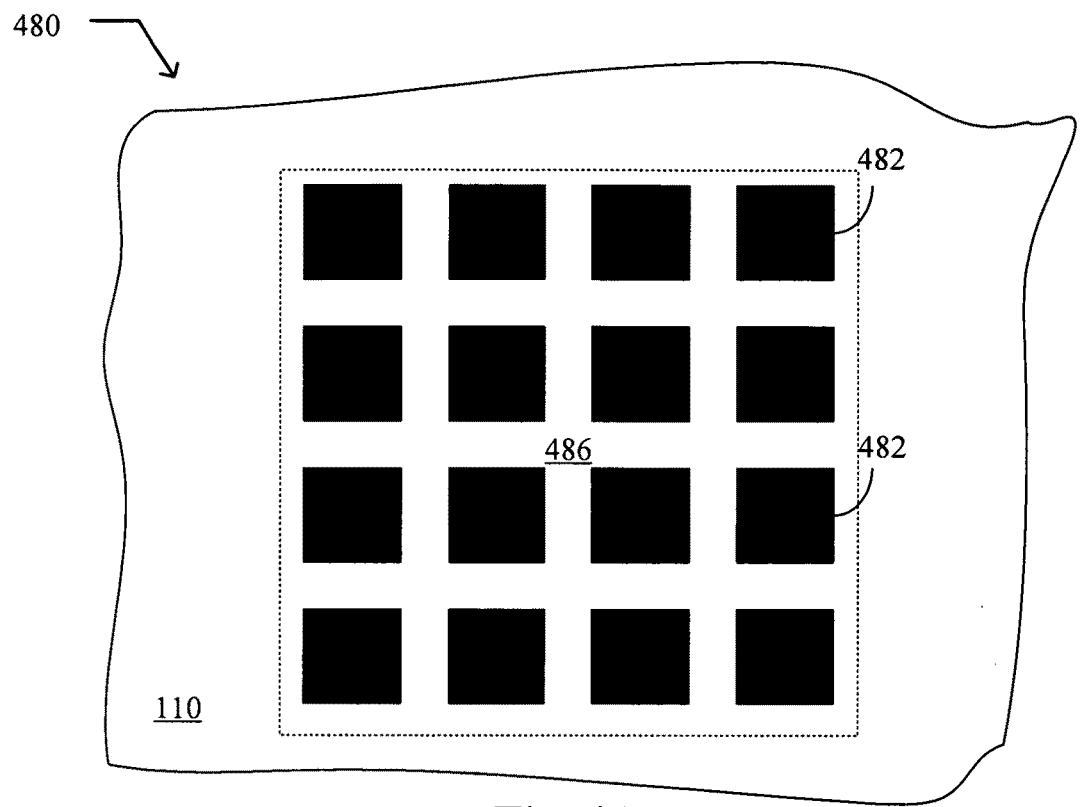
FIG. 4A is a top plan view of a portion of an implantable device including one or more energy emitters in the form of a patterned energy emitter, according to one illustrated embodiment.
Figure 4B:
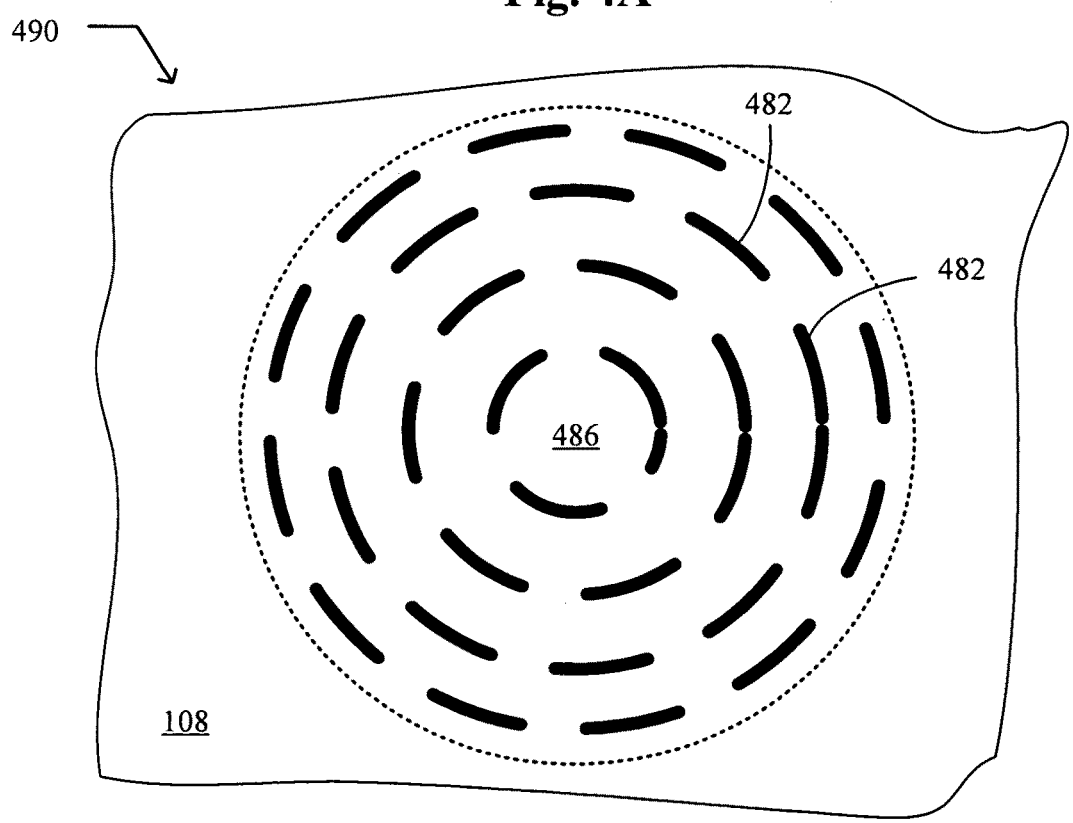
FIG. 4B is a top plan view of a portion of an implantable device including one or more energy emitters in the form of a patterned energy emitter, according to one illustrated embodiment.
Figure 5A:
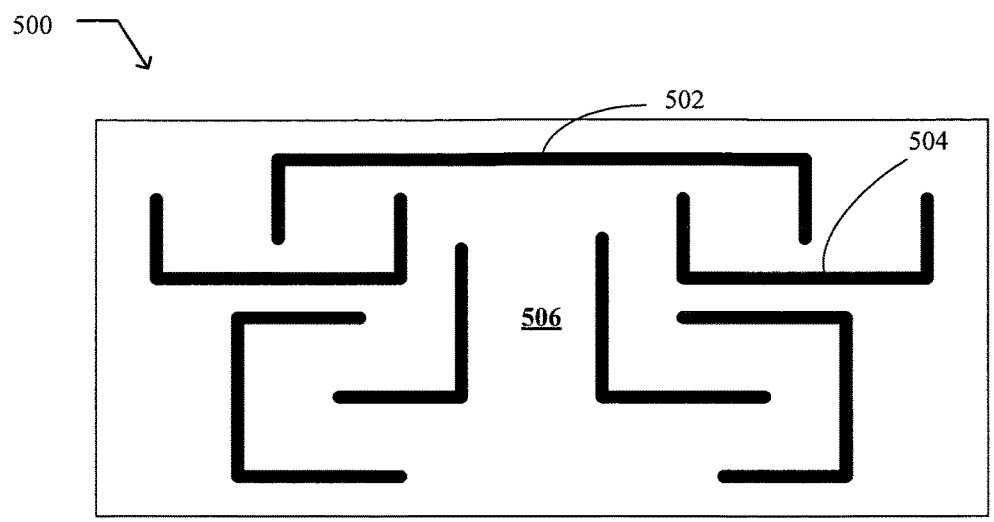
FIG. 5A is a top plan view of a portion of an implantable device including one or more energy emitters in the form of a patterned energy emitter, according to one illustrated embodiment.
Figure 5B:
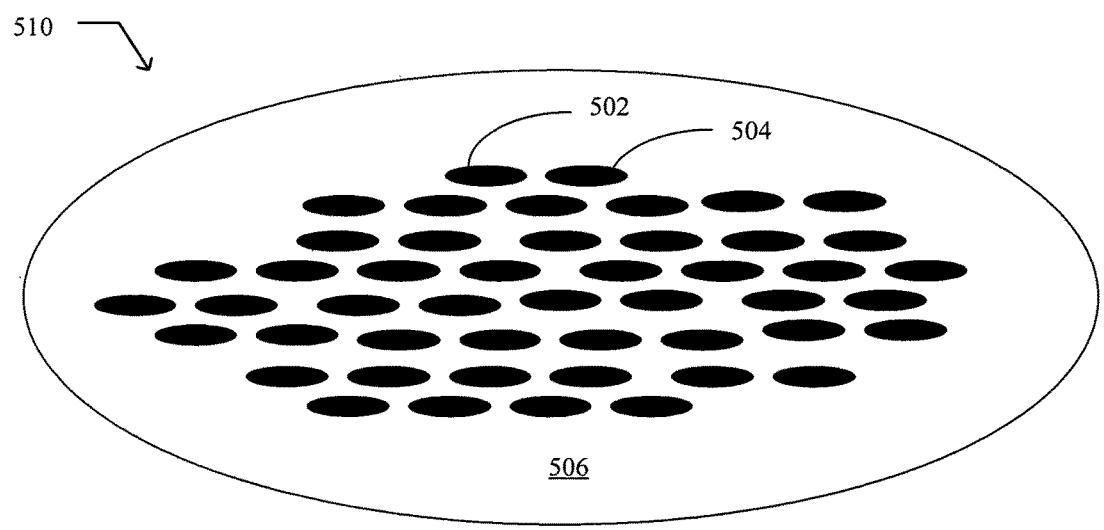
FIG. 5B is a top plan view of a portion of an implantable device including one or more energy emitters in the form of a patterned energy emitter, according to one illustrated embodiment.

Referring to FIGS. 4A and 4B, in an embodiment, the one or more energy emitters 302 include a patterned energy emitter 480 having one or more conductive traces 482 that are deposited, etched, or otherwise applied to a substrate to form one or more patterned electrodes. For example, lithographic techniques can be used to form a conductive trace layout 490, onto a surface of a substrate 486. The lithographic process for forming the conductive trace layouts 490 can include for example, but not limited to, applying a resist film (e.g., spin-coating a photoresist film) onto the substrate, exposing the resist with an image of a circuit layout (e.g., the geometric pattern of one or more conductive traces), heat treating the resist, developing the resist, transferring the layout onto the substrate, and removing the remaining resist. Transferring the layout onto the substrate 486 can include, but is not limited to, using techniques like subtractive transfer, etching, additive transfer, selective deposition, impurity doping, ion implantation, and the like. Referring to FIGS. 5A and 5B, in an embodiment, patterned energy emitters 500, 510 can include, but are not limited to, two or more electrodes 502, 504 forming a pattern. In an embodiment, A patterned energy emitter 500 includes two or more electrodes 502, 504 separated by an insulating material 506. In an embodiment, the patterned energy emitter 500 delivers an energy stimulus of a character and for a time sufficient to provide a temporally controllable, spatially patterned, energy stimulus. In an embodiment, the patterned energy emitter 500 delivers an energy stimulus of a character and for a time sufficient to provide a spatial distribution-controllable spatially patterned energy stimulus.

Figure 6:
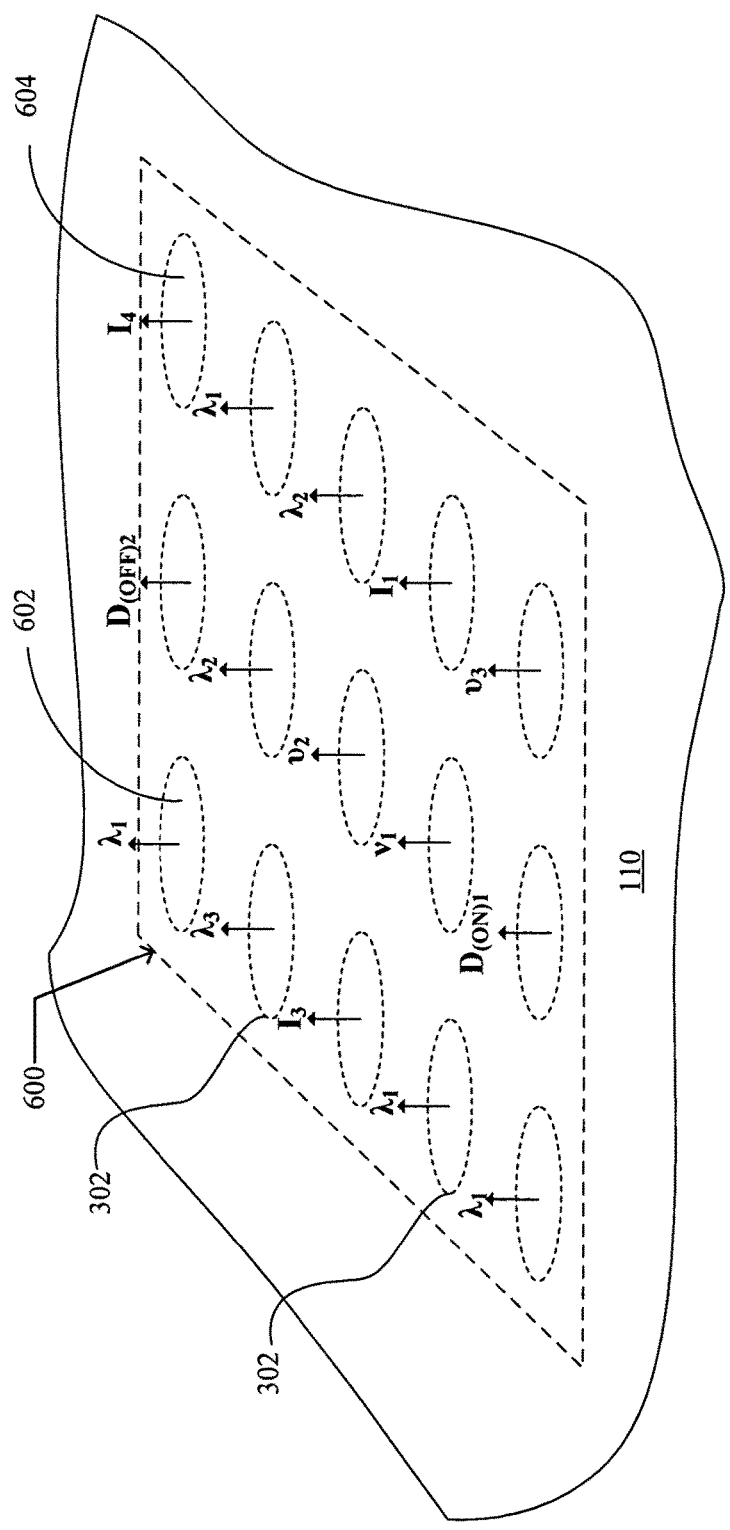
FIG. 6 is a top plan view of portion of an implantable device including one or more energy emitters according to one illustrated embodiment.

Referring to FIG. 6, in an embodiment, the one or more energy emitters 302 are arranged to provide an illumination pattern 600 comprising at least a first region 602 and a second region 604. In an embodiment, the second region 604 of the illumination pattern 600 comprises at least one of an illumination intensity ($I_n$), an energy-emitting pattern, a peak emission wavelength ($a_n$), an ON-pulse duration ($D_{(ON)n}$), an OFF-pulse duration ($D_{(OFF)n}$), and a pulse frequency ($a_n$) different from the first region 602. The one or more energy emitters 302 can provide a spatially patterned sterilizing stimulus having a peak emission wavelength in at least one of an x-ray, an ultraviolet, a visible, an infrared, a near infrared, a terahertz, microwave, and a radio frequency spectrum, or combinations thereof, to at least a portion of tissue proximate an implantable device 102. In an embodiment, the one or more energy emitters 302 provide a spatially patterned optical energy stimulus. The implantable device 102 can include, but is not limited to, a patterned-light emitting source. In an embodiment, the patterned-light emitting source is configured to provide a spatially patterned energy stimulus to at least one of biological fluid and tissue proximate the implantable device 102.

In an embodiment, at least one of the one or more energy emitters 302 is configured to provide a spatially patterned energy stimulus having at least a first region and a second region 604 different from the first region 602. In an embodiment, the first 602 region comprises one of a spatially patterned electromagnetic energy stimulus, a spatially patterned electrical energy stimulus, a spatially patterned ultrasonic energy stimulus, or a spatially patterned thermal energy stimulus, and the second region 604 comprises a spatially patterned energy stimulus that is different from that in first region 602; that is of a spatially patterned electromagnetic energy stimulus, a spatially patterned electrical energy stimulus, a spatially patterned ultrasonic energy stimulus, or a spatially patterned thermal energy stimulus. In an embodiment, the spatially patterned energy stimulus is adapted to provide a voltage across at least a portion of cells of tissue proximate an outer surface 108 of the implantable device 102. In an embodiment, the spatially patterned energy stimulus is adapted to provide a voltage across a region proximate the implantable device 102, and to inactivate an infectious agents present within the region. In an embodiment, the spatially patterned energy stimulus is adapted to provide a voltage across at least a portion of tissue proximate the implantable device 102, and to induce pore formation in a plasma membrane of at least a portion of infectious agents within the region. In an embodiment, the voltage is of sufficient strength or duration to exceed a nominal dielectric strength of at least one cell plasma membrane.

In an embodiment, an energy emitter 302 is operably coupled to a plurality of waveguides 902 and is configured to deliver a multiplex energy stimulus having, for example, two or more peak emission wavelengths. In an embodiment, a multiplex energy stimulus can be routed to two or more waveguides 902 based on a wavelength, an intensity, a spectral power distribution, a waveguide-specific address, or the like. Once routed, the a plurality of waveguides 902 can deliver a spatially patterned energy stimulus having at least a first region and a second region 604 different from the first region 602 where the difference depends on the selection rule (e.g., spectral power distribution, irradiance, peak power, intensity, phase, polarization, frequency, repetition rate, bandwidth, waveguide-specific address, or the like) used to route the energy stimulus.

With continued reference to FIG. 3, the system 100 can include, but is not limited to, one or more controllers 402 such as a processor (e.g., a microprocessor) 404, a central processing unit (CPU) 406, a digital signal processor (DSP) 408, an application-specific integrated circuit (ASIC) 410, a field programmable gate array (FPGA) 412, or the like, or any combinations thereof, and can include discrete digital or analog circuit elements or electronics, or combinations thereof. The system 100 can include, but is not limited to, one or more field programmable gate arrays 412 having a plurality of programmable logic components. The system 100 can include, but is not limited to, one or more an application specific integrated circuits having a plurality of predefined logic components. In an embodiment, at least one controller 402 is operably coupled to one or more energy emitters 302. In an embodiment, the system 100 includes one or more controllers 402 configured to concurrently or sequentially operate multiple energy emitters 302.

In an embodiment, one or more controllers 402 are configured to automatically control at least one waveform characteristic (e.g., intensity, frequency, pulse intensity, pulse duration, pulse ratio, pulse repetition rate, or the like) associated with the delivery of one or more energy stimuli. For example, pulsed waves can be characterized by the fraction of time the energy stimulus is present over one pulse period. This fraction is called the duty cycle and is calculated by dividing the pulse time ON by the total time of a pulse period (e.g., time ON plus time OFF). In an embodiment, a pulse generator 320 is configured to electronically generate pulsed periods and non-pulsed (or inactive) periods.

In an embodiment, the controller 402 is configured to control at least one parameter associated with a delivery of the energy stimulus. In an embodiment, the controller 402 is configured to control at least one parameter associated with a spatial illumination field modulation, a spatial illumination field intensity, or a spatial illumination delivery pattern. In an embodiment, the controller 402 is configured to control at least one of an excitation intensity, an excitation frequency, an excitation pulse frequency, an excitation pulse ratio, an excitation pulse intensity, an excitation pulse duration time, an excitation pulse repetition rate, an energy stimulus delivery regimen, an ON-rate, and an OFF-rate. In an embodiment, the system 100 includes at least one processor 404 communicably coupled to at least one of the one or more energy emitters 302 and configured to control at least one of a duration time, an amount of energy (e.g., a fluence, peak power, average power, operational fluence, or the like), a delivery schedule, a delivery pattern, an excitation amount, an excitation type, and a delivery location associated with the delivery of the energy stimulus.

In an embodiment, the implantable device 102 are, for example, wirelessly coupled to a controller 402 that communicates with the implantable device 102 via wireless communication. Non-limiting examples of wireless communication include optical connections, ultraviolet connections, infrared, BLUETOOTH®, Internet connections, radio, network connections, and the like. The system 100 can include, but is not limited to, means for generating a response 460 based on a comparison, of a detected at least one of an emitted energy and a remitted energy to at least one heuristically determined parameter, including one or more controllers 402.

In an embodiment, the system 100 includes at least one controller 402 operably coupled to the one or more energy emitters 302 and configured to control at least one parameter associated with the delivery of the energy stimulus. In an embodiment, the at least one controller 402 is configured to control at least one of a duration time, an amount of energy, an excitation amount, an excitation type, a delivery location, and a spatial-pattern stimulation configuration associated with the delivery of the energy stimulus.

The system 100 can include, but is not limited to, one or more memories 414 that, for example, store instructions or data, for example, volatile memory (e.g., Random Access Memory (RAM) 416, Dynamic Random Access Memory (DRAM), or the like), non-volatile memory (e.g., Read-Only Memory (ROM) 418, Electrically Erasable Programmable Read-Only Memory (EEPROM), Compact Disc Read-Only Memory (CD-ROM), or the like), persistent memory, or the like. Further non-limiting examples of one or more memories 414 include Erasable Programmable Read-Only Memory (EPROM), flash memory, and the like. The one or more memories 414 can be coupled to, for example, one or more controllers 402 by one or more instruction, data, or power buses 420.

The system 100 can include, but is not limited to, one or more databases 422. In an embodiment, a database 422 includes at least one of inflammation indication parameter data, infection indication parameter data, diseased tissue indication parameter data, and the like. In an embodiment, a database 422 includes at least one of absorption coefficient data, extinction coefficient data, scattering coefficient data, and the like. In an embodiment, a database 422 includes at least one of stored reference data such as infection marker data, inflammation marker data, infective stress marker data, a systemic inflammatory response syndrome data, sepsis marker data, and the like. In an embodiment, a database 422 includes information associated with a disease state of a biological subject. In an embodiment, a database 422 includes measurement data. In an embodiment, a database 422 includes at least one of psychosis state indication information, psychosis trait indication information, and predisposition for a psychosis indication information. In an embodiment, a database 422 includes at least one of infection indication information, inflammation indication information, diseased state indication information, and diseased tissue indication information. In an embodiment, a database 422 includes at least one of cryptographic protocol information, regulatory compliance protocol information (e.g., FDA regulatory compliance protocol information, or the like), regulatory use protocol information, authentication protocol information, authorization protocol information, delivery regimen protocol information, activation protocol information, encryption protocol information, decryption protocol information, treatment protocol information, and the like. In an embodiment, a database 422 includes at least one of energy stimulus control delivery information, energy emitter control information, power control information, and the like.

In an embodiment, the system 100 is configured to compare an input associated with at least one characteristic associated with a biological subject to a database 422 of stored reference values, and to generate a response based in part on the comparison. In an embodiment, the system 100 is configured to compare an input associated with at least one physiological characteristic associated with a biological subject to a database 422 of stored reference values, and to generate a response based in part on the comparison.

In an embodiment, the at least one characteristic associated with a biological subject includes real-time detected information associated with tissue or biological fluid proximate an implantable device 102. In an embodiment, the at least one characteristic associated with a biological subject includes real-time detected information associated with a biological fluid received within one or more fluid-flow passageways 106. In an embodiment, the system 100 is configured to compare an input associated with at least one characteristic associated with a biological fluid received within one or more fluid-flow passageways 106 to a database 422 of stored reference values, and to generate a response based in part on the comparison.

In an embodiment, the response includes at least one of a visual representation, an audio representation (e.g., an alarm, an audio waveform representation of a tissue region, or the like), a haptic representation, and a tactile representation (e.g., a tactile diagram, a tactile display, a tactile graph, a tactile interactive depiction, a tactile model (e.g., a multidimensional model of an infected tissue region, or the like), a tactile pattern (e.g., a refreshable Braille display), a tactile-audio display, a tactile-audio graph, or the like). In an embodiment, the response includes generating at least one of a visual, an audio, a haptic, and a tactile representation of at least one of biological fluid spectral information, tissue spectral information, fat spectral information, muscle spectral information, bone spectral information, blood component spectral information, and the like. In an embodiment, the response includes generating at least one of a visual, an audio, a haptic, and a tactile representation of at least one physical or biochemical characteristic associated with a biological subject.

In an embodiment, the response includes initiating one or more treatment protocols. In an embodiment, the response includes initiating at least one treatment regimen. In an embodiment, the response includes delivering an energy stimulus. In an embodiment, the response includes delivering an active agent. In an embodiment, the response includes concurrently or sequentially delivering an energy stimulus and an active agent.

In an embodiment, the response includes at least one of a response signal, a control signal, a change to a sterilizing stimulus parameter (e.g., an electrical sterilizing stimulus, an electromagnetic sterilizing stimulus, an ultrasonic sterilizing stimulus, or a thermal sterilizing stimulus), and the like. In an embodiment, the response includes at least one of a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, and the like.

In an embodiment, the response includes at least one of a change to a sterilizing stimulus spatial pattern parameter (e.g., an electrical sterilizing stimulus spatial pattern parameter, an electromagnetic sterilizing stimulus spatial pattern parameter, an ultrasonic sterilizing stimulus spatial pattern parameter, or a thermal sterilizing stimulus spatial pattern parameter), and a change in a sterilizing stimulus delivery regiment parameter (e.g., an electrical sterilizing stimulus delivery regiment parameter, an electromagnetic sterilizing stimulus delivery regiment parameter, an ultrasonic sterilizing stimulus delivery regiment parameter, or a thermal sterilizing stimulus delivery regiment parameter), or the like.

In an embodiment, the response includes at least one of activating an authorization protocol, activating an authentication protocol, activating a software update protocol, activating a data transfer protocol, and activating an infection sterilization diagnostic protocol. In an embodiment, the response includes sending information associated with at least one of an authentication protocol, an authorization protocol, a delivery protocol, an activation protocol, an encryption protocol, and a decryption protocol.

In an embodiment, a database 422 includes at least one of stored reference data such as characteristic biological fluid (e.g., cerebrospinal fluid) component signature data, characteristic blood component signature data, characteristic tissue signature data, and the like. In an embodiment, a database 422 includes information indicative of one or more spectral events associated with transmitted optical energy or a remitted optical energy from at least one of a biological tissue and biological fluid.

In an embodiment, a database 422 includes at least one of cerebrospinal fluid spectral information, blood spectral information, tissue spectral information, fat spectral information, muscle spectral information, and bone spectral information. In an embodiment, a database 422 includes at least one of modeled tissue (e.g., blood, bone, muscle, tendons, organs, fluid-filled cysts, ventricles, or the like) spectral information or modeled biological fluid spectral information. In an embodiment, a database 422 includes at least one of modeled biological fluid spectral information, modeled blood spectral information, modeled fat spectral information, modeled muscle spectral information, and modeled bone spectral information.

In an embodiment, a database 422 includes at least one of inflammation indication parameter data, infection indication parameter data, diseased tissue indication parameter data, or the like. In an embodiment, a database 422 includes at least one of absorption coefficient data, extinction coefficient data, scattering coefficient data, and the like. In an embodiment, a database 422 includes stored reference data such as characteristic spectral signature data. In an embodiment, a database 422 includes stored reference data such as infection marker data, inflammation marker data, infective stress marker data, a systemic inflammatory response syndrome data, sepsis marker data, or the like. In an embodiment, a database 422 includes information associated with a disease state of a biological subject. In an embodiment, a database 422 includes measurement data.

In an embodiment, the system 100 is configured to compare an input associated with a biological subject to a database 422 of stored reference values, and to generate a response based in part on the comparison. In an embodiment, the system 100 is configured to compare an output of one or more of the plurality of logic components and to determine at least one parameter associated with a cluster centroid deviation derived from the comparison. In an embodiment, the system 100 is configured to compare a measurand associated with the biological subject to a threshold value associated with a spectral model and to generate a response based on the comparison. In an embodiment, the system 100 is configured to generate the response based on the comparison of a measurand that modulates with a detected heart beat of the biological subject to a target value associated with a spectral model.

In an embodiment, the system 100 is configured to compare the measurand associated with the biological subject to the threshold value associated with a spectral model and to generate a real-time estimation of the formation of an obstruction of a flow in a fluid-flow passageway 106 based on the comparison. In an embodiment, the system 100 is configured to compare an input associated with at least one characteristic associated with, for example, a tissue proximate an implantable device 102 to a database 422 of stored reference values, and to generate a response based in part on the comparison.

The system 100 can include, but is not limited to, one or more data structures (e.g., physical data structures) 424. In an embodiment, a data structure 424 includes information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, a pH level, or the like. The system 100 can include, but is not limited to, at least one of inflammation indication parameter data, infection indication parameter data, diseased tissue indication parameter data, and the like configured as a data structure 424. In an embodiment, a data structure 424 includes information associated with least one parameter associated with a cytokine plasma concentration or an acute phase protein plasma concentration. In an embodiment, a data structure 424 includes information associated with a disease state of a biological subject. In an embodiment, a data structure 424 includes measurement data. In an embodiment, the controller 402 includes a processor 404 configured to execute instructions, and a memory 414 that stores instructions configured to cause the processor 404 to generate a second response from information encoded in a data structure 424.

The system 100 can include, but is not limited to, one or more computer-readable memory media (CRMM) 426 having cerebrospinal fluid information configured as a data structure, the data structure 424 including at least one of psychosis state marker information, psychosis trait marker information, and psychosis indication information. The system 100 can include, but is not limited to, one or more computer-readable memory media 426 having cerebrospinal fluid information configured as a data structure, the data structure 424 including at least one of psychosis state indication information, psychosis trait indication information, and predisposition for a psychosis indication information. The system 100 can include, but is not limited to, one or more computer-readable memory media 426 having cerebrospinal fluid information configured as a data structure 424, the data structure 424 including at least one of infection indication information, inflammation indication information, diseased state indication information, and diseased tissue indication information.

In an embodiment, a data structure 424 includes cerebrospinal fluid spectral information. In an embodiment, the cerebrospinal fluid spectral information includes one or more heuristically determined parameters associated with at least one in vivo or in vitro determined metric. For example, information associated with cerebrospinal fluid components can be determined by one or more in vivo or in vitro technologies or methodologies including, for example, high resolution proton magnetic resonance spectroscopy, nanoprobe nuclear magnetic resonance spectroscopy, in vivo micro-dialysis, flow cytometry, or the like. Non-limiting examples of heuristics include a heuristic protocol, heuristic algorithm, threshold information, a threshold level, a target parameter, or the like. The system 100 can include, but is not limited to, a means for generating one or more heuristically determined parameters associated with at least one in vivo or in vitro determined metric including one or more data structures 424. The system 100 can include, but is not limited to, a means for generating a response based on a comparison, of a detected at least one of an emitted energy and a remitted energy to at least one heuristically determined parameter, including one or more data structures 424.

In an embodiment, a data structure 424 includes one or more heuristics. In an embodiment, the one or more heuristics include a heuristic for determining a rate of change associated with at least one physical parameter associated with a biological fluid. In an embodiment, the one or more heuristics include a heuristic for determining the presence of an infectious agent. In an embodiment, the one or more heuristics include a heuristic for determining at least one dimension of an infected tissue region. In an embodiment, the one or more heuristics include a heuristic for determining a location of an infection. In an embodiment, the one or more heuristics include a heuristic for determining a rate of change associated with a biochemical marker within the one or more fluid-flow passageways 106. In an embodiment, the one or more heuristics include a heuristic for determining a biochemical marker aggregation rate. In an embodiment, the one or more heuristics include a heuristic for determining a type of biochemical marker. In an embodiment, the one or more heuristics include a heuristic for generating at least one initial parameter. In an embodiment, the one or more heuristics include a heuristic for forming an initial parameter set from one or more initial parameters. In an embodiment, the one or more heuristics include a heuristic for generating at least one initial parameter, and for forming an initial parameter set from the at least one initial parameter. In an embodiment, the one or more heuristics include at least one pattern classification and regression protocol.

In an embodiment, a data structure 424 includes information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, a pH level, or the like. The system 100 can include, but is not limited to, at least one of inflammation indication parameter data, infection indication parameter data, diseased tissue indication parameter data, and the like configured as a data structure 424. In an embodiment, a data structure 424 includes information associated with least one parameter associated with a cytokine plasma concentration or an acute phase protein plasma concentration. In an embodiment, a data structure 424 includes information associated with a disease state of a biological subject. In an embodiment, a data structure 424 includes measurement data.

The system 100 can include, but is not limited to, one or more computer-readable media drives 426, interface sockets, Universal Serial Bus (USB) ports, memory card slots, and the like, and one or more input/output components 428 such as, for example, a graphical user interface 430, a display, a keyboard 432, a keypad, a trackball, a joystick, a touch-screen, a mouse, a switch, a dial, and the like, and any other peripheral device. In an embodiment, the system 100 includes one or more user input/output components 428 that operably couple to at least one controller 402 to control (electrical, electromechanical, software-implemented, firmware-implemented, or other control, or combinations thereof) at least one parameter associated with the energy delivery associated with the one or more energy emitters 302. The system 100 can include, but is not limited to, one or more modules optionally operable for communication with one or more input/output components 428 that are configured to relay user output and/or input. In an embodiment, a module includes one or more instances of electrical, electromechanical, software-implemented, firmware-implemented, or other control devices. Such device include one or more instances of memory 414, controllers 402, ports, valves 132, antennas, power, or other supplies; logic modules or other signaling modules; gauges or other such active or passive detection components; or piezoelectric transducers, shape memory elements, micro-electro-mechanical system (MEMS) elements, or other actuators.

The computer-readable media drive 426 or memory slot can be configured to accept signal-bearing medium (e.g., computer-readable memory media, computer-readable recording media, or the like). In an embodiment, a program for causing the system 100 to execute any of the disclosed methods can be stored on, for example, a computer-readable recording medium (CRMM) 434, a signal-bearing medium, and the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transmission logic, reception logic, etc.), etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, and the like.

In an embodiment, the system 100 includes signal-bearing media in the form of one or more logic devices (e.g., programmable logic devices, complex programmable logic device, field-programmable gate arrays, application specific integrated circuits, or the like) comprising, for example, a data structure 424 including one or more look-up tables. The system 100 can include, but is not limited to, signal-bearing media having biological fluid information configured as a data structure 424. In an embodiment, the data structure 424 includes at least one of psychosis state indication information, psychosis trait indication information, and predisposition for a psychosis indication information. In an embodiment, the data structure 424 includes at least one of infection indication information, inflammation indication information, diseased state indication information, and diseased tissue indication information.

The system 100 can include, but is not limited to, at least one sensor components 440 including one or more sensors 442. In an embodiment, the sensor component 440 is configured to detect (e.g., assess, calculate, evaluate, determine, gauge, measure, monitor, quantify, resolve, sense, or the like) at least one characteristic (e.g., a spectral characteristic, a spectral signature, a physical quantity, an environmental attribute, a physiologic characteristic, or the like) associated with a biological subject. In an embodiment, the sensor component 440 is in optical communication along an optical path with at least one of the one or more energy emitters 302.

In an embodiment, the sensor component 440 is configured to detect spectral information associated with a real-time change in one or more parameters associated with a biological fluid. For example, in an embodiment, the sensor component 440 is configured to detect at least one of an emitted energy and a remitted energy associated with a real-time change in one or more parameters associated with a biological fluid. In an embodiment, the system 100 includes means for detecting at least one characteristic associated with a biological subject including at least one sensor component 440 having one or more sensors 442 and at least one controller 402 operably coupled to the at least one sensor component 440.

In an embodiment, the at least one characteristic associated with a biological subject includes a characteristic associated with tissue proximate the implantable. In an embodiment, the at least one characteristic associated with a biological subject includes a characteristic associated with a biological fluid of the biological subject. In an embodiment, the at least one characteristic associated with a biological subject includes a physiological characteristic of the biological subject. In an embodiment, the at least one characteristic associated with a biological subject includes a characteristic associated with a cerebrospinal fluid of the biological subject. In an embodiment, the at least one characteristic associated with a biological subject includes a characteristic associated with a tissue of the biological subject. In an embodiment, the at least one characteristic associated with a biological subject includes a specimen of the biological subject. In an embodiment, the at least one characteristic associated with a biological subject includes one or more spectroscopic properties (e.g., tissue spectroscopic properties, biological fluid spectroscopic properties, infectious agent spectroscopic properties, biomarker spectroscopic properties, or the like). In an embodiment, the at least one characteristic associated with a biological subject includes at least one characteristic (e.g., a spectral characteristic, a spectral signature, a physical quantity, a relative quantity, an environmental attribute, a physiologic characteristic, or the like) associated with a region within the biological subject. In an embodiment, the at least one characteristic associated with a biological subject includes a characteristic associated with a fluid-flow passageway 106 obstruction, a hematological abnormality, or a body fluid flow abnormality (e.g., a cerebrospinal fluid abnormality). In an embodiment, the at least one characteristic associated with a biological subject includes a characteristic associated with a biological fluid flow vessel. In an embodiment, the at least one characteristic associated with a biological subject includes a characteristic associated with one or more cerebrospinal fluid components. In an embodiment, the at least one characteristic associated with a biological subject includes a characteristic associated with one or more imaging probes attached, targeted to, conjugated, bound, or associated with at least one inflammation markers. In an embodiment, the at least one characteristic associated with a biological subject includes a characteristic associated with one or more imaging probes attached, targeted to, conjugated, bound, or associated with at least one blood components. In an embodiment, the at least one characteristic associated with a biological subject includes a characteristic associated with one or more blood components. In an embodiment, the at least one characteristic associated with a biological subject includes a characteristic associated with one or more cerebrospinal fluid components.

In an embodiment, one or more of the sensors 442 are configured to determine at least one characteristic associated with a biological fluid received within one or more fluid-flow passageways 106. In an embodiment, one or more of the sensors 442 are configured to detect at least one of a characteristic of a biological fluid proximate the implantable device 102, a characteristic of a tissue proximate the implantable device 102, and a physiological characteristic of the biological subject.

In an embodiment, one or more of the sensors 442 are configured to detect at least one physiological characteristic associated with a biological subject. For example, physiological characteristics such as, for example pH can be used to assess blood flow, a cell metabolic state (e.g., anaerobic metabolism, or the like), the presence of an infectious agent, a disease state, and the like. In an embodiment, the implantable device 102 includes one or more sensors 442 configured to determine at least one of a physiological characteristic of a biological subject, and a characteristic associated with a tissue proximate the implantable device 102. Among physiological characteristics examples include, but are not limited to, at least one of a temperature, a regional or local temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, an intracranial pressure, a respiratory rate, a vital statistic, and the like. In an embodiment, the at least one physiological characteristic includes at least one of a temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, an intracranial pressure, and a respiratory rate.

In an embodiment, the at least one physiological characteristic includes at least one hematological parameter. In an embodiment, the hematological parameter is associated with a hematological abnormality. In an embodiment, the at least one physiological characteristic includes one or more parameters associated with at least one of leukopenia, leukophilia, lymphocytopenia, lymphocytophilia, neutropenia, neutrophilia, thrombocytopenia, disseminated intravascular coagulation, bacteremia, and viremia.

In an embodiment, the at least one physiological characteristic includes at least one of an infection marker, an inflammation marker, an infective stress marker, a systemic inflammatory response syndrome marker, and a sepsis marker. In an embodiment, the infection marker includes at least one of a red blood cell count, a lymphocyte level, a leukocyte count, a myeloid count, an erythrocyte sedimentation rate, and a C-reactive protein level. In an embodiment, the at least one physiological characteristic includes at least one of a cytokine plasma concentration and an acute phase protein plasma concentration.

The implantable device 102 can include, but is not limited to, circuitry for performing a comparison of the determined at least one characteristic associated with the tissue or a biological fluid proximate the implantable device 102 to stored reference data following the delivery of the energy stimulus. Circuitry can include one or more components operably coupled (e.g., communicatively coupled, electromagnetically, magnetically, ultrasonically, optically, inductively, electrically, capacitively coupleable, or the like) to each other. In an embodiment, circuitry can include one or more remotely located components. In an embodiment, remotely located components are operably coupled via wireless communication. In an embodiment, remotely located components are operably coupled via one or more receivers, transmitters, transceivers, and the like.

The implantable device 102 can include, but is not limited to, circuitry configured to generate a response based at least in part on the comparison. The implantable device 102 can include, but is not limited to, one or more processors 404 configured to perform a comparison of the at least one characteristic associated with the tissue or a biological fluid proximate the implantable device 102 stored reference data following delivery of the sterilizing stimulus, and to generate a response based at least in part on the comparison.

In an embodiment, the one or more energy emitters 302 are configured to direct an in vivo generated pulsed energy stimulus along an optical path for a time sufficient to interact with one or more regions within the biological subject and for a time sufficient for a portion of the in vivo generated pulsed energy stimulus to reach a portion of the sensor component 440 that is in optical communication along the optical path. In an embodiment, the one or more energy emitters 302 are configured to direct optical energy along an optical path for a time sufficient to interact with one or more regions within the biological subject and with at least a portion of the optical energy sensor component 440. In an embodiment, one or more of the energy emitters 302 are configured to emit a pulsed optical energy stimulus along an optical path for a time sufficient to interact with a cerebrospinal fluid received within the one or more fluid-flow passageways 106, such that a portion of the pulsed optical energy stimulus is directed to a portion of the sensor component 440 that is in optical communication along the optical path.

In an embodiment, the sensor component 440 includes an imaging spectrometer. In an embodiment, the sensor component 440 comprises at least one of a photo-acoustic imaging spectrometer, a thermo-acoustic imaging spectrometer, and a photo-acoustic/thermo-acoustic tomographic imaging spectrometer. In an embodiment, optical energy sensor component includes at least one of a thermal detector, a photovoltaic detector, or a photomultiplier detector. In an embodiment, the optical energy sensor component includes at least one of a charge coupled device, a complementary metal-oxide-semiconductor device, a photodiode image sensor device, a Whispering Gallery Mode (WGM) micro cavity device, and a scintillation detector device.

In an embodiment, the sensor component 440 is configured to detect at least one of an emitted energy and a remitted energy. In an embodiment, the sensor component 440 is configured to detect at least one of an emitted energy and a remitted energy associated with a biological subject. In an embodiment, the sensor component 400 is configured to detect an optical energy absorption profile of a portion of a tissue or biological fluid within the biological subject. In an embodiment, the sensor component 440 is configured to detect an excitation radiation and an emission radiation associated with a portion of a tissue or biological fluid within a biological subject.

In an embodiment, the sensor component 440 is configured to detect at least one of an energy absorption profile and an energy reflection profile of a region within a biological subject. The system 100 can include, but is not limited to, means for detecting at least one of an emitted energy and a remitted energy including an interrogation energy source and one or more sensor components 440 having one or more sensors 442. In an embodiment, the sensor component 440 includes at least one of a time-integrating optical component 444, a linear time-integrating component 446, a nonlinear optical component 448, and a temporal autocorrelating component 450. In an embodiment, the sensor component 440 includes one or more one-, two-, or three-dimensional photodiode arrays.

Among sensors 442 examples include, but are not limited to, acoustic wave sensors, aptamer-based sensors, biosensors, blood volume pulse sensors, cantilevers, conductance sensors, electrochemical sensors, fluorescence sensors, force sensors, heat sensors (e.g., thermistors, thermocouples, or the like), high resolution temperature sensors, differential calorimeter sensors, optical sensors, goniometry sensors, potentiometer sensors, resistance sensors, respiration sensors, sound sensors (e.g., ultrasound), Surface Plasmon Band Gap sensor (SPRBG), physiological sensors, surface plasmon sensors, and the like. Further non-limiting examples of sensors include affinity sensors, bioprobes, biostatistics sensors, enzymatic sensors, in-situ sensors (e.g., in-situ chemical sensor), ion sensors, light sensors (e.g., visible, infrared, or the like), microbiological sensors, microhotplate sensors, micron-scale moisture sensors, nanosensors, optical chemical sensors, single particle sensors, and the like. Further non-limiting examples of sensors include chemical sensors, cavitand-based supramolecular sensors, nucleic acid sensors, deoxyribonucleic acid sensors (e.g., electrochemical DNA sensors, or the like), supramolecular sensors, and the like. In an embodiment, at least one of the one or more sensors 442 is configured to detect or measure the presence or concentration of specific target chemicals (e.g., blood components, biological fluid component, cerebral spinal fluid component, infectious agents, infection indication chemicals, inflammation indication chemicals, diseased tissue indication chemicals, biological agents, molecules, ions, or the like).

Further non-limiting examples of the one or more sensors 442 include chemical transducers, ion sensitive field effect transistors (ISFETs), ISFET pH sensors, membrane-ISFET devices (MEMFET), microelectronic ion-sensitive devices, potentiometric ion sensors, quadruple-function ChemFET (chemical-sensitive field-effect transistor) integrated-circuit sensors, sensors with ion-sensitivity and selectivity to different ionic species, and the like.

Further non-limiting examples of the one or more sensors 442 can be found in the following documents (the contents of which are incorporated herein by reference): U.S. Pat. No. 7,396,676 (issued Jul. 8, 2008) and U.S. Pat. No. 6,831,748 (issued Dec. 14, 2004).

In an embodiment, the one or more sensors 442 include one or more electrochemical transducers, photochemical transducer, optical transducers, piezoelectrical transducers, or thermal transducers. In an embodiment, the one or more sensors 442 include one or more thermal detectors, photovoltaic detectors, or photomultiplier detectors. In an embodiment, the one or more sensors 442 include one or more charge coupled devices, complementary metal-oxide-semiconductor devices, photodiode image sensor devices, whispering gallery mode micro cavity devices, or scintillation detector devices. In an embodiment, the one or more sensors 442 include one or more ultrasonic transducers 314. In an embodiment, the one or more sensors 442 include one or more conductivity sensor. In an embodiment, the one or more sensors 442 include one or more spectrometers.

In an embodiment, the one or more sensors 442 include one or more density sensors. In an embodiment, the one or more density sensors include one or more optical density sensors. In an embodiment, the one or more density sensors include one or more refractive index sensors. In an embodiment, the one or more refractive index sensors include one or more fiber optic refractive index sensors.

In an embodiment, the one or more sensors 442 include one or more surface plasmon resonance sensors. In an embodiment, the one or more sensors 442 include one or more localized surface plasmon resonance sensors. In an embodiment, surface plasmon resonance based sensors detect target molecules suspended in a fluid, for example, by reflecting light off thin metal films in contact with the fluid. Adsorbing molecules cause changes in the local index of refraction, resulting in changes in the resonance conditions of the surface plasmon waves. In an embodiment, detection of target molecules includes monitoring shifts in the resonance conditions of the surface plasmon waves due to changes in the local index of refraction associates with adsorption of target molecules.

In an embodiment, the one or more sensors 442 include one or more acoustic biosensors, amperometric biosensors, calorimetric biosensors, optical biosensors, or potentiometric biosensors. In an embodiment, the one or more sensors 442 include one or more fluid flow sensors. In an embodiment, the one or more sensors 442 include one or more differential electrodes. In an embodiment, the one or more sensors 442 include one or more biomass sensors. In an embodiment, the one or more sensors 442 include one or more immuno sensors.

In an embodiment, the one or more sensors 442 include one or more functionalized cantilevers. In an embodiment, the one or more sensors 442 include a light transmissive support and a reflective metal layer. In an embodiment, the one or more sensors 442 include a biological molecule capture layer. In an embodiment, the biological molecule capture layer includes an array of different binding molecules that specifically bind one or more target molecules.

In an embodiment, the system 100 is configured to initiate one or more treatment protocols. In an embodiment, the system 100 is configured to initiate at least one treatment regimen based on a detected spectral event. In an embodiment, the system 100 is configured to initiate at least one treatment regimen based on a detected biomarker event. In an embodiment, the system 100 is configured to initiate at least one treatment regimen based on a detected infection. In an embodiment, the system 100 is configured to initiate at least one treatment regimen based on a detected cerebrospinal fluid pressure. In an embodiment, the system 100 is configured to initiate at least one treatment regimen based on a detected a fluid vessel abnormalities (e.g., an obstruction), a detected biological fluid abnormality (e.g., cerebrospinal fluid abnormalities, hematological abnormalities, components concentration or level abnormalities, flow abnormalities, or the like), a detected biological parameter, or the like.

Many of the disclosed embodiments can be electrical, electromechanical, software-implemented, firmware-implemented, or other otherwise implemented, or combinations thereof. Many of the disclosed embodiments can be software or otherwise in memory, such as one or more executable instruction sequences or supplemental information as described herein. For example, in an embodiment, the implantable device 102 can include, but is not limited to, one or more controllers 402 configured to perform a comparison of the at least one characteristic associated with the biological subject to stored reference data, and to generate a response based at least in part on the comparison. In an embodiment, the generated response includes at least one of a response signal, a change to a sterilizing stimulus parameter, a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, and a change in a sterilizing stimulus delivery regimen parameter.

The system 100 can include for example, but not limited to, one or more sensors 442 configured to determine at least one characteristic associated with a biological fluid of the biological subject. In an embodiment, the one or more sensors 442 are configured to determine at least one characteristic associated with a cerebrospinal fluid of the biological subject. In an embodiment, the at least one characteristic associated with the cerebrospinal fluid includes at least one of an autofluorescence, an immunofluorescence, and an indirect immunofluorescence. In an embodiment, the at least one characteristic associated with the cerebrospinal fluid includes flow or pressure information. In an embodiment, the at least one characteristic associated with the cerebrospinal fluid includes at least one of an optical density an opacity, and a refractivity. In an embodiment, the at least one characteristic associated with the cerebrospinal fluid includes at least one parameter associated with a psychosis state marker or a psychosis trait marker. In an embodiment, the at least one characteristic associated with the cerebrospinal fluid includes at least one psychiatric disorder indication parameter. In an embodiment, the at least one characteristic associated with the cerebrospinal fluid includes at least one of an infection indication parameter, an inflammation indication parameter, a diseased state indication parameter (e.g., an absence, a presence, or a severity indication parameter), and a diseased tissue indication parameter.

In an embodiment, the at least one characteristic associated with the cerebrospinal fluid includes at least one of a psychotic disorder indication parameter, a psychotic state indication parameter, a psychotic trait indication parameter, a psychosis indication parameter, and a predisposition for a psychosis indication parameter. In an embodiment, the at least one characteristic associated with the cerebrospinal fluid includes at least one of a psychotic disorder indication, psychotic state indication, a psychotic trait indication, a psychosis indication, and a predisposition for a psychosis indication.

In an embodiment, at least one of the one or more sensors 442 is configured to detect a fluorescence associated with an autofluorescent material within a cerebrospinal fluid received within at least one of the one or more fluid-flow passageways 106. In an embodiment, at least one of the one or more sensors 442 is configured to detect an autofluorescence associated with monocytes within a cerebrospinal fluid received within at least one of the one or more fluid-flow passageways 106. In an embodiment, at least one of the one or more sensors 442 is configured to detect an autofluorescence associated with amyloids within a cerebrospinal fluid received within at least one of the one or more fluid-flow passageways 106.

In an embodiment, the at least one characteristic associated with the cerebrospinal fluid includes at least one of an electromagnetic energy absorption parameter, an energy stimulus emission parameter, an energy stimulus scattering parameter, an energy stimulus reflectance parameter, an energy stimulus phase shift parameter, an energy stimulus dephasing parameter, and an energy stimulus depolarization parameter. In an embodiment, the at least one characteristic associated with the cerebrospinal fluid includes at least one of an electromagnetic energy absorption parameter, an electromagnetic energy emission parameter, an electromagnetic energy scattering parameter, an electromagnetic energy reflectance parameter, an electromagnetic energy phase shift parameter, an electromagnetic energy dephasing parameter, and an electromagnetic energy depolarization parameter. In an embodiment, the at least one characteristic associated with the cerebrospinal fluid includes at least one of an absorbance, a reflectivity, and a transmittance. In an embodiment, the at least one characteristic associated with the cerebrospinal fluid includes at least one of a refraction and a scattering.

In an embodiment, the sensor component 440 is configured to detect spectral information associated with the cerebrospinal fluid. For example, In an embodiment, the sensor component 440 is configured to detect at least one of an absorption coefficient, an extinction coefficient, and a scattering coefficient associated with the cerebrospinal fluid. In an embodiment, the at least one characteristic associated with the cerebrospinal fluid includes at least one of an absorption coefficient, an extinction coefficient, and a scattering coefficient.

In an embodiment, the sensor component 440 is configured to detect spectral information associated with one or more cerebrospinal fluid components. In an embodiment, the sensor component 440 is configured to detect an energy absorption of one or more cerebrospinal fluid components. Non-limiting examples of detectable cerebrospinal fluid components include adenosine deaminase, albumin, calcium, chloride, C-reactive protein, creatine kinase, creatinine, cystatin C, cytokines, glucose, hydrogencarbonate, immunoglobulin G, interleukins, lactate, lactate dehydrogenase, lipids, lymphocytes, monocytes, mononuclear cells, myelin basic protein, neuron-specific enolase, potassium, proteins, S-100 protein, small molecules, sodium, $\beta_2$-microglobulin, and the like.

In an embodiment, at least one controller 402 is operably coupled to the sensor component 440 and configured to process an output associated with one or more sensors 442. In an embodiment, the system 100 includes one or more controllers 402 configured to concurrently or sequentially operate multiple sensors 442. In an embodiment, the system 100 includes one or more controllers 402 configured to perform a comparison of the at least one characteristic associated with the cerebrospinal fluid to stored reference data, and to generate a response based at least in part on the comparison. In an embodiment, one or more of one or more sensors 440 are configured to detect at least one of an emitted energy and a remitted energy, and to generate a response based on the detected at least one of the emitted energy and the remitted energy.

In an embodiment, the system 100 includes a controller 402 operably coupled to the one or more sensors 440 and configured to perform a comparison of at least one characteristic associated with the cerebrospinal fluid to stored reference data, and to generate a response based at least in part on the comparison. In an embodiment, the response includes at least one of a visual representation, an audio representation, a haptic representation, and a tactile representation. In an embodiment, the response includes generating spectral information associated with a biological fluid component.

In an embodiment, the response includes a psychiatric disorder probability score. In an embodiment, the generated response includes at least one of a response signal, a control signal, a display, a change to an energy stimulus parameter, a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, or a change in an energy stimulus delivery regimen parameter.

In an embodiment, one or more controllers 402 are configured to automatically control one or more of a frequency, a duration, a pulse rate, a duty cycle, or the like associated with an ultrasonic energy generated by the one or more transducers 314 based on a sensed parameter. In an embodiment, one or more controllers 402 are configured to automatically control one or more of a frequency, a duration, a pulse rate, a duty cycle, or the like associated with the ultrasonic energy generated by the one or more transducers 314 based on a sensed parameter associated with a region within the biological subject.

The system 100 can include for example, but not limited to, one or more sensors 442 configured to determine at least one characteristic associated with a biological specimen (e.g., biological fluid, tissue, or the like) proximate a surface (e.g., outer surface 108 or inner surface 110, or the like) of the implantable device 102. In an embodiment, the system 100 is configured to determine one or more tissue spectroscopic properties, such as, for example, a transport scattering coefficient or an absorption coefficient.

In an embodiment, the at least one characteristic associated with a biological specimen proximate a surface of the implantable device 102 includes at least one of an inflammation indication parameter, an infection indication parameter, a diseased state indication parameter, and a diseased tissue indication parameter. In an embodiment, the at least one characteristic associated with a biological specimen proximate a surface of the implantable device 102 includes at least one of an inflammation indication parameter, an infection indication parameter, a diseased state indication parameter, and a diseased tissue indication parameter. In an embodiment, the at least one characteristic associated with a biological specimen proximate a surface of the implantable device 102 includes at least one parameter associated with an amount of energy-activatable disinfecting agent present in at least a portion of the tissue proximate a surface of the implantable device 102, a sodium ion content, a chloride content, a superoxide anion content, or a hydrogen peroxide content. In an embodiment, the at least one characteristic associated with a biological specimen proximate a surface of the implantable device 102 includes at least one of an absorption coefficient, an extinction coefficient, and a scattering coefficient.

In an embodiment, the at least one characteristic associated with a biological specimen proximate a surface of the implantable device 102 includes at least one parameter associated with an infection marker, an inflammation marker, an infective stress marker, a systemic inflammatory response syndrome marker, or a sepsis marker. In an embodiment, the infection marker includes at least one of a red blood cell count, a lymphocyte level, a leukocyte count, a myeloid count, an erythrocyte sedimentation rate, and a C-reactive protein level.

In an embodiment, the at least one characteristic associated with a biological specimen proximate a surface of the implantable device 102 includes at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, or a pH level. In an embodiment, the at least one characteristic associated with a biological specimen proximate a surface of the implantable device 102 includes at least one parameter associated with a cytokine plasma concentration or an acute phase protein plasma concentration. In an embodiment, the at least one characteristic associated with a biological specimen proximate a surface of the implantable device 102 includes at least one parameter associated with a leukocyte level. In an embodiment, the controller is communicatively coupled to the one or more sensors 442 configured to determine the at least one characteristic associated with a biological specimen proximate a surface of the implantable device 102.

In an embodiment, one or more sensors 442 are configured to determine at least one characteristic associated with a tissue proximate the implantable device 102. In an embodiment, the at least one characteristic associated with the tissue proximate the implantable device 102 includes at least one of a transmittance, an energy stimulus frequency change, energy stimulus frequency shift, an energy stimulus phase change, and energy stimulus phase shift. In an embodiment, the at least one characteristic associated with the tissue proximate the implantable device 102 includes at least one of a fluorescence, an intrinsic fluorescence, a tissue fluorescence, and a naturally occurring fluorophore fluorescence. In an embodiment, the at least one characteristic associated with the tissue proximate the implantable device 102 includes at least one of an electrical conductivity, and electrical polarizability, and an electrical permittivity. In an embodiment, the at least one characteristic associated with the tissue proximate the implantable device 102 includes at least one of a thermal conductivity, a thermal diffusivity, a tissue temperature, and a regional temperature.

In an embodiment, the controller 402 is configured to perform a comparison of the at least one characteristic associated with the tissue proximate the at least one outer surface 108 to stored reference data, and to generate a response based at least in part on the comparison. The system 100 can include for example, but not limited to, one or more processors 404 configured to perform a comparison of the at least one characteristic associated with a biological specimen proximate a surface of the implantable device 102 to stored reference data, and to generate a response based at least in part on the comparison. In an embodiment, the system 100 is configured to compare an input associated with at least one characteristic associated with a tissue proximate an implantable device 102 to a data structure 424 including reference values, and to generate a response based in part on the comparison. In an embodiment, the system 100 is configured to compare an input associated with at least one physiological characteristic associated with a biological subject to a data structure 424 including reference values, and to generate a response based in part on the comparison. In an embodiment, the system 100 is configured to compare an input associated with at least one characteristic associated with a tissue proximate an implantable device 102 to a data structure 424 including reference values, and to generate a response based in part on the comparison.

In an embodiment, the sensor component 440 is configured to detect at least one of an emitted energy and a remitted energy associated with a tissue of a biological subject. Blood is a tissue composed of, among other components, formed elements (e.g., blood cells such as erythrocytes, leukocytes, thrombocytes, or the like) suspend in a matrix (plasma). The heart, blood vessels (e.g., arteries, arterioles, capillaries, veins, venules, or the like), and blood components, make up the cardiovascular system. The cardiovascular system, among other things, moves oxygen, gases, and wastes to and from cells and tissues, maintains homeostasis by stabilizing body temperature and pH, and helps fight diseases. In an embodiment, the sensor component 440 is configured to detect at least one of an emitted energy and a remitted energy associated with a portion of a cardiovascular system. In an embodiment, the sensor component 440 is configured to detect at least one of an emitted energy and a remitted energy associated with one or more blood components within a biological subject. In an embodiment, the sensor component 440 is configured to detect at least one of an emitted energy and a remitted energy associated with one or more formed elements within a biological subject. In an embodiment, the sensor component 440 is configured to detect spectral information associated with one or more of one or more blood components. In an embodiment, the sensor component 440 is configured to detect at least one of an emitted energy and a remitted energy associated with a real-time change in one or more parameters associated with at least one blood component within a biological subject. In an embodiment, the sensor component 440 is configured to detect an energy absorption of one or more blood components.

Non-limiting examples of detectable blood components include erythrocytes, leukocytes (e.g., basophils, granulocytes, eosinophils, monocytes, macrophages, lymphocytes, neutrophils, or the like), thrombocytes, acetoacetate, acetone, acetylcholine, adenosine triphosphate, adrenocorticotrophic hormone, alanine, albumin, aldosterone, aluminum, amyloid proteins (non-immunoglobulin), antibodies, apolipoproteins, ascorbic acid, aspartic acid, bicarbonate, bile acids, bilirubin, biotin, blood urea Nitrogen, bradykinin, bromide, cadmium, calciferol, calcitonin (ct), calcium, carbon dioxide, carboxyhemoglobin (as HbcO), cell-related plasma proteins, cholecystokinin (pancreozymin), cholesterol, citric acid, citrulline, complement components, coagulation factors, coagulation proteins, complement components, c-peptide, c-reactive protein, creatine, creatinine, cyanide, 11-deoxycortisol, deoxyribonucleic acid, dihydrotestosterone, diphosphoglycerate (phosphate), or the like.

Further non-limiting examples of detectable blood components include to dopamine, enzymes, epidermal growth factor, epinephrine, ergothioneine, erythrocytes, erythropoietin, folic acid, fructose, furosemide glucuronide, galactoglycoprotein, galactose (children), gamma-globulin, gastric inhibitory peptide, gastrin, globulin, $\alpha$-1-globulin, $\alpha$-2-globulin, $\alpha$-globulins, $\beta$-globulin, $\beta$-globulins, glucagon, glucosamine, glucose, immunoglobulins (antibodies), lipase p, lipids, lipoprotein (sr 12-20), lithium, low-molecular weight proteins, lysine, lysozyme (muramidase), $\alpha$-2-macroglobulin, $\gamma$-mobility (non-immunoglobulin), pancreatic polypeptide, pantothenic acid, para-aminobenzoic acid, parathyroid hormone, pentose, phosphorated, phenol, phenylalanine, phosphatase, acid, prostatic, phospholipid, phosphorus, prealbumin, thyroxine-binding, proinsulin, prolactin (female), prolactin (male), proline, prostaglandins, prostate specific antigen, protein, protoporphyrin, pseudoglobulin I, pseudoglobulin II, purine, pyridoxine, pyrimidine nucleotide, pyruvic acid, CCL5 (RANTES), relaxin, retinol, retinol-binding protein, riboflavin, ribonucleic acid, secretin, serine, serotonin (5-hydroxytryptamine), silicon, sodium, solids, somatotropin (growth hormone), sphingomyelin, succinic acid, sugar, sulfates, inorganic, sulfur, taurine, testosterone (female), testosterone (male), triglycerides, triiodothyronine, tryptophan, tyrosine, urea, uric acid, water, miscellaneous trace components, and the like.

Among $\alpha$-Globulins examples include, but are not limited to, $\alpha$1-acid glycoprotein, $\alpha$1-antichymotrypsin, $\alpha$1-antitrypsin, $\alpha$1B-glycoprotein, $\alpha$1-fetoprotein, $\alpha$1-microglobulin, $\alpha$1T-glycoprotein, $\alpha$2HS-glycoprotein, $\alpha$2-macroglobulin, 3.1 S Leucine-rich $\alpha$2-glycoprotein, 3.8 S histidine-rich $\alpha$2-glycoprotein, 4 S $\alpha$2, $\alpha$1-glycoprotein, 8 S $\alpha$3-glycoprotein, 9.5 S $\alpha$1-glycoprotein (serum amyloid P protein), Corticosteroid-binding globulin, ceruloplasmin, GC globulin, haptoglobin (e.g., Type 1-1, Type 2-1, or Type 2-2), inter-$\alpha$-trypsin inhibitor, pregnancy-associated $\alpha$2-glycoprotein, serum cholinesterase, thyroxine-binding globulin, transcortin, vitamin D-binding protein, Zn-$\alpha$2-glycoprotein, and the like. Among $\beta$-Globulins, examples include, but are not limited to, hemopexin, transferrin, $\beta$2-microglobulin, $\beta$2-glycoprotein I, $\beta$2-glycoprotein II, (C3 proactivator), $\beta$2-glycoprotein III, C-reactive protein, fibronectin, pregnancy-specific $\beta$1-glycoprotein, ovotransferrin, and the like. Among immunoglobulins examples include, but are not limited to, immunoglobulin G (e.g., IgG, $IgG_1$, $IgG_2$, $IgG_3$, $IgG_4$), immunoglobulin A (e.g., IgA, $IgA_1$, $IgA_2$), immunoglobulin M, immunoglobulin D, immunoglobulin E, $\kappa$ Bence Jones protein, $\gamma$ Bence Jones protein, J Chain, and the like.

Among apolipoproteins examples include, but are not limited to, apolipoprotein A-I (HDL), apolipoprotein A-II (HDL), apolipoprotein C-I (VLDL), apolipoprotein C-II, apolipoprotein C-III (VLDL), apolipoprotein E, and the like. Among $\gamma$-mobility (non-immunoglobulin) examples include, but are not limited to, 0.6 S $\gamma$2-globulin, 2 S $\gamma$2-globulin, basic Protein B2, post-$\gamma$-globulin ($\gamma$-trace), and the like. Among low-molecular weight proteins examples include, but are not limited to, lysozyme, basic protein B1, basic protein B2, 0.6 S $\gamma$2-globulin, 2 S $\gamma$2-globulin, post $\gamma$-globulin, and the like.

Among complement components examples include, but are not limited to, C1 esterase inhibitor, C1q component, C1r component, C1s component, C2 component, C3 component, C3a component, C3b-inactivator, C4 binding protein, C4 component, C4a component, C4-binding protein, C5 component, C5a component, C6 component, C7 component, C8 component, C9 component, factor B, factor B (C3 proactivator), factor D, factor D (C3 proactivator convertase), factor H, factor H ($\beta_1$H), properdin, and the like. Among coagulation proteins examples include, but are not limited to, antithrombin III, prothrombin, antihemophilic factor (factor VIII), plasminogen, fibrin-stabilizing factor (factor XIII), fibrinogen, thrombin, and the like.

Among cell-Related Plasma Proteins examples include, but are not limited to, fibronectin, $\beta$-thromboglobulin, platelet factor-4, serum Basic Protease Inhibitor, and the like. Among amyloid proteins (Non-Immunoglobulin) examples include, but are not limited to, amyloid-Related apoprotein (apoSAA1), AA (FMF) (ASF), AA (TH) (AS), serum amyloid P component (9.5 S 7$\alpha$1-glycoprotein), and the like. Among miscellaneous trace components examples include, but are not limited to, varcinoembryonic antigen, angiotensinogen, and the like.

In an embodiment, the sensor component 440 is configured to determine at least one characteristic (e.g., a spectral characteristic, a spectral signature, a physical quantity, a relative quantity, an environmental attribute, a physiologic characteristic, or the like) associated with a region within the biological subject. In an embodiment, the sensor component 440 is configured to determine at least one characteristic associated with a fluid-flow passageway 106 obstruction, a hematological abnormality, or a body fluid flow abnormality (e.g., a cerebrospinal fluid abnormality). In an embodiment, the sensor component 440 is configured to determine at least one characteristic associated with a portion of the tissue within the biological subject. In an embodiment, the sensor component 440 is configured to determine at least one characteristic associated with a biological fluid flow passageway.

In an embodiment, a controller 402 is configured to perform a comparison of the at least one characteristic associated with the with the cerebrospinal fluid to stored reference data, and to initiate a treatment protocol based at least in part on the comparison. In an embodiment, a controller 402 is configured to perform a comparison of the at least one characteristic associated with the with the cerebrospinal fluid to stored reference data, and to cause at least one of an emission of an energy stimulus from the one or more energy emitters to a cerebrospinal fluid received within at least one of the one or more fluid-flow passageways 106, and a delivery of an active agent from at least one disinfecting agent reservoir to an interior of at least one of the one or more fluid-flow passageways 106.

In an embodiment, the sensor component 440 is configured to determine at least one characteristic associated with one or more biological markers or biological components (e.g., cerebrospinal fluid components). In an embodiment, the sensor component 440 is configured to determine at least one characteristic associated with a tissue proximate the implantable device 102. In an embodiment, the sensor component 440 is configured to determine a spatial dependence associated with the least one characteristic. In an embodiment, the sensor component 440 is configured to determine a temporal dependence associated with the least one characteristic. In an embodiment, the sensor component 440 is configured to concurrently or sequentially determine at least one spatial dependence associated with the least one characteristic and at least one temporal dependence associated with the least one characteristic.

In an embodiment, the sensor component 440 is configured to determine at least one spectral parameter associated with one or more imaging probes (e.g., chromophores, fluorescent agents, fluorescent marker, fluorophores, molecular imaging probes, quantum dots, radio-frequency identification transponders (RFIDs), x-ray contrast agents, or the like). In an embodiment, the sensor component 440 is configured to determine at least one characteristic associated with one or more imaging probes attached, targeted to, conjugated, bound, or associated with at least one inflammation markers. See, e.g., the following documents (the contents of which are incorporated herein by reference): Jaffer et al., Arterioscler. Thromb. Vasc. Biol. 2002; 22; 1929-1935 (2002); Kalchenko et al., J. of Biomed. Opt. 11(5):50507 (2006).

In an embodiment, the one or more imaging probes include at least one carbocyanine dye label. In an embodiment, the sensor component 440 is configured to determine at least one characteristic associated with one or more imaging probes attached, targeted to, conjugated, bound, or associated with at least one biomarker or biological fluid component.

In an embodiment, the one or more imaging probes include at least one fluorescent agent. In an embodiment, the one or more imaging probes include at least one quantum dot. In an embodiment, the one or more imaging probes include at least one radio-frequency identification transponder. In an embodiment, the one or more imaging probes include at least one x-ray contrast agent. In an embodiment, the one or more imaging probes include at least one molecular imaging probe. A non-limiting approach includes systems, devices, methods, and compositions including, among other things, one or more imaging probes.

Among imaging probes examples include, but are not limited to, fluorescein (FITC), indocyanine green (ICG) and rhodamine B. Non-limiting examples of other fluorescent dyes for use in fluorescence imaging include a number of red and near infrared emitting fluorophores (600-1200 nm) including cyanine dyes such as Cy5, Cy5.5, and Cy7 (Amersham Biosciences, Piscataway, N.J., USA) or a variety of Alexa Fluor dyes such as Alexa Fluor 633, Alexa Fluor 635, Alexa Fluor 647, Alexa Fluor 660, Alexa Fluor 680, Alexa Fluor 700, Alexa Fluor 750 (Molecular Probes-Invitrogen, Carlsbad, Calif., USA; see, also, U.S. Patent Pub. No. 2005/0171434 (published Aug. 4, 2005) (the contents of which are incorporated herein by reference), and the like.

Further non-limiting examples of imaging probes include IRDye800, IRDye700, and IRDye680 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS, ADS 821-NS (American Dye Source, Montreal, Calif.), NIAD-4 (ICx Technologies, Arlington, Va.), and the like. Further non-limiting examples of fluorophores include BODIPY-FL, europium, green, yellow and red fluorescent proteins, luciferase, and the like. Quantum dots of various emission/excitation properties can be used as imaging probes. See, e.g., Jaiswal, et al. Nature Biotech. 21:47-51 (2003) (the contents of which are incorporated herein by reference). Further non-limiting examples of imaging probes include those including antibodies specific for leukocytes, anti-fibrin antibodies, monoclonal anti-diethylene triamine pentaacetic acid (DTPA), DTPA labeled with Technetium-99m ($^{99m}$TC), and the like.

In an embodiment, the sensor component 440 is configured to detect at least one of an emitted energy and a remitted energy associated with a biomarker. Among biomarker examples include, but are not limited to, one or more substances that are measurable indicators of a biological state and can be used as indicators of normal disease state, pathological disease state, and/or risk of progressing to a pathological disease state. In some instances, a biomarker can be a normal blood component that is increased or decreased in the pathological state. A biomarker can also be a substance that is not normally detected in biological sample, fluid, or tissue, but is released into circulation because of the pathological state. In some instances, a biomarker can be used to predict the risk of developing a pathological state. For example, plasma measurement of lipoprotein-associated phospholipase A2 (Lp-PLA2) is approved by the U.S. Food & Drug Administration (FDA) for predicting the risk of first time stroke. In other instances, the biomarker can be used to diagnose an acute pathological state. For example, elevated plasma levels of S-100b, B-type neurotrophic growth factor (BNGF), von Willebrand factor (vWF), matrix metalloproteinase-9 (MMP-9), and monocyte chemoattractant protein-1 (MCP-1) are highly correlated with the diagnosis of stroke (see, e.g., Reynolds, et al., *Early biomarkers of stroke*. Clin. Chem. 49:1733-1739 (2003), which is incorporated herein by reference).

Further non-limiting examples of biomarkers include high-sensitivity C-reactive protein (hs-CRP), cardiac troponin T (cTnT), cardiac troponin I (cTnI), N-terminal-pro B-type natriuretic peptide (NT-proBNP), D-dimer, P-selectin, E-selectin, thrombin, interleukin-10, fibrin monomers, phospholipid microparticles, creatine kinase, interleukin-6, tumor necrosis factor-alpha, myeloperoxidase, intracellular adhesion molecule-1 (ICAM1), vascular adhesion molecule (VCAM), matrix metalloproteinase-9 (MMP9), ischemia modified albumin (IMA), free fatty acids, choline, soluble CD40 ligand, insulin-like growth factor, (see, e.g., Giannitsis, et al. *Risk stratification in pulmonary embolism based on biomarkers and echocardiography*. Circ. 112:1520-1521 (2005), Barnes, et al., *Novel biomarkers associated with*

*deep venous throbosis: A comprehensive review*. Biomarker Insights 2:93-100 (2007); Kamphuisen, *Can anticoagulant treatment be tailored with biomarkers in patients with venous thromboembolism?* J. Throm. Haemost. 4:1206-1207 (2006); Rosalki, et al., *Cardiac biomarkers for detection of myocardial infarction: Perspectives from past to present*. Clin. Chem. 50:2205-2212 (2004); Apple, et al., *Future biomarkers for detection of ischemia and risk stratification in acute coronary syndrome*, Clin. Chem. 51:810-824 (2005), which are incorporated herein by reference).

In an embodiment, the sensor component 440 is configured to detect at least one characteristic associated with one or more biological fluid components. In an embodiment, the at least one characteristic includes at least one of absorption coefficient information, extinction coefficient information, and scattering coefficient information associated with the at least one molecular probe. In an embodiment, the at least one characteristic includes spectral information indicative of a rate of change, an accumulation rate, an aggregation rate, or a rate of change associated with at least one physical parameter associated with a biological fluid component.

In an embodiment, the sensor component 440 is configured to detect at least characteristic associated with a biological subject. In an embodiment, the at least one characteristic includes at least one of a transmittance, an energy frequency change, a frequency shift, an energy phase change, and a phase shift. In an embodiment, the at least one characteristic includes at least one of a fluorescence, an intrinsic fluorescence, a tissue fluorescence, and a naturally occurring fluorophore fluorescence. In an embodiment, the at least one characteristic includes at least one of an electrical conductivity, and electrical polarizability, and an electrical permittivity. In an embodiment, the at least one characteristic includes at least one of a thermal conductivity, a thermal diffusivity, a tissue temperature, and a regional temperature.

In an embodiment, the at least one characteristic associated with a biological subject includes at least one parameter associated with a doppler optical coherence tomograph. (See, e.g., Li et al., *Feasibility of Interstitial Doppler Optical Coherence Tomography for In Vivo Detection of Microvascular Changes During Photodynamic Therapy*, Lasers in surgery and medicine 38(8):754-61. (2006), which is incorporated herein by reference; see, also U.S. Pat. No. 7,365,859 (issued Apr. 29, 2008), which is incorporated herein by reference).

In an embodiment, the at least one characteristic associated with a biological subject includes spectral signature information associated with an implant device. For example, in an embodiment, the at least one characteristic includes implant device spectral signature information associated with at least one of a bio-implants, bioactive implants, breast implants, cochlear implants, dental implants, neural implants, orthopedic implants, ocular implants, prostheses, implantable electronic device, implantable medical devices, and the like. Further non-limiting examples of implant devices include replacements implants (e.g., joint replacements implants such, for example, elbows, hip (an example of which is shown on FIG. 1), knee, shoulder, wrists replacements implants, or the like), subcutaneous drug delivery devices (e.g., implantable pills, drug-eluting stents, or the like), shunts (e.g., cardiac shunts, lumbo-peritoneal shunts, cerebrospinal fluid shunts, cerebral shunts, pulmonary shunts, portosystemic shunts, portacaval shunts, or the like), stents (e.g., coronary stents, peripheral vascular stents, prostatic stents, ureteral stents, vascular stents, or the like), biological fluid flow controlling implants, and the like. Further non-limiting examples of implant device include artificial hearts, artificial joints, artificial prosthetics, catheters, contact lens, mechanical heart valves, subcutaneous sensors, urinary catheters, vascular catheters, and the like.

In an embodiment, the at least one characteristic includes at least one parameter associated with a diseased state. Inflammation is a complex biological response to insults that can arise from, for example, chemical, traumatic, or infectious stimuli. It is a protective attempt by an organism to isolate and eradicate the injurious stimuli as well as to initiate the process of tissue repair. The events in the inflammatory response are initiated by a complex series of interactions involving inflammatory mediators, including those released by immune cells and other cells of the body. Histamines and eicosanoids such as prostaglandins and leukotrienes act on blood vessels at the site of infection to localize blood flow, concentrate plasma proteins, and increase capillary permeability. Chemotactic factors, including certain eicosanoids, complement, and especially cytokines known as chemokines, attract particular leukocytes to the site of infection. Other inflammatory mediators, including some released by the summoned leukocytes, function locally and systemically to promote the inflammatory response. Platelet activating factors and related mediators function in clotting, which aids in localization and can trap pathogens. Certain cytokines, interleukins and TNF, induce further trafficking and extravasation of immune cells, hematopoiesis, fever, and production of acute phase proteins. Once signaled, some cells and/or their products directly affect the offending pathogens, for example by inducing phagocytosis of bacteria or, as with interferon, providing antiviral effects by shutting down protein synthesis in the host cells.

Oxygen radicals, cytotoxic factors, and growth factors can also be released to fight pathogen infection or to facilitate tissue healing. This cascade of biochemical events propagates and matures the inflammatory response, involving the local vascular system, the immune system, and various cells within the injured tissue. Under normal circumstances, through a complex process of mediator-regulated pro-inflammatory and anti-inflammatory signals, the inflammatory response eventually resolves itself and subsides. For example, the transient and localized swelling associated with a cut is an example of an acute inflammatory response. However, in certain cases resolution does not occur as expected. Prolonged inflammation, known as chronic inflammation, leads to a progressive shift in the type of cells present at the site of inflammation and is characterized by simultaneous destruction and healing of the tissue from the inflammatory process, as directed by certain mediators. Rheumatoid arthritis is an example of a disease associated with persistent and chronic inflammation.

Non-limiting suitable techniques for optically measuring a diseased state may be found in, for example, U.S. Pat. No. 7,167,734 (issued Jan. 23, 2007), which is incorporated herein by reference. In an embodiment, the at least one characteristic includes at least one of an electromagnetic energy absorption parameter, an electromagnetic energy emission parameter, an electromagnetic energy scattering parameter, an electromagnetic energy reflectance parameter, and an electromagnetic energy depolarization parameter. In an embodiment, the at least one characteristic includes at least one of an absorption coefficient, an extinction coefficient, and a scattering coefficient.

In an embodiment, the at least one characteristic associated with a biological subject includes at least one parameter associated with an infection marker (e.g., an infectious agent marker), an inflammation marker, an infective stress marker, a systemic inflammatory response syndrome marker, or a sepsis marker. Non-limiting examples of infection makers, inflammation markers, and the like may be found in, for example, Imam et al., *Radiotracers for imaging of infection and inflammation—A Review*, World J. Nucl. Med. 40-55 (2006), which is incorporated herein by reference. Non-limiting characteristics associated with an infection marker, an inflammation marker, an infective stress marker, a systemic inflammatory response syndrome marker, or a sepsis marker include at least one of an inflammation indication parameter, an infection indication parameter, a diseased state indication parameter, and a diseased tissue indication parameter.

In an embodiment, the response includes generating a visual, an audio, a haptic, or a tactile representation of at least one spectral parameter associated with a detected infection marker. In an embodiment, the response includes generating a visual, an audio, a haptic, or a tactile representation of at least one physical parameter indicative of at least one dimension of infected tissue region.

In an embodiment, the at least one characteristic associated with a biological subject includes at least one of a tissue water content, an oxy-hemoglobin concentration, a deoxy-hemoglobin concentration, an oxygenated hemoglobin absorption parameter, a deoxygenated hemoglobin absorption parameter, a tissue light scattering parameter, a tissue light absorption parameter, a hematological parameter, and a pH level.

In an embodiment, the at least one characteristic associated with a biological subject includes at least one hematological parameter. Non-limiting examples of hematological parameters include an albumin level, a blood urea level, a blood glucose level, a globulin level, a hemoglobin level, erythrocyte count, a leukocyte count, and the like. In an embodiment, the infection marker includes at least one parameter associated with a red blood cell count, a lymphocyte level, a leukocyte count, a myeloid count, an erythrocyte sedimentation rate, or a C-reactive protein level. In an embodiment, the at least one characteristic includes at least one parameter associated with a cytokine plasma level or an acute phase protein plasma level. In an embodiment, the at least one characteristic includes at least one parameter associated with a leukocyte level.

In an embodiment, a controller 402 is configured to compare a measurand associated with the biological subject to a threshold value associated with a tissue spectral model and to generate a response based on the comparison. In an embodiment, a controller 402 is configured to generate the response based on the comparison of a measurand that modulates with a detected heart beat of the biological subject to a target value associated with a tissue spectral model. In an embodiment, a controller 402 is configured to concurrently or sequentially operate multiple energy emitters 302. In an embodiment, a controller 402 is configured to compare an input associated with at least one characteristic associated with, for example, a tissue proximate an implantable device 102 to a database 422 of stored reference values, and to generate a response based in part on the comparison.

The response can include, but is not limited to, at least one of a response signal, an absorption parameter, an extinction parameter, a scattering parameter, a comparison code, a comparison plot, a diagnostic code, a treatment code, an alarm response, and a test code based on the comparison of a detected optical energy absorption profile to characteristic spectral signature information. In an embodiment, the response includes at least one of a display, a visual representation (e.g., a visual depiction representative of the detected (e.g., assessed, calculated, evaluated, determined, gauged, measured, monitored, quantified, resolved, sensed, or the like) information) component, a visual display of at least one spectral parameter, and the like. In an embodiment, the response includes a visual representation indicative of a parameter associated with an infection present in a region of a tissue proximate one or more sensors 442. In an embodiment, the response includes a generating a representation (e.g., depiction, rendering, modeling, or the like) of at least one physical parameter associated with a biological specimen.

Figure 7:
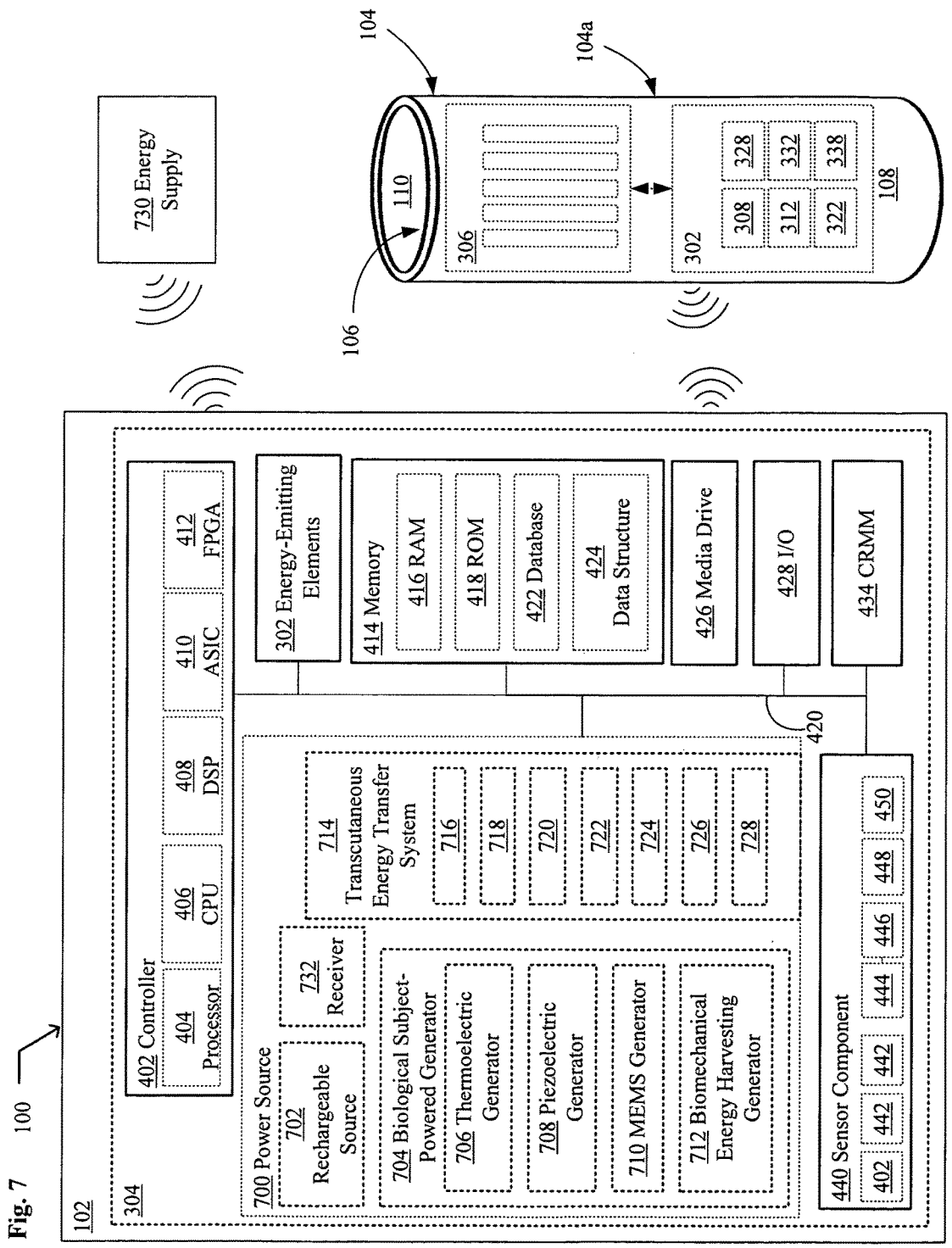
FIG. 7 is a schematic diagram of a system including an implantable device according to one illustrated embodiment.

Referring to FIG. 7, the implantable device 102 can include, but is not limited to, one or more power sources 700. In an embodiment, the power source 700 is electromagnetically, magnetically, ultrasonically, optically, inductively, electrically, or capacitively coupleable to at least one of the energy emitters 302 and the sensor component 440. In an embodiment, the power source 700 is carried by the implantable device 102. In an embodiment, the power source 700 comprises at least one rechargeable power source 702.

In an embodiment, the implantable device 102 includes one or more biological-subject (e.g., human)-powered generators 704. In an embodiment, the biological-subject-powered generator 704 is configured to harvest energy from for example, but not limited to, motion of one or more joints. In an embodiment, the biological-subject-powered generator 704 is configured to harvest energy generated by the biological subject using at least one of a thermoelectric generator 706, piezoelectric generator 708, electromechanical generator 710 (e.g., a microelectromechanical systems (MEMS) generator, or the like), biomechanical-energy harvesting generator 712, and the like.

In an embodiment, the biological-subject-powered generator 704 is configured to harvest thermal energy generated by the biological subject. In an embodiment, a thermoelectric generator 706 is configured to harvest heat dissipated by the biological subject. In an embodiment, the biological-subject-powered generator 704 is configured to harvest energy generated by any physical motion or movement (e.g., walking,) by biological subject. For example, in an embodiment, the biological-subject-powered generator 704 is configured to harvest energy generated by the movement of a joint within the biological subject. In an embodiment, the biological-subject-powered generator 704 is configured to harvest energy generated by the movement of a fluid (e.g., biological fluid) within the biological subject.

Among power sources 700 examples include, but are not limited to, one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, and the like. Further non-limiting examples of power sources 700 include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, biomechanical-energy harvesting generators, and the like. In an embodiment, the implantable device 102 includes one or more generators configured to harvest mechanical energy from for example, ultrasonic waves, mechanical vibration, blood flow, and the like. In an embodiment, the implantable device 102 includes one or more power receivers 732 configured to receive power from an in vivo or ex vivo power source.

In an embodiment, the power source 700 includes at least one of a thermoelectric generator, a piezoelectric generator, an electromechanical generator, and a biomechanical-energy harvesting generator, and at least one of a button cell, a chemical battery cell, a fuel cell, a secondary cell, a lithium ion cell, a micro-electric patch, a nickel metal hydride cell, silver-zinc cell, a capacitor, a super-capacitor, a thin film secondary cell, an ultra-capacitor, and a zinc-air cell. In an embodiment, the power source 700 includes at least one rechargeable power source.

In an embodiment, the implantable device 102 includes a power source 700 including at least one of a thermoelectric generator a piezoelectric generator, an electromechanical generator, and a biomechanical-energy harvesting generator. In an embodiment, the power source is configured to manage a duty cycle associated with emitting an effective amount of the energy stimulus from the one or more energy emitters 302. In an embodiment, the power source 700 is configured to manage a duty cycle associated with emitting an effective amount of a sterilizing energy stimulus from the one or more energy emitters 302. In an embodiment, the one or more energy emitters 302 are configured to provide a voltage across at least a portion of the tissue proximate the implantable device 102 from a power source 700 coupled to the implantable device 102.

The implantable device 102 can include a transcutaneous energy transfer system 714. In an embodiment, the transcutaneous energy transfer system 714 is configured to transfer power from an in vivo power source to the implantable device 102. In an embodiment, the transcutaneous energy transfer system 714 is configured to transfer power to the implantable device 102 and to recharge a power source 700 within the implantable device 102. In an embodiment, the implantable device 102 can include, but is not limited to, at least one of a battery, a capacitor, and a mechanical energy store (e.g., a spring, a flywheel, or the like).

In an embodiment, the transcutaneous energy transfer system 714 is electromagnetically, magnetically, ultrasonically, optically, inductively, electrically, or capacitively coupleable to an in vivo power supply. In an embodiment, the transcutaneous energy transfer system 714 is electromagnetically, magnetically, ultrasonically, optically, inductively, electrically, or capacitively coupleable to the energy emitter component 304. In an embodiment, the transcutaneous energy transfer system 714 includes at least one electromagnetically coupleable power supply 716, magnetically coupleable power supply 718, ultrasonically coupleable power supply 720, optically coupleable power supply 722, inductively coupleable power supply 724, electrically coupleable power supply 726, or capacitively coupleable power supply 728. In an embodiment, the energy transcutaneous transfer system 714 is configured to wirelessly receive power from a remote power supply 730.

The transcutaneous energy transfer system 714 can include, but is not limited to, an inductive power supply. In an embodiment, the inductive power supply includes a primary winding operable to produce a varying magnetic field. The implantable device 102 can include, but is not limited to, a secondary winding electrically coupled to one or more energy emitters 302 for providing a voltage to tissue proximate the implantable device 102 in response to the varying magnetic field of the inductive power supply. In an embodiment, the transcutaneous energy transfer system 714 includes a secondary coil configured to provide an output voltage ranging from about 10 volts to about 25 volts. In an embodiment, the transcutaneous energy transfer system 714 is configured to manage a duty cycle associated with emitting an effective amount of the sterilizing energy stimulus from one or more energy emitters 302. In an embodiment, the transcutaneous energy transfer system 714 is configured to transfer power to the implantable device 102 and to recharge a power source 700 within the implantable device 102. In an embodiment, the power source 700 is configured to wirelessly receive power from a remote power supply 730. In an embodiment, the in vivo power source includes at least one of a thermoelectric generator, a piezoelectric generator, a microelectromechanical systems generator, and a biomechanical-energy harvesting generator.

Figure 8:
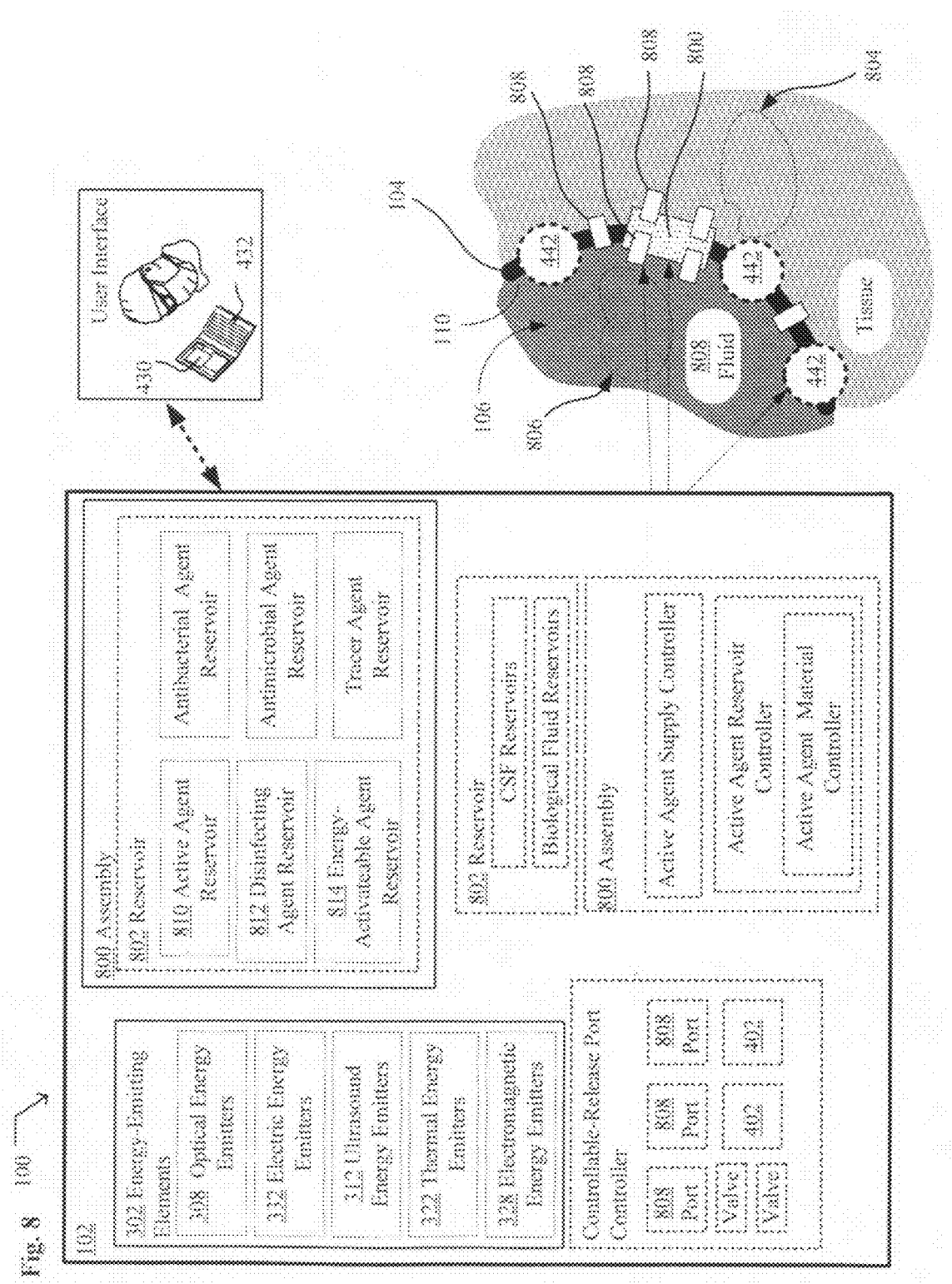
FIG. 8 is a schematic diagram of a system including an implantable device according to one illustrated embodiment.

FIG. 8 shows a system 100 in which one or more methodologies or technologies can be implemented such as, for example, managing a transport of biological fluids and actively detecting, treating, or preventing an infection (e.g., an implant-associated infection, a hematogenous implant-associated infection, or the like), a biological fluid abnormality, or the like. A non-limiting approach for treating or preventing an infection, biological fluid abnormality, or the like includes systems, devices, and methods for administrating a perioperative antibiotic prophylaxis to a patient. Another non-limiting approach includes systems, devices, methods, and compositions for actively forming an antimicrobial agent, in vivo. Another non-limiting approach includes systems, devices, methods, and compositions for impeding bacterial adherence to the implantable device 102 surfaces. Another non-limiting approach includes systems, devices, methods, and compositions for actively impeding biofilm formation on the implantable device 102. Another non-limiting approach includes systems, devices, and methods including coating the implantable device 102 with active agent compositions having, for example, anti-biofilm activity. Another non-limiting approach includes systems, devices, and methods including coating the implantable device 102 with one or more coatings having self-cleaning properties. Another non-limiting approach includes systems, devices, and methods including an implant with a self-cleaning coating having self-cleaning, and anti-bacterial activity. Another non-limiting approach includes systems, devices, and methods including an implantable device 102 having one or more self-cleaning surfaces. Yet another non-limiting approach includes systems, devices, and methods configured to treat or reduce the concentration of an infectious agent in the immediate vicinity of the implantable device 102.

In an embodiment, at least a portion of an inner or an outer surface of the implantable device 102 includes one or more coatings, functionalized surfaces, surface treatments, immuno-stimulating coatings, and the like. In an embodiment, at least a portion of one or more of the fluid-flow passageways 106 includes one or more coatings, functionalized surfaces, surface treatments, immuno-stimulating coatings, and the like. In an embodiment, at least a portion of the body structure 104 includes one or more coatings, functionalized surfaces, surface treatments, immuno-stimulating coatings, and the like.

Among the one or more coatings, functionalized surfaces, surface treatments, immuno-stimulating coatings, and the like, examples include, but are not limited to, polymeric compositions that resist bacterial adhesion, antimicrobial coating, coatings that controllably release antimicrobial agents, quaternary ammonium silane coatings, chitosan coatings, and the like. Further non-limiting examples of coatings, functionalized surfaces, surface treatments, immuno-stimulating coatings, and the like may be found in, for example, the following documents (the contents of which are incorporated herein by reference): U.S. Pat. No. 7,348,021 (issued Mar. 25, 2008), U.S. Pat. No. 7,217,425 (issued May 15, 2007), U.S. Pat. No. 7,151,139 (issued Dec. 19, 2006), and U.S. Pat. No. 7,143,709 (issued Dec. 5, 2006). In an embodiment, at least a portion of an inner or an outer surface of the implantable device 102 includes one or more self-cleaning coating materials. Examples of self-cleaning coating (e.g., Lotus Effect) materials include, but are not limited to titanium dioxide, superhydrophobic materials, carbon nanotubes with nanoscopic paraffin coating, or the like. Further non-limiting examples of self-cleaning (e.g., non fouling) coating materials include antimicrobial, and nonfouling zwitterionic polymers, zwitterionic surface forming materials, zwitterionic polymers, poly(carboxybetaine methacrylate) (pCBMA), poly(carboxybetaine acrylic amide) (pCBAA), poly(oligo(ethylene glycol)methyl ether methacrylate) (pOEGMA), poly(N,N-dimethyl-N-(ethoxycarbonylmethyl)-N-[2'-(methacryloyloxy)ethyl]-ammonium bromide), cationic pC8NMA, switchable pCBMA-1 C2, pCBMA-2, and the like. See, e.g., WO 2008/083390 (published Jul. 10, 2008) (the contents of which are incorporated herein by reference).

Further non-limiting examples of coatings include superhydrophobic conducting polypyrrole films, coating, or components that are electrically switchable between an oxidized state and a neutral state, resulting in reversibly switchable superhydrophobic and superhydrophilic properties (see, e.g., Lahann et al., *A Reversibly Switching Surface*, 299 (5605): 371-374 (2003) 21:47-51 (2003), the contents of which are incorporated herein by reference); coatings including electrically isolatable fluid-support structures (see, e.g., U.S. Pat. No. 7,535,692 (issued May 19, 2009), the contents of which are incorporated herein by reference); coatings including a plurality of volume-tunnable nanostructures (see, e.g., U.S. Patent Publication No. 2008/0095977 (published Apr. 24, 2008), the contents of which are incorporated herein by reference); coatings including re-entrant surface structures (see, e.g., Tuteja et al., *Robust Omniphobic Surfaces*, Epub 2008 Nov. 10, 105(47):18200-5 (2008), the contents of which are incorporated herein by reference); coatings including superhydrophobic conducting polypyrrole materials, coatings including zwitterionic polymers (see, e.g., Cheng et al., *A Switchable Biocompatible Polymer Surface with Self-Sterilizing and Nonfouling Capabilities*, Agnew. Chem. Int. Ed. 8831-8834 (2008), the contents of which are incorporated herein by reference); or the like.

In an embodiment, the implantable device 102 includes at least one active agent assembly 800 including one or more reservoirs 802. In an embodiment, the implantable device 102 includes one or more active agent assemblies 800 configured to deliver at least one active agent from the at least one reservoir 802 to at least one of a region 804 proximate an outer surface 108 and a region 806 proximate an inner surface 110 of the implantable device 102. In an embodiment, the implantable device 102 includes one or more active agent reservoirs 802 including at least one active agent composition. Among active agents, examples include, but are not limited to, adjuvants, allergens, analgesics, anesthetics, antibacterial agents, antibiotics, antifungals, anti-inflammatory agents (e.g., nonsteroidal anti-inflammatory drugs), antimicrobials, antioxidants, antipyretics, anti-tumor agents, antivirals, bio-control agents, biologics or bio-therapeutics, chemotherapy agents, disinfecting agents, energy-activatable active agents, immunogens, immunological adjuvants, immunological agents, immuno-modulators, immuno-response agents, immuno-stimulators (e.g., specific immuno-stimulators, non-specific immuno-stimulators, or the like), immuno-suppressants, non-pharmaceuticals (e.g., cosmetic substances, or the like), pharmaceuticals, protease inhibitors or enzyme inhibitors, receptor agonists, receptor antagonists, therapeutic agents, tolerogens, toll-like receptor agonists, toll-like receptor antagonists, vaccines, or combinations thereof.

Further non-limiting examples of active agents include nonsteroidal anti-inflammatory drugs such as acemetacin, aclofenac, aloxiprin, amtolmetin, aproxen, aspirin, azapropazone, benorilate, benoxaprofen, benzydamine hydrochloride, benzydamine hydrochloride, bromfenal, bufexamac, butibufen, carprofen, celecoxib, choline salicylate, clonixin, desoxysulindac, diflunisal, dipyone, droxicam, etodolac, etofenamate, etoricoxib, felbinac, fenbufen, fenoprofen, fentiazac, fepradinol, floctafenine, flufenamic acid, indomethacin, indoprofen, isoxicam, ketorolac, licofelone, lomoxicam, loxoprofen, magnesium salicylate, meclofenamic acid, meclofenamic acid, mefenamic acid, meloxicam, morniflumate, niflumic acid, nimesulide, oxaprozen, phenylbutazone, piketoprofen, piroxicam, pirprofen, priazolac, propyphenazone, proquazone, rofecoxib, salalate, salicylamide, salicylic acid, sodium salicylate, sodium thiosalicylate, sulindac, suprofen, tenidap, tenoxicam, tiaprofenic acid, tolmetin, tramadol, trolamine salicylate, zomepirac, or the like. Further non-limiting examples of active agents include energy (e.g., chemical energy, electrical resistance, laser energy, terahertz energy, microwave energy, optical energy, radio frequency energy, sonic energy, thermal energy, thermal resistance heating energy or ultrasonic energy, or the like)-activatable active agents, and the like.

In an embodiment, the active agent includes at least one active agent that selectively targets bacteria. For example, in an embodiment, the active agent includes at least one bacteriophage that can, for example, selectively target bacteria. Bacteriophages generally comprise an outer protein hull enclosing genetic material. The genetic material can be ssRNA, dsRNA, ssDNA, or dsDNA. Bacteriophages are generally smaller than the bacteria they destroy generally ranging from about 20 nm to about 200 nm. Non-limiting examples of bacteriophages include T2, T4, T6, phiX-174, MS2, or the like). In an embodiment, the active agent includes at least one energy-activatable agent that selectively targets bacteria. For example, in an embodiment, the active agent includes at least one triplet excited-state photosensitizer that can, for example, selectively target bacteria.

Further non-limiting examples of active agents include triplet excited-state photosensitizers, reactive oxygen species, reactive nitrogen species, any other inorganic or organic ion or molecules that include oxygen ions, free radicals, peroxides, or the like. Further non-limiting examples of active agents include compounds, molecules, or treatments that elicit a biological response from any biological subject. Further non-limiting examples of disinfecting agents include therapeutic agents (e.g., antimicrobial therapeutic agents), pharmaceuticals (e.g., a drug, a therapeutic compound, pharmaceutical salts, or the like) non-pharmaceuticals (e.g., a cosmetic substance, or the like), neutraceuticals, antioxidants, phytochemicals, homeopathic agents, and the like. Further non-limiting examples of disinfecting agents include peroxidases (e.g., haloperoxidases such as chloroperoxidase, or the like), oxidoreductase (e.g., myeloperoxidase, eosinophil peroxidase, lactoperoxidase, or the like) oxidases, and the like.

Further non-limiting examples of active agents include one or more pore-forming toxins. Non limiting examples of pore-forming toxins include beta-pore-forming toxins, e.g., hemolysin, Panton-Valentine leukocidin S, aerolysin, Clostridial epsilon-toxin; binary toxins, e.g., anthrax, *C. perfringens* Iota toxin, *C. difficile* cytolethal toxins; cholesterol-dependent cytolysins; pneumolysin; small pore-forming toxins; and gramicidin A.

Further non-limiting examples of active agents include one or more pore-forming antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. More than 800 different antimicrobial peptides have been identified or predicted from nucleic acid sequences, a subset of which are available in a public database (see, e.g., Wang & Wang, *Nucleic Acids Res.* 32:D590-D592, 2004); http://aps.unmc.edu/AP/main.php, which is incorporated herein by reference). More specific examples of antimicrobial peptides include, but are not limited to, anionic peptides, e.g., maximin H5 from amphibians, small anionic peptides rich in glutamic and aspartic acids from sheep, cattle and humans, and dermcidin from humans; linear cationic alpha-helical peptides, e.g., cecropins (A), androvin, moricin, ceratotoxin, and melittin from insects, cecropin P1 from *Ascaris* nematodes, magainin 2, dermaseptin, bombinin, brevinin-1, esculentins and buforin II from amphibians, pleurocidin from skin mucous secretions of the winter flounder, seminalplasmin, BMAP, SMAP (SMAP29, ovispirin), PMAP from cattle, sheep and pigs, CAP 18 from rabbits and LL37 from humans; cationic peptides enriched for specific amino acids, e.g., praline-containing peptides including abaecin from honeybees, praline- and arginine-containing peptides including apidaecins from honeybees, drosocin from *Drosophila*, pyrrhocoricin from European sap-sucking bug, bactenicins from cattle (Bac7), sheep and goats and PR-39 from pigs, praline- and phenylalanine-containing peptides including prophenin from pigs, glycine-containing peptides including hymenoptaecin from honeybees, glycine- and praline-containing peptides including coleoptericin and holotricin from beetles, tryptophan-containing peptides including indolicidin from cattle, and small histidine-rich salivary polypeptides, including histatins from humans and higher primates; anionic and cationic peptides that contain cysteine and from disulfide bonds, e.g., peptides with one disulphide bond including brevinins, peptides with two disulfide bonds including alpha-defensins from humans (HNP-1, HNP-2, cryptidins), rabbits (NP-1) and rats, beta-defensins from humans (HBD1, DEFB118), cattle, mice, rats, pigs, goats and poultry, and rhesus theta-defensin (RTD-1) from rhesus monkey, insect defensins (defensin A); and anionic and cationic peptide fragments of larger proteins, e.g., lactoferricin from lactoferrin, casocidin 1 from human casein, and antimicrobial domains from bovine alpha-lactalbumin, human hemoglobin, lysozyme, and ovalbumin (see, e.g., Brogden, *Nat. Rev. Microbiol.* 3:238-250, 2005, which is incorporated herein by reference).

Further non-limiting examples of active agents include antibacterial drugs. Non-limiting examples of antibacterial drugs include beta-lactam compounds such as penicillin, methicillin, nafcillin, oxacillin, cloxacillin, dicloxacillin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxime, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, silfamethizole, sulfadiazine, sulfamethoxazole, sulfapyridine, and sulfadoxine; fluoroquinolones such as ciprofloxacin, gatifloxacin, gemifloxacin, levofloxacin, lomefloxacin, moxifloxacin, norfloxacin, and ofloxacin; antimycobacteria drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole.

Further non-limiting examples of active agents include antifungal agents. Non-limiting examples of antifungal agents include anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

Further non-limiting examples of active agents include anti-parasite agents. Non-limiting examples of anti-parasite agents include antimalaria drugs such as chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins; treatments for amebiasis such as metronidazole, iodoquinol, paromomycin, diloxanide furoate, pentamidine, sodium stibogluconate, emetine, and dehydroemetine; and other anti-parasite agents such as pentamidine, nitazoxanide, suramin, melarsoprol, eflornithine, nifurtimox, clindamycin, albendazole, and tinidazole. Further non-limiting examples of active agents include ionic silver, (SilvaSorb®, Medline Industries, Inc), anti-microbial silver compositions (Arglaes®, Medline Industries, Inc), or the like. Further non-limiting examples of active agents include superoxide-forming compositions. Further non-limiting examples of active agents include oxazolidinones, gram-positive antibacterial agents, or the like. See, e.g., U.S. Pat. No. 7,322,965 (issued Jan. 29, 2008), which is incorporated herein by reference. In an embodiment, the active agent includes one or more antimicrobial agents. In an embodiment, the antimicrobial agent is an antimicrobial peptide. Amino acid sequence information for a subset of these can be found as part of a public database (see, e.g., Wang & Wang, *Nucleic Acids Res.* 32:D590-D592, 2004); http://aps.unmc.edu/AP/main.php, which is incorporated herein by reference). Alternatively, a phage library of random peptides can be used to screen for peptides with antimicrobial properties against live bacteria, fungi and/or parasites. The DNA sequence corresponding to an antimicrobial peptide can be generated ex vivo using standard recombinant DNA and protein purification techniques.

In an embodiment, one or more of the active agent include chemicals suitable to disrupt or destroy cell membranes. For example, some oxidizing chemicals can withdraw electrons from a cell membrane causing it to, for example, become destabilized. Destroying the integrity of cell membranes of, for example, a pathogen can lead to cell death.

In an embodiment, the implantable device 102 includes one or more active agent assemblies 800 configured to deliver at least one active agent from the at least one reservoir 802 to at least one of a region proximate an outer and an inner surface of the implantable device 102. In an embodiment, at least one of the one or more active agent assemblies 800 is configured to deliver one or more active agents in a spatially patterned distribution. In an embodiment, at least one of the one or more active agent assemblies 800 is configured to deliver one or more active agents in a temporally patterned distribution. In an embodiment, the implantable device 102 includes a plurality of spaced apart release ports 808 adapted to deliver one or more active agents in a spatially patterned distribution. In an embodiment, the implantable device 102 includes a plurality of spaced apart controllable-release ports 808 adapted to deliver one or more active agents in a spatially patterned distribution. In an embodiment, a controller 402 is operably coupled to the active agent assembly 800 and configured to control at least one of an active agent delivery rate, an active agent delivery amount, a active agent delivery composition, a port release rate, a port release amount, and a port release pattern. In an embodiment, the controller 402 is operably coupled to the active agent assembly and configured to actively control one or more of the plurality of spaced apart release ports. In an embodiment, at least one controller 402 is operably coupled to one or more of the spaced-apart controllable-release ports 808 and configured to control at least one of a port release rate, a port release amount, and a port release pattern associated with a delivery of the one or more active agents. In an embodiment, at least one processor 404 is operably coupled to the active agent assembly 800 and configured to control at least one of a port release rate, a port release amount, and a port release pattern associated with the delivery of the one or more active agents from the at least one active agent reservoir 810 to an interior of at least one of the one or more fluid-flow passageways 106.

In an embodiment, at least one controller 402 is operably coupled to one or more of the plurality of spaced apart release ports 808 and configured to actuate one or more of the plurality of spaced apart release ports 808 between an active agent discharge state and an active agent retention state. In an embodiment, the implantable device 102 includes one or more active agent assemblies 800 including one or more active agent reservoirs 810 configured to deliver at least one active agent from the at least one active agent reservoirs 810 to at least one of a region 804 proximate an outer surface 108 and a region 806 proximate an inner surface 110 of the implantable device 102.

In an embodiment, the active agent assembly 800 comprises a disinfecting agent assembly including at least one disinfecting agent reservoir 812. In an embodiment, the disinfecting agent assembly is configured to deliver one or more disinfecting agents from the at least one disinfecting agent reservoir 812 to an interior of at least one of the one or more fluid-flow passageways 106. In an embodiment, the active agent assembly 800 comprises an energy-activatable agent assembly including at least one energy-activatable agent reservoir 814. In an embodiment, the energy-activatable agent assembly is configured to deliver one or more energy-activatable agents from the at least one energy-activatable agent reservoir 814 to an interior of at least one of the one or more fluid-flow passageways 106.

In an embodiment, the implantable device 102 includes one or more active agent assemblies 800 configured to deliver at least one energy-activatable agent from at least one reservoir 802 to, for example, an interior of one or more fluid-flow passageways 106. Non-limiting examples of energy-activatable active agents include radiation absorbers, light energy absorbers, X-ray absorbers, photoactive agents, and the like. Non-limiting examples of photoactive agents include, but are not limited to photoactive antimicrobial agents (e.g., eudistomin, photoactive porphyrins, photoactive $TiO_2$, antibiotics, silver ions, antibodies, nitric oxide, or the like), photoactive antibacterial agents, photoactive antifungal agents, and the like. Further non-limiting examples of energy-activatable agent includes energy-activatable disinfecting agents, photoactive agents, or a metabolic precursor thereof. In an embodiment, the at least one energy-activatable agent includes at least one X-ray absorber. In an embodiment, the at least one energy-activatable agent includes at least one radiation absorber.

In an embodiment, the active agent assembly 800 is configured to deliver at least one energy-activatable disinfecting agent from at least one reservoir 802 to a biological fluid 808 received within one or more fluid-flow passageways 106. In an embodiment, the implantable device 102 includes one or more active agent assemblies 800 configured to deliver at least one energy-activatable disinfecting agent from the at least one active agent reservoir to tissue 810 proximate at least one surface of the implantable device 102. In an embodiment, at least one of the one or more active agent assemblies 800 is configured to deliver at least one energy-activatable disinfecting agent in a spatially patterned distribution. In an embodiment, the active agent assembly 800 is configured to deliver at least one energy-activatable steroid to tissue proximate the at least one outer surface 108 of the implantable device 102.

The at least one active agent reservoir 802 can include, for example, but not limited to an acceptable carrier. In an embodiment, at least one active agent is carried by, encapsulated in, or forms part of, an energy-sensitive (e.g., energy-activatable), carrier, vehicle, vesicle, pharmaceutical vehicle, pharmaceutical carrier, pharmaceutically acceptable vehicle, pharmaceutically acceptable carrier, or the like.

Non-limiting examples of carriers include any matrix that allows for transport of, for example, a disinfecting agent across any tissue, cell membranes, and the like of a biological subject, or that is suitable for use in contacting a biological subject, or that allows for controlled release formulations of the compositions disclosed herein. Further non-limiting examples of carriers include at least one of creams, liquids, lotions, emulsions, diluents, fluid ointment bases, gels, organic and inorganic solvents, degradable or non-degradable polymers, pastes, salves, vesicle, and the like. Further non-limiting examples of carriers include cyclic oligosaccharides, ethasomes, hydrogels, liposomes, micelle, microspheres, nisomes, non-ionic surfactant vesicles, organogels, phospholipid surfactant vesicles, phospholipid surfactant vesicles, transfersomes, virosomes. Further non-limiting examples of energy-sensitive carriers and the like include electrical energy-sensitive, light sensitive, pH-sensitive, ion-sensitive, sonic energy sensitive, ultrasonic energy sensitive carriers.

In an embodiment, one or more active agents are carried by energy-sensitive vesicles (e.g., energy-sensitive cyclic oligosaccharides, ethasomes, hydrogels, liposomes, micelles, microspheres, nisomes, non-ionic surfactant vesicles, organogels, phospholipid surfactant vesicles, transfersomes, virosomes, and the like.). In an embodiment, at least one of the one or more energy emitters 302 is configured to provide energy of a character and for a time sufficient to liberate at least a portion of an active agent carried by the energy-sensitive vesicles.

In an embodiment, the implantable device 102 includes one or more biological fluid reservoirs. In an embodiment, the implantable device 102 includes one or more biological specimen reservoirs. In an embodiment, the implantable device 102 includes one or more cerebrospinal fluid reservoirs. In an embodiment, the implantable device 102 includes one or more active agent assemblies 800 configured to receive one or more biological fluids. In an embodiment, the biological fluid reservoir is placed under the scalp of a user. In an embodiment, the biological fluid reservoir is configured to allow for the removal of cerebrospinal fluid with a syringe. In an embodiment, the reservoir is configured to detect bacteria, cancer cells, blood, or proteins of a fluid sample received within. In an embodiment, the biological fluid reservoir is configured to allow the injection or introduction of antibiotics for cerebrospinal fluid infection or chemotherapy medication. In an embodiment, the reservoir includes circuitry configured to detect at least one physical quantity, environmental attribute, or physiologic characteristic associated with, for example, a shunting process.

In an embodiment, the one or more active agent assemblies 800 are configured to deliver one or more tracer agents. In an embodiment, the implantable device 102 includes one or more active agent assemblies 800 configured to deliver at least one tracer agent from at least one reservoir 802. In an embodiment, the implantable device 102 includes one or more active agent assemblies 800 including one or more tracer agent reservoirs 810 configured to deliver at least one tracer agent. In an embodiment, active agent assembly 800 is further configured to concurrently or sequentially deliver one or more tracer agents and one or more energy-activatable disinfecting agents. In an embodiment, the active agent assembly 800 is further configured to deliver one or more tracer agents for indicating the presence or concentration of one or more energy-activatable disinfecting agents in at least a region proximate the implantable device 102. In an embodiment, the active agent assembly 800 is further configured to deliver one or more tracer agents for indicating the response of the one or more energy-activatable disinfecting agents to energy emitted from the one or more energy-emitting emitters 302.

Among tracer agents, examples include one or more in vivo clearance agents, magnetic resonance imaging agents, contrast agents, dye-peptide compositions, fluorescent dyes, or tissue specific imaging agents. In an embodiment, the one or more tracer agents include at least one fluorescent dye. In an embodiment, the one or more tracer agents include indocyanine green.

In an embodiment, at least one of the one or more fluid-flow passageways 106 includes a photoactive agent. In an embodiment, at least one of the one or more fluid-flow passageways 106 includes a photoactive coating material. In an embodiment, at least one of the one or more fluid-flow passageways 106 includes a photoactive agent configured to emit ultraviolet light energy in the presence of an energy stimulus. In an embodiment, at least one of the one or more fluid-flow passageways 106 includes a photoactive agent configured to emit ultraviolet light energy in the presence of an electrical potential. In an embodiment, at least one of the one or more fluid-flow passageways 106 includes a photoactive agent having one or more photoabsorption bands in the visible region of the electromagnetic spectrum.

Figure 9:
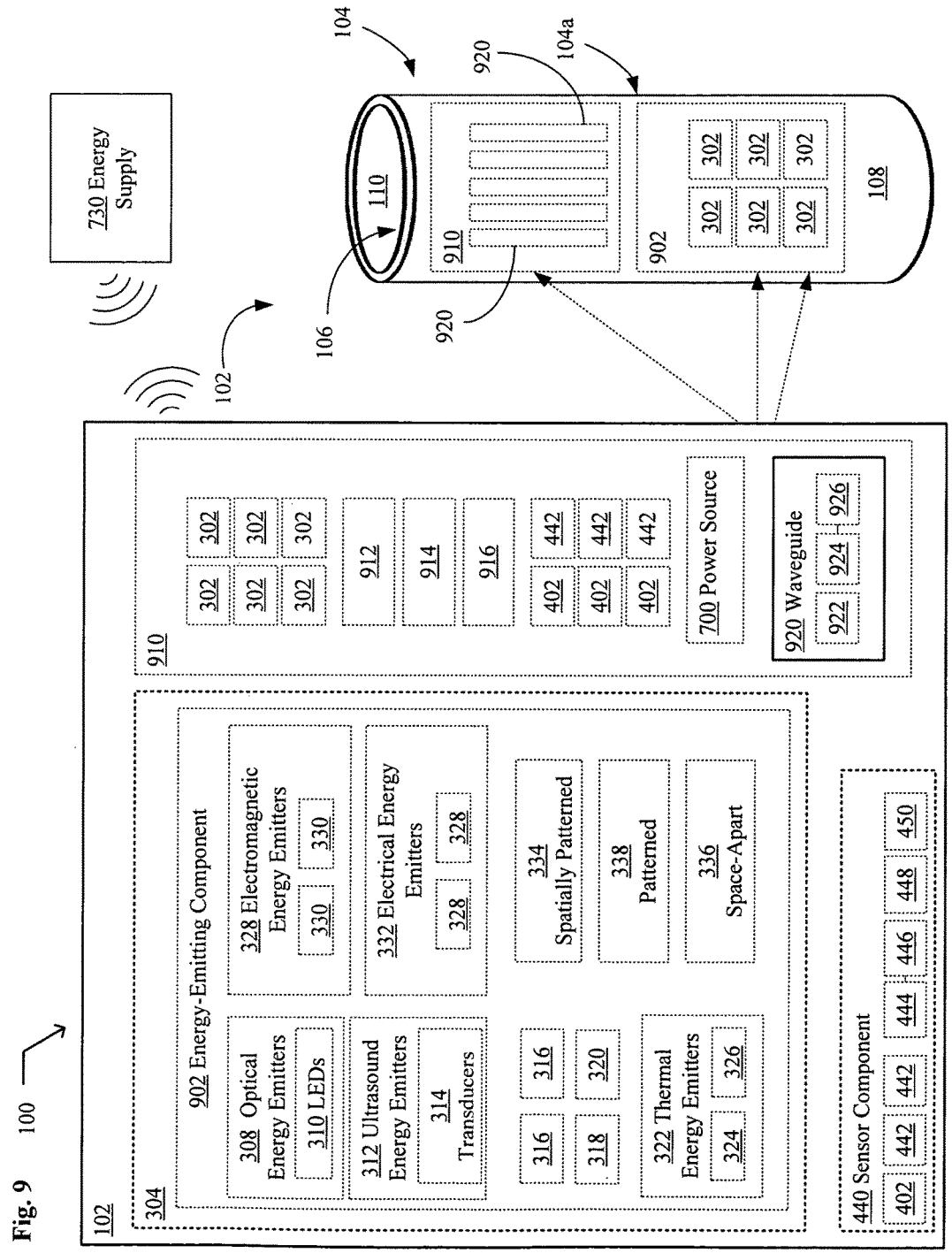
FIG. 9 is a schematic diagram of a system including an implantable device according to one illustrated embodiment.

Referring to FIG. 9, in an embodiment, the system 100 includes at least one energy-emitting component 902. Among energy-emitting components 902 examples include, but are not limited to, electric circuits, electrical conductors, electrodes (e.g., nano- and micro-electrodes, patterned-electrodes, electrode arrays (e.g., multi-electrode arrays, microfabricated multi-electrode arrays, patterned-electrode arrays, or the like), electrocautery electrodes, or the like), cavity resonators, conducting traces, ceramic patterned electrodes, electro-mechanical components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency UV light-emitting diodes, or the like), arc flashlamps, incandescent emitters, transducers, heat sources, continuous wave bulbs, a quantum dot, ultrasound emitting elements, ultrasonic transducers, thermal energy emitting elements, and the like.

In an embodiment, the at least one energy-emitting component 902 is configured to provide an energy stimulus. In an embodiment, the energy-emitting component 902 includes a patterned-energy emitting source 338. In an embodiment, the energy-emitting component 902 includes one or more energy emitters 302.

In an embodiment, the at least one energy-emitting component 902 includes a plurality of electrodes 330, the plurality of electrodes 330 configured to provide a spatially patterned sterilizing energy stimulus. In an embodiment, the at least one energy-emitting component 902 includes a plurality of light emitting diodes 310 configured to provide a spatially patterned sterilizing energy stimulus. In an embodiment, the at least one energy-emitting component 902 is configured to provide an illumination pattern comprising at least a first region and a second region, the second region having at least one of an illumination intensity, an energy-emitting pattern, a peak emission wavelength, an ON-pulse duration, an OFF-pulse duration, and a pulse frequency different from the first region. In an embodiment, the at least one energy-emitting component 902 is configured to deliver electromagnetic radiation of a character and for a time sufficient to induce PCD without substantially inducing necrosis of a tissue proximate the outer portion of the one or more fluid-flow passageways 106. In an embodiment, the at least one energy-emitting component 902 configured to deliver a sufficient amount of an ultraviolet radiation to induce cell death by PCD. In an embodiment, the at least one energy-emitting component 902 is configured to deliver an effective dose of optical energy at which a cell preferentially undergoes PCD compared to necrosis. In an embodiment, the at least one energy-emitting component 902 is configured to deliver a sufficient amount of an optical energy to initiate ultraviolet energy induced PCD. In an embodiment, the at least one energy-emitting component 902 includes at least one ultraviolet energy emitter. In an embodiment, the at least one energy-emitting component 902 includes at least one ultraviolet B energy emitter. In an embodiment, the at least one energy-emitting component 902 includes at least one ultraviolet C energy emitter. In an embodiment, the at least one energy-emitting component 902 comprises a peak emission wavelength ranging from about 100 nanometers to about 400 nanometers. In an embodiment, energy-emitting component 902 comprises a peak emission wavelength ranging from about 100 nanometers to about 320 nanometers. In an embodiment, energy-emitting component 902 comprises a peak emission wavelength ranging from about 280 nanometers to about 320 nanometers.

In an embodiment, the system 100 includes at least one actively controllable excitation component 910 including one or more energy emitters 302. In an embodiment, the actively controllable excitation component 910 is configured to deliver at least one of an electromagnetic sterilizing energy stimulus, an electrical sterilizing energy stimulus, an ultrasonic sterilizing energy stimulus, and a thermal sterilizing energy stimulus. In an embodiment, the actively controllable excitation component 910 is operable to emit a sterilizing energy stimulus having one or more peak emission wavelengths in the infrared, visible, or ultraviolet spectrum, or combinations thereof. In an embodiment, the actively controllable excitation component 910 includes one or more energy emitters 302 configured to deliver at least one of an electrical sterilizing energy stimulus, an electromagnetic sterilizing energy stimulus, an ultrasonic sterilizing energy stimulus, and a thermal sterilizing energy stimulus of sufficient strength or duration to attenuate an activity of an infectious agent proximate the outer portion of the one or more fluid-flow passageways. In an embodiment, the actively controllable excitation component 910 includes one or more energy emitters 302 configured to deliver at least one of an electrical sterilizing energy stimulus, an electromagnetic sterilizing energy stimulus, an ultrasonic sterilizing energy stimulus, and a thermal sterilizing energy stimulus of sufficient strength or duration to cause the death of one or more pathogens proximate the outer portion of the one or more fluid-flow passageways. In an embodiment, the actively controllable excitation component 910 includes one or more energy emitters 302 configured to deliver a sufficient amount of at least one of an electrical sterilizing energy stimulus, an electromagnetic sterilizing energy stimulus, an ultrasonic sterilizing energy stimulus, and a thermal sterilizing energy stimulus, in vivo, to induce PCD without substantially inducing necrosis of an infectious agent proximate the outer portion of the one or more fluid-flow passageways.

In an embodiment, the actively controllable excitation component 910 includes a spatially patterned energy-emitting element 912 configured to provide a spatially patterned energy stimulus. In an embodiment, the actively controllable excitation component 304 includes a spatially patterned energy-emitting element configured to provide a spatially patterned energy stimulus, the spatially patterned energy-emitting element 912 having a plurality of spaced apart energy emitters 302. In an embodiment, the actively controllable excitation component 910 includes at least one energy-emitting component 902, the at least one energy-emitting component 902 configured to provide a spatially patterned light energy stimulus.

In an embodiment, the actively controllable excitation component 910 includes one or more spatially patterned energy-emitting elements 914 configured to provide a spatially patterned energy stimulus. In an embodiment, at least one spatially patterned energy-emitting element 914 includes a plurality of spaced-apart energy emitters 202. The actively controllable excitation component 910 can include, but is not limited to, at least one patterned electrode 916. In an embodiment, at least one patterned electrode 916 is configured to provide a spatially patterned energy stimulus. In an embodiment, the power source 902 is electromagnetically, magnetically, ultrasonically, optically, inductively, electrically, or capacitively coupleable to the actively controllable excitation component 910.

In an embodiment, the implantable device 102 includes one or more actively controllable excitation components 910 configured to deliver and energy stimulus to a region proximate at least one of an outer surface 108 and an inner surface 110 of the body structure 104. In an embodiment, the implantable device 102 includes one or more actively controllable excitation components 910 configured to deliver and energy stimulus to an interior of one or more fluid-flow passageways 106. In an embodiment, the implantable device 102 includes one or more actively controllable excitation components 304 configured to deliver and energy stimulus to an exterior of the body structure 104. In an embodiment, the implantable device 102 includes one or more actively controllable excitation components 910 configured to deliver energy to a region within the biological subject. In an embodiment, an average integrated energy flux of the actively controllable excitation component 910 is less than about 80 milli-joules per square centimeter. In an embodiment, average integrated energy flux of the actively controllable excitation component 910 is less than about 35 milli-joules per square centimeter. In an embodiment, an average integrated energy flux of the actively controllable excitation component 910 is less than about 15 milli-joules per square centimeter. In an embodiment, an average energy density of the actively controllable excitation component 910 ranges from about less than about 15 milli-joules per square centimeter to about less than about 80 milli-joules per square centimeter.

In an embodiment, the system 100 includes at least one controller 402 operably coupled to the actively controllable excitation component 910. In an embodiment, the at least one controller 402 is configured to control at least one parameter associated with the delivery of the energy stimulus. In an embodiment, the system 100 includes at least one sensor 442 and at least one controller 402 operably coupled to the actively controllable excitation component 910. In an embodiment, the at least one controller 402 is configured to control at least one parameter associated with the delivery of the energy stimulus based on a detected parameter.

In an embodiment, actively controllable excitation component 910 is configured to reduce the concentration of an infectious agent in the immediate vicinity of an implant. In an embodiment, the actively controllable excitation component 910 is operable to concurrently or sequentially deliver at least a first sterilizing energy stimulus and a second sterilizing energy stimulus, in vivo, to tissue proximate the first outer surface 108. In an embodiment, at least one of the first sterilizing energy stimulus and the second sterilizing energy stimulus comprises a peak emission wavelength in the x-ray, ultraviolet, visible, infrared, near infrared, terahertz, microwave, or radio frequency spectrum; and a controller 402 communicatively coupled to the actively controllable excitation component 910, the controller 402 configured to regulate at least one parameter associated with the delivery of a sterilizing energy stimulus.

In an embodiment, the second energy stimulus comprises at least one of an illumination intensity, an energy-emitting pattern, a peak emission wavelength, an ON-pulse duration, an OFF-pulse duration, and a pulse frequency different from the first energy stimulus. In an embodiment, the actively controllable excitation component 910 is configured to concurrently or sequentially generate at least a first sterilizing energy stimulus and a second sterilizing energy stimulus. In an embodiment, one or more controllers 402 are configured to control at least one parameter associated with the delivery of at least one of the first sterilizing energy stimulus and the second sterilizing energy stimulus. For example, in an embodiment, at least one controller 402 is configured to control at least one of an excitation intensity, an excitation frequency, an excitation pulse frequency, an excitation pulse ratio, an excitation pulse intensity, an excitation pulse duration time, and an excitation pulse repetition rate associated with the delivery of at least one of the first sterilizing energy stimulus and the second sterilizing energy stimulus. In an embodiment, at least one controller 402 is configured to control at least one of a first and a second sterilizing energy stimulus delivery regimen parameter, a temporal sterilizing energy stimulus delivery pattern parameter, a spaced-apart sterilizing energy stimulus delivery pattern parameter, a spatial electric field modulation parameter, a spatial electric field magnitude parameter, a spatial electric field distribution parameter, an ON-rate, or an OFF-rate associated with the delivery of at least one of the first sterilizing energy stimulus and the second sterilizing energy stimulus. In an embodiment, at least one controller 402 is configured to control at least one parameter associated with the delivery of the first sterilizing energy stimulus, and at least one other controller 402 is configured to control at least one parameter associated with the delivery of the second sterilizing stimulus.

In an embodiment, actively controllable excitation component 910 is energetically, electrically, photonically, thermally or ultrasonically coupleable, via one or more waveguides 920, to an exterior 108 of the implantable device 102. In an embodiment, actively controllable excitation component 910 is energetically, electrically, photonically, thermally or ultrasonically coupleable, via one or more waveguides 920, to an interior 110 of at least one of the one or more fluid-flow passageways 106. In an embodiment, actively controllable excitation component 910 includes at least one of an ultrasonic energy waveguide 922, an optical energy waveguide 924, an electromagnetic energy waveguide 926, and the like.

In an embodiment, the actively controllable excitation component 910 is configured to provide a voltage across a region proximate the implantable device 102 from a power source 700 coupled to the implantable device 102. In an embodiment, the voltage is sufficient to exceed a nominal dielectric strength of a cell plasma membrane without substantially interfering with a normal operation of the implantable device 102. In an embodiment, the voltage is sufficient to reduce the concentration of an infectious agent in the immediate vicinity of an implant.

Figure 10:
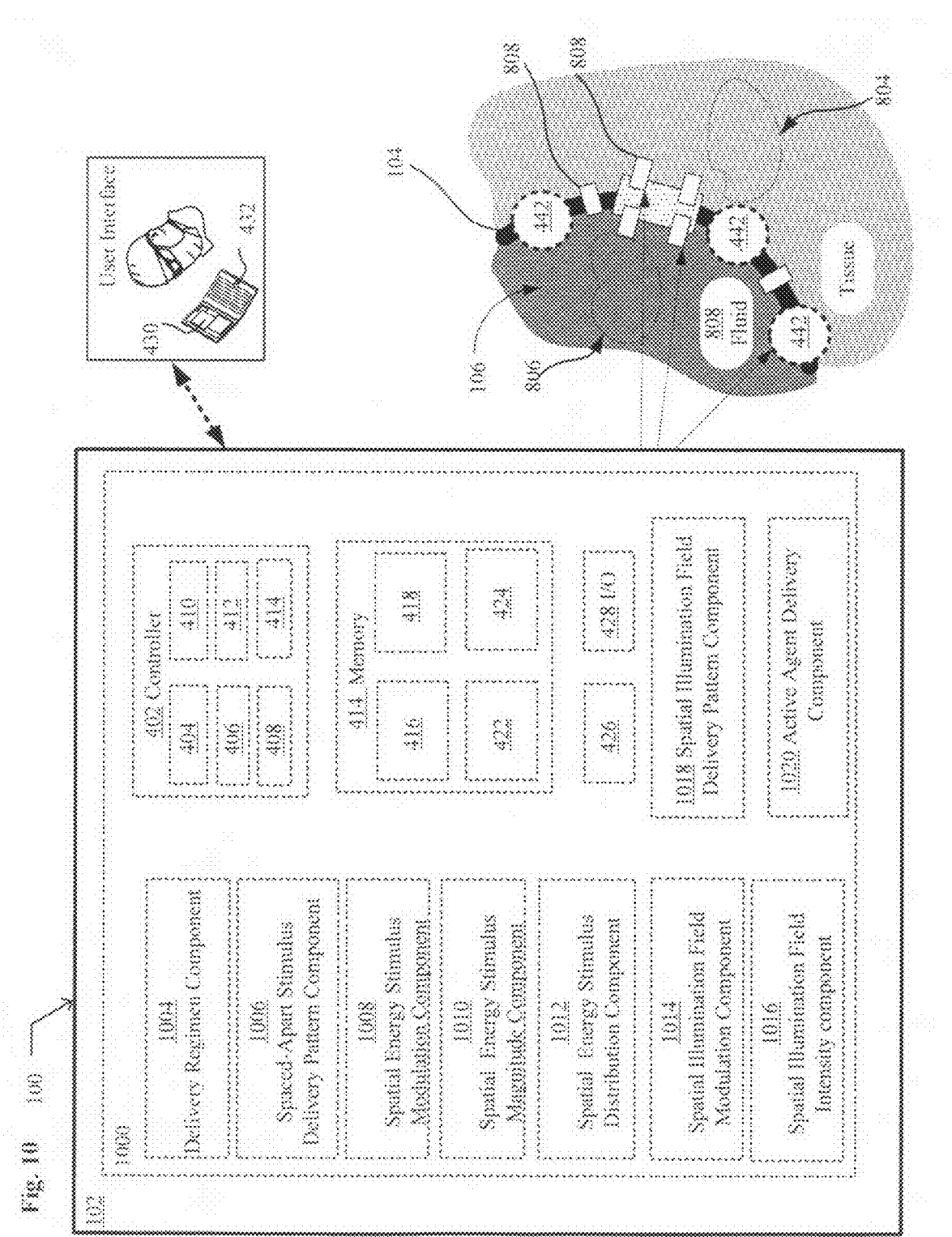
FIG. 10 is a schematic diagram of a system including an implantable device according to one illustrated embodiment.

Referring to FIG. 10, in an embodiment, the system 100 includes a control means 1000. The control means 1000 can include for example, but not limited to, electrical, electro-mechanical, software, firmware, or other control components, or combinations thereof. In an embodiment, the control means 1000 includes electrical circuitry configured to for example, but not limited to, control at least one of an energy stimulus delivery regimen parameter, a temporal sterilizing energy stimulus delivery pattern parameter, a spaced-apart energy stimulus delivery pattern parameter, a spatial energy stimulus modulation parameter, a spatial energy stimulus magnitude parameter, and a spatial energy stimulus distribution parameter associated with the delivery of the energy stimulus. In an embodiment, the control means 1000 includes electrical circuitry configured to for example, but not limited to, control the one or more controllable-release ports configured to deliver the at least one scaffold-forming material to the first outer surface 108. Further non-limiting examples of circuitry can be found, among other things, in U.S. Pat. No. 7,236,821 (issued Jun. 26, 2001), the contents of which is incorporated herein by reference.

In a general sense, those skilled in the art will recognize that the various aspects described herein (which can be implemented, individually and/or collectively, by a wide range of hardware, software, firmware, and/or any combination thereof) can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein can be implemented in an analog or digital fashion or some combination thereof.

In an embodiment, the control means 1000 includes one or more electro-mechanical systems configured to for example, control at least one of a sterilizing stimulus delivery regimen parameter, a temporal sterilizing energy stimulus delivery pattern parameter, a spaced-apart sterilizing stimulus delivery pattern parameter, a spatial sterilizing stimulus modulation parameter, a spatial sterilizing stimulus magnitude parameter, and a spatial sterilizing stimulus distribution parameter associated with the delivery of the sterilizing stimulus. In an embodiment, the control means 1000 includes one or more electro-mechanical systems configured to for example, but not limited to, control the one or more controllable-release ports configured to deliver the at least one active agent to the first outer surface 108. In a general sense, the various embodiments described herein can be implemented, individually and/or collectively, by various types of electro-mechanical systems having a wide range of electrical components such as hardware, software, firmware, and/or virtually any combination thereof; and a wide range of components that can impart mechanical force or motion such as rigid bodies, spring or torsional bodies, hydraulics, electro-magnetically actuated devices, and/or virtually any combination thereof.

Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Non-limiting examples of electro-mechanical systems include a variety of consumer electronics systems, medical devices, as well as other systems such as motorized transport systems, factory automation systems, security systems, and/or communication/computing systems. The term, electro-mechanical, as used herein is not necessarily limited to a system that has both electrical and mechanical actuation except as context may dictate otherwise.

In an embodiment, the system 100 includes a control means 1000 for operably coupling to at least one of a plurality of energy emitters 302, an energy emitting component 902, an actively controllable excitation component 910, and the like. In an embodiment, the control means 1000 is operable to control at least one component associated with the delivery of an energy stimulus. Such components can include for example, but not limited to, a delivery regimen component 1004, a spaced-apart energy stimulus delivery pattern component 1006, a spatial energy stimulus modulation component 1008, a spatial energy stimulus magnitude component 1010, a spatial energy stimulus distribution component 1012, or the like. In an embodiment, the control means 1000 is operable to control at least one of a spatial illumination field modulation component 1014, a spatial illumination field intensity component 1016, and a spatial illumination delivery pattern component 1018. In an embodiment, the control means 1000 is operable to control at least one sterilizing stimulus delivery regimen parameter selected from an excitation intensity, an excitation frequency, an excitation pulse frequency, an excitation pulse ratio, an excitation pulse intensity, an excitation pulse duration time, an excitation pulse repetition rate, an ON-rate, or an OFF-rate. A "duty cycle" includes, but is not limited to, a ratio of a pulse duration ($\tau$) relative to a pulse period (T). For example, a pulse train having a pulse duration of 10 as and a pulse signal period of 40 as, corresponds to a duty cycle (D=$\tau$/T) of 0.25. In an embodiment, the control means 1000 is operable to manage a duty cycle associated with emitting an effective amount of the electrical sterilizing stimulus from the actively controllable excitation component 910.

In an embodiment, the control means 1000 is operable to control at least one component 1020 associated with the delivery of an active agent. Such components can include for example, but not limited to, a delivery rate component, a delivery amount component, a delivery composition component, a port release rate component, a port release amount component, a port release pattern component, or the like.

The control means 1000 can include, but is not limited to, one or more controllers 402 such as a processor (e.g., a microprocessor) 404, a central processing unit (CPU) 406, a digital signal processor (DSP) 408, an application-specific integrated circuit (ASIC) 410, a field programmable gate array 412, and the like, and combinations thereof, and can include discrete digital and/or analog circuit elements or electronics. In an embodiment, the control means 1000 is configured to wirelessly couple to an implantable device 102 that communicates via wireless communication with the control means 1000. Non-limiting examples of wireless communication include optical connections, audio, ultraviolet connections, infrared, BLUETOOTH®, Internet connections, network connections, and the like.

In an embodiment, the control means 1000 includes at least one controller 402 and at least one sensor component 440. In an embodiment, the at least one controller 402 is communicably coupled to at least one of the actively controllable excitation component 910 and the sensor component 440, and is configured to control at least one parameter associated with the delivery of an energy stimulus based on detected information associated with the sensor component 440.

In an embodiment, the control means 1000 is operably coupled to the one or more sensors 442, and is configured to determine the at least one characteristic associated with the tissue proximate the implantable device 102. In an embodiment, the control means 1000 is configured to perform a comparison of the at least one characteristic associated with the tissue proximate the implantable device 102 to stored reference data, and to generate a response based at least in part on the comparison.

In an embodiment, the control means 1000 is operably coupled to the one or more sensors 442, and is configured to determine the at least one physiological characteristic of the biological subject. In an embodiment, the control means 1000 is configured to perform a comparison of the determined at least one physiological characteristic of the biological subject to stored reference data, and to generate a response based at least in part on the comparison. In an embodiment, the generated response includes at least one of a response signal, a change to a sterilizing stimulus parameter, a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, and a change in a sterilizing stimulus delivery regimen parameter.

In an embodiment, the control means 1000 includes at least one controller 402, which is communicably coupled to the actively controllable excitation component 910. In an embodiment, the control means 1000 is configured to control at least one of a duration time, an amount of energy, an excitation amount, an excitation type, a delivery location, and a spatial-pattern stimulation configuration associated with the delivery of the energy stimulus.

The control means 1000 can include, but is not limited to, one or more memories 414 that store instructions or data, for example, volatile memory (e.g., random access memory (RAM) 416, dynamic random access memory (DRAM), or the like) non-volatile memory (e.g., read-only memory (ROM) 418, electrically erasable programmable read-only memory (EEPROM), compact disc read-only memory (CD-ROM), or the like), persistent memory, and the like. Further non-limiting examples of one or more memories 414 include erasable programmable read-only memory (EPROM), flash memory, and the like. The one or more memories can be coupled to, for example, one or more controllers by one or more instruction, data, or power buses.

The control means 1000 can include a computer-readable media drive or memory slot 426, and one or more input/output components 428 such as, for example, a graphical user interface, a display, a keyboard, a keypad, a trackball, a joystick, a touch-screen, a mouse, a switch, a dial, and the like, and any other peripheral device. The control means 1000 can further include one or more databases 422, and one or more data structures 424. The computer-readable media drive or memory slot can be configured to accept computer-readable memory media. In an embodiment, a program for causing the system 100 to execute any of the disclosed methods can be stored on a computer-readable recording medium. Non-limiting examples of computer-readable memory media include CD-R, CD-ROM, DVD, flash memory, floppy disk, hard drive, magnetic tape, magnetooptic disk, MINIDISC, non-volatile memory card, EEPROM, optical disk, optical storage, RAM, ROM, system memory, web server, and the like.

In an embodiment, the control means 1000 is adapted to apply a potential across a plurality of energy emitters 302 having parameters selected to produce superoxide species in an interstitial fluid proximate the plurality of energy emitters 302 when the implantable device 102 is implanted within the biological subject. In an embodiment, the applied potential is sufficient to produce superoxide species in an interstitial fluid proximate the plurality of energy emitters 302 when the implantable device 102 is implanted within the biological subject.

Figure 11:
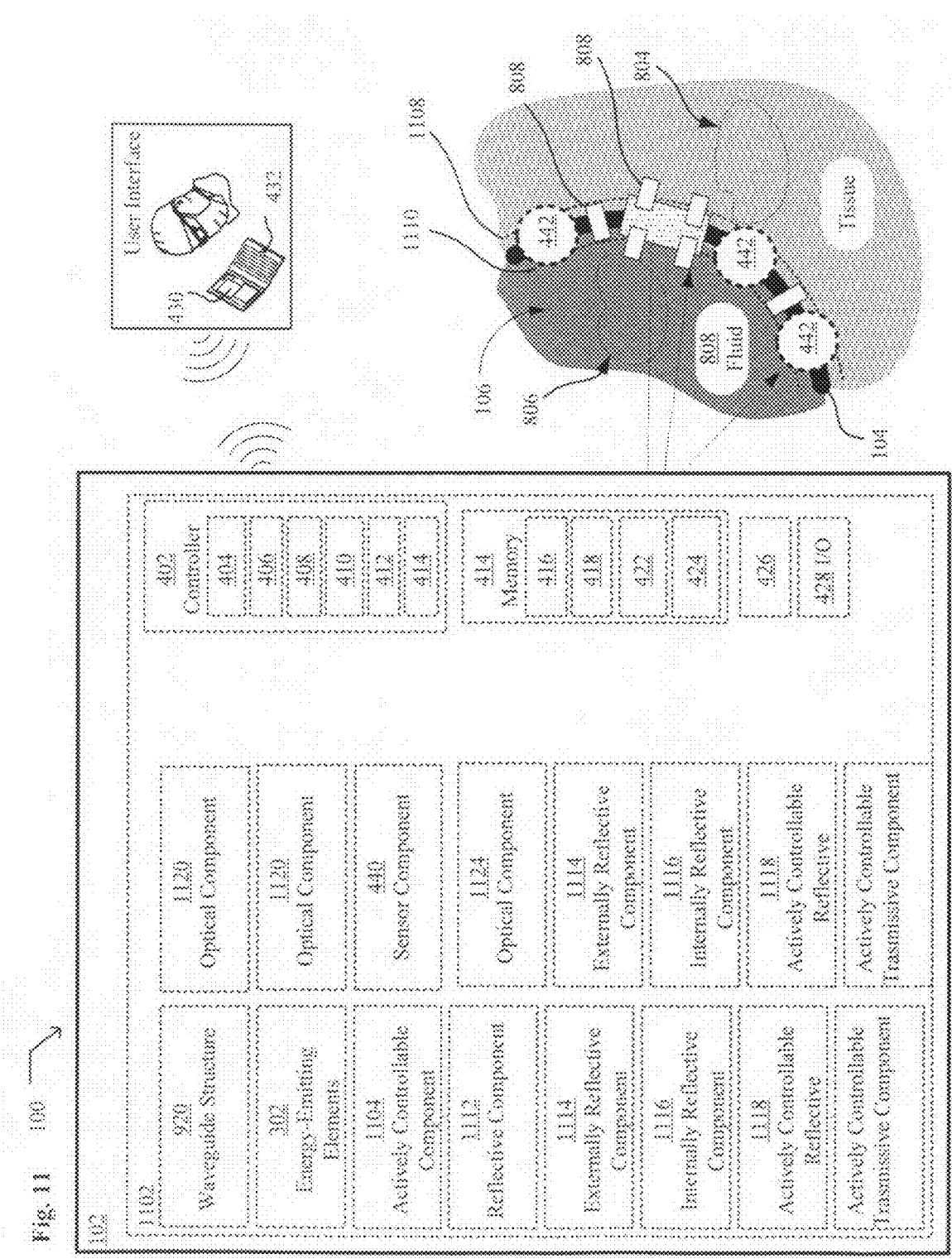
FIG. 11 is a schematic diagram of a system including an implantable device according to one illustrated embodiment.

FIG. 11 shows a system 100 in which one or more methodologies or technologies can be implemented such as, for example, managing a transport of biological fluids, delivering energy stimuli, and actively detecting, treating, or preventing an infection, or the like. In an embodiment, the implantable device 102 includes means for reflecting 1102 at least a portion of an emitted energy stimulus within an interior of at least one of the one or more fluid-flow passageways 106. In an embodiment, the means for reflecting 1102 an emitted energy stimulus includes one or more reflective materials, one or more waveguides 920, and one or more controllers 402. In an embodiment, the means for reflecting 1102 an emitted energy stimulus can include one or more mechanical components, electro-mechanical components for generating, transmitting, or receiving waves (e.g., ultrasonic waves, electromagnetic waves, or the like), or the like.

The one or more waveguides 920 can take a variety of shapes, configurations, and geometric including, but not limited to, cylindrical, conical, planar, parabolic, regular or irregular forms. In an embodiment, two or more optical waveguides 920 can be coupled (e.g., optically coupled) to form, for example, an array of waveguides 920. In an embodiment, the waveguide 920 comprises a laminate including one or more optically active coatings. In an embodiment, two or more optical waveguides 920 can be arranged to form a part of patterned energy emitting component. In an embodiment, multiple optical waveguides 920 are formed from a single substrate or structure. Waveguides 920 can include any structure suitable to directing electromagnetic energy waves. Non-limiting examples of waveguides 920 include electromagnetic waveguides, optical waveguides (e.g., optical fibers, photonic-crystal fibers, or the like), acoustic waveguides (e.g., ultrasonic energy waveguides), multi-energy waveguides, or the like. Further non-limiting examples of waveguides 920 include lens structures, light-diffusing structures, mirror structures, mirrored surfaces, reflective coatings, reflective materials, reflective surfaces, or combinations thereof. Further non-limiting examples of waveguides include etchings, facets, grooves, thin-films, optical micro-prisms, lenses (e.g., micro-lenses, or the like), diffusing elements, diffractive elements (e.g., gratings, cross-gratings, or the like), texturing, and the like.

In an embodiment, one or more energy emitters 302 are energetically coupled to the exterior or interior surfaces 108, 110 of a body structure 104 via one or more waveguides 920. In an embodiment, a portion of the exterior surface 108 or interior surface 110 of a body structure 104 includes a mirrored or reflective surfaces such as, for example, a film, a coating, an optically active coating, a mirrored or reflective substrate, or the like. In an embodiment, the one or more waveguides 920 include at least one of a transparent, translucent, or light-transmitting material, and combinations or composites thereof. Among transparent, translucent, or light-transmitting materials, examples include those materials that offer a low optical attenuation rate to the transmission or propagation of light waves. Examples of transparent, translucent, or light-transmitting materials include but are not limited to crystals, epoxies, glasses, borosilicate glasses, optically clear materials, semi-clear materials, plastics, thermo plastics, polymers, resins, thermal resins, and the like, or combinations or composites thereof. In an embodiment, the one or more waveguides 920 include at least one of an optically transparent, optically translucent, and light-transmitting component. In an embodiment, the one or more waveguides 920 include at least one optically transparent, translucent, or light-transmitting material.

Non-limiting examples of optically transparent, translucent, or light-transmitting material include one or more of acetal copolymers, acrylic, glass, AgBr, AgCl, $Al_2O_3$, GeAsSe glass, $BaF_2$, $CaF_2$, CdTe, AsSeTe glass, CsI, diamond, GaAs, Ge, ITRAN materials, KBr, thallium bromide-Iodide, LiF, $MgF_2$, NaCl, polyethylene, Pyrex, Si, $SiO_2$, ZnS, ZnSe, thermoplastic polymers, or thermoset polymers, or composites thereof.

Further non-limiting examples of optically transparent, translucent, or light-transmitting material include one or more of acrylonitrile butadaine styrene polymers, cellulosic, epoxy, ethylene butyl acrylate, ethylene tetrafluoroethylene, ethylene vinyl alcohol, fluorinated ethylene propylene, furan, nylon, phenolic, poly[2,2,4-trifluoro-5-trifluoromethoxy-1,3-dioxole-co-tetrafluoroethylene], poly[2,2-bistrifluoromethyl-4,5-difluoro-1,3-dioxole-co-tetrafluoroethylene], poly[2,3-(perfluoroalkenyl) perfluorotetrahydrofuran], polyacrylonitrile butadiene styrene, polybenzimidazole, polycarbonate, polyester, polyetheretherketone, polyetherimide, polyethersulfone, polyethylene, polyimide, polymethyl methacrylate, polynorbornene, polyperfluoroalkoxyethylene, polystyrene, polysulfone, polyurethane, polyvinyl chloride, polyvinylidene fluoride, diallyl phthalate, thermoplastic elastomer, transparent polymers, or vinyl ester, or composites thereof.

In an embodiment, at least a portion of a body structure 104 defining the one or more fluid-flow passageways 106 includes one or more actively controllable reflective or transmissive components 1104 configured to outwardly transmit or internally reflect an energy stimulus propagated through at least one of the one or more fluid-flow passageways 106. In an embodiment, a controller 402 is operably coupled to at least one of the one or more actively controllable reflective and transmissive components 1104. In an embodiment, a controller 402 is configured to cause an outward-transmission or internal-reflection of an energy stimulus propagated through at least one of the one or more fluid-flow passageways 106 based on, for example, detected information from a sensor component 440.

In an embodiment, the implantable device 102 includes means for reflecting at least a portion of an emitted energy stimulus within an interior of at least one of the one or more fluid-flow passageways 106. In an embodiment, the means for reflecting at least a portion of an emitted energy stimulus includes at least one waveguide 920, one or more energy emitters 302, and one or more controllers 402. In an embodiment, the implantable device 102 includes means for laterally reflecting or longitudinally reflecting electromagnetic radiation transmitted within an interior of at least one of the one or more fluid-flow passageways 106. In an embodiment, means for laterally reflecting or longitudinally reflecting electromagnetic radiation includes at least one waveguide 920, one or more energy emitters 302, and one or more controllers 402.

In an embodiment, at least a portion of a body structure 104 defining the one or more fluid-flow passageways 106 includes an optical material that permits the transmission of at least a portion of an emitted energy stimulus from an interior of at least one of the one or more fluid-flow passageways 106 to an exterior of at least one of the one or more fluid-flow passageways 106. In an embodiment, at least a portion of a body structure 104 defining the one or more fluid-flow passageways includes an optical material that internally reflects at least a portion of an emitted energy stimulus present within an interior of at least one of the one or more fluid-flow passageways 106. In an embodiment, at least a portion of a body structure 104 defining the one or more fluid-flow passageways 106 includes an optical material that internally reflects at least a portion of an emitted energy stimulus within an interior of at least one of the one or more fluid-flow passageways 106, without substantially permitting the transmission of the emitted energy stimulus through an exterior of the body structure.

In an embodiment, the implantable device 102 includes one or more optical materials forming at least a portion of a body structure 104 defining the one or more fluid-flow passageways 106. In an embodiment, the one or more optical materials are configured to limit an amount of the energy stimulus that can traverse within the one or more fluid-flow passageways 106 and through an outer surface 108 of the body structure 104. In an embodiment, the implantable device 102 includes one or more optical materials on at least a portion of a body structure 104 defining the one or more fluid-flow passageways 106 to internally reflect at least a portion of an emitted energy stimulus from the one or more energy emitters 302 into an interior of at least one of the one or more fluid-flow passageways 106. In an embodiment, the implantable device 102 includes at least one outer internally reflective coating 1108 on a body structure 104 defining the one or more fluid-flow passageways 106. In an embodiment, the implantable device 102 includes at least one inner internally reflective coating 1110 on a body structure 104 defining the one or more fluid-flow passageways 106.

In an embodiment, at least a portion of the one or more fluid-flow passageways 106 includes an optical material that internally directs at least a portion of an emitted energy stimulus along a substantially longitudinal direction of at least one of the one or more fluid-flow passageways 106. In an embodiment, at least a portion of the one or more fluid-flow passageways 106 includes an optical material that internally directs at least a portion of an emitted energy stimulus along a substantially lateral direction of at least one of the one or more fluid-flow passageways 106.

In an embodiment, at least one of the one or more fluid-flow passageways 106 includes a surface configured to laterally internally reflect or longitudinally internally reflect electromagnetic radiation transmitted therethrough. For example, in an embodiment, at least a portion of a body structure defining the one or more fluid-flow passageways 106 includes a reflective surface 1112 capable of reflecting at least about 50 percent of an energy stimulus emitted by the one or more energy emitters that impinges on the reflective surface. In an embodiment, at least a portion of a body structure defining the one or more fluid-flow passageways 106 includes a reflective surface 1112 that is reflective at a first wavelength and transmissive at a second wavelength different than the first wavelength. In an embodiment, at least one of the one or more fluid-flow passageways 106 includes one or more internally reflective components 1114 configured to manage a delivery of light to a biological fluid received within the one or more fluid-flow passageways 106, and to manage a collection of reflected light from the biological fluid.

In an embodiment, at least a portion of the one or more fluid-flow passageways 106 includes an optical component 1120 that directs a first portion of an emitted energy stimulus along a substantially lateral direction in one or more regions of at least one of the one or more fluid-flow passageways 106 and an optical component 1122 that directs a second portion of the emitted energy stimulus along a substantially longitudinal direction in one or more regions of at least one of the one or more fluid-flow passageways 106. In an embodiment, at least a portion of the one or more fluid-flow passageways 106 includes a first optical component configured to direct at least a portion of an emitted energy stimulus along a substantially lateral direction in a first region of at least one of the one or more fluid-flow passageways 106 and a second optical component configured to direct at least a portion of the emitted energy stimulus along a substantially lateral direction in a second region of the one or more fluid-flow passageways 106, the second region different from the first region. In an embodiment, at least a portion of the one or more fluid-flow passageways 106 includes a first optical component that directs at least a portion of an emitted energy stimulus along a substantially longitudinal direction in a first region of at least one of the one or more fluid-flow passageways 106 and a second optical component that directs at least a portion of the emitted energy stimulus along a substantially longitudinal direction in a second region of the one or more fluid-flow passageways 106, the second region different from the first region. In an embodiment, at least a portion of the one or more fluid-flow passageways 106 includes a first optical component configured to direct at least a portion of an emitted energy stimulus along a substantially lateral direction in a first region of at least one of the one or more fluid-flow passageways 106 and a second optical component configured to direct at least a portion of the emitted energy stimulus along a substantially lateral direction in a second region of the one or more fluid-flow passageways 106, the second region different from the first region.

In an embodiment, at least one of the one or more fluid-flow passageways 106 includes at least one of an outer surface and an inner surface that is reflective to at least one of electromagnetic energy, ultrasonic energy, and thermal energy. In an embodiment, at least one of the one or more fluid-flow passageways 106 includes an inner surface that is internally reflective to electromagnetic radiation. In an embodiment, at least one of the one or more fluid-flow passageways 106 includes a surface that is internally reflective to ultraviolet radiation. In an embodiment, at least one of the one or more fluid-flow passageways 106 includes a surface that is internally reflective to infrared radiation. In an embodiment, at least one of the one or more fluid-flow passageways 106 includes a surface having a reflective coating.

In an embodiment, at least one of the one or more fluid-flow passageways 106 includes a reflective material. In an embodiment, the reflective material comprises at least one of aluminum, barium sulfate, gold, silver, titanium dioxide, and zinc oxide. In an embodiment, at least one of the one or more fluid-flow passageways 106 includes an ultraviolet energy reflective material. In an embodiment, the ultraviolet energy reflective material comprises barium sulfate.

In an embodiment, at least a portion of a body structure 104 defining the one or more fluid-flow passageways 106 includes an optical transparent, optical translucent, or light-transmitting component 1124 that directs at least a portion of an emitted energy stimulus into an interior of at least one of the one or more fluid-flow passageways 106. In an embodiment, the optical transparent, optical translucent, or light-transmitting component 1124 includes one or more waveguides 920. In an embodiment, the optical transparent, optical translucent, or light-transmitting component 1124 includes one or more optical energy waveguides 920. In an embodiment, the optical transparent, optical translucent, or light-transmitting component 1124 comprises a light-transmitting material. In an embodiment, the optical transparent, optical translucent, or light-transmitting component 1124 comprises one or more optical fibers. In an embodiment, the optical transparent, optical translucent, or light-transmitting component 1124 extends substantially longitudinally along at least one of the one or more fluid-flow passageways 106. In an embodiment, the optical transparent, optical translucent, or light-transmitting component 1124 extends substantially laterally within at least one of the one or more fluid-flow passageways 106. In an embodiment, the optical transparent, optical translucent, or light-transmitting component 1124 extends substantially helically within at least one of the one or more fluid-flow passageways 106.

In an embodiment, the implantable device 102 includes one or more optical waveguides 920 received within at least one of the one or more fluid-flow passageways 106. In an embodiment, the one or more optical waveguides 920 are photonically coupleable to at least one of the one or more energy emitters 302 and configured to direct an emitted energy stimulus into an interior of at least one of the one or more fluid-flow passageways 106.

Figure 12:
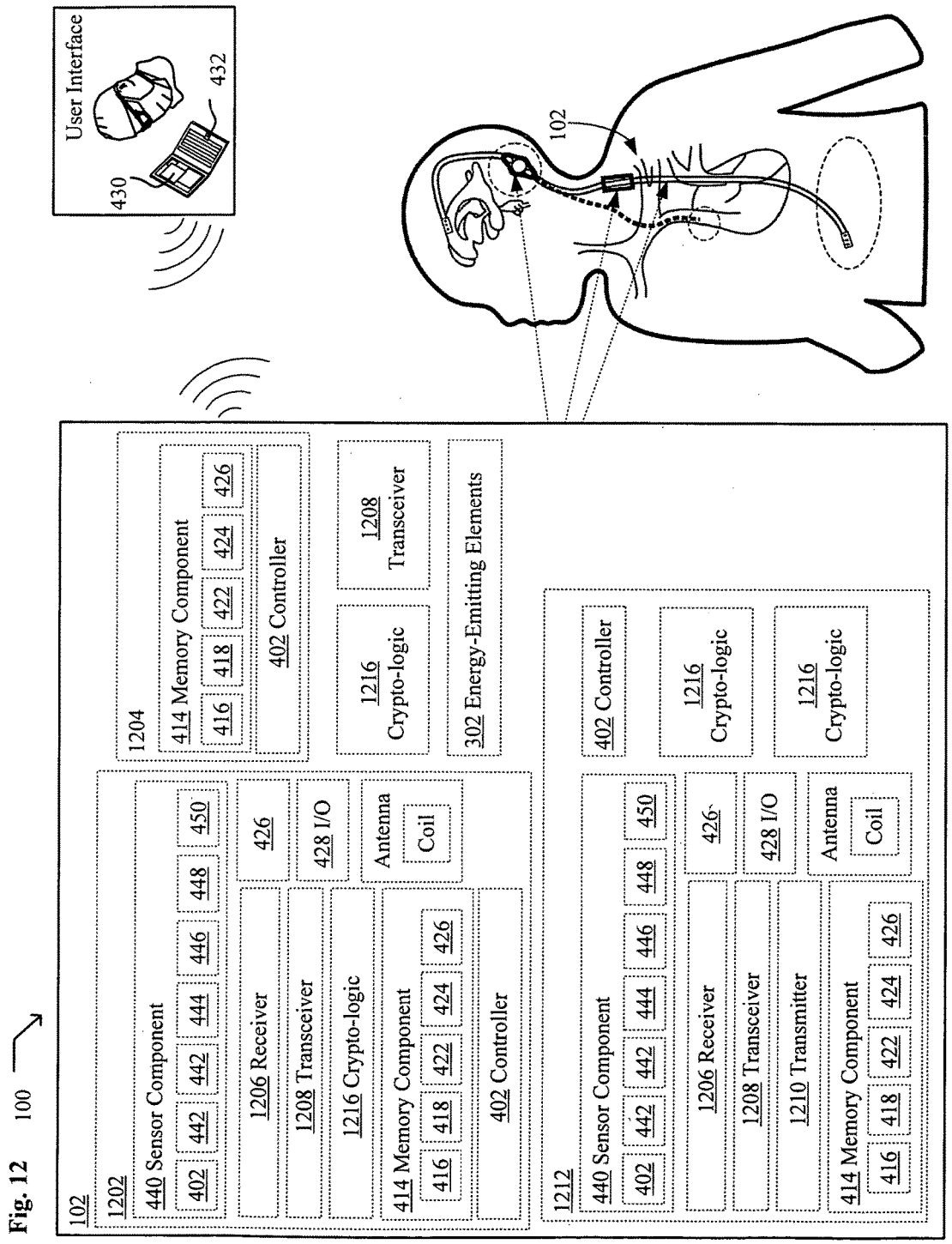
FIG. 12 is a schematic diagram of a system including an implantable device according to one illustrated embodiment.

Referring to FIG. 12, the system 100 can include one or more implantable devices 102 including for example, but not limited to, circuitry configured to obtain information 1202, and circuitry configured to store the obtained information 1204. In an embodiment, the circuitry configured to obtain information 1202 includes circuitry configured to obtain information associated with a delivery of the energy stimulus. In an embodiment, the circuitry configured to obtain information 1202 includes circuitry configured to obtain at least one of a command stream, a software stream, and a data stream. In an embodiment, the circuitry configured to obtain information includes at least one of a receiver and a transceiver configured to obtain information regarding a target detection set of one or more characteristics associated with the biological subject.

The implantable device 102 can include, but is not limited to, one or more controllers 402 configured to perform a comparison of, for example, a characteristic associated with a biological subject to obtained information, and to generate a response based at least in part on the comparison. In an embodiment, the generated response includes causing the obtained information to be stored in one or more data structures 424.

The system 100 can include one or more implantable devices 102 including for example, but not limited to, one or more receivers 1206, transceivers 1208, or transmitters 1210. In an embodiment, at least one of the one or more receiver 1206, transceivers 1208, and transmitters 1210, can be, for example, wirelessly coupled to a controller 402 that communicates with a control unit of the system 100 via wireless communication. In an embodiment, at least one of the one or more receivers 1206 and transceivers 1208 is configured to acquire information associated with a set of targets, markers, or the like for detection. In an embodiment, at least one of the one or more receivers 1206 and transceivers 1208 is configured to acquire information associated with a set of physiological characteristic for detection. In an embodiment, at least one of the one or more receivers 1206 and transceivers 1208 is configured to acquire information associated with one or more physiological characteristics for detection. In an embodiment, at least one of the one or more receivers 1206 and transceivers 1208 is configured to acquire information associated with one or more cerebrospinal fluid characteristics for detection.

In an embodiment, at least one receiver 1206 is configured to acquire information associated with a delivery of an energy stimulus. In an embodiment, the at least one receiver 1206 is configured to acquire data. In an embodiment, the at least one receiver 1206 is configured to acquire software. In an embodiment, the at least one receiver 1206 is configured to receive data from one or more distal sensors 442. In an embodiment, the at least one receiver 1206 is configured to receive stored reference data. In an embodiment, the at least one receiver 1206 is configured to acquire at least one of instructions, instructions associated with a delivery of an energy stimulus, instructions associated with a delivery of an active agent, information associated with a biological sample, instructions associated with a biological fluid, instructions associated with a disease state, and the like.

In an embodiment, the at least one receiver 1206 is configured to acquire information based at least in part on a detected characteristic associated with a cerebrospinal fluid received within at least one of the one or more fluid-flow passageways 106. In an embodiment, the at least one receiver 1206 is configured to acquire information based at least in part on a detected characteristic associated with a tissue proximate the one or more fluid-flow passageways 106. In an embodiment, the at least one receiver 1206 is configured to acquire information based at least in part on a detected physiological characteristic associated with the biological subject. In an embodiment, the at least one receiver 1206 is configured to acquire information associated with delivery of an active agent.

In an embodiment, the system 100 includes one or more receivers 1206 configured to acquire spectral information (e.g., radio frequency (RF) information) emitted by an in vivo biological sample. In an embodiment, the one or more receivers 1206 include one or more of analog-to-digital converters, signal amplifier, matching networks, oscillators, power amplifiers, RF receive coils, RF synthesizers, or signal filters. In an embodiment, the system 100 includes one or more transceivers 1208 (e.g., RF transceivers 1208) configured to generate RF excitation pulses that interacts with, for example, an in vivo target.

The system 100 can include one or more implantable devices 102 including for example, but not limited to, circuitry for providing information 1212. In an embodiment, the circuitry for providing information 1212 includes circuitry for providing status information regarding the implantable device. In an embodiment, the circuitry for providing information 1212 includes circuitry for providing information regarding at least one characteristic associated with a biological subject. For example, in an embodiment, the circuitry for providing information 1212 includes circuitry for providing information regarding at least one characteristic associated with a tissue or biological fluid proximate the implantable device 102. In an embodiment, the circuitry for providing information includes circuitry for providing information regarding at least one physiological characteristic associated with the biological subject. In an embodiment, the circuitry for providing information 1212 includes circuitry for providing information regarding at least one characteristic associated with the cerebrospinal fluid of the biological subject. In an embodiment, the circuitry for providing information 1212 includes circuitry for providing information regarding at least one characteristic associated with a tissue proximate the one or more fluid-flow passageways 106.

The system 100 can include one or more implantable devices 102 including for example, but not limited to, at least one transmitter 1210 configured to send information. The system 100 can include one or more implantable devices 102 including for example, but not limited to, circuitry for transmitting information. In an embodiment, the at least one transmitter 1210 is configured to send information based at least in part on a detected characteristic associated with a cerebrospinal fluid received within at least one of the one or more fluid-flow passageways 106. In an embodiment, the at least one transmitter 1210 is configured to send a request for transmission of at least one of data, a command, an authorization, an update, and a code The system 100 can include one or more implantable devices 102 including for example, but not limited to, one or more cryptographic logic components 1216. In an embodiment, at least one of the one or more cryptographic logic components 1216 is configured to implement at least one cryptographic process, or cryptographic logic, or combinations thereof. Non-limiting examples of a cryptographic process include one or more processes associated with cryptographic protocols, decryption protocols, encryption protocols, regulatory compliance protocols (e.g., FDA regulatory compliance protocols, or the like), regulatory use protocols, authentication protocols, authorization protocols, treatment regimen protocols, activation protocols, encryption protocols, decryption protocols, and the like. Non-limiting examples of a cryptographic logic include one or more crypto-algorithms signal-bearing media, crypto controllers (e.g., crypto-processors), cryptographic modules (e.g., hardware, firmware, or software, or combinations thereof for implementing cryptographic logic, or cryptographic processes), and the like.

In an embodiment, the cryptographic logic component 1216 is configured to implement at least one cryptographic process or cryptographic logic. In an embodiment, the cryptographic logic component 1216 is configured to implement one or more processes associated with at least one of a cryptographic protocol, a decryption protocol, an encryption protocol, a regulatory compliance protocol, a regulatory use protocol, an authentication protocol, an authorization protocol, a delivery protocol, an activation protocol, an encryption protocol, and a decryption protocol. In an embodiment, the cryptographic logic component 1216 includes one or more crypto-algorithms, signal-bearing media, crypto controllers, or cryptographic modules.

In an embodiment, the cryptographic logic component 1216 is configured to generate information associated with at least one of an authentication protocol, an authorization protocol, a delivery protocol (e.g., a sterilizing energy stimulus delivery protocol), an activation protocol, an encryption protocol, and a decryption protocol. In an embodiment, the cryptographic logic component 1216 is configured to generate information associated at least one of an authorization instruction, an authentication instruction, a prescription dosing instruction, a sterilizing energy stimulus administration instruction, and a prescribed regimen instruction.

In an embodiment, the cryptographic logic component 1216 is configured to generate information associated with at least one of an instruction stream, an encrypted data stream, an authentication data stream, and an authorization data stream. In an embodiment, the cryptographic logic component 1216 is configured to generate information associated with at least one of an activation code, an error code, a command code, and an authorization code. In an embodiment, the cryptographic logic component 1216 is configured to generate information associated with at least one of a cryptographic protocol, a decryption protocol, an encryption protocol, a regulatory compliance protocol, and regulatory use protocol.

Figure 13:
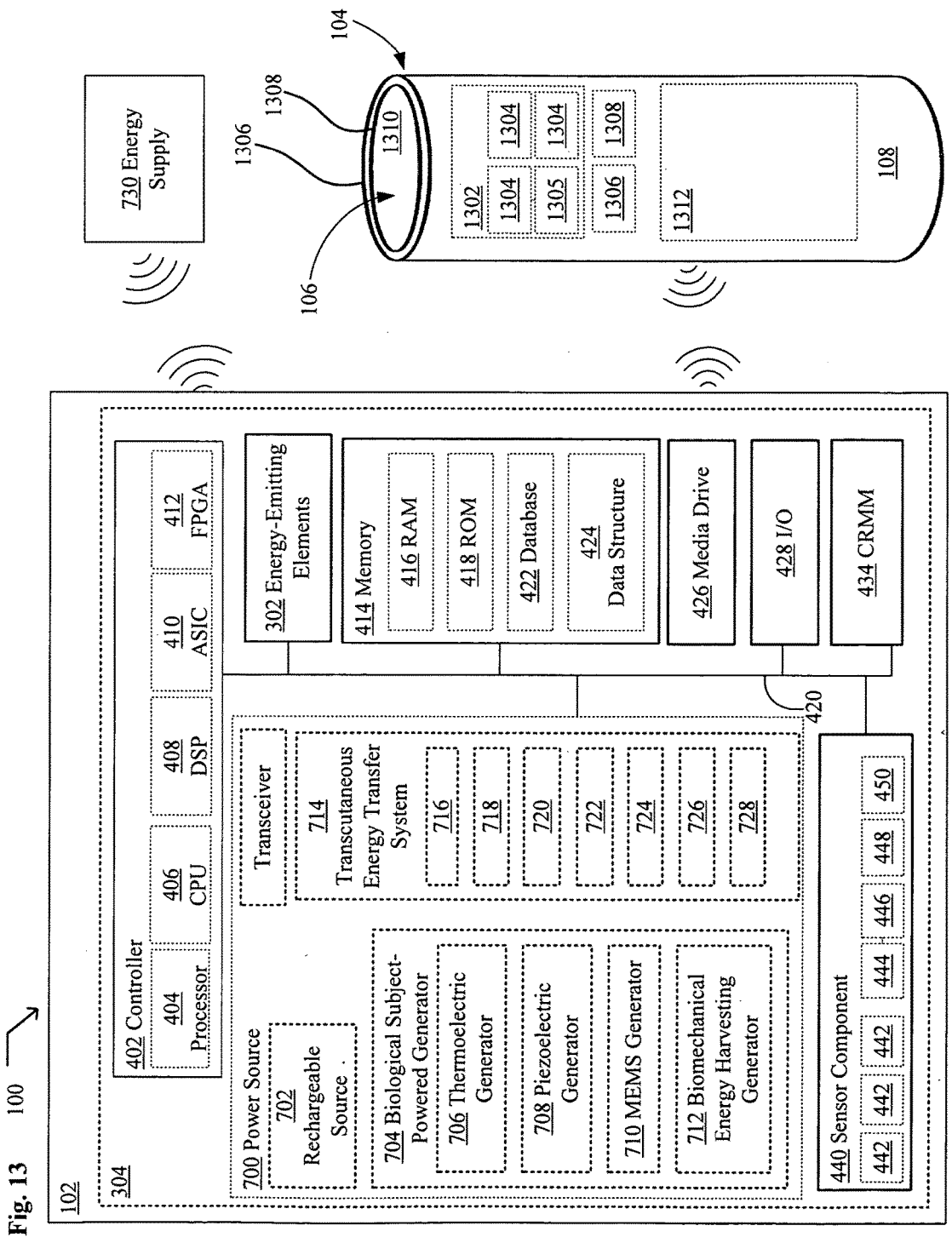
FIG. 13 is a schematic diagram of a system including an implantable device according to one illustrated embodiment.

Referring to FIG. 13, in an embodiment, the implantable device 102 includes a body structure 104 including one or more components 1302 that are energetically actuatable between an optically transparent state and an optically reflective state.

In an embodiment, an indwelling shunt apparatus includes a body structure 104 having an outer surface and an inner surface defining one or more fluid-flow passageways 106 configured to receive a cerebrospinal fluid of a biological subject. In an embodiment, the body structure 104 includes a plurality of actuatable regions 1302 that are independently actuatable between at least a first transmissive state and a second transmissive state. In an embodiment, a sensor component 440 including one or more sensors 442 configured to detect at least one characteristic associated with a biological sample proximate at least one of the outer surface and the inner surface of the body structure 104. In an embodiment, the at least one characteristic associated with the biological sample includes at least one of an autofluorescence, an immunofluorescence, or an indirect immunofluorescence. In an embodiment, the indwelling shunt apparatus includes one or more energy emitters 302 configured to emit an energy stimulus based at least in part on at least one detected characteristic associated with the biological sample.

In an embodiment, at least one of the plurality of actuatable regions 1302 is energetically actuatable between an optically transparent state and an optically reflective state. In an embodiment, at least one of the plurality of actuatable regions 1302 includes one or more actively controllable reflective or transmissive components. Non-limiting examples of actively controllable reflective or transmissive components include liquid crystal components that are actively controllable between a reflective state and a transmissive state, electrochromic components that are actively controllable between a reflective state and a transmissive state, and the like.

In an embodiment, at least one of the plurality of actuatable regions 1302 is controllably actuatable between an optically transparent state and an optically reflective state. In an embodiment, at least one of the plurality of actuatable regions 1302 is actively controllable between a transmissive state and a reflective state. In an embodiment, at least one of the plurality of actuatable regions 1302 is actively controllable between a transmissive state and a less transmissive state. In an embodiment, at least one of the plurality of actuatable regions 1302 is configured to outwardly transmit or internally reflect an energy stimulus propagated through at least one of the one or more fluid-flow passageways 106.

In an embodiment, the sensor component 440 is configured to detect at least one of a characteristic of a cerebrospinal fluid received within one or more fluid-flow passageways 106, a characteristic of a tissue proximate the one or more fluid-flow passageways 106, and a physiological characteristic of the biological subject.

In an embodiment, the indwelling shunt includes a controller 402 operably coupled to at least one of the plurality of actuatable regions, the controller 402 configured to cause an outward-transmission or internal-reflection of an energy stimulus propagated through at least one of the one or more fluid-flow passageways 106 based on detected information from the sensor component 440.

In an embodiment, the sensor component 440 includes one or more electrochemical transducers, photochemical transducer, optical transducers, piezoelectrical transducers, or thermal transducers. In an embodiment, the sensor component 440 includes one or more thermal detectors, photovoltaic detectors, or photomultiplier detectors. In an embodiment, the sensor component 440 includes one or more charge coupled devices, complementary metal-oxide-semiconductor devices, photodiode image sensor devices, whispering gallery mode micro cavity devices, or scintillation detector devices. In an embodiment, the sensor component 440 includes one or more ultrasonic transducers.

In an embodiment, the sensor component 440 includes one or more density sensors. In an embodiment, the one or more density sensors include one or more optical density sensors. In an embodiment, the one or more density sensors include one or more refractive index sensors. In an embodiment, the one or more refractive index sensors include one or more fiber optic refractive index sensors.

In an embodiment, the sensor component 440 includes one or more surface plasmon resonance sensors. In an embodiment, the sensor component 440 includes one or more localized surface plasmon resonance sensors. In an embodiment, the sensor component 440 includes a light transmissive support and a reflective metal layer. In an embodiment, the sensor component includes one or more acoustic biosensors, amperometric biosensors, calorimetric biosensors, optical biosensors, or potentiometric biosensors. In an embodiment, the sensor component 440 includes one or more fluid flow sensors. In an embodiment, the sensor component 440 includes one or more differential electrodes.

In an embodiment, the sensor component 440 includes one or more biological mass sensors. In an embodiment, the sensor component 440 includes one or more immuno sensors. In an embodiment, the sensor component 440 includes one or more functionalized cantilevers. In an embodiment, the sensor component 440 includes a biological molecule capture layer. In an embodiment, the sensor component 440 includes biological molecule capture layer having an array of different binding molecules that specifically bind one or more target molecules. In an embodiment, the sensor component 440 includes a spectrometer (e.g., a mass spectrometer, nuclear magnetic resonance spectrometer, UV-VIS spectrometer, and the like).

In an embodiment, at least one of the one or more sensors 442 is configured to detect a fluorescence associated with an autofluorescent material of biological sample proximate at least one of the outer surface and the inner surface of the body structure 104. In an embodiment, at least one of the one or more sensors 442 is configured to detect at least one of an emitted energy and a remitted energy, and to generate a response based on the detected at least one of the emitted energy or the remitted energy. In an embodiment, the indwelling shunt includes one or more optical materials on at least a portion of a body structure 104 to internally reflect at least a portion of an emitted energy stimulus from the one or more energy emitters 302 into an interior of at least one of the one or more fluid-flow passageways 106.

In an embodiment, at least one of the one or more fluid-flow passageways 106 includes a surface region 1304 that is energetically actuatable between an optically transparent state and an optically reflective state. In an embodiment, at least one of the one or more fluid-flow passageways 106 includes one or more regions 1305 that are controllably actuatable between an optically transparent state and an optically reflective state. In an embodiment, at least one of the one or more fluid-flow passageways 106 includes one or more regions 1308 that are actively controllable between a transmissive state and a reflective state. In an embodiment, at least one of the one or more fluid-flow passageways 106 includes one or more regions 1310 that are actively controllable between a transmissive state and a less transmissive state. In an embodiment, at least one of the one or more fluid-flow passageways 106 includes one or more liquid crystal components that are actively controllable between a transmissive state and a less transmissive state. In an embodiment, at least one of the one or more fluid-flow passageways 106 includes one or more electrochromic components that are actively controllable between a transmissive state and a less transmissive state.

In an embodiment, the implantable device 102 includes a body structure 104 having one or more actively controllable reflective or transmissive components 1312 configured to outwardly transmit or internally reflect an energy stimulus propagated through at least one of the one or more fluid-flow passageways 106. The implantable device 102 can further include a sensor component 440 configured to detect at least one of a characteristic of a cerebrospinal fluid received within one or more fluid-flow passageways 106, a characteristic of a tissue proximate the one or more fluid-flow passageways 106, and a physiological characteristic of the biological subject. The implantable device 102 can further include one or more actively controllable reflective or transmissive components 1312 configured to outwardly transmit or internally reflect an energy stimulus propagated through at least one of the one or more fluid-flow passageways 106. The implantable device 102 can further include a controller 402 operably coupled to at least one of the one or more actively controllable reflective and transmissive components 1312. In an embodiment, the controller 402 is configured to cause an outward-transmission or internal-reflection of an energy stimulus propagated through at least one of the one or more fluid-flow passageways 106 based on detected information from the sensor component 440.

In an embodiment, a body structure 104 defining at least one of the one or more fluid-flow passageways 106 includes a self-cleaning coating composition. In an embodiment, the self-cleaning coating composition comprises an energy-activatable self-cleaning material. In an embodiment, the self-cleaning coating composition comprises a chemically activatable self-cleaning material. In an embodiment, the self-cleaning coating composition comprises one or more of titanium dioxide, superhydrophobic materials, or carbon nanotubes with nanoscopic paraffin coatings. In an embodiment, the self-cleaning coating composition comprises one or more of non-fouling zwitterionic polymers, zwitterionic surface forming materials, zwitterionic polymers, poly(carboxybetaine methacrylate) (pCBMA), poly(carboxybetaine acrylic amide) (pCBAA), poly(oligo(ethylene glycol) methyl ether methacrylate) (pOEGMA), poly(N, N-dimethyl-N-(ethoxycarbonylmethyl)-N-[2'-(methacryloyloxy) ethyl]-ammonium bromide), cationic pC8NMA, switchable pCBMA-1 C2, or pCBMA-2.

In an embodiment, the self-cleaning coating composition comprises one or more antimicrobial agents. In an embodiment, at least one of the one or more fluid-flow passageways 106 includes a coating configured to generate a reactive oxygen specie or a reactive nitrogen specie when exposed to an energy stimulus. In an embodiment, at least one of the one or more fluid-flow passageways 106 includes a self-cleaning coating configured to hydrolyze when exposed to an energy stimulus. In an embodiment, at least one of the one or more fluid-flow passageways 106 includes a self-cleaning coating configured to degrade when exposed to an energy stimulus. In an embodiment, at least one of the one or more fluid-flow passageways 106 includes one or more reflective materials and one or more self-cleaning materials. In an embodiment, at least one of the one or more fluid-flow passageways 106 includes one or more reflective coatings and one or more self-cleaning coatings.

Referring to FIG. 13, in an embodiment, the implantable device 102 includes a body structure 104 including one or more components 1302 that are energetically actuatable among a plurality of wettability states. It may be possible to affect adhesion of, for example, bacteria and biofilm formation by changing the functional and chemical character of a surface on an implantable device 102. It may also be possible to modulate the adhesion and biofilm formation by modulating the functional and chemical character of a surface on an implantable device 102. By modulating the functional and chemical character of a surface on an implantable device 102, it may also be possible to affect the transport properties of a fluid exposed to the surface on an implantable device 102. Controllable wettability components can be made using a variety of methodologies and technologies including, for example, spray pyrolysis, electro-deposition, electro-deposition onto laser-drilled polymer molds, laser cutting and electro-polishing, laser micromachining, surface micro-machining, soft lithography, x-ray lithography, LIGA techniques (e.g., X-ray lithography, electroplating, and molding), conductive paint silk screen techniques, conventional pattering techniques, injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, or the like), complementary-symmetry/metal-oxide semiconductor (CMOS) technology, deep x-ray exposure techniques, and the like.

Further examples of methodologies and technologies for making controllable wettability components can found in the following documents (the contents of which are incorporated herein by reference): Feng et al., *Reversible Super-hydrophobicity to Super-hydrophilicity Transition of Aligned ZnO Nanorod Films*, J. Am. Chem. Soc., 126, 62-63 (2004), Lin et al., Electrically Tunable Wettability of Liquid Crystal/Polymer Composite Films, Optics Express 16(22): 17591-598 (2008), Wang et al., *Photoresponsive Surfaces with Controllable Wettability*, Journal of Photochemistry and Photobiology C: Photochemistry Reviews, 8(1): 18-29 (2007), U.S. Pat. No. 6,914,279 (issued Jul. 5, 2005), and U.S. Patent Publication No. 2008/0223717 (published Sep. 18, 2008).

The wettability of a substrate can be determined using various technologies and methodologies including contact angle methods, the Goniometer method, the Whilemy method, or the Sessile drop technique. Wetting is a process by which a liquid interacts with a solid. Wettability (the degree of wetting) is determined by a force balance between adhesive and cohesive force and is often characterized by a contact angle. The contact angle is the angle made by the intersection of the liquid/solid interface and the liquid/air interface. Alternatively, it is the angle between a solid sample's surface and the tangent of a droplet's ovate shape at the edge of the droplet. Contact angle measurements provide a measure of interfacial energies and conveys direct information regarding how hydrophilic or hydrophobic a surface is. For example, superhydrophilic surfaces have contact angles less than about 5°, hydrophilic surfaces have contact angles less than about 90°, hydrophobic surfaces have contact angles greater than about 90°, and superhydrophobic surfaces have contact angles greater than about 150°.

In an embodiment, the implantable device 102 includes a body structure 104 including one or more components 1302 having switchable wetting properties. In an embodiment, the implantable device 102 includes a body structure 104 including one or more components 1302 that are energetically actuatable between at least a first wettability and a second wettability. In an embodiment, the one or more components 1302 are acoustically, chemically, electrochemically, electrically, optically, thermally, or photochemically actuatable between at least a first wettability and a second wettability.

In an embodiment, the one or more components 1302 include at least one photo-responsive material. Non-limiting examples of photo-responsive materials include SnO, $SnO_2$, $TiO_2$, $W_2O_3$, ZnO, ZnO, and the like. In an embodiment, the one or more components 1302 include at least one film, coating, or material including SnO, $SnO_2$, $TiO_2$, $W_2O_3$, ZnO, ZnO, or the like. In an embodiment, the one or more components 1302 are UV-manipulatable between at least a first wettability and a second wettability. In an embodiment, the one or more components 1302 include one or more ZnO nano-rod films, coatings, or materials that are UV-manipulatable between a superhydrophobic state and superhydrophilic state. In an embodiment, the one or more components 1302 include at least one electrochemically active material. Non-limiting examples of electrochemically active materials include electrochemically active polymers (e.g., polyaniline, polyethylenethioxythiophene, conjugated polymer poly(3-hexylthiophene), or the like), and the like.

In an embodiment, the one or more components 1302 include one or more superhydrophobic conducting polypyrrole films, coatings, or components that are electrically switchable between an oxidized state and a neutral state, resulting in reversibly switchable superhydrophobic and superhydrophilic properties. See, e.g., Lahann et al., *A Reversibly Switching Surface*, 299 (5605): 371-374 (2003) 21:47-51 (2003), the contents of which are incorporated herein by reference). In an embodiment, the one or more components 1302 include one or more electrically isolatable fluid-support structures. See, e.g., U.S. Pat. No. 7,535,692 (issued May 19, 2009), the contents of which are incorporated herein by reference). In an embodiment, the one or more components 1302 include a plurality of volume-tunnable nanostructures. See, e.g., U.S. Patent Publication No. 2008/0095977 (published Apr. 24, 2008), the contents of which are incorporated herein by reference). In an embodiment, the one or more components 1302 include one or more tunable (electrically tunable) superhydrophobic conducting polypyrrole films, coatings, or components. See, e.g., Krupenki et al, *Electrically Tunable Superhydrophobic Nanostructured Surfaces*, Bell Labs Technical Journal 10 (3): 161-170 (2009), the contents of which are incorporated herein by reference). In an embodiment, the one or more components 1302 include one or more electrically tunable crystal/polymer composites. In an embodiment, the one or more components 1302 include a switchable surface. See e.g., Gras et al., *Intelligent Control of Surface Hydrophobicity*, ChemPhysChem 8(14): 2036-2050(2007).

In an embodiment, at least one of the one or more fluid-flow passageways 106 includes one or more surface regions 1304 that are energetically actuatable between a substantially hydrophobic state and a substantially hydrophilic state. In an embodiment, at least one of the one or more fluid-flow passageways 106 includes a surface region 1304 that is energetically actuatable between at least a first hydrophilic state and a second hydrophilic state. In an embodiment, at least one of the one or more fluid-flow passageways 106 includes a surface region 1304 that is energetically actuatable between a hydrophobic state and a hydrophilic state. In an embodiment, at least one of the one or more fluid-flow passageways 106 includes a surface region 1304 having a material that is switchable between a zwitterionic state and a non-zwitterionic state. In an embodiment, at least one of the one or more fluid-flow passageways 106 includes at least one of an antimicrobial coating 1306 and a non-fouling coating 1308. In an embodiment, at least one of the one or more fluid-flow passageways 106 includes an antimicrobial 1306 and a non-fouling coating 1308. In an embodiment, at least one of the one or more fluid-flow passageways 106 includes a surface region 1304 that is energetically actuatable between an antimicrobial state and a non-fouling state.

Figure 14:
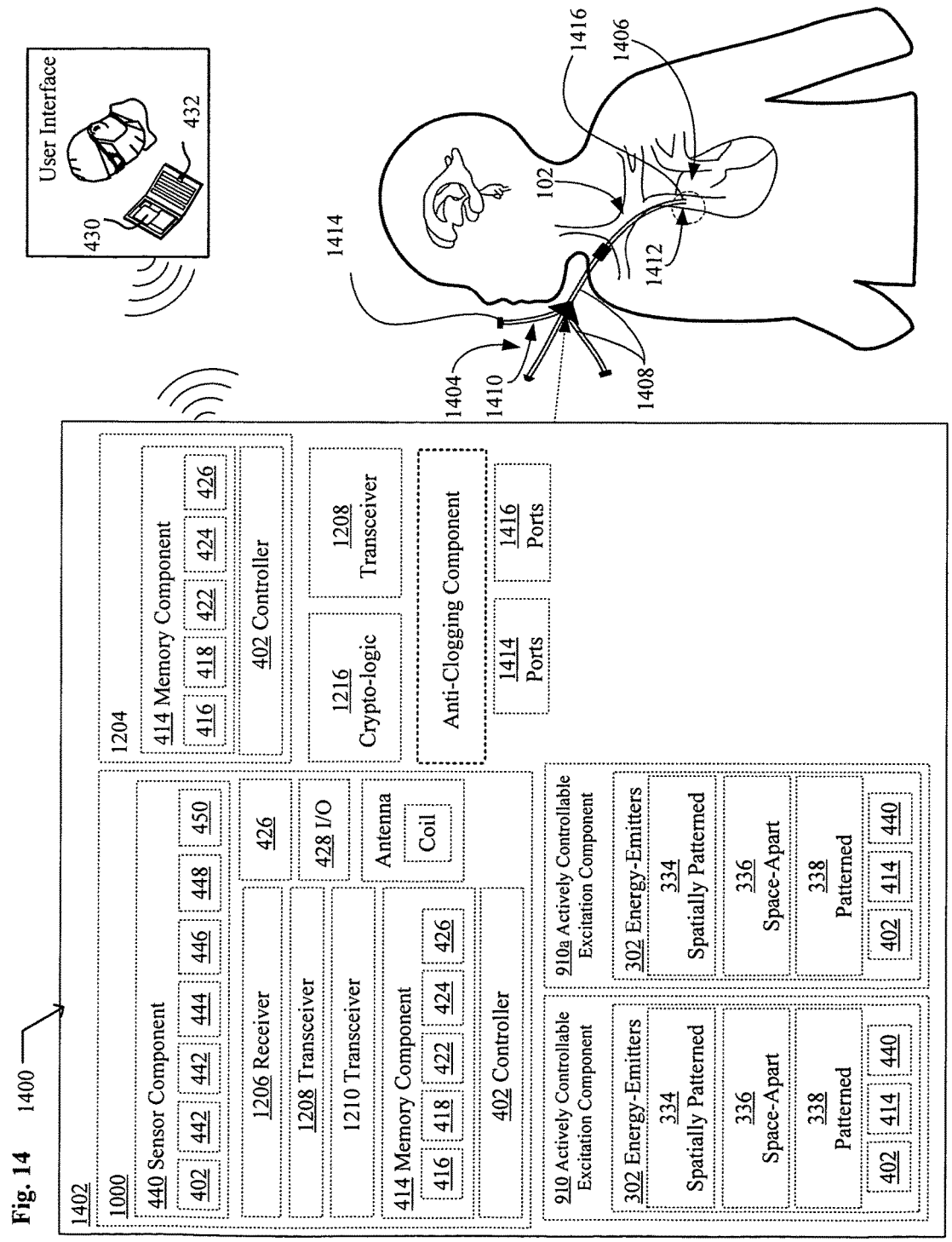
FIG. 14 is a schematic diagram of a system including an implantable device according to one illustrated embodiment.

Referring to FIG. 14, in an embodiment, an implantable fluid management device 1400 includes a catheter assembly 1402 defining one or more fluid-flow passageways 106 configured to receive a biological fluid of a subject. The catheter assembly 1402 can include, but is not limited to, a proximal portion 1404, a distal portion 1406, and one or more tubular structures 1408 including an inflow fluid-flow passageway 1410 and an outflow fluid-flow passageway 1412. In an embodiment, the inflow fluid-flow passageway 1410 is configured in fluid communication to one or more inflow ports 1414, and the outflow fluid-flow passageway 1412 is configured in fluid communication to one or more outflow ports 1416

In an embodiment, an implantable fluid management device 1400 includes an actively controllable excitation component 910 configured to independently deliver, in vivo, at least one of a first sterilizing energy stimulus to a biological fluid received within at least one of the one or more fluid-flow passageways 106 and a second sterilizing energy stimulus to a tissue proximate an outer surface of the implantable fluid management device. In an embodiment, the actively controllable excitation component 910 is configured to concurrently or sequentially deliver the first sterilizing energy stimulus to a biological fluid received within at least one of the one or more fluid-flow passageways 106 and the second sterilizing energy stimulus to a region proximate an outer surface of the implantable fluid management device 1400. In an embodiment, the first sterilizing energy stimulus or the second sterilizing energy stimulus comprises an electromagnetic stimulus, an electrical stimulus, an ultrasonic stimulus, or a thermal stimulus. In an embodiment, the first sterilizing energy stimulus comprises one of an electrical sterilizing energy stimulus, an electromagnetic sterilizing energy stimulus, an ultrasonic sterilizing energy stimulus, or a thermal sterilizing energy stimulus, and the second sterilizing energy stimulus comprises a different one of an electrical sterilizing energy stimulus, an electromagnetic sterilizing energy stimulus, an ultrasonic sterilizing energy stimulus, or a thermal sterilizing energy stimulus. In an embodiment, the actively controllable excitation component 910 is configured to concurrently or sequentially deliver at least a first energy stimulus and a second energy stimulus, the second energy stimulus different from the first energy stimulus. In an embodiment, the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus.

In an embodiment, the implantable fluid management device 1400 is configured to provide an illumination pattern to a biological fluid received within at least one of the one or more fluid-flow passageways 106, the illumination pattern comprising at least a first region and a second region, the second region having at least one of an illumination intensity, an energy-emitting pattern, a peak emission wavelength, an ON-pulse duration, an OFF-pulse duration, and a pulse frequency different from the first region. In an embodiment, the implantable fluid management device 1400 is configured to provide an illumination pattern to a tissue proximate a surface of the implantable fluid management device implantable fluid management device 1400. In an embodiment, the actively controllable excitation component 910 is configured to provide an illumination pattern to a biological fluid received within at least one of the one or more fluid-flow passageways 106. In an embodiment, the illumination pattern includes at least a first region and a second region, the second region having at least one of an illumination intensity, an energy-emitting pattern, a peak emission wavelength, an ON-pulse duration, an OFF-pulse duration, and a pulse frequency different from the first region. In an embodiment, the actively controllable excitation component 910 is configured to provide an illumination pattern to a tissue or biological fluid proximate a surface of the implantable fluid management device 1400.

In an embodiment, an implantable fluid management device 1400 includes a first actively controllable excitation component 910 configured to deliver, in vivo, a first sterilizing energy stimulus to a biological fluid received within at least one of the one or more fluid-flow passageways 106, and a second actively controllable excitation component 910a configured to deliver, in vivo, a second sterilizing energy stimulus to a tissue proximate an outer surface of the implantable fluid management device 1400. In an embodiment, an implantable fluid management device 1400 includes a control means 1000 operably coupled to at least one of the first actively controllable excitation component 910 and the actively controllable excitation component 910a. In an embodiment, the implantable fluid management device 1400 is configured to concurrently or sequentially deliver the first sterilizing energy stimulus to a biological fluid received within at least one of the one or more fluid-flow passageways 106 and the second sterilizing energy stimulus to a tissue proximate an outer surface of the implantable fluid management device 1400. In an embodiment, the first sterilizing energy stimulus or the second sterilizing energy stimulus comprises an electromagnetic stimulus, an electrical stimulus, an ultrasonic stimulus, or a thermal stimulus. In an embodiment, the first sterilizing energy stimulus comprises one of an electrical sterilizing energy stimulus, an electromagnetic sterilizing energy stimulus, an ultrasonic sterilizing energy stimulus, or a thermal sterilizing energy stimulus, and the second sterilizing energy stimulus comprises a different one of an electrical sterilizing energy stimulus, an electromagnetic sterilizing energy stimulus, an ultrasonic sterilizing energy stimulus, or a thermal sterilizing energy stimulus. In an embodiment, the implantable fluid management device 1400 is configured to concurrently or sequentially deliver at least a first energy stimulus and a second energy stimulus, the second energy stimulus different from the first energy stimulus. In an embodiment, the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus.

Figure 15:
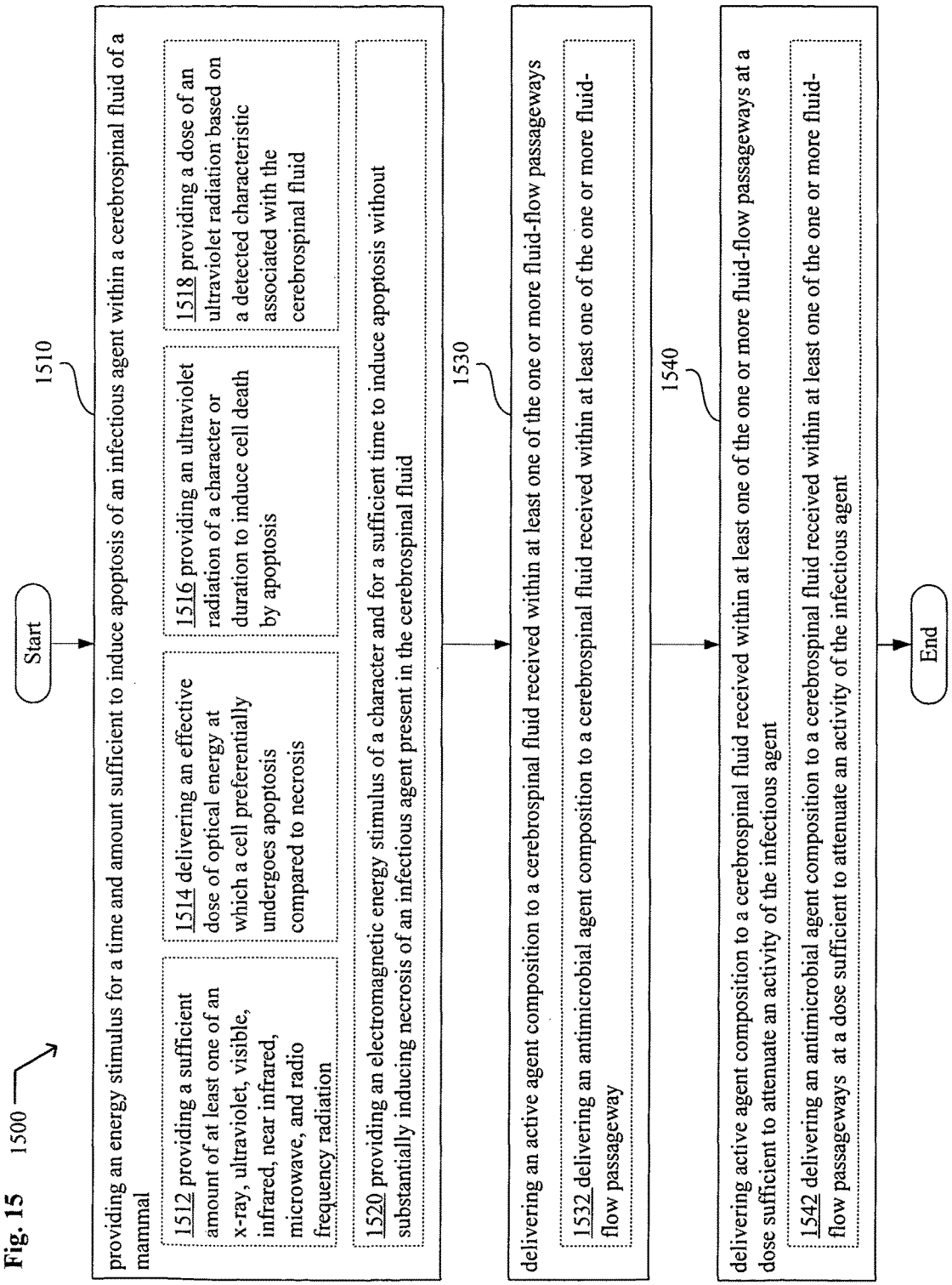
FIG. 15 is a flow diagram of a method according to one illustrated embodiment.

FIG. 15 shows an example of an in vivo method 1500 of treating an infectious agent. At 1510, the method 1500 includes providing an energy stimulus for a time and amount sufficient to induce PCD of an infectious agent within a cerebrospinal fluid of a mammal, the cerebrospinal fluid received within one or more fluid-flow passageways 106 of an indwelling implant including one or more energy-emitting components 902 energetically coupleable to an interior of the one or more fluid-flow passageways 106. At 1512, providing the sufficient amount of the energy stimulus includes providing a sufficient amount of at least one of an x-ray, ultraviolet, visible, infrared, near infrared, terahertz, microwave, and radio frequency radiation. At 1514, providing the sufficient amount of the energy stimulus includes delivering an effective dose of optical energy at which a cell preferentially undergoes PCD compared to necrosis. At 1516, providing the sufficient amount of the energy stimulus includes providing an ultraviolet radiation of a character or duration to induce cell death by PCD. At 1518, providing the sufficient amount of the energy stimulus includes providing a dose of an ultraviolet radiation based on a detected characteristic associated with the cerebrospinal fluid. At 1520, providing the sufficient amount of the energy stimulus includes providing an electromagnetic energy stimulus of a character and for a sufficient time to induce PCD without substantially inducing necrosis of an infectious agent present in the cerebrospinal fluid.

Figure 16:
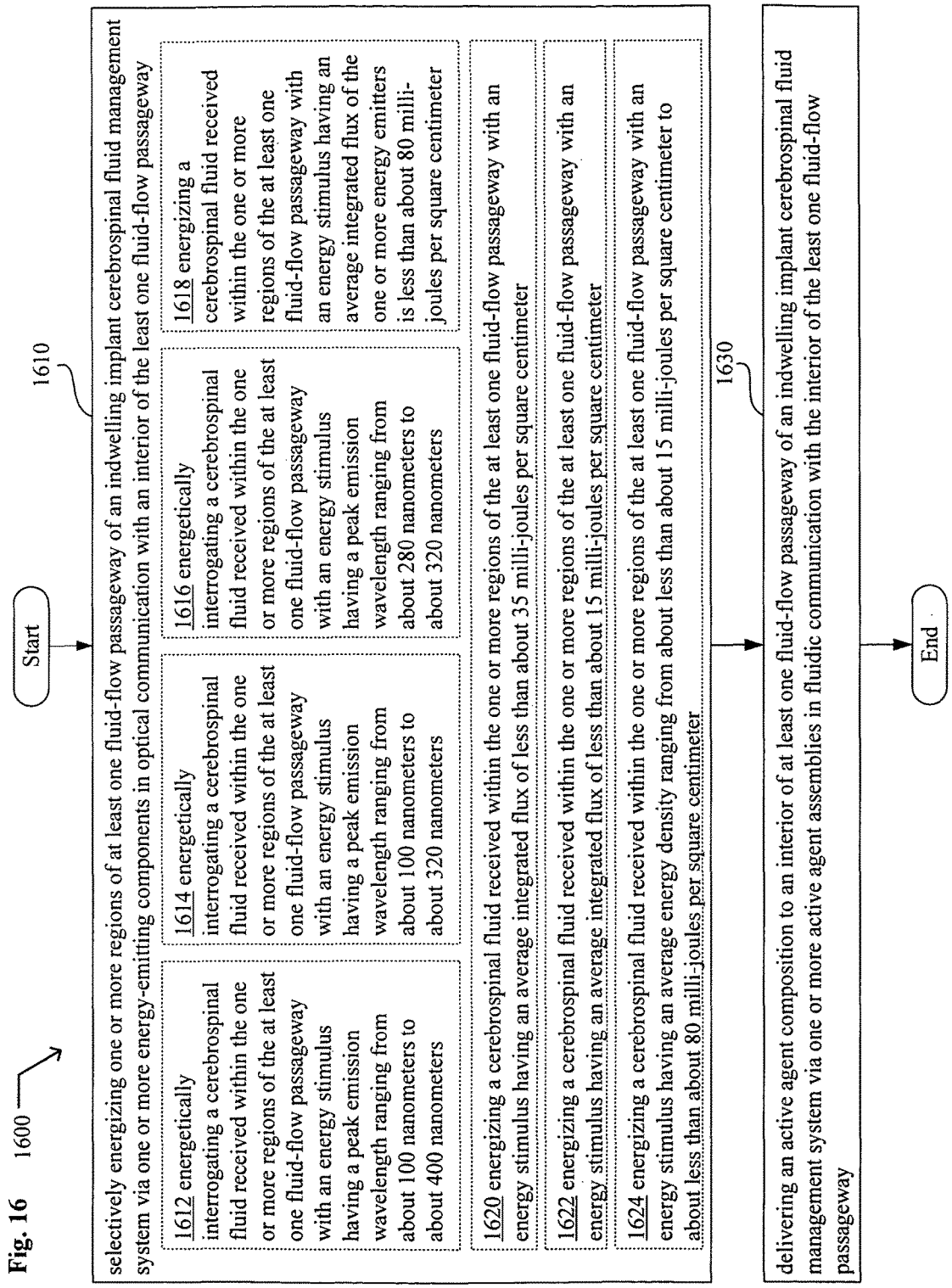
FIG. 16 is a flow diagram of a method according to one illustrated embodiment.

At 1530, the method 1500 can further include delivering an active agent composition (e.g., an antimicrobial agent composition, or the like) to a cerebrospinal fluid received within at least one of the one or more fluid-flow passageways 106. At 1532, delivering an active agent composition includes delivering an active agent composition (e.g., an antimicrobial agent composition, or the like) to a cerebrospinal fluid received within at least one of the one or more fluid-flow passageways 106. At 1540, the method 1500 can further include delivering an antimicrobial agent composition to a cerebrospinal fluid received within at least one of the one or more fluid-flow passageways 106 at a dose sufficient to attenuate an activity of the infectious agent. At 1542, delivering an active agent composition includes delivering an antimicrobial agent composition to a cerebrospinal fluid received within at least one of the one or more fluid-flow passageways 106 at a dose sufficient to attenuate an activity of the infectious agent FIG. 16 shows an example of a method 1600 inhibiting a microbial colonization in the cerebrospinal fluid of a biological subject. At 1610, the method 1600 includes selectively energizing one or more regions of at least one fluid-flow passageway 106 of an indwelling implant cerebrospinal fluid management system via one or more energy-emitting components 902 in optical communication with an interior of the least one fluid-flow passageway 106. At 1612, selectively energizing includes energetically interrogating a cerebrospinal fluid received within the one or more regions of the at least one fluid-flow passageway 106 with an energy stimulus having a peak emission wavelength ranging from about 100 nanometers to about 400 nanometers. At 1614, selectively energizing includes energetically interrogating a cerebrospinal fluid received within the one or more regions of the at least one fluid-flow passageway 106 with an energy stimulus having a peak emission wavelength ranging from about 100 nanometers to about 320 nanometers. At 1616, selectively energizing includes energetically interrogating a cerebrospinal fluid received within the one or more regions of the at least one fluid-flow passageway 106 with an energy stimulus having a peak emission wavelength ranging from about 280 nanometers to about 320 nanometers. At 1618, selectively energizing includes energizing a cerebrospinal fluid received within the one or more regions of the at least one fluid-flow passageway 106 with an energy stimulus having an operational fluence of the one or more energy emitters 302 is less than about 80 milli-joules per square centimeter. At 1620, selectively energizing includes energizing a cerebrospinal fluid received within the one or more regions of the at least one fluid-flow passageway 106 with an energy stimulus having an operational fluence of less than about 35 milli-joules per square centimeter. At 1622, selectively energizing includes energizing a cerebrospinal fluid received within the one or more regions of the at least one fluid-flow passageway 106 with an energy stimulus having an operational fluence of less than about 15 milli-joules per square centimeter. At 1624, selectively energizing includes energizing a cerebrospinal fluid received within the one or more regions of the at least one fluid-flow passageway 106 with an energy stimulus having an average energy density ranging from about less than about 15 milli-joules per square centimeter to about less than about 80 milli-joules per square centimeter.

At 1630, the method 1600 includes delivering an active agent composition to an interior of at least one fluid-flow passageway of an indwelling implant cerebrospinal fluid management system via one or more active agent assemblies in fluidic communication with the interior of the least one fluid-flow passageway.

Figure 17:
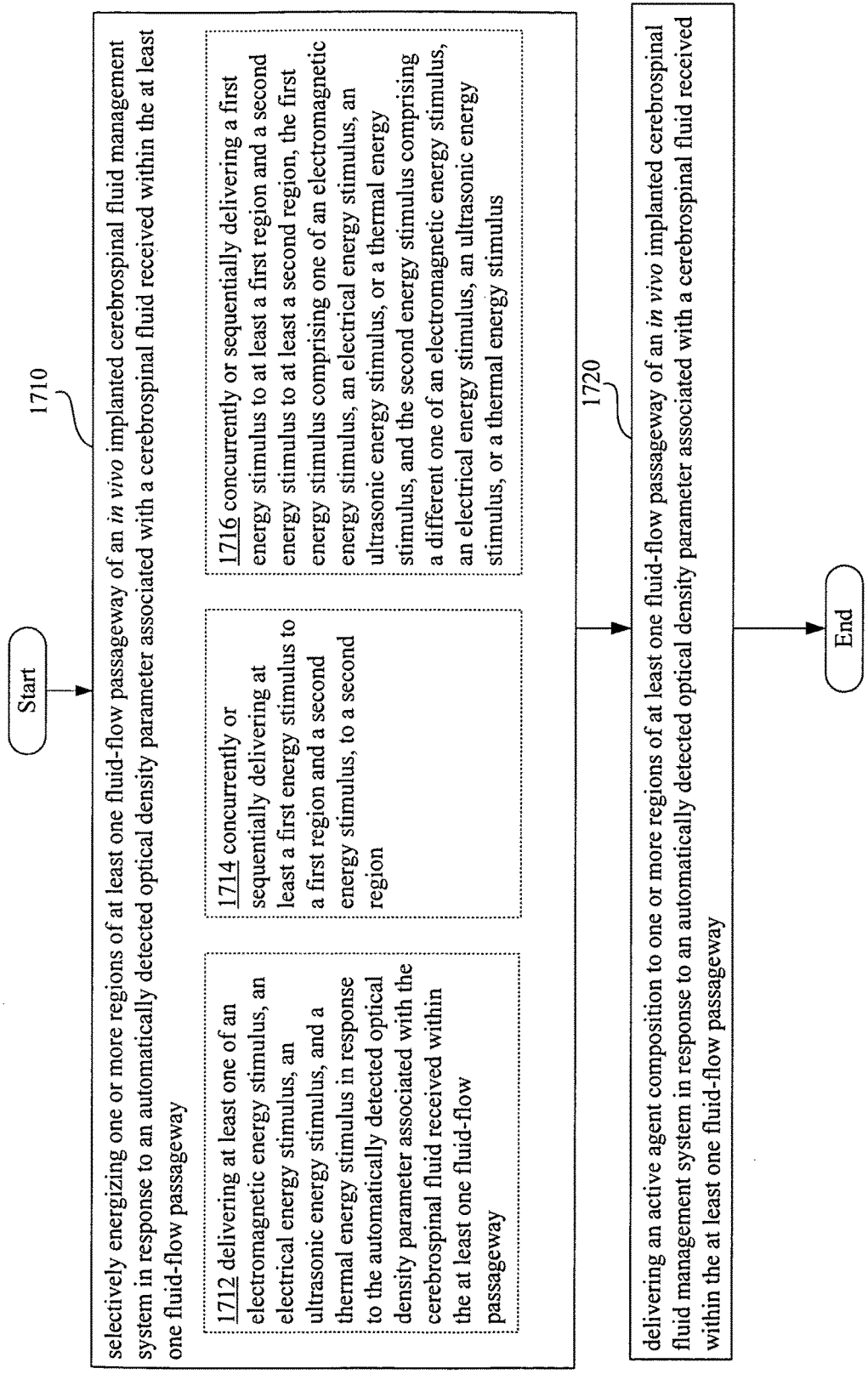
FIG. 17 is a flow diagram of a method according to one illustrated embodiment.

FIG. 17 shows an example of a method 1700. At 1710, the method 1700 includes selectively energizing one or more regions of at least one fluid-flow passageway 106 of an in vivo implanted cerebrospinal fluid management system in response to an automatically detected optical density parameter associated with a cerebrospinal fluid received within the at least one fluid-flow passageway 106. At 1712, selectively energizing one or more regions of the at least one fluid-flow passageway 106 includes delivering at least one of an electromagnetic energy stimulus, an electrical energy stimulus, an ultrasonic energy stimulus, and a thermal energy stimulus in response to the automatically detected optical density parameter associated with the cerebrospinal fluid received within the at least one fluid-flow passageway 106. At 1714, selectively energizing one or more regions of the at least one fluid-flow passageway 106 includes concurrently or sequentially delivering at least a first energy stimulus to a first region and a second energy stimulus to a second region. At 1716, selectively energizing one or more regions of the at least one fluid-flow passageway 106 includes concurrently or sequentially delivering a first energy stimulus to at least a first region and a second energy stimulus to at least a second region, the first energy stimulus comprising one of an electromagnetic energy stimulus, an electrical energy stimulus, an ultrasonic energy stimulus, or a thermal energy stimulus, and the second energy stimulus comprising a different one of an electromagnetic energy stimulus, an electrical energy stimulus, an ultrasonic energy stimulus, or a thermal energy stimulus.

At 1720, the method 1700 includes delivering an active agent composition to one or more regions of at least one fluid-flow passageway of an in vivo implanted cerebrospinal fluid management system in response to an automatically detected optical density parameter associated with a cerebrospinal fluid received within the at least one fluid-flow passageway.

Figure 18:
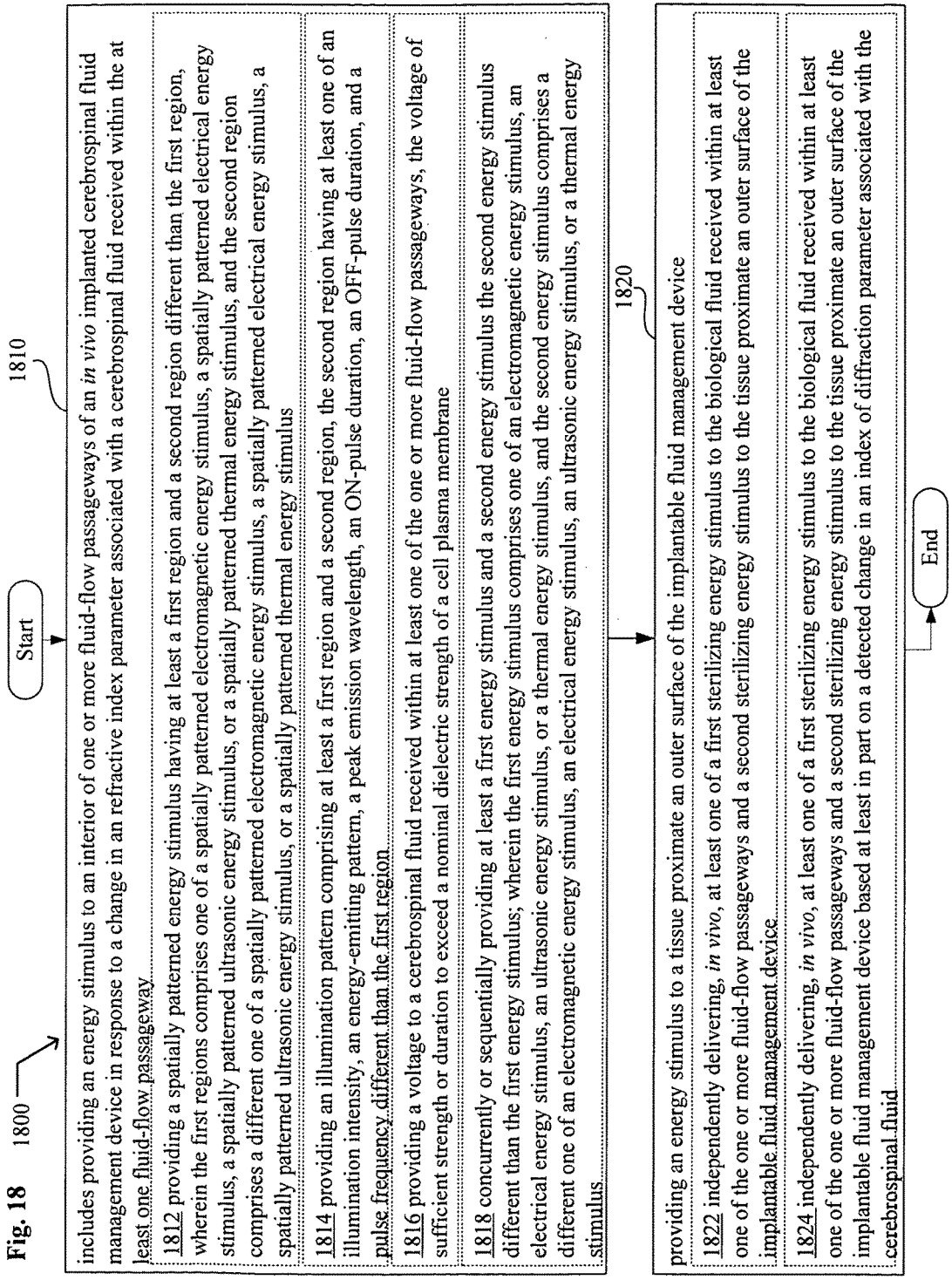
FIG. 18 is a flow diagram of a method according to one illustrated embodiment.

FIG. 18 shows an example of a method 1800. At 1810, the method 1800 includes providing an energy stimulus to an interior of one or more fluid-flow passageways 106 of an in vivo implanted cerebrospinal fluid management device in response to a change in a refractive index parameter associated with a cerebrospinal fluid received within the at least one fluid-flow passageway 106. At 1812, providing the energy stimulus includes providing a spatially patterned energy stimulus having at least a first region and a second region different from the first region. In an embodiment, the first regions comprises one of a spatially patterned electromagnetic energy stimulus, a spatially patterned electrical energy stimulus, a spatially patterned ultrasonic energy stimulus, or a spatially patterned thermal energy stimulus, and the second region comprises a different one of a spatially patterned electromagnetic energy stimulus, a spatially patterned electrical energy stimulus, a spatially patterned ultrasonic energy stimulus, or a spatially patterned thermal energy stimulus. At 1814, providing the energy stimulus includes providing an illumination pattern comprising at least a first region and a second region, the second region having at least one of an illumination intensity, an energy-emitting pattern, a peak emission wavelength, an ON-pulse duration, an OFF-pulse duration, and a pulse frequency different from the first region. At 1816, providing the energy stimulus includes providing a voltage to a cerebrospinal fluid received within at least one of the one or more fluid-flow passageways 106, the voltage of sufficient strength or duration to exceed a nominal dielectric strength of a cell plasma membrane. At 1818, providing the energy stimulus includes concurrently or sequentially providing at least a first energy stimulus and a second energy stimulus the second energy stimulus different from the first energy stimulus. In an embodiment, the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus.

At 1820, the method 1800 can further include providing an energy stimulus to a tissue proximate an outer surface of the implantable fluid management device. At 1822, providing the energy stimulus includes independently delivering, in vivo, at least one of a first sterilizing energy stimulus to the biological fluid received within at least one of the one or more fluid-flow passageways 106 and a second sterilizing energy stimulus to the tissue proximate an outer surface of the implantable fluid management device. At 1824, providing the energy stimulus includes independently delivering, in vivo, at least one of a first sterilizing energy stimulus to the biological fluid received within at least one of the one or more fluid-flow passageways 106 and a second sterilizing energy stimulus to the tissue proximate an outer surface of the implantable fluid management device based at least in part on a detected change in a refractive index parameter associated with the cerebrospinal fluid.

Figure 19:
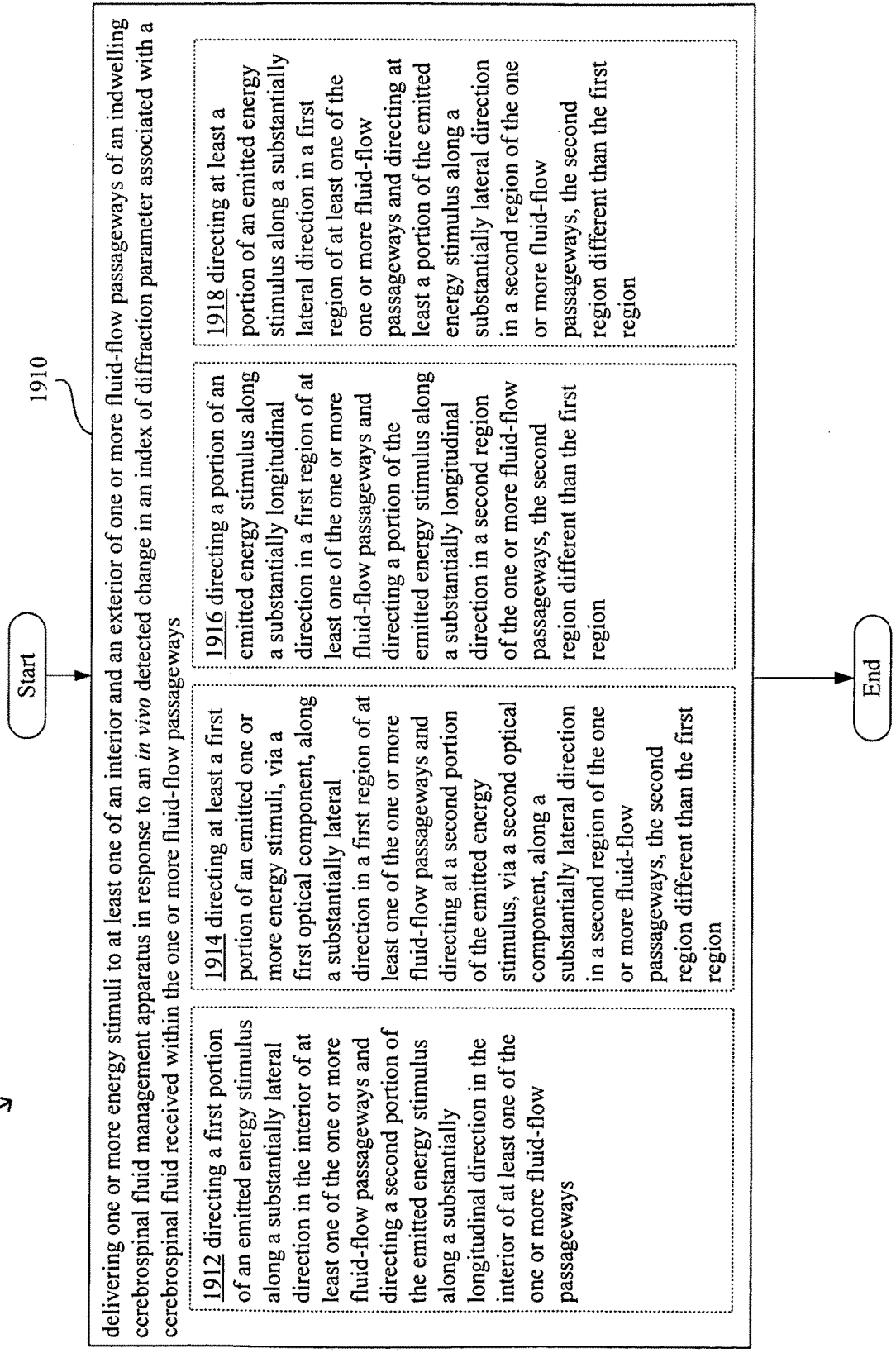
FIG. 19 is a flow diagram of a method according to one illustrated embodiment.

FIG. 19 shows an example of a method 1900. At 1910, the method 1900 includes delivering one or more energy stimuli to at least one of an interior and an exterior of one or more fluid-flow passageways 106 of an indwelling cerebrospinal fluid management apparatus in response to an in vivo detected change in a refractive index parameter associated with a cerebrospinal fluid received within the one or more fluid-flow passageways 106. At 1912, delivering the one or more energy stimuli includes directing a first portion of an emitted energy stimulus along a substantially lateral direction in the interior of at least one of the one or more fluid-flow passageways 106 and directing a second portion of the emitted energy stimulus along a substantially longitudinal direction in the interior of at least one of the one or more fluid-flow passageways 106. At 1914, delivering the one or more energy stimuli includes directing at least a first portion of an emitted one or more energy stimuli, via a first optical component, along a substantially lateral direction in a first region of at least one of the one or more fluid-flow passageways 106 and directing at a second portion of the emitted energy stimulus, via a second optical component, along a substantially lateral direction in a second region of the one or more fluid-flow passageways 106, the second region different from the first region. At 1916, delivering the one or more energy stimuli includes directing a portion of an emitted energy stimulus along a substantially longitudinal direction in a first region of at least one of the one or more fluid-flow passageways 106 and directing a portion of the emitted energy stimulus along a substantially longitudinal direction in a second region of the one or more fluid-flow passageways 106, the second region different from the first region. At 1918, delivering the one or more energy stimuli includes directing at least a portion of an emitted energy stimulus along a substantially lateral direction in a first region of at least one of the one or more fluid-flow passageways 106 and directing at least a portion of the emitted energy stimulus along a substantially lateral direction in a second region of the one or more fluid-flow passageways 106, the second region different from the first region.

FIG. 20 shows an example of a method 2000. At 2010, the method 2000 includes concurrently or sequentially delivering two or more energy stimuli to an interior and an exterior of one or more fluid-flow passageways 106 of an indwelling cerebrospinal fluid management apparatus in response to a detected parameter associated with one or more of a cerebrospinal fluid received within the one or more fluid-flow passageways 106, a detected parameter associated with a tissue proximate an outer surface of the one or more fluid-flow passageways 106, or a characteristic associated with a biological subject. At 2012, concurrently or sequentially delivering the two or more energy stimuli includes concurrently or sequentially delivering at least a first energy stimulus and a second energy stimulus, the second energy stimulus different from the first energy stimulus. In an embodiment, the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus. At 2014, concurrently or sequentially delivering the two or more energy stimuli includes concurrently or sequentially delivering a first electrical stimulus and a second electrical stimulus, in vivo, to target tissue proximate the implanted or inserted surgical implant, the first electrical stimulus or the second electrical stimulus of a character or duration to inhibit scar formation, and the other of the first electrical stimulus or the second electrical stimulus of a character or duration to promote growth of tissue. At 2016, concurrently or sequentially delivering the two or more energy stimuli includes concurrently or sequentially delivering the first sterilizing energy stimulus to a biological fluid received within at least one of the one or more fluid-flow passageways 106 and the second sterilizing energy stimulus to a tissue proximate an outer surface of the indwelling cerebrospinal fluid management apparatus.

FIG. 21 shows an example of a method 2100. At 2110, the method 2100 includes comparing, via integrated circuitry, one or more characteristics communicated from an implanted shunt device to stored reference data, the one or more characteristics including at least one of information associated with a cerebrospinal fluid received within one or more fluid-flow passageways 106 of the implanted shunt device, information associated with a tissue proximate an outer surface of the implanted shunt device, and information associated with a physiological characteristic of the biological subject. At 2120, the method 2100 includes initiating a treatment protocol based at least in part on the comparison. At 2122, initiating the treatment protocol includes selectively energizing one or more regions proximate a surface of the implanted shunt device via one or more energy-emitters based at least in part on the comparison. At 2124, initiating the treatment protocol includes delivering an active agent composition to one or more regions proximate a surface of the implanted shunt device via one or more active agent assemblies based at least in part on the comparison. At 2126, initiating the treatment protocol includes activating an authorization protocol, activating an authentication protocol, activating an energy stimulus protocol, activating an active agent delivery protocol, or activating an infection sterilization diagnostic protocol based at least in part on the comparison.

Figure 22:
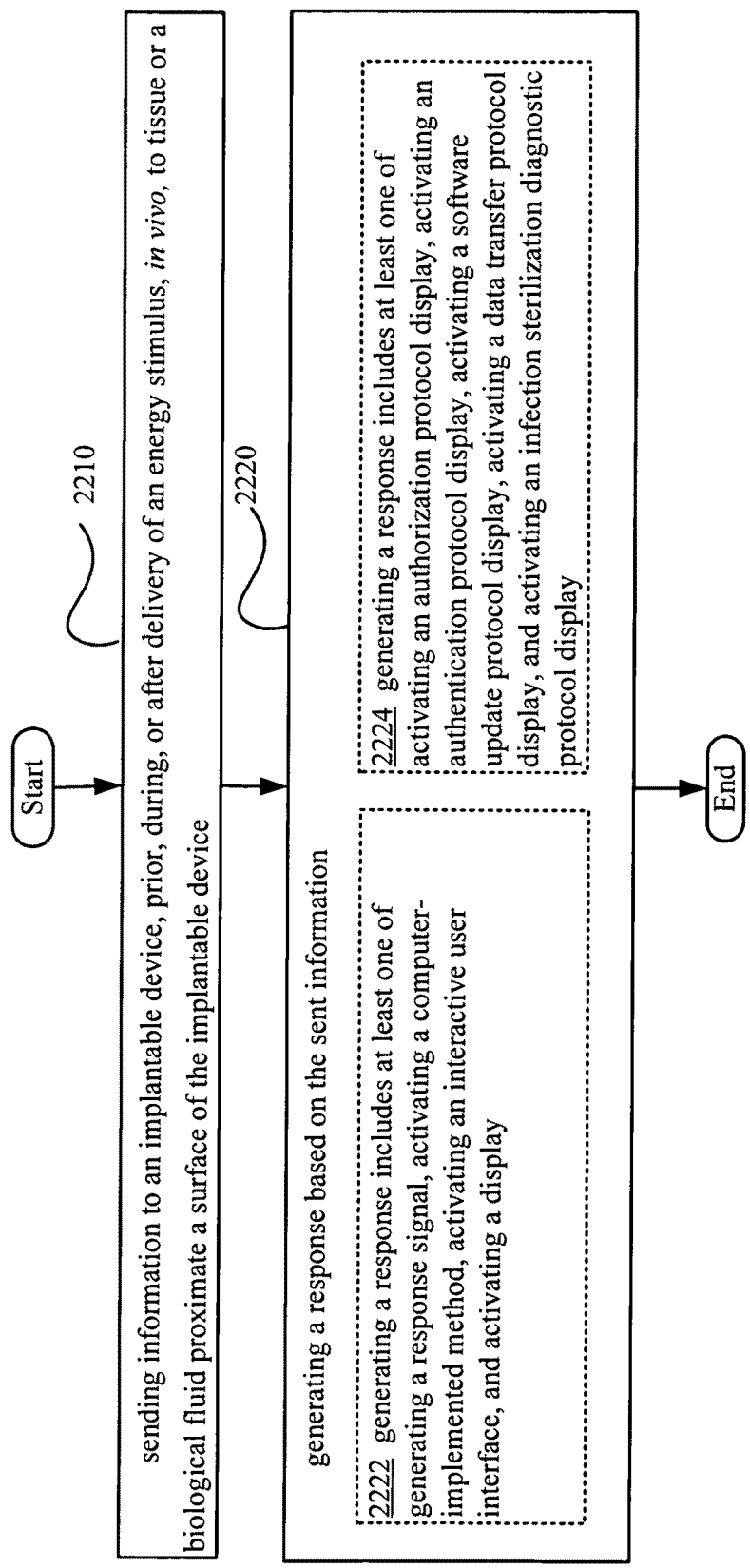
FIG. 22 is a flow diagram of a method according to one illustrated embodiment.

FIG. 22 shows an example of a method 2200. At 2210, the method 2200 includes sending information to an implantable device 102, prior, during, or after delivery of an energy stimulus, in vivo, to tissue or biological fluid proximate a surface of the implantable device 102. In an embodiment, sending information to an implantable device 102 includes sending information to an implantable device 102, prior, during, or after delivery of at least one of an electrical sterilizing stimulus, an electromagnetic sterilizing stimulus, an ultrasonic sterilizing stimulus, and a thermal sterilizing stimulus. At 2220, the method 2200 includes generating a response based on the sent information. At 2222, generating the response can include at least one of generating a response signal, activating a computer-implemented method, activating an interactive user interface, and activating a display. At 2224, generating the response can include at least one of activating an authorization protocol display, activating an authentication protocol display, activating a software update protocol display, activating a data transfer protocol display, and activating an infection sterilization diagnostic protocol display.

Figure 23:
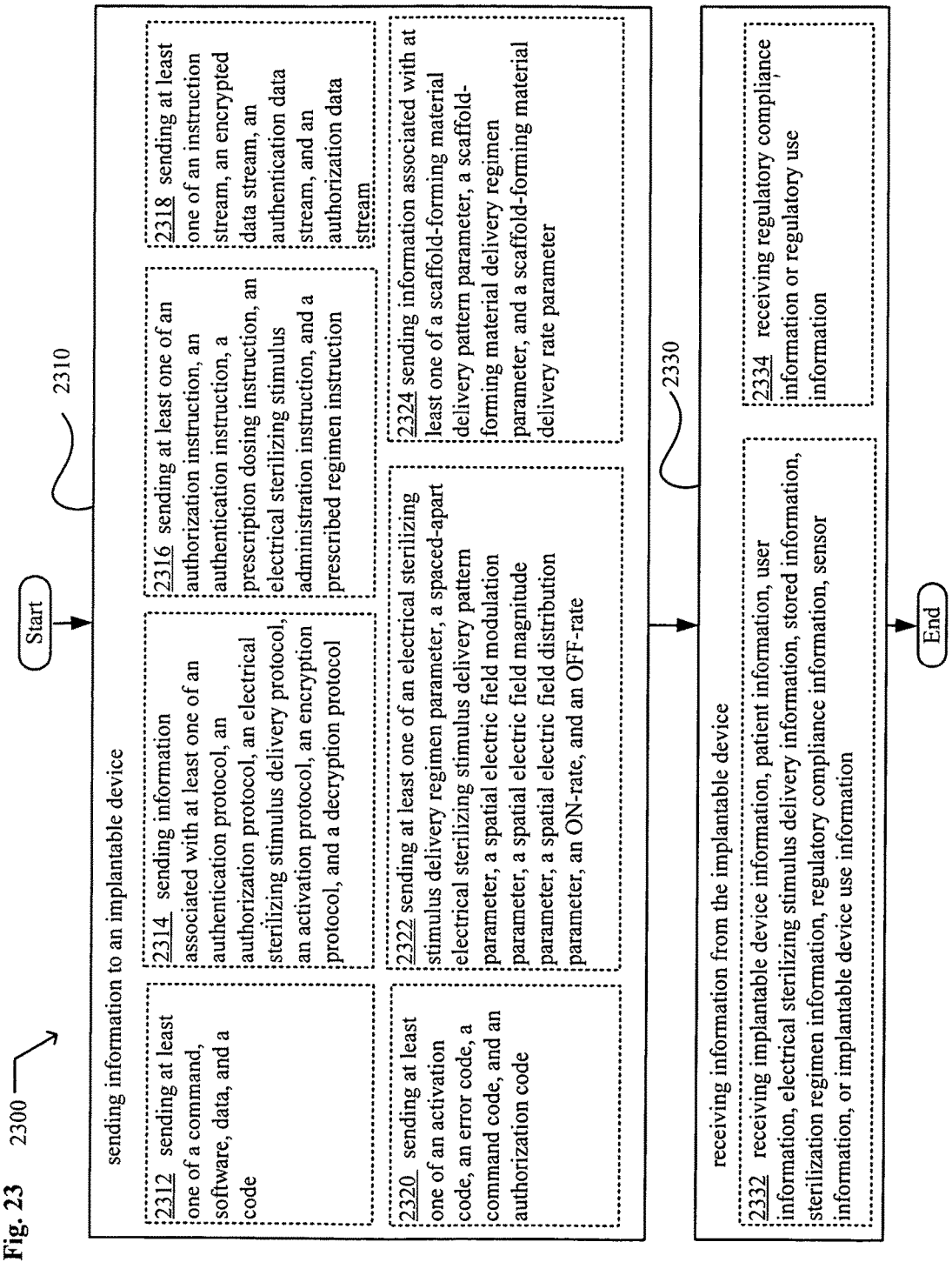
FIG. 23 is a flow diagram of a method according to one illustrated embodiment.

FIG. 23 shows an example of a method 2300. At 2310, the method 2300 includes sending information to an implantable device that includes: one or more fluid-flow passageways 106, an actively controllable excitation component 910 configured to deliver an electrical sterilizing stimulus, in vivo, to tissue or a biological fluid proximate a surface of the implantable device 102, and a controller 402 communicatively coupled to the actively controllable excitation component 910. At 2312, sending information can include sending at least one of a command, software, data, and a code. At 2314, sending information can include sending information associated with at least one of an authentication protocol, an authorization protocol, a delivery protocol, an activation protocol, an encryption protocol, and a decryption protocol. In an embodiment, sending information includes sending information associated with at least one of an electrical sterilizing stimulus delivery protocol, an electromagnetic sterilizing stimulus delivery protocol, an ultrasonic sterilizing stimulus delivery protocol, and a thermal sterilizing stimulus delivery protocol. At 2316, sending information includes sending at least one of an authorization instruction, an authentication instruction, a prescription dosing instruction, a sterilizing stimulus administration instruction, and a prescribed regimen instruction. At 2318, sending information includes sending at least one of an instruction stream, an encrypted data stream, an authentication data stream, and an authorization data stream. At 2320, sending information includes sending at least one of an activation code, an error code, a command code, and an authorization code. In an embodiment, sending information includes sending at least one of patient information, sensor information, detected data, physiological sensor data, and physiological reference data. At 2322, sending information includes sending at least one of a sterilizing stimulus delivery regimen parameter, a temporal sterilizing energy stimulus delivery pattern parameter, a spaced-apart sterilizing stimulus delivery pattern parameter, a spatial electric field modulation parameter, a spatial electric field magnitude parameter, a spatial electric field distribution parameter, an ON-rate, and an OFF-rate. At 2324, sending information includes sending information associated with at least one of an active agent delivery pattern parameter, an active agent delivery regimen parameter, and an active agent delivery rate parameter. In an embodiment, sending information includes sending information associated with at least one of an electrical sterilizing stimulus delivery pattern parameter, an electromagnetic sterilizing stimulus delivery pattern parameter, an ultrasonic sterilizing stimulus delivery pattern parameter, and a thermal sterilizing stimulus delivery pattern parameter. In an embodiment, sending information includes sending information associated with at least one of an electrical sterilizing stimulus delivery regimen parameter, an electromagnetic sterilizing stimulus delivery regimen parameter, an ultrasonic sterilizing stimulus delivery regimen parameter, and a thermal sterilizing stimulus delivery regimen parameter.

At 2330, the method 2300 includes receiving information from the implantable device 102. At 2332, receiving information from the implantable device 102 includes receiving implantable device information, patient information, user information, sterilizing stimulus delivery information, stored information, sterilization regimen information, regulatory compliance information, sensor information, or implantable device use information. At 2334, receiving information from the implantable device 102 includes receiving regulatory compliance information or regulatory use information. In an embodiment, receiving information includes receiving sensor data. In an embodiment, receiving information includes receiving a control signal. In an embodiment, receiving information includes receiving a request for transmission of information. In an embodiment, receiving information includes receiving a request for transmission of at least one of data, a command, an authorization, an update, and a code.

Figure 24:
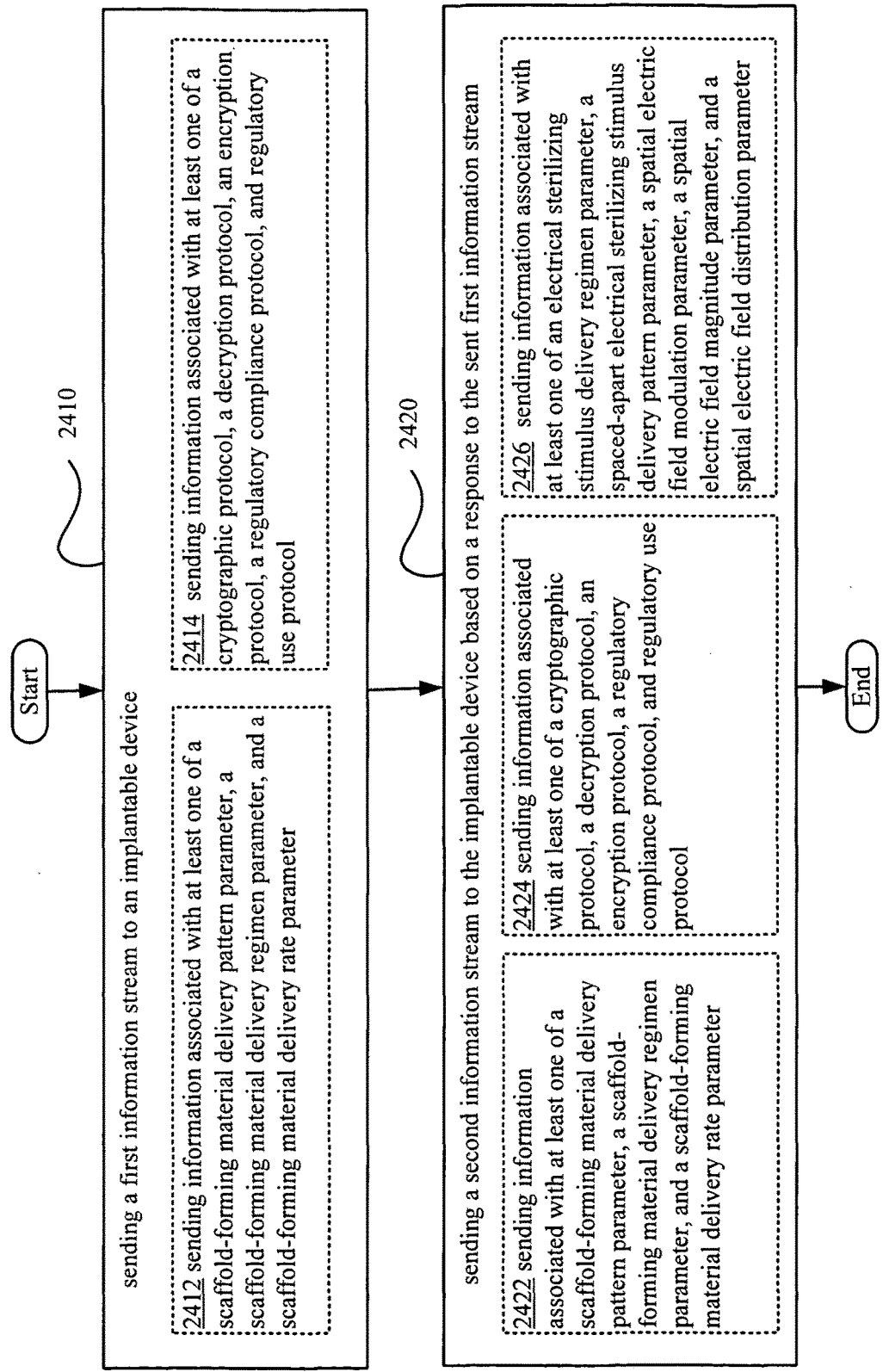
FIG. 24 is a flow diagram of a method according to one illustrated embodiment.

FIG. 24 shows an example of a method 2400. At 2410, the method 2400 includes sending a first information stream to an implantable device 102. At 2412, sending the first information stream includes sending information associated with at least one of an active agent delivery pattern parameter, an active agent delivery regimen parameter, and an active agent delivery rate parameter. At 2414, sending the first information stream includes sending information associated with at least one of a cryptographic protocol, a decryption protocol, an encryption protocol, a regulatory compliance protocol, and regulatory use protocol. At 2420, the method 2400 includes sending a second information stream to the implantable device 102 based on a response to the sent first information stream. At 2422, sending the second information stream includes sending information associated with at least one of an active agent delivery pattern parameter, an active agent delivery regimen parameter, and an active agent delivery rate parameter. At 2424, sending the second information stream includes sending information associated with at least one of a cryptographic protocol, a decryption protocol, an encryption protocol, a regulatory compliance protocol, and regulatory use protocol. At 2426, sending the second information stream includes sending information associated with at least one of a sterilizing energy stimulus delivery regimen parameter, a spaced-apart sterilizing energy stimulus delivery pattern parameter, a spatial electric field modulation parameter, a spatial electric field magnitude parameter, and a spatial electric field distribution parameter.

Figure 25:
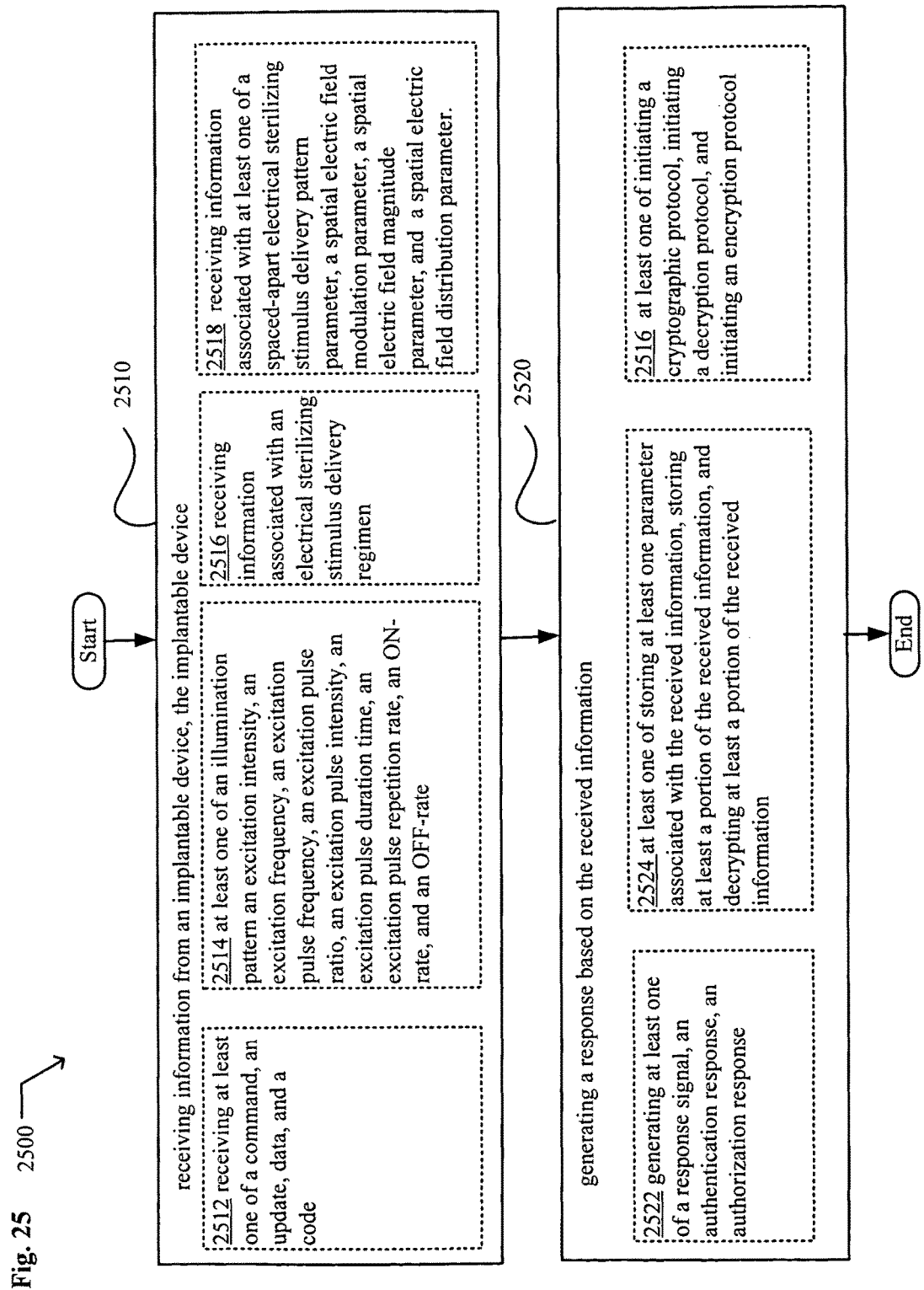
FIG. 25 is a flow diagram of a method according to one illustrated embodiment.

FIG. 25 shows an example of a method 2500. At 2510, the method 2500 includes receiving information from an implantable device 102 that includes: one or more fluid-flow passageways 106, an actively controllable excitation component 910 configured to deliver a sterilizing energy stimulus, in vivo, to tissue or a biological fluid proximate a surface of the implantable device 102, and a controller 402 communicatively coupled to the actively controllable excitation component. At 2512, receiving information includes receiving at least one of a command, an update, data, and a code. At 2514, receiving information includes receiving information associated with at least one of an illumination pattern an excitation intensity, an excitation frequency, an excitation pulse frequency, an excitation pulse ratio, an excitation pulse intensity, an excitation pulse duration time, an excitation pulse repetition rate, an ON-rate, and an OFF-rate. At 2516, receiving information includes receiving information associated with an electrical sterilizing stimulus delivery regimen. At 2518, receiving information includes receiving information associated with at least one of a spaced-apart electrical sterilizing stimulus delivery pattern parameter, a spatial electric field modulation parameter, a spatial electric field magnitude parameter, and a spatial electric field distribution parameter. In an embodiment, receiving information includes receiving sensor data. In an embodiment, receiving information includes receiving a control signal. In an embodiment, receiving information includes receiving a request for transmission of information. In an embodiment, receiving information includes receiving a request for transmission of at least one of data, a command, an authorization, an update, and a code.

At 2520, the method 2500 includes generating a response based on the received information. At 2522, generating the response includes generating at least one of a response signal, an authentication response, and an authorization response. At 2524, generating the response includes at least one of storing at least one parameter associated with the received information, storing at least a portion of the received information, and decrypting at least a portion of the received information. At 2526, generating the response includes at least one of initiating a cryptographic protocol, initiating a decryption protocol, and initiating an encryption protocol. In an embodiment, generating the response includes generating at least one of a control signal, data, a command, an authorization, an update, and a code.

Figure 26A:
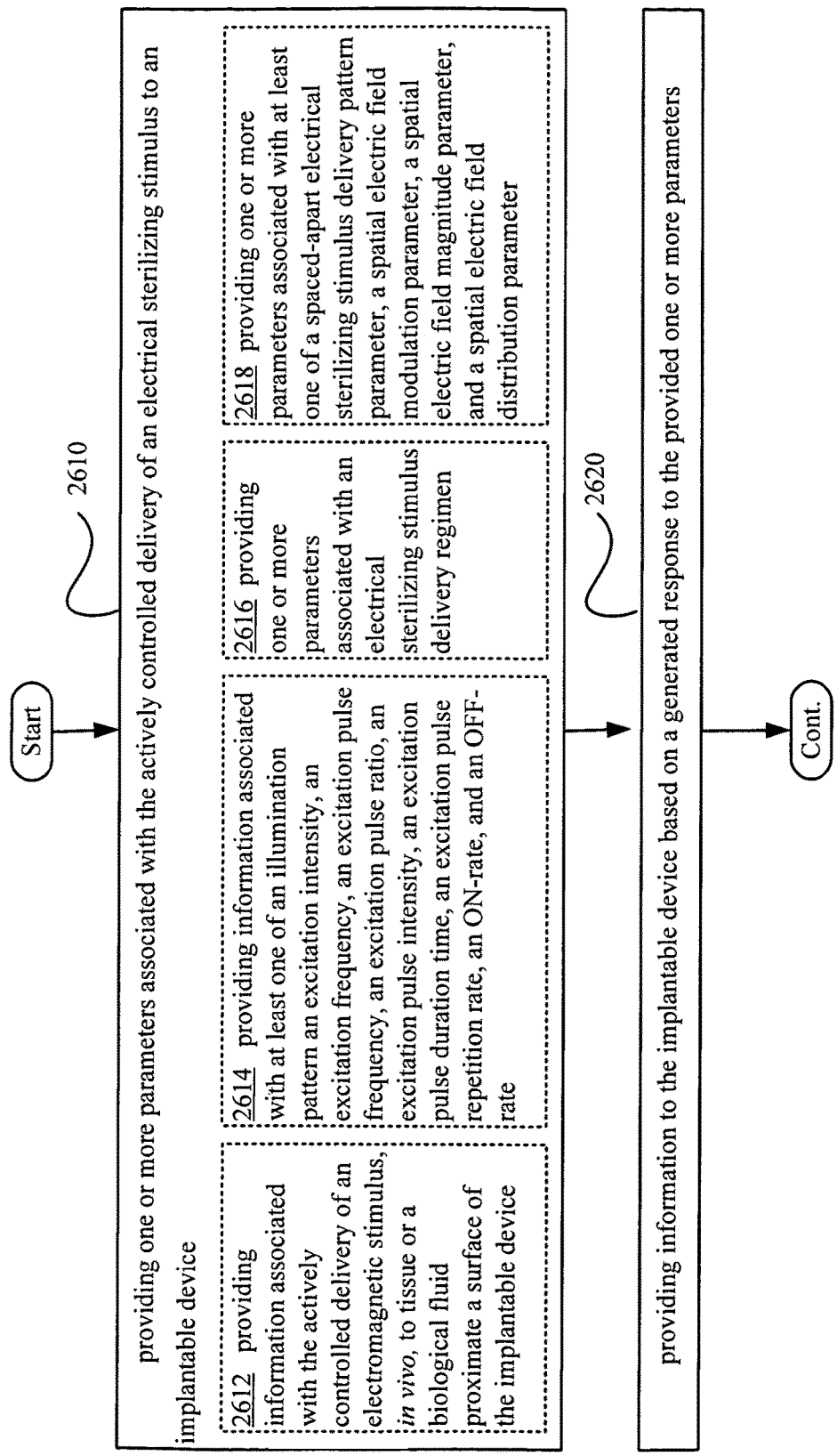
FIGS. 26A and 26B are flow diagrams of a method according to one illustrated embodiment.
Figure 26B:
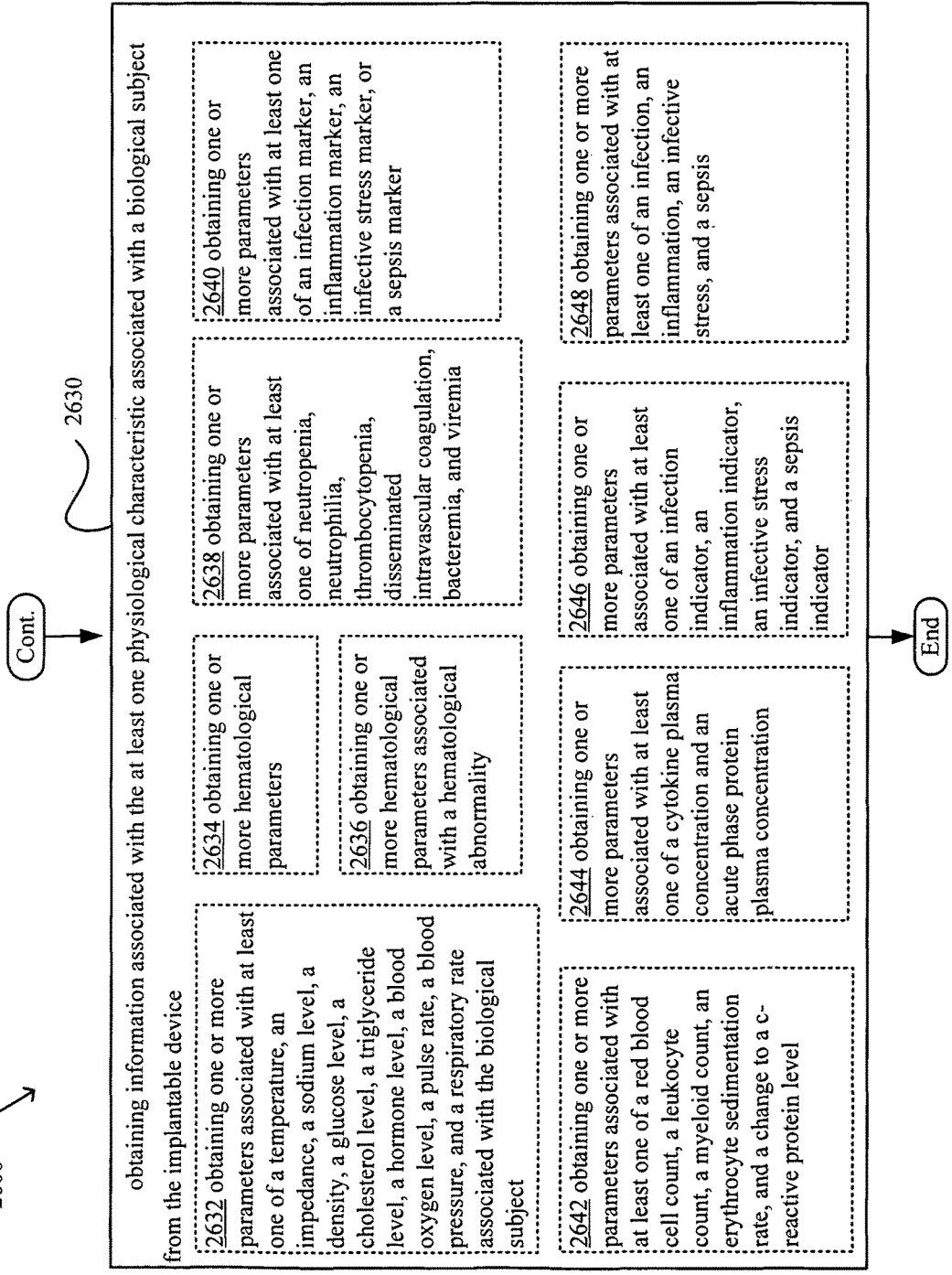

FIGS. 26A and 26B show an example of a method 2600. At 2610, the method 2600 includes providing one or more parameters associated with the actively controlled delivery of a sterilizing energy stimulus to an implantable device 102. In an embodiment, providing the one or more parameters includes providing information to the implantable device 102, the information associated with the actively controlled delivery of at least one of an electrical sterilizing stimulus, an electromagnetic sterilizing stimulus, an ultrasonic sterilizing stimulus, and a thermal sterilizing stimulus, in vivo, to tissue or a biological fluid proximate the implantable device 102. In an embodiment, providing the one or more parameters includes providing information associated with the actively controlled delivery of an electrical stimulus, in vivo, to tissue or a biological fluid proximate a surface of the implantable device 102. At 2612, providing the one or more parameters includes providing information associated with the actively controlled delivery of an electromagnetic stimulus, in vivo, to tissue proximate a first outer surface of the implantable device 102. At 2614, providing the one or more parameters includes providing information associated with at least one of an illumination pattern an excitation intensity, an excitation frequency, an excitation pulse frequency, an excitation pulse ratio, an excitation pulse intensity, an excitation pulse duration time, an excitation pulse repetition rate, an ON-rate, and an OFF-rate. At 2616, providing the one or more parameters includes providing one or more parameters associated with an electrical sterilizing stimulus delivery regimen. At 2618, providing the one or more parameters includes providing one or more parameters associated with at least one of a spaced-apart electrical sterilizing stimulus delivery pattern parameter, a spatial electric field modulation parameter, a spatial electric field magnitude parameter, and a spatial electric field distribution parameter. In an embodiment, providing the one or more parameters includes providing information associated with the actively controlled delivery of an ultrasonic stimulus, in vivo, to tissue proximate a first outer surface of the implantable device. In an embodiment, providing the one or more parameters includes providing information associated with the actively controlled delivery of a thermal stimulus, in vivo, to tissue proximate a first outer surface of the implantable device. In an embodiment, providing the one or more parameters includes providing information associated with a spatial-pattern of the sterilizing energy stimulus. In an embodiment, providing the one or more parameters includes providing information associated with a spatial-pattern distribution of the sterilizing energy stimulus. In an embodiment, providing the one or more parameters includes providing information associated with a temporal-pattern of the sterilizing energy stimulus. In an embodiment, providing the one or more parameters includes providing the one or more parameters based at least in part on obtained information.

At 2620 the method 2600 includes providing information to the implantable device 102 based on a generated response to the provided one or more parameters. In an embodiment, providing the one or more parameters includes providing the one or more parameters based at least in part on obtained information. In an embodiment, providing the one or more parameters includes providing the one or more parameters in response to the obtained information. At 2630, the method 2600 includes obtaining information associated with the at least one physiological characteristic associated with a biological subject from the implantable device 102. At 2632, obtaining information includes obtaining one or more parameters associated with at least one of a temperature, an impedance, a sodium level, a density, a glucose level, a lipoprotein level, a cholesterol level, a triglyceride level, a hormone level, a blood oxygen level, a pulse rate, a blood pressure, an intracranial pressure, and a respiratory rate associated with the biological subject. At 2634, obtaining information includes obtaining one or more hematological parameters. At 2636, obtaining information includes obtaining one or more hematological parameters associated with a hematological abnormality. At 2638, obtaining information includes obtaining one or more parameters associated with at least one of leukopenia, leukophilia, lymphocytopenia, lymphocytophilia, neutropenia, neutrophilia, thrombocytopenia, disseminated intravascular coagulation, bacteremia, and viremia. At 2640, obtaining information includes obtaining one or more parameters associated with at least one of an infection marker, an inflammation marker, an infective stress marker, a systemic inflammatory response syndrome marker, and a sepsis marker. At 2642, obtaining information includes obtaining one or more parameters associated with at least one of a red blood cell count, a lymphocyte level, a leukocyte count, a myeloid count, an erythrocyte sedimentation rate, and a change to C-reactive protein level. At 2644, obtaining information includes obtaining one or more parameters associated with at least one of a cytokine plasma concentration and an acute phase protein plasma concentration. At 2646, obtaining information includes obtaining one or more parameters associated with at least one of an infection indicator, an inflammation indicator, an infective stress indicator, and a sepsis indicator. At 2648, obtaining information includes obtaining one or more parameters associated with at least one of an infection, an inflammation, an infective stress, or a sepsis. In an embodiment, obtaining information includes obtaining one or more parameters associated with at least one of an infection, an inflammation, an infective stress, and a sepsis.

FIG. 27 shows an example of a method 2700. At 2710, the method 2700 includes providing a first information to an implantable device 102. At 2720, the method 2700 includes obtaining a second information from the implant based on a response to the first information. At 2730, the method 2700 includes providing information to the implantable device 102 based on the second information.

FIG. 28 shows an example of a method 2800. At 2810, the method 2800 includes receiving information from an implantable device 102, during delivery of a sterilizing energy stimulus, in vivo, to tissue or biological fluid proximate a surface of the implantable device 102. At 2820, the method 1600 includes generating a response based on the received information.

FIG. 29 shows an example of a method 2900. At 2910, the method 2900 includes receiving information from an implantable device 102, after delivery of a sterilizing energy stimulus, in vivo, to tissue or a biological fluid proximate the implantable device 102. At 2920, the method 2900 includes generating a response based on the received information.

FIG. 30 shows an example of a method 3000. At 3010, the method 3000 includes receiving information from an implantable device 102, before delivery of a sterilizing energy stimulus, in vivo, to a biological fluid or tissue proximate an inner or an outer surface of the implantable device 102. At 3020, the method 3000 includes generating a response based on the received information. At 3022, generating the response includes activating a third-party device. At 3024, generating the response includes activating an authorization protocol. At 3026, generating the response includes activating an authentication protocol. At 3028, generating the response includes activating a software update protocol. At 3030, generating the response includes activating a data transfer protocol. At 3032, generating the response includes activating an infection sterilization diagnostic protocol.

FIG. 31 shows an example of a method 3100 of treating scar formation post surgery. Following an injury to a tissue, localized release of inflammatory mediators may occur as a result of damaged endothelial cells and platelet aggregation at the site of injury. This inflammatory response is a normal part of the wound repair process, preventing infection and promoting fibrosis and wound closure. Inflammatory mediators such as transforming growth factor (TGF) β family, platelet-derived growth factors (PDGF), and epidermal growth factors (EGF) stimulate fibroblast proliferation and matrix secretion, and promote leukocyte recruitment. The recruited leukocytes release additional mediators such as fibroblast growth factors (FGF), vascular endothelial growth factors (VEGF), and other factors that reinforce fibroblast proliferation and differentiation, fight infection, and increase vascular permeability and ingrowth. Although important in the wound healing process, inflammatory mediators such as TGF-β have been implicated in scar formation. Accordingly, it can be possible to attenuate scar formation by regulating the activity of mediators involved in the wound repair process. In an embodiment, astroglial cells, in their immature, activated state, can be used to reduce secondary cell death (necrosis) glial scar formation, promote axon regeneration, or promote blood vessel growth. See, e.g., U.S. Pat. No. 4,900,553. For example, in an embodiment, a method of reducing glial scar formation includes inducing apoptosis in reactive astrocytes (e.g., microglia, endothelial cells, fibroblasts, or the like), providing one or more neural stem cells, nonreactive astrocytes or the like, and providing a stimulus (an electrical, an electromagnetic, an ultrasonic, or a thermal stimulus, or the like) of a character and duration to promote growth of the one or more neural stem cells, or nonreactive astrocytes.

At 3110, the method 3100 includes implanting or inserting a surgical implant comprising a photoactivatable steroid composition into a biological subject. In an embodiment, implanting or inserting the surgical implant includes implanting or inserting a surgical implant comprising a photoactivatable steroid composition including one or more growth promoting materials. At 3120, the method 3100 includes photoactivating the photoactivatable steroid composition. At 3122, photoactivating the photoactivatable steroid composition includes activating an actively controllable excitation component 910 so as to deliver a sterilizing energy stimulus of a character and for a time sufficient to photoactivate at least a portion of the photoactivatable steroid composition. In an embodiment, photoactivating the photoactivatable steroid composition includes controlling an actively controllable excitation component 910 so as to deliver a sterilizing energy stimulus of a character and for a time sufficient to stimulate non-scarring tissue formation. In an embodiment, the method 3100 can further include concurrently or sequentially delivering a first electrical stimulus and a second electrical stimulus, in vivo, to target tissue proximate the implanted or inserted surgical implant. In an embodiment, the first electrical stimulus or the second electrical stimulus is of a character and duration to inhibit growth of tissue of a first type, and the other of the first electrical stimulus or the second electrical stimulus is of a character and duration to promote growth of tissue of a second type. In an embodiment, the method 3100 includes concurrently or sequentially delivering a first electrical stimulus and a second electrical stimulus, in vivo, to target tissue proximate the implanted or inserted surgical implant, such than the first electrical stimulus or the second electrical stimulus is of a character and duration to inhibit (e.g., minimize, reduce, prevent, or the like) a scar formation process, and the other of the first electrical stimulus or the second electrical stimulus is of a character and duration to promote growth of tissue. In an embodiment, the method 3100 can further include concurrently or sequentially delivering a spatially patterned electrical stimulus including a first electrical stimulus and a second electrical stimulus, in vivo, to target tissue proximate the implanted or inserted surgical implant, the first electrical stimulus or the second electrical stimulus of a character and duration to inhibit scar formation in a first region proximate the implanted device and the other of the first electrical stimulus or the second electrical stimulus of a character and duration to promote growth of tissue in a second region proximate the implanted, the second region differing in at least one of area, volume, and location of the first region.

FIG. 32 shows an example of a method 3200 of treating scar formation post surgery. At 3210, the method 3200 includes photoactivating a photoactivatable steroid composition carried by an implanted surgical implant. At 3212, photoactivating the photoactivatable steroid composition includes activating an actively controllable excitation component 910 to deliver a space-apart light energy patterned having a sufficient strength or duration to photoactivate at least a portion of the photoactivatable steroid composition.

Figure 33:
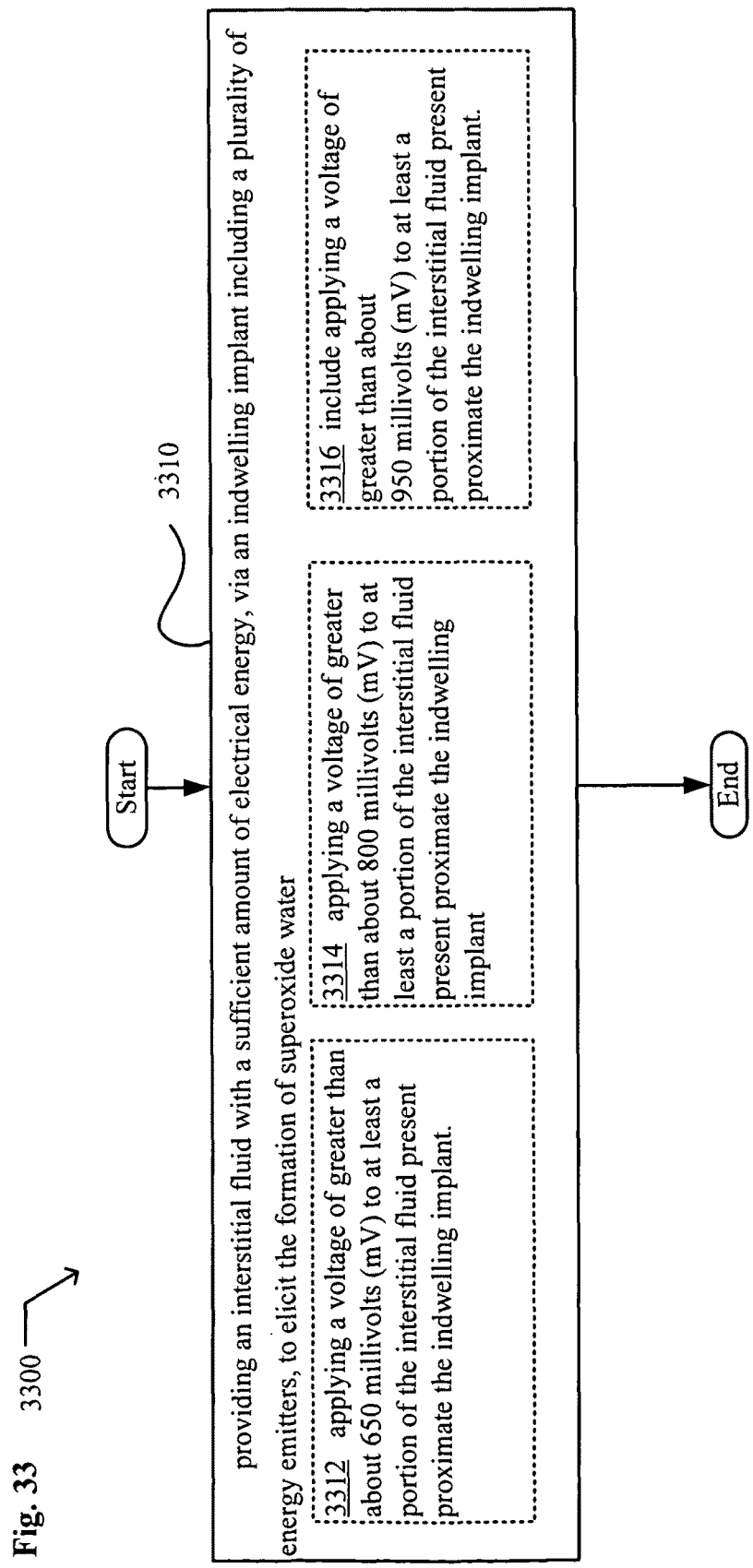

FIG. 33 shows an example of a method 3300 of forming an antimicrobial agent, in vivo. At 3310, the method 3300 includes providing an interstitial fluid with a sufficient amount of electrical energy, via an indwelling implant including a plurality of energy emitters 302, to elicit the formation of superoxidized water. In an embodiment, the resulting superoxidized water can affect one or more healing or growth promoting properties to tissue or a biological fluid. At 3312, providing the interstitial fluids with the sufficient amount of electrical energy includes applying a voltage of greater than about 650 millivolts (mV) to at least a portion of the interstitial fluid proximate the indwelling implant. At 3314, providing the interstitial fluids with the sufficient amount of electrical energy includes applying a voltage of greater than about 800 millivolts (mV) to at least a portion of the interstitial fluid proximate the indwelling implant. Applying a sufficient voltage to tissue infected with, for example, pathogenic bacteria, can lead to a reduction of the pathogenic bacteria in at least a portion of the infected tissue. At 3316, providing the interstitial fluids with the sufficient amount of electrical energy includes applying a voltage of greater than about 950 millivolts (mV) to at least a portion of the interstitial fluid proximate the indwelling implant.

Figure 34:
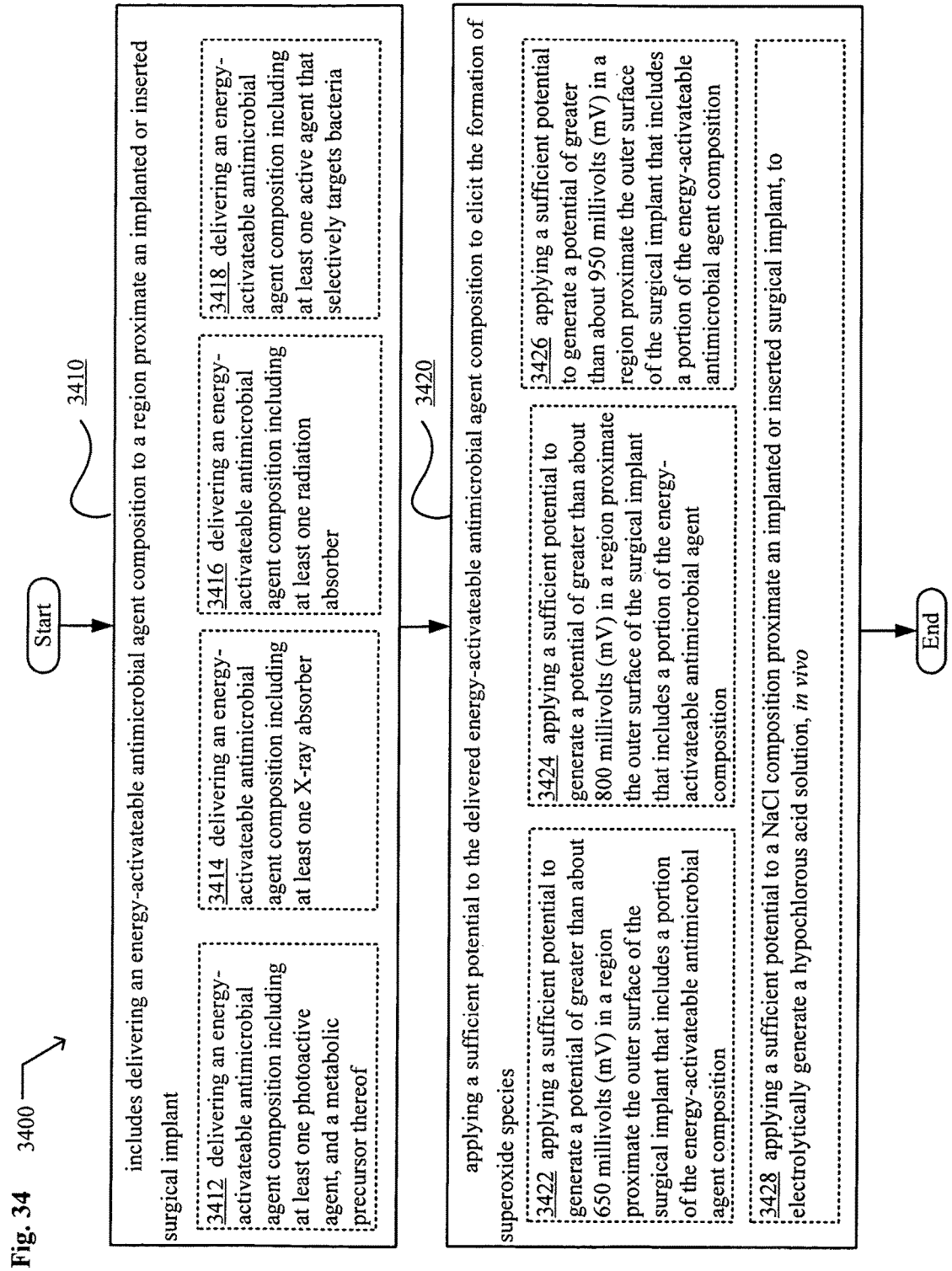
FIG. 34 is a flow diagram of a method according to one illustrated embodiment.

FIG. 34 shows an example of a method 3400 of forming an antimicrobial agent, in vivo. At 3410, the method 3400 includes delivering an energy-activatable antimicrobial agent composition to a region (e.g., a region within a fluid-flow passageway 106, a region proximate an inner or an outer surface of an implantable device 102, or the like) proximate an implanted or inserted surgical implant, the implanted or inserted surgical implant including at least one antimicrobial agent reservoir, the antimicrobial agent reservoir configured to deliver an energy-activatable antimicrobial agent composition to tissue proximate an outer surface of the surgical implant, and a plurality of electrodes, the plurality of electrodes operable to energize an energy-activatable antimicrobial agent composition in the presence of an applied potential. Among antimicrobial agent compositions, examples include, but are not limited to, diluted solutions of NaCl, hypochlorous acid solutions (HAS), oxidative reduction potential aqueous compositions, STER-ILOX TX (PuriCore Inc.), STERILOX Solutions (PuriCore Inc.), MICROCYN (Nofil Corp.), superoxidized aqueous compositions, superoxidized water, superoxide dismutase compositions, physiologically balanced ionized acidic solutions, and the like. Further non-limiting examples of antimicrobial agent compositions can be found in, for example, the following documents (the contents of which are incorporated herein by reference): U.S. Pat. No. 7,276,255 (issued Oct. 2, 2007), U.S. Pat. No. 7,183,048 (issued Feb. 27, 2007), U.S. Pat. No. 6,506,416 (issued Jan. 14, 2003), U.S. Pat. No. 6,426,066 (issued Jul. 30, 2002), and U.S. Pat. No. 5,622,848 (Apr. 22, 1997); and U.S. Patent Nos. 2007/0196357 (published Aug. 23, 2007), 2007/0173755 (published Jul. 26, 2007), and 2005/0142157 (published Jun. 30, 2005).

At 3412, delivering an energy-activatable antimicrobial agent composition includes delivering an energy-activatable antimicrobial agent composition including at least one photoactive agent, or a metabolic precursor thereof. At 3414, delivering an energy-activatable antimicrobial agent composition includes delivering an energy-activatable antimicrobial agent composition including at least one X-ray absorber. At 3416, delivering an energy-activatable antimicrobial agent composition includes delivering an energy-activatable antimicrobial agent composition including at least one radiation absorber. At 3418, delivering an energy-activatable antimicrobial agent composition includes delivering an energy-activatable antimicrobial agent composition including at least one active agent that selectively targets bacteria.

At 3420, the method 3400 includes applying a sufficient potential to the delivered energy-activatable antimicrobial agent composition to elicit the formation of superoxide species. At 3422, applying the sufficient potential to the delivered energy-activatable antimicrobial agent composition includes applying a sufficient potential to generate a potential of greater than about 650 millivolts (mV) in a region proximate the outer surface of the surgical implant that includes a portion of the energy-activatable antimicrobial agent composition. At 3424, applying the sufficient potential to the delivered energy-activatable antimicrobial agent composition includes applying a sufficient potential to generate a potential of greater than about 800 millivolts (mV) in a region proximate the outer surface of the surgical implant that includes a portion of the energy-activatable antimicrobial agent composition. At 3426, applying the sufficient potential to the delivered energy-activatable antimicrobial agent composition includes applying a sufficient potential to generate a potential of greater than about 950 millivolts (mV) in a region proximate the outer surface of the surgical implant that includes a portion of the energy-activatable antimicrobial agent composition. In an embodiment, the antimicrobial agent compositions ranges in pH from about 5.0 to about 6.5. At 3428, applying the sufficient potential to the delivered energy-activatable antimicrobial agent composition includes applying a sufficient potential to a NaCl composition proximate an implanted or inserted surgical implant, to electrolytically generate a hypochlorous acid solution (HAS), in vivo, in a region. In an embodiment, the pH of the generated HAS ranges from about 5.5 to about 6.2.

Figure 35:
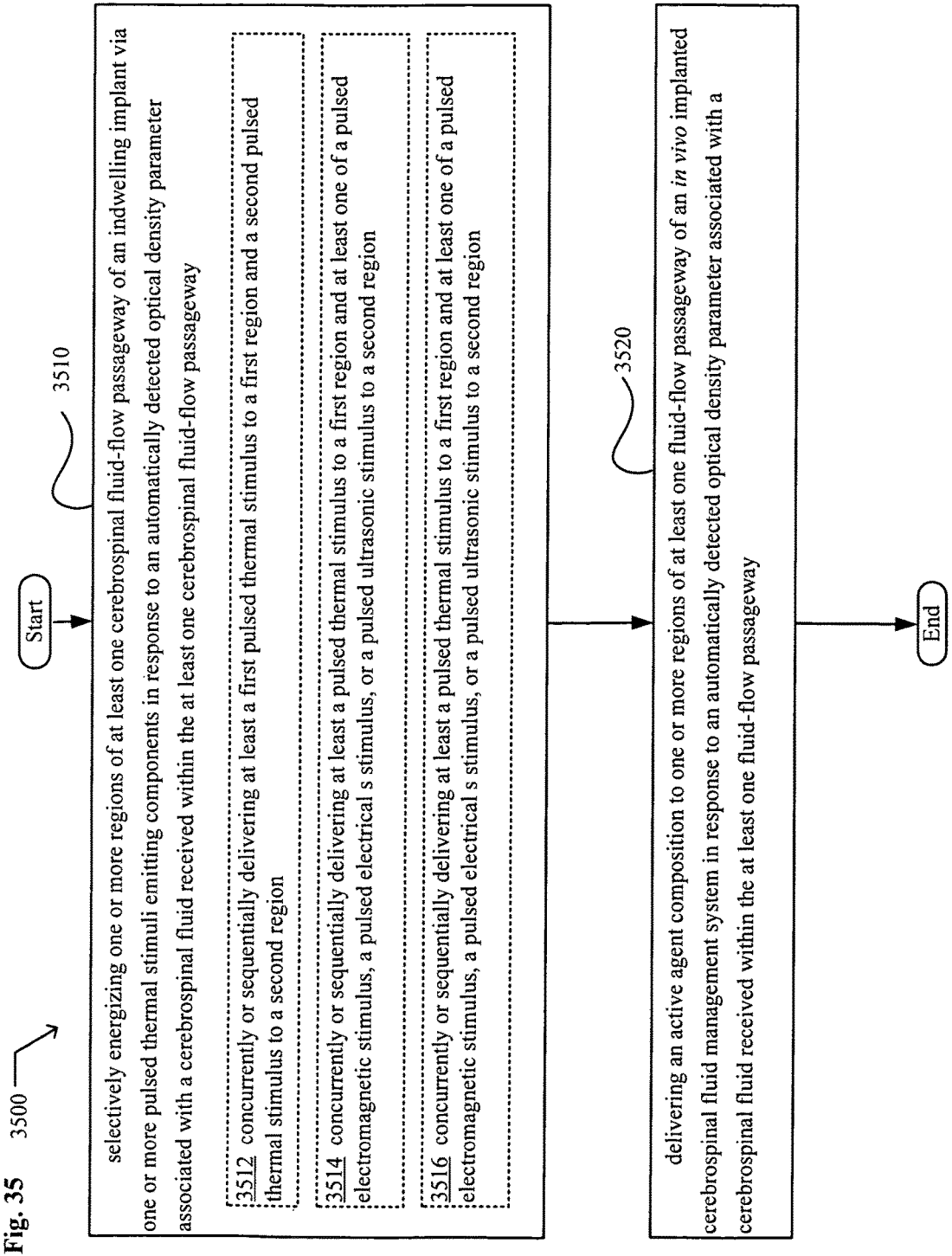
FIG. 35 is a flow diagram of a method according to one illustrated embodiment.

FIG. 35 shows an example of a method 3500 of inhibiting a microbial colonization in the cerebrospinal fluid of a biological subject. At 3510, the method 3500 includes selectively energizing one or more regions of at least one cerebrospinal fluid-flow passageway 106 of an indwelling implant 102 via one or more pulsed thermal stimuli emitting components in response to an automatically detected optical density parameter associated with a cerebrospinal fluid received within the at least one cerebrospinal fluid-flow passageway 106. At 3512, selectively energizing includes concurrently or sequentially delivering at least a first pulsed thermal stimulus to a first region and a second pulsed thermal stimulus to a second region. At 3514, selectively energizing includes concurrently or sequentially delivering a pulsed thermal stimulus to a first region and at least one of a pulsed electromagnetic stimulus, a pulsed electrical s stimulus, or a pulsed ultrasonic stimulus to a second region. At 3520, the method 3500 can include delivering an active agent composition to one or more regions of at least one fluid-flow passageway 106 of an in vivo implanted cerebrospinal fluid management system 100 in response to an automatically detected optical density parameter associated with a cerebrospinal fluid received within the at least one fluid-flow passageway 106.

Figure 36:
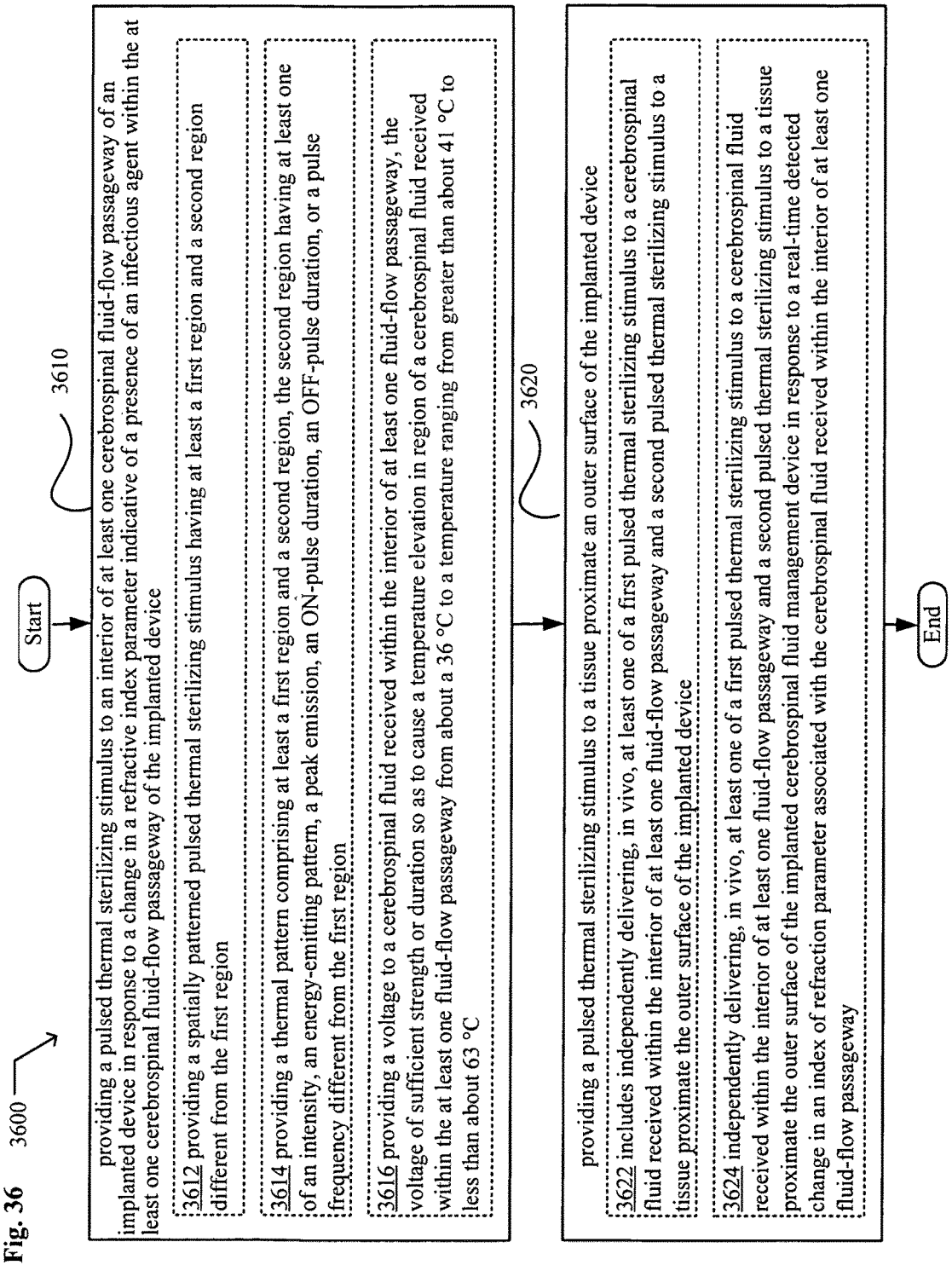
FIG. 36 is a flow diagram of a method according to one illustrated embodiment.

FIG. 36 shows an example of a method 3600. At 3610, the method 3600 includes providing a pulsed thermal sterilizing stimulus to an interior of at least one cerebrospinal fluid-flow passageway 106 of an implanted device 102 in response to a change in a refractive index parameter indicative of a presence of an infectious agent within the at least one cerebrospinal fluid-flow passageway 106 of the implanted device 102. At 3612, providing the pulsed thermal sterilizing stimulus includes providing a spatially patterned pulsed thermal sterilizing stimulus having at least a first region and a second region different from the first region. At 3614, providing the pulsed thermal sterilizing stimulus includes providing a thermal pattern comprising at least a first region and a second region, the second region having at least one of an intensity, an energy-emitting pattern, a peak emission, an ON-pulse duration, an OFF-pulse duration, or a pulse frequency different from the first region. At 3616, providing the pulsed thermal sterilizing stimulus includes providing a voltage to a cerebrospinal fluid received within the interior of at least one fluid-flow passageway 106, the voltage of sufficient strength or duration so as to cause a temperature elevation in region of a cerebrospinal fluid received within the at least one fluid-flow passageway 106 from about a 36° C. to a temperature ranging from greater than about 41° C. to less than about 63° C.

At 3620, the method 3600 can include providing a pulsed thermal sterilizing stimulus to a tissue proximate an outer surface of the implanted device 102. At 3622, providing the pulsed thermal sterilizing stimulus includes independently delivering, in vivo, at least one of a first pulsed thermal sterilizing stimulus to a cerebrospinal fluid received within the interior of at least one fluid-flow passageway 106 and a second pulsed thermal sterilizing stimulus to a tissue proximate the outer surface of the implanted device 102. At 3624, providing the pulsed thermal sterilizing stimulus includes independently delivering, in vivo, at least one of a first pulsed thermal sterilizing stimulus to a cerebrospinal fluid received within the interior of at least one fluid-flow passageway 106 and a second pulsed thermal sterilizing stimulus to a tissue proximate the outer surface of the implanted cerebrospinal fluid management device 102 in response to a real-time detected change in an index of refraction parameter associated with the cerebrospinal fluid received within the interior of at least one fluid-flow passageway 106.

Figure 37:
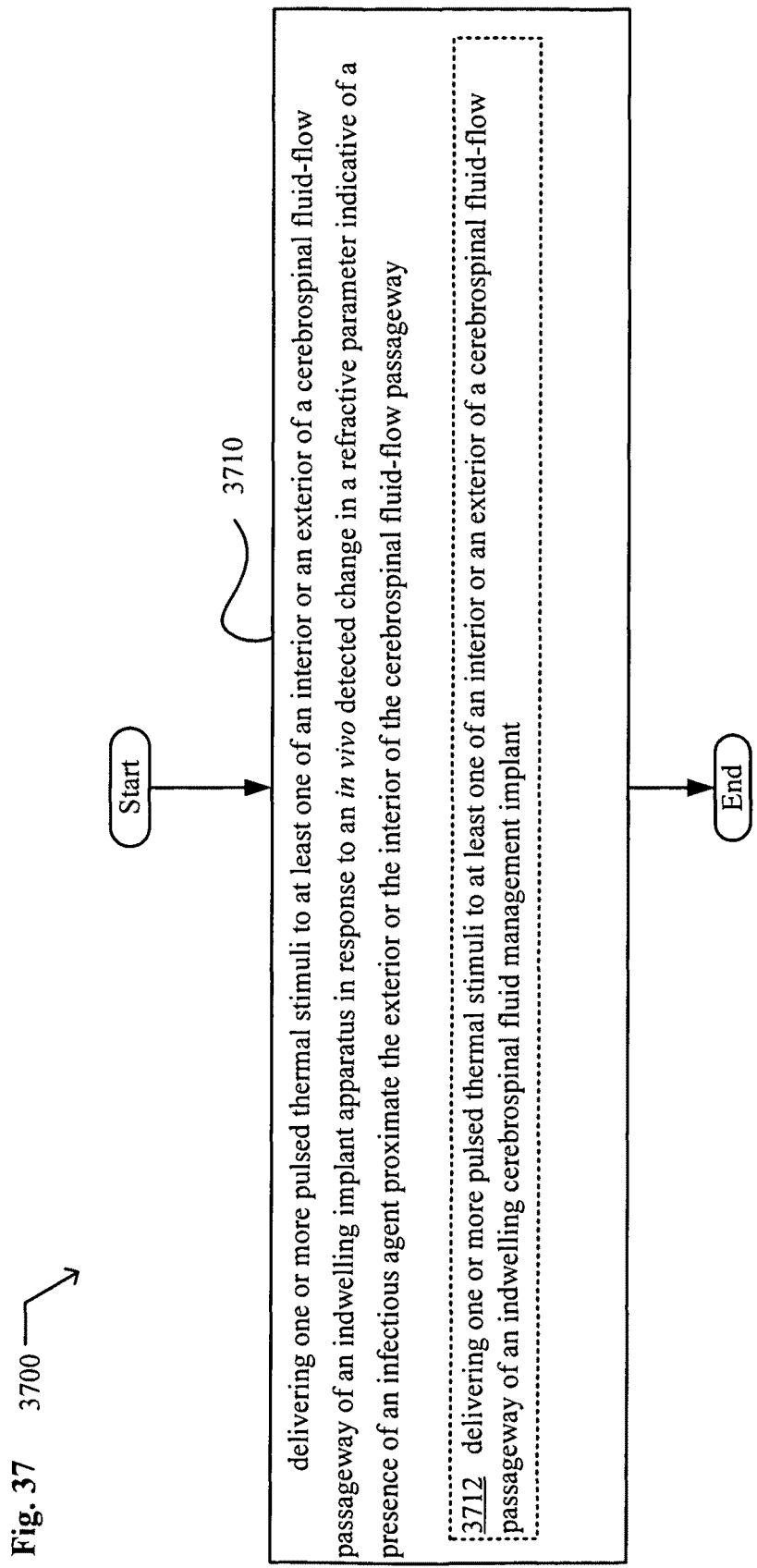
FIG. 37 is a flow diagram of a method according to one illustrated embodiment.

FIG. 37 shows an example of a method 3700. At 3710, the method 3700 includes delivering one or more pulsed thermal stimuli to at least one of an interior or an exterior of a cerebrospinal fluid-flow passageway 106 of an indwelling implant apparatus 102 in response to an in vivo detected change in a refractive parameter indicative of a presence of an infectious agent proximate the exterior or the interior of the cerebrospinal fluid-flow passageway 106. At 3712, delivering the one or more pulsed thermal stimuli includes delivering one or more pulsed thermal stimuli to at least one of an interior or an exterior of a cerebrospinal fluid-flow passageway 106 of an indwelling cerebrospinal fluid management implant 102.

FIG. 38 shows an example of a method 3800. At 3810, the method 3800 includes concurrently or sequentially delivering two or more energy stimuli to an interior surface 110 and an exterior surface 108 of a body structure 104 of an indwelling apparatus in response to a detected parameter associated with one or more of a cerebrospinal fluid received within the interior of the body structure 104, a detected parameter associated with a tissue proximate the exterior surface 108, or a physiological characteristic associated with a biological subject.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system can be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware, or virtually any combination thereof. Further, the use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A shunt assembly, comprising:
a body structure defining one or more fluid-flow passageways configured to receive a biological fluid of a biological subject;
a sensor component for detecting an infectious agent proximate to the body structure;
a sterilizing energy emitter configured to emit a sterilizing energy stimulus to the biological fluid or to the infectious agent proximate to the body structure; and
means for reflecting at least a portion of the emitted energy stimulus within an interior of at least one of the one or more fluid-flow passageways.

2. The shunt assembly of claim 1, wherein the means for reflecting at least a portion of an emitted energy stimulus includes one or more energy emitters configured to emit the energy stimulus to an interior at least one of the one or more fluid-flow passageways, and an optical material that internally reflects at least a portion of an emitted energy stimulus present within an interior of at least one of the one or more fluid-flow passageways.

3. The shunt assembly of claim 1, wherein the means for reflecting at least a portion of an emitted energy stimulus includes an optical material that internally reflects at least a portion of an emitted energy stimulus within an interior of at least one of the one or more fluid-flow passageways, without substantially permitting the transmission of the emitted energy stimulus through an exterior of the body structure.

4. The shunt assembly of claim 1, wherein the means for reflecting at least a portion of an emitted energy stimulus includes an optical material that internally directs at least a portion of an emitted energy stimulus along a substantially lateral direction of at least one of the one or more fluid-flow passageways.

5. The shunt assembly of claim 1, wherein the means for reflecting at least a portion of an emitted energy stimulus includes a reflective surface capable of reflecting at least about 50 percent of an energy stimulus emitted by the one or more energy emitters that impinges on the reflective surface.

6. The shunt assembly of claim 1, wherein the means for reflecting at least a portion of an emitted energy stimulus includes a reflective surface that is reflective at a first wavelength and transmissive at a second wavelength different from the first wavelength.

7. The shunt assembly of claim 1, wherein the means for reflecting at least a portion of an emitted energy stimulus includes one or more internally reflective components configured to manage a delivery of light to a biological fluid received within the one or more fluid-flow passageways, and to manage a collection of reflected light from the biological fluid.

8. The shunt assembly of claim 1, wherein the means for reflecting at least a portion of an emitted energy stimulus includes an optical component that directs a first portion of an emitted energy stimulus along a substantially lateral direction in one or more regions of at least one of the one or more fluid-flow passageways and an optical component that directs a second portion of the emitted energy stimulus along a substantially longitudinal direction in one or more regions of at least one of the one or more fluid-flow passageways.

9. The shunt assembly of claim 1, wherein the means for reflecting at least a portion of an emitted energy stimulus includes a first optical component configured to direct at least a portion of an emitted energy stimulus along a substantially lateral direction in a first region of at least one of the one or more fluid-flow passageways and a second optical component configured to direct at least a portion of the emitted energy stimulus along a substantially lateral direction in a second region of the one or more fluid-flow passageways, the second region different from the first region.

10. The shunt assembly of claim 1, wherein the means for reflecting at least a portion of an emitted energy stimulus includes a first optical component that directs at least a portion of an emitted energy stimulus along a substantially longitudinal direction in a first region of at least one of the one or more fluid-flow passageways and a second optical component that directs at least a portion of the emitted energy stimulus along a substantially longitudinal direction in a second region of the one or more fluid-flow passageways, the second region different from the first region.

11. The shunt assembly of claim 1, wherein at least a portion of the body structure is configured to sufficiently internally reflect at least a portion of an emitted energy stimulus to generate an evanescent electromagnetic field across one or more regions of the body structure.

12. The shunt assembly of claim 1, wherein at least a portion of the body structure is configured to sufficiently internally reflect at least a portion of an emitted energy stimulus to cause an evanescent electromagnetic field to emanate from at least a portion of the body structure.

13. The shunt assembly of claim 1, wherein at least a portion of the body structure is configured to internally reflect at least a portion of an emitted energy stimulus within an interior of at least one of the one or more fluid-flow passageways.

14. The shunt assembly of claim 1, wherein at least a portion of the body structure is configured to totally internally reflect at least a portion of an emitted energy-stimulus propagated within an interior of at least one of the one or more fluid-flow passageways.

15. The shunt assembly of claim 1, wherein the infectious agent is in a biofilm.

16. The shunt assembly of claim 1, wherein the sensor component is configured to perform a real-time comparison of a measurand associated with a biological sample proximate one or more regions of at least one surface of the implantable device to stored reference data.

17. The shunt assembly of claim 1, wherein the sensor component is configured to detect at least one physiological characteristic associated with an infectious agent.

18. The shunt assembly of claim 1, further comprising a controller operably coupled to the sensor component and to the sterilizing energy emitter, the controller configured to automatically control at least one characteristic associated with sterilizing energy stimulus.

19. A shunt assembly, comprising:
a body structure defining one or more fluid-flow passageways configured to receive a biological fluid of a biological subject; at least a portion of the body structure configured to reflecting at least a portion of an emitted energy stimulus within the interior of at least one of the one or more fluid-flow passageways;
a sensor component for detecting an infectious agent proximate to the body structure; and
one or more energy emitters configured to emit the energy stimulus to an interior at least one of the one or more fluid-flow passageways;
wherein at least a portion of a body structure defining the one or more fluid-flow passageways includes a reflective surface capable of reflecting at least about 50 percent of an energy stimulus emitted by the one or more energy emitters that impinges on the reflective surface.

20. The shunt assembly of claim 19, wherein the at least a portion of the body structure is configured to laterally internally reflect or longitudinally internally reflect electromagnetic radiation transmitted within the interior of at least one of the one or more fluid-flow passageways.

21. The shunt assembly of claim 19, further comprising:
one or more optical materials forming at least a portion of a body structure defining the one or more fluid-flow passageways, the one or more optical materials configured to limit an amount of the energy stimulus that can traverse within the one or more fluid-flow passageways and through an outer surface of the body structure.

22. The shunt assembly of claim 19, further comprising:
one or more optical materials on at least a portion of a body structure defining the one or more fluid-flow passageways to internally reflect at least a portion of an emitted energy stimulus from the one or more energy emitters into an interior of at least one of the one or more fluid-flow passageways.

23. The shunt assembly of claim 19, further comprising:
at least one outer internally reflective coating on a body structure defining the one or more fluid-flow passageways.

24. The shunt assembly of claim 19, further comprising:
at least one inner internally reflective coating on a body structure defining the one or more fluid-flow passageways.

25. The shunt assembly of claim 19, wherein at least one of the one or more fluid-flow passageways includes a surface configured to laterally internally reflect or longitudinally internally reflect electromagnetic radiation transmitted there through.

26. The shunt assembly of claim 19, wherein at least a portion of a body structure defining the one or more fluid-flow passageways includes a reflective surface that is reflective at a first wavelength and transmissive at a second wavelength different from the first wavelength.

27. The shunt assembly of claim 19, wherein at least one of the one or more fluid-flow passageways includes one or more internally reflective components configured to manage a delivery of light to a biological fluid received within the one or more fluid-flow passageways, and to manage a collection of reflected light from the biological fluid.

28. The shunt assembly of claim 19, wherein at least one of the one or more fluid-flow passageways includes at least one of an outer surface and an inner surface that is reflective to at least one of electromagnetic energy, ultrasonic energy, and thermal energy.

29. The shunt assembly of claim 19, wherein the infectious agent is in a biofilm.

30. The shunt assembly of claim 19, wherein the sensor component is configured to perform a real-time comparison of a measurand associated with a biological sample proximate one or more regions of at least one surface of the implantable device to stored reference data.

31. The shunt assembly of claim 19, wherein the sensor component is configured to detect at least one physiological characteristic associated with an infectious agent.

32. The shunt assembly of claim 19, further comprising a controller operably coupled to the sensor component and to at least one of the one or more energy emitters, the controller configured to automatically control at least one characteristic associated with sterilizing energy stimulus.

* * * * *

UNITED STATES PATENT AND TRADEMARK OFFICE
CERTIFICATE OF CORRECTION

| | | |
|---|---|---|
| PATENT NO. | : 9,687,670 B2 | Page 1 of 1 |
| APPLICATION NO. | : 12/800798 | |
| DATED | : June 27, 2017 | |
| INVENTOR(S) | : Ralph F. Dacey, Jr. et al. | |

It is certified that error appears in the above-identified patent and that said Letters Patent is hereby corrected as shown below:

In the Specification

Column 2, Line 6 "Ser. No. 12/800,760, entitled SYSTEMS, DEVICES, AND" should read --Ser. No. 12/800,766, entitled SYSTEMS, DEVICES, AND--

In the Claims

Column 106, Line 44, Claim 19 "stimulus to an interior at least one of the one or more" should read --stimulus to an interior of at least one of the one or more--

Signed and Sealed this
Tenth Day of October, 2017

Joseph Matal
*Performing the Functions and Duties of the*
*Under Secretary of Commerce for Intellectual Property and*
*Director of the United States Patent and Trademark Office*